US008450304B2

(12) United States Patent
Zhang et al.

(10) Patent No.: US 8,450,304 B2
(45) Date of Patent: May 28, 2013

(54) 4-AZETIDINYL-1-HETEROARYL-CYCLOHEXANOL ANTAGONISTS OF CCR2

(75) Inventors: Xuqing Zhang, Audubon, PA (US); Heather Rae Hufnagel, Glenmoore, PA (US); Cuifen Hou, Spring House, PA (US); Dana L. Johnson, Upper Black Eddy, PA (US); Zhihua Sui, Spring House, PA (US); Barry Fegely, Quakertown, PA (US); David Breslin, Telford, PA (US)

(73) Assignee: Janssen Pharmaceutica N.V. (BE)

( * ) Notice: Subject to any disclaimer, the term of this patent is extended or adjusted under 35 U.S.C. 154(b) by 359 days.

(21) Appl. No.: 12/633,861

(22) Filed: Dec. 9, 2009

(65) Prior Publication Data
US 2010/0144695 A1 Jun. 10, 2010

Related U.S. Application Data

(60) Provisional application No. 61/121,272, filed on Dec. 10, 2008, provisional application No. 61/167,295, filed on Apr. 7, 2009.

(51) Int. Cl.
*C07D 401/08* (2006.01)
*C07D 403/08* (2006.01)
*C07D 407/14* (2006.01)
*A61K 31/506* (2006.01)

(52) U.S. Cl.
USPC ...... 514/210.19; 514/269; 514/339; 514/363; 514/365; 514/367; 514/369; 514/370; 514/372; 514/374; 514/375; 514/397; 514/406; 544/311; 546/268.1; 548/136; 548/179; 548/187; 548/194; 548/204; 548/214; 548/217; 548/236; 548/314.7; 548/375.1; 548/953

(58) Field of Classification Search
USPC ............ 544/311; 546/268.1; 548/136, 179, 548/187, 194, 204, 214, 217, 236, 314.7, 548/375.1, 953; 514/210.19, 269, 339, 363, 514/365, 367, 369, 370, 372, 374, 375, 397, 514/406
See application file for complete search history.

(56) References Cited

U.S. PATENT DOCUMENTS

| | | | |
|---|---|---|---|
| 6,245,799 B1 | 6/2001 | Asselin et al. | |
| 6,255,315 B1 | 7/2001 | Patane et al. | |
| 8,269,015 B2 * | 9/2012 | Zhang et al. | 546/268.1 |
| 2003/0004151 A1 | 1/2003 | Cherney et al. | |
| 2006/0069123 A1 | 3/2006 | Xia et al. | |
| 2006/0135502 A1 | 6/2006 | Cherney et al. | |
| 2006/0252751 A1 | 11/2006 | Xue et al. | |
| 2010/0144695 A1 | 6/2010 | Zhang et al. | |
| 2010/0267688 A1 | 10/2010 | Zhang et al. | |
| 2010/0267689 A1 | 10/2010 | Zhang et al. | |

FOREIGN PATENT DOCUMENTS

| | | |
|---|---|---|
| EP | 1201239 | 5/2002 |
| WO | WO 9857641 | 12/1998 |
| WO | WO 0134598 | 5/2001 |
| WO | WO 2004/050024 | 6/2004 |
| WO | WO 2005/060665 | 7/2005 |
| WO | WO 2006/073592 | 7/2006 |
| WO | WO 2007003965 | 1/2007 |
| WO | WO 2007/053498 | 5/2007 |
| WO | WO 2007/130712 | 11/2007 |
| WO | WO 2010/068663 | 6/2010 |
| WO | WO 2010/1210 11 | 10/2010 |
| WO | WO 2010/1210 36 | 10/2010 |
| WO | WO 2010/1210 46 | 10/2010 |

OTHER PUBLICATIONS

Havlioglu et al., Slit Proteins potential endogenous modulators of inflammation, Neurovirology, 8, pp. 486-495, 2002.*
Banker et al., Prodrugs, Modern Pharmaceutics, Third Edition, Revised and Expanded, pp. 451 and 596, 1996.*
Wolff, Some Consideration for prodrug design, Burgers Medicinal Chemistry and Drug Discovery, 5th Edition, vol. I: Principles and Practice, pp. 975-977, 1995.*
Damasio, Alzheimer's Disease and related dementias, Cecil Textbook of Medicine, 20th Edition, vol. 2, pp. 1992-1996, 1996.*
Simone, Oncology: Introduction, Cecil Textbook of Medicine, 20th Edition, vol. 1, pp. 1004-1010, 1996.*
Gura et al., Systems for identifying new drugs are often faulty, Science, 278:1041-1042, 1997.*
Johnson et al., Relationships between drug activity in NCI preclinical in vitro and in vivo models and early clinical trials, British Journal of Cancer, 84(10):1424-1431,2001.*
Ulrich, Chapter 4: Crystallization, Kirk-Othmer Encyclopedia of Chemical Technology, Aug. 2002.*
West, Solid Solutions, Solid State Chemistry and its applications, pp. 358 & 365, 1988.*
Lima et al., Bioisosterism: A Useful Strategy for Molecular Modification and Drug Design, Current Medicinal Chemistry, 2005, 12, pp. 23-49.*
Thornber, C.W. Isosterism and Molecular Modification in Drug Design. Royal Society of Chemistry. 1979, pp. 563-580.*
Bundgaard, et al., "Design of Prodrugs: Bioreversible Derivatives for Various Functional Groups and Chemical Entities", Elsevier Science Publishers, 1985, pp. 1-4, Chapter 1.

(Continued)

*Primary Examiner* — Deepak Rao
(74) *Attorney, Agent, or Firm* — Mary A. Appollina

(57) ABSTRACT

The present invention comprises compounds of Formula (I).

Formula (I)

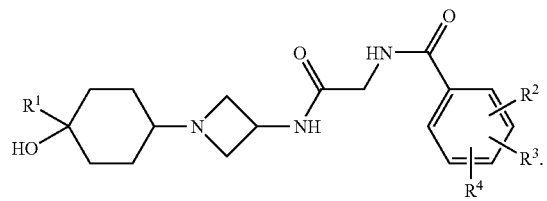

wherein: $R^1$, $R^2$, $R^3$, and $R^4$ are as defined in the specification. The invention also comprises pharmaceutical compositions comprising the compounds of formula (I) and methods of preventing, treating or ameliorating a CCR2 mediated syndrome, disorder or disease, for example, type II diabetes, obesity or asthma, by administering the compounds of formula (I).

25 Claims, 2 Drawing Sheets

OTHER PUBLICATIONS

Bryn, et al., "Hydrates and Solvates", Solid State Chemistry of Drugs, 2$^{nd}$ Edition, 1999, pp. 232-247, Chapter 10, Polymorphs.

Han, et al., "Targeted Prodrug Design to Optimize Drug Delivery", AAPS PHARMSCI, 2000, vol. 2 (1) pp. 1-11.

Morissette, et al., "High-throughput crystallization: polymorphs, salts, co-crystals and solvates of pharmaceutical solids", Advanced Drug Delivery Reviews, 2004, pp. 275-300, vol. 56.

Vippagunta, et al., "Crystalline Solids", Advanced Drug Delivery Reviews, 2001, pp. 3-26, vol. 48.

Thornber, "Isosterism and Molecular Modification in Drug Design", Royal Society of Chemistry, 1979, pp. 563-580.

Golub, et al., "Molecular Classification of Cancer: Class Discovery and Class Prediction by Gene Expression Monitoring", Science, 1999, pp. 531-537, vol. 286.

Lala, et al., "role of nitric oxide in tumor progression: Lessions from experimental tumors", Cancer and Metastasis Reviews, 1998, pp. 91-106, 17(1).

Dawson, et al, "Targeting Monocyte Chemoattractant Protein-1 Signalling in Disease", Expert Opin. Ther. Targets, 2003, vol. 7(1), pp. 35-48.

Seebach, et al, "Safe One-Pot Carbon-Carbon Bond Formation with Lithiated Nitrosamines Including Denitrosation by Sequential Reduction with Lithium a Aluminium Hydride and Raney-Nickel", Synthesis, 1979, vol. 6, pp. 423-424.

Gdaniec, et al., "Conformation and Stereodynamics of N,N-Dinitroso-2,4,6,8-tetraaryl-3,7-diazabicyclo [3.3.1] nonanes", J. Org. Chem., 1997 vol. 62, pp. 5619-5622.

Abdel-Magid, et al., "Reductive Amination of Aldehydes and Ketones with Sodium Triacetoxyborohydride. Studies on Direct and Indirect Reductive Amination Procedures", J. Org. Chem, 1996, vol. 61, pp. 3849-3862.

Chan, et al., "1,5-BIS (Trimethylsiloxy)-1,5-Dimethoxy-1-4-Pentadienes. Cyclopropance Synthesis Via Intramolecular Coupling", Tetrahedron Letters, 1982 vol. 23, No. 8, pp. 799-802.

Rollins, "Monocyte chemoattractant protein 1: a potential regulator of monocyte recruitment in inflammatory disease", 89Mol. Med. Today, 1996 vol. 2, pp. 198.

Das, B. et al. "A Highly Chemoselective Boc Protection of Amines using Sulfonic-Acid-Functionalized Silica As an Efficient Heterogeneous Recyclable Catalyst", Tetrahedron Lett. 2006, 47, 7551-7556.

Ingersoll, A. W. et. al., "Hippuric Acid", Organic Syntheses 1932, XII, vol. 12. pp. 40.

Xia M, Sui Z, "Recent Developments in CCR2 Antagonists", *Expert Opin. Ther. Patents*, 2009, 19(3), 295-303.

U.S. Appl. No. 12/760,832, filed Apr. 15, 2010.
U.S. Appl. No. 12/760,855, filed Apr. 15, 2010.
U.S. Appl. No. 12/761,080, filed Apr. 15, 2010.
PCT/US2009/067307 International Search Report, Aug. 2, 2010.
U.S. Appl. No. 12/760,832 Notice of Allowance, dated May 18, 2012.
U.S. Appl. No. 12/760,832 Office Action, dated Feb. 3, 2012.
U.S. Appl. No. 12/760,832 Office Action, dated Dec. 20, 2011.
U.S. Appl. No. 12/760,855 Notice of Allowance, dated Aug. 3, 2012.
U.S. Appl. No. 12/760,855 Notice of Allowance, dated Feb. 22, 2012.
U.S. Appl. No. 12/760,855 Office Action, dated Sep. 15, 2011.
U.S. Appl. No. 12/761,080 Notice of Abandonment, dated Nov. 9, 2011.
U.S. Appl. No. 12/761,080 Notice of Allowance and Fee(s) Due, dated Jul. 25, 2011.
U.S. Appl. No. 12/761,080 Office Action, dated Feb. 11, 2011.
U.S. Appl. No. 13/280,690 Notice of Allowance dated Jun. 27, 2012.
U.S. Appl. No. 13/280,690 Office Action, dated Mar. 26, 2012.
U.S. Appl. No. 13/280,690 Office Action dated Dec. 8, 2011.

Silva, A., et al., Mini Rev. Med. Chem 2005 vol. 5, pp. 893-914.

Lanter, et al., "The discovery of Novel Cyclohexylamide CCR2 Antagonists", Bioorganic & Medicinal Chemistry Letters, Pergamon; 2011, vol. 21, No. 24, pp. 7496-7501.

Tamura, Inhibition of CCR2 Amelolorates Insulin Resistance and Hepatic Steatosis in db/db Mice, 2008, Arterioscler Thromb Vasc Biol. p. 2195-2201.

Barnes, et. al. New Drugs for Asthma, 2004, Nature Reviews: Drug Discovery, vol. 3, p. 831-844.

Horuk, et al., Chemokine Receptor Antagonists: overcoming developmental hurdles, 2009, Nature Reviews: Drug Discovery, vol. 8, pp. 23-22.

Kang, CCR2 antagonism improves insulin resistance, lipid metabolism, and diabetic nephropathy in type 2 diabetic mice, 2010, Kidney Internation, vol. 78, p. 883-894.

Palmqvist, Chemokines and their receptors as potential targets for the treatment of asthma, 2007, British Journal of Pharmacology, vol. 151, p. 725-736'.

\* cited by examiner

US 8,450,304 B2

4-AZETIDINYL-1-HETEROARYL-CYCLOHEXANOL ANTAGONISTS OF CCR2

CROSS-REFERENCE TO RELATED APPLICATIONS

This application claims priority from U.S. Provisional Application Ser. Nos. 61/121,272 filed Dec. 10, 2008 and 61/167,295 filed Apr. 7, 2009, the contents of each of which are hereby incorporated by reference in their entirety.

FIELD OF THE INVENTION

The invention is directed to substituted dipiperidine compounds, which are antagonists to the chemoattractant cytokine receptor 2 (CCR2), pharmaceutical compositions, and methods for use thereof. More particularly, the CCR2 antagonists are substituted piperidyl acrylamide compounds useful for preventing, treating or ameliorating a CCR2 mediated syndrome, disorder or disease.

BACKGROUND OF THE INVENTION

CCR2 is a member of the GPCR family of receptors, as are all known chemokine receptors, and are expressed by monocytes and memory T-lymphocytes. The CCR2 signaling cascade involves activation of phospholipases (PLCβ2), protein kinases (PKC), and lipid kinases (PI-3 kinase).

Chemoattractant cytokines (i.e., chemokines) are relatively small proteins (8-10 kD), which stimulate the migration of cells. The chemokine family is divided into four subfamilies based on the number of amino acid residues between the first and second highly conserved cysteines.

Monocyte chemotactic protein-1 (MCP-1) is a member of the CC chemokine subfamily (wherein CC represents the subfamily having adjacent first and second cysteines) and binds to the cell-surface chemokine receptor 2 (CCR2). MCP-1 is a potent chemotactic factor, which, after binding to CCR2, mediates monocyte and lymphocyte migration (i.e., chemotaxis) toward a site of inflammation. MCP-1 is also expressed by cardiac muscle cells, blood vessel endothelial cells, fibroblasts, chondrocytes, smooth muscle cells, mesangial cells, alveolar cells, T-lymphocytes, marcophages, and the like.

After monocytes enter the inflammatory tissue and differentiate into macrophages, monocyte differentiation provides a secondary source of several proinflammatory modulators, including tumor necrosis factor-α (TNF-α), interleukin-1 (IL-1), IL-8 (a member of the CXC chemokine subfamily, wherein CXC represents one amino acid residue between the first and second cysteines), IL-12, arachidonic acid metabolites (e.g., PGE$_2$ and LTB$_4$), oxygen-derived free radicals, matrix metalloproteinases, and complement components.

Animal model studies of chronic inflammatory diseases have demonstrated that inhibition of binding between MCP-1 and CCR2 by an antagonist suppresses the inflammatory response. The interaction between MCP-1 and CCR2 has been implicated (see Rollins B J, Monocyte chemoattractant protein 1: a potential regulator of monocyte recruitment in inflammatory disease, *Mol. Med. Today,* 1996, 2:198; and Dawson J, et al., Targeting monocyte chemoattractant protein-1 signaling in disease, *Expert Opin. Ther. Targets,* 2003 Feb. 7 (1):35-48) in inflammatory disease pathologies such as psoriasis, uveitis, atherosclerosis, rheumatoid arthritis (RA), multiple sclerosis, Crohn's Disease, nephritis, organ allograft rejection, fibroid lung, renal insufficiency, type II diabetes and diabetic complications, diabetic nephropathy, diabetic retinopathy, diabetic retinitis, diabetic microangiopathy, tuberculosis, sarcoidosis, invasive staphylococcia, inflammation after cataract surgery, allergic rhinitis, allergic conjunctivitis, chronic urticaria, Chronic Obstructive Pulmonary Disease (COPD), allergic asthma, periodontal diseases, periodonitis, gingivitis, gum disease, diastolic cardiomyopathies, cardiac infarction, myocarditis, chronic heart failure, angiostenosis, restenosis, reperfusion disorders, glomerulonephritis, solid tumors and cancers, chronic lymphocytic leukemia, chronic myelocytic leukemia, multiple myeloma, malignant myeloma, Hodgkin's disease, and carcinomas of the bladder, breast, cervix, colon, lung, prostate, and stomach. Monocyte migration is inhibited by MCP-1 antagonists (either antibodies or soluble, inactive fragments of MCP-1), which have been shown to inhibit the development of arthritis, asthma, and uveitis. Both MCP-1 and CCR2 knockout (KO) mice have demonstrated that monocyte infiltration into inflammatory lesions is significantly decreased. In addition, such KO mice are resistant to the development of experimental allergic encephalomyelitis (EAE, a model of human MS), cockroach allergen-induced asthma, atherosclerosis, and uveitis. Rheumatoid arthritis and Crohn's Disease patients have improved during treatment with TNF-α antagonists (e.g., monoclonal antibodies and soluble receptors) at dose levels correlated with decreases in MCP-1 expression and the number of infiltrating macrophages.

MCP-1 has been implicated in the pathogenesis of seasonal and chronic allergic rhinitis, having been found in the nasal mucosa of most patients with dust mite allergies. MCP-1 has also been found to induce histamine release from basophils in vitro. During allergic conditions, both allergens and histamines have been shown to trigger (i.e., to up-regulate) the expression of MCP-1 and other chemokines in the nasal mucosa of people with allergic rhinitis, suggesting the presence of a positive feedback loop in such patients.

There remains a need for small molecule CCR2 antagonists for preventing, treating or ameliorating a CCR2 mediated inflammatory syndrome, disorder or disease resulting from MCP-1 induced monocyte and lymphocyte migration to a site of inflammation.

All documents cited herein are incorporated by reference.

DETAILED DESCRIPTION OF THE INVENTION

Figure 1:
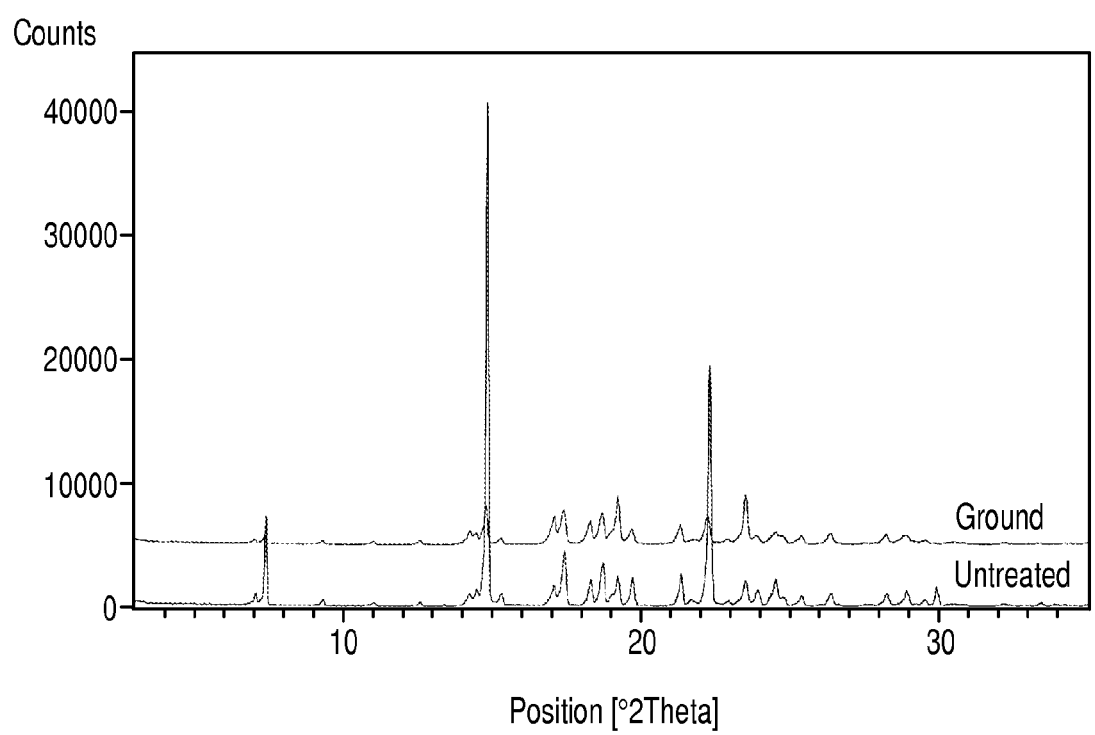
FIG. 1 is comparison of the X-ray diffraction patterns of untreated and ground samples of compound 40a (freebase monohydrate) expressed in terms of ° 2θ.

The invention comprises compounds of Formula (I).

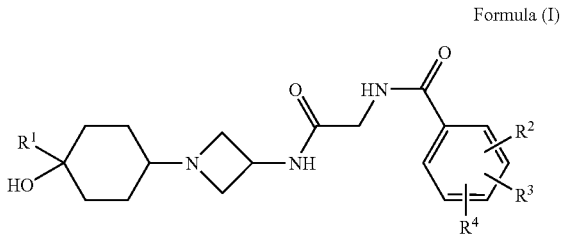

Formula (I)

wherein:
R¹ is

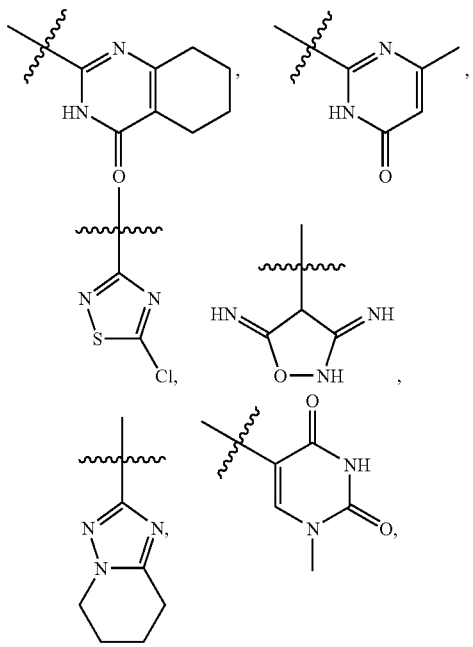

pyridyl, pyridyl-N-oxide, 1H-pyridin-2-onyl, indolyl, pyrazinyl, 3-H-thiazol-2-onyl, pyrimidyl, benzooxazolyl, oxazolyl, thiazolyl, isothiazolyl, pyrazolyl, imidazolyl, thiophenyl, furyl, [1,2,4]oxadiazolyl or [1,3,4]thiadiazolyl; wherein said pyridyl, pyridyl-N-oxide, pyrimidyl, pyrazolyl, imidazolyl, thiophenyl, or thiazolyl is optionally substituted with one substituent selected from the group consisting of $OC_{(1-4)}$ alkyl, $OC_{(3-6)}$ocycloalkyl, $OCH_2CF_3$, $OCH_2Ph$, F, CN, $CH_2CN$, $C_{(1-4)}$alkyl, $CH_2CF_3$, $N(C_{(1-4)}alkyl)_2$, $C_{(1-4)}$alkylOH, $Si(CH_3)_3$, —C≡CH, $SCH_3$, $S(O)CH_3$, $SO_2CH_3$, pyrrolidinyl, OH, $NH_2$, NHCN, $CO_2H$, $CONH_2$, $NHCO_2C_{(1-4)}$ alkyl, $N(SO_2CH_3)_2$, $NHSO_2CH_3$, $NHC(O)CF_3$, $NHC_{(1-4)}$ alkyl, $NHCO_2H$, $NHCO_2C_{(1-4)}$alkyl, $NHCOC_{(1-4)}$alkyl, $NHCONH_2$, $NHCONHC_{(1-4)}$alkyl, and Br; or said pyridyl may be substituted with one $OCH_3$ group and one $CH_3$; or wherein said pyrimidyl is optionally substituted with one $N(C_{(1-4)}alkyl)_2$ group or one or two $OCH_3$ groups; or wherein said thiazolyl is optionally substituted on two adjacent carbon atoms to form fused bicyclic system benzothiazol-2-yl, or wherein said benzothiazol-2-yl is optionally substituted with Br or $OCH_3$; or wherein said 1H-pyridin-2-onyl is optionally substituted with one substituent selected from the group consisting of $CH_2CN$, $C_{(1-4)}$alkyl, $CH_2CF_3$, and $CH_2CH_2OH$, or said 1H-pyridin-2-onyl may be optionally substituted with up to 2 methyl groups; or wherein said [1,2,4]oxadiazolyl is optionally substituted on any carbon atom with $CCl_3$, or pyrrolidinyl, or alternatively both hydrogens on said carbon atom of said [1,2,4]oxadiazolyl may be replaced by an oxo group;

R² is $C_{(1-4)}$alkyl, $NH_2$, $NO_2$, $NHCH_2CH_2OH$, $N(C_{(1-4)}$alkyl$)_2$, $N(SO_2CH_3)_2$, CN, F, Cl, Br, $CF_3$, $C_{(3-6)}$cycloalkyl, heterocyclyl, $OCF_3$, $OCF_2H$, $CF_2H$, or $OC_{(1-4)}$alkyl;

R³ is H, F, Cl, $CF_3$, or $OC_{(1-4)}$alkyl; alternatively, R² and R³ may be taken together with their attached phenyl to form a benzo[1,3]dioxolyl, 2,3-dihydro-benzofuranyl, or 2,3-dihydro-benzo[1,4]dioxinyl group;

R⁴ is H, $OC_{(1-4)}$alkyl, or F;

and solvates, hydrates, tautomers, prodrugs, and pharmaceutically acceptable salts thereof.

An embodiment of the invention comprises compounds of Formula (Ia).

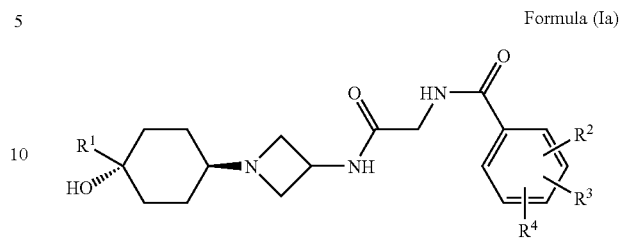

Formula (Ia)

wherein R¹, R², R³ and R⁴ are as defined above for Formula (I).

Another embodiment of the invention comprises compounds of Formula (I) and/or Formula (Ia) wherein:
R¹ is

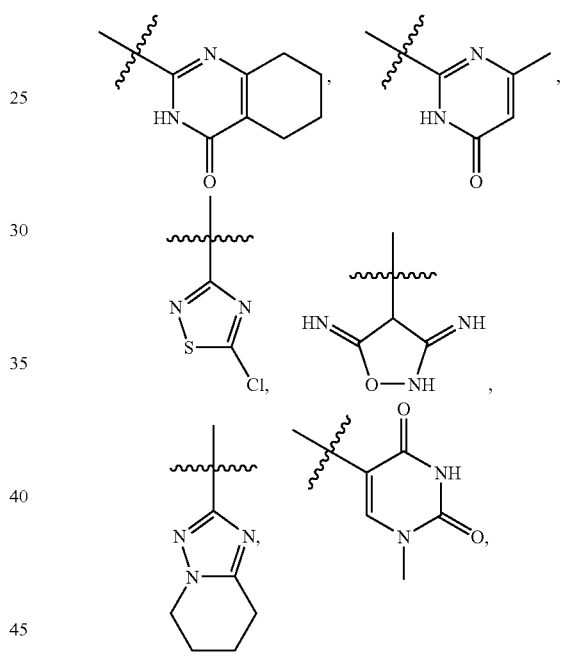

pyridyl, pyridyl-N-oxide, 1H-pyridin-2-onyl, indolyl, pyrazinyl, 3-H-thiazol-2-onyl, pyrimidyl, methyl substituted imidazolyl, methyl substituted pyrazolyl optionally substituted with Br, thiophenyl optionally substituted with Br, benzooxazolyl, oxazolyl, thiazolyl, isothiazolyl, [1,2,4]oxadiazolyl or [1,3,4]thiadiazolyl; wherein said pyridyl, pyridyl-N-oxide, or thiazolyl is optionally substituted with one substituent selected from the group consisting of $OC_{(1-4)}$alkyl, $OC_{(3-6)}$ cycloalkyl, $OCH_2CF_3$, $OCH_2Ph$, F, CN, $CH_2CN$, $C_{(1-4)}$alkyl, $CH_2CF_3$, $N(C_{(1-4)}alkyl)_2$, $C_{(1-4)}$alkylOH, $Si(CH_3)_3$, —C≡CH, $SCH_3$, $S(O)CH_3$, $SO_2CH_3$, pyrrolidinyl, OH, $NH_2$, NHCN, $CO_2H$, $CONH_2$, $NHCO_2C_{(1-4)}$alkyl, $N(SO_2CH_3)_2$, $NHSO_2CH_3$, $NHC(O)CH_3$, $NHC(O)CF_3$, $NHC_{(1-4)}$alkyl, and Br; or said pyridyl may be substituted with one $OCH_3$ group and one $CH_3$; wherein said pyrimidyl is optionally substituted with one $N(C_{(1-4)}alkyl)_2$ group or one or two $OCH_3$ groups; wherein said thiazolyl is optionally substituted on two adjacent carbon atoms to form fused bicyclic system benzothiazol-2-yl, wherein said benzothiazol-2-yl is optionally substituted with Br or $OCH_3$; wherein said 1H-pyridin-2-onyl is optionally substituted with one substituent selected from the group consisting of CH$_2$CN, C$_{(1-4)}$alkyl, CH$_2$CF$_3$, and CH$_2$CH$_2$OH, or said 1H-pyridin-2-onyl may be optionally substituted with up to 2 methyl groups; wherein said [1,2,4]oxadiazolyl is optionally substituted on any carbon atom with CCl$_3$, or pyrrolidinyl, alternatively both hydrogens on said carbon atom may be replaced by an oxo group;

R$^2$ is C$_{(1-4)}$alkyl, NH$_2$, NO$_2$, NHCH$_2$CH$_2$OH, N(C$_{(1-4)}$alkyl)$_2$, N(SO$_2$CH$_3$)$_2$, CN, F, Cl, Br, CF$_3$, pyrrolidinyl, OCF$_3$, OCF$_2$H, CF$_2$H, or OC$_{(1-4)}$alkyl;

R$^3$ is H, F, Cl, CF$_3$, or OC$_{(1-4)}$alkyl; alternatively, R$^2$ and R$^3$ may be taken together with their attached phenyl to form a benzo[1,3]dioxolyl group;

R$^4$ is H, OCH$_3$, or F;

and solvates, hydrates, tautomers, prodrugs, and pharmaceutically acceptable salts thereof.

Another embodiment of the invention comprises compounds of Formula (I) and/or Formula (Ia) wherein:

R$^1$ is pyridyl, pyridyl-N-oxide, pyrimidyl, methyl substituted imidazolyl, methyl substituted pyrazolyl optionally substituted with Br, thiophenyl optionally substituted with Br, benzooxazolyl, oxazolyl, thiazolyl, isothiazolyl, or [1,3,4]thiadiazolyl; wherein said pyridyl, pyridyl-N-oxide, or thiazolyl is optionally substituted with one substituent selected from the group consisting of OC$_{(1-4)}$alkyl, OC$_{(3-6)}$cycloalkyl, OCH$_2$CF$_3$, OCH$_2$Ph, F, CN, C$_{1-4}$alkyl, N(C$_{(1-4)}$alkyl)$_2$, C$_{(1-4)}$alkylOH, Si(CH$_3$)$_3$, —C≡CH, SCH$_3$, S(O)CH$_3$, SO$_2$CH$_3$, pyrrolidinyl, OH, NH$_2$, NHCN, and Br; or said pyridyl may be substituted with one OCH$_3$ group and one CH$_3$; wherein said pyrimidyl is optionally substituted with one N(C$_{(1-4)}$alkyl)$_2$ group or one or two OCH$_3$ groups; wherein said thiazolyl is optionally substituted on two adjacent carbon atoms to form fused bicyclic system benzothiazol-2-yl, wherein said benzothiazol-2-yl is optionally substituted with Br or OCH$_3$;

R$^2$ is NH$_2$, NO$_2$, NHCH$_2$CH$_2$OH, N(CH$_3$)$_2$, N(SO$_2$CH$_3$)$_2$, CN, F, Cl, Br, CF$_3$, pyrrolidinyl, or OCH$_3$;

R$^3$ is H, F, Cl, CF$_3$, or OCH$_3$; alternatively, R$^2$ and R$^3$ may be taken together with their attached phenyl to form a benzo[1,3]dioxolyl group;

R$^4$ is H, or F;

and solvates, hydrates, tautomers, prodrugs, and pharmaceutically acceptable salts thereof.

Another embodiment of the invention comprises compounds of Formula (I) and/or Formula (Ia) wherein:

R$^1$ is pyridyl, pyridyl-N-oxide, pyrimidyl, methyl substituted imidazolyl, methyl substituted pyrazolyl optionally substituted with Br, thiophenyl optionally substituted with Br, benzooxazolyl, oxazolyl, thiazolyl, isothiazolyl, or [1,3,4]thiadiazolyl; wherein said pyridyl or pyridyl-N-oxide is optionally substituted with one substituent selected from the group consisting of OC$_{(1-4)}$alkyl, OC$_{(3-6)}$cycloalkyl, OCH$_2$CF$_3$, OCH$_2$Ph, F, CN, C$_{(1-4)}$alkyl, N(C$_{(1-4)}$alkyl)$_2$, and Br; or said pyridyl may be substituted with one OCH$_3$ group and one CH$_3$; wherein said pyrimidyl is optionally substituted with one N(C$_{1-4}$alkyl)$_2$ group or one or two OCH$_3$ groups; wherein said thiazolyl is optionally substituted with C$_{(1-4)}$alkyl, CH$_2$OH, Si(CH$_3$)$_3$, —C≡CH, SCH$_3$, S(O)CH$_3$, SO$_2$CH$_3$, OH, NH$_2$, N(C$_{(1-4)}$alkyl)$_2$, pyrrolidinyl, OC$_{(1-4)}$alkyl, NHCN, or said thiazolyl may be substituted on two adjacent carbon atoms to form fused bicyclic system benzothiazol-2-yl, wherein said benzothiazol-2-yl is optionally substituted with Br;

R$^2$ is NH$_2$, NO$_2$, NHCH$_2$CH$_2$OH, N(CH$_3$)$_2$, N(SO$_2$CH$_3$)$_2$, CN, F, Cl, Br, CF$_3$, pyrrolidinyl, or OCH$_3$;

R$^3$ is H, F, Cl, CF$_3$, or OCH$_3$; alternatively, R$^2$ and R$^3$ may be taken together with their attached phenyl to form a benzo[1,3]dioxolyl group;

R$^4$ is H, or F;

and solvates, hydrates, tautomers, prodrugs, and pharmaceutically acceptable salts thereof.

Another embodiment of the invention comprises compounds of Formula (I) and/or Formula (Ia) wherein:

R$^1$ is pyridyl, methoxy substituted pyridyl-N-oxide, pyrimidyl, methyl substituted imidazolyl, methyl substituted pyrazolyl optionally substituted with Br, thiophenyl optionally substituted with Br, benzooxazolyl, oxazolyl, thiazolyl, isothiazolyl, or [1,3,4]thiadiazolyl; wherein said pyridyl is optionally substituted with one substituent selected from the group consisting of OCH$_3$, OCH$_2$CH$_3$, OCH(CH$_3$)$_2$, OC(CH$_3$)$_3$, cyclobutoxy, OCH$_2$CF$_3$, OCH$_2$Ph, F, CN, CH$_3$, N(CH$_3$)$_2$, and Br; or said pyridyl may be substituted with one OCH$_3$ group and one CH$_3$; wherein said pyrimidyl is optionally substituted with one N(CH$_3$)$_2$ group or one or two OCH$_3$ groups; wherein said thiazolyl is optionally substituted with CH$_2$OH, Si(CH$_3$)$_3$, CH$_3$, CH$_2$CH$_3$, CH(CH$_3$)$_2$, —C≡CH, SCH$_3$, S(O)CH$_3$, SO$_2$CH$_3$, OH, NH$_2$, N(CH$_3$)$_2$, pyrrolidinyl, OCH$_3$, OCH(CH$_3$)$_2$, NHCN, or said thiazolyl may be substituted on two adjacent carbon atoms to form fused bicyclic system benzothiazol-2-yl, wherein said benzothiazol-2-yl is optionally substituted with Br;

R$^2$ is CF$_3$, F, Cl, CN, OCH$_3$,

R$^3$ is H, F, Cl, CF$_3$, alternatively, R$^2$ and R$^3$ may be taken together with their attached phenyl to form a benzo[1,3]dioxolyl group;

R$^4$ is H, F;

and solvates, hydrates, tautomers, prodrugs, and pharmaceutically acceptable salts thereof.

Another embodiment of the invention is a compound which is selected from the group consisting of:

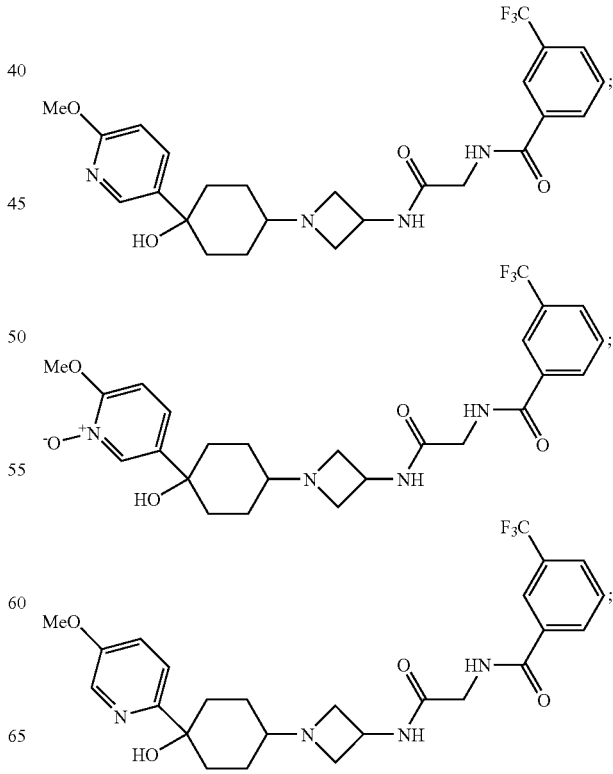

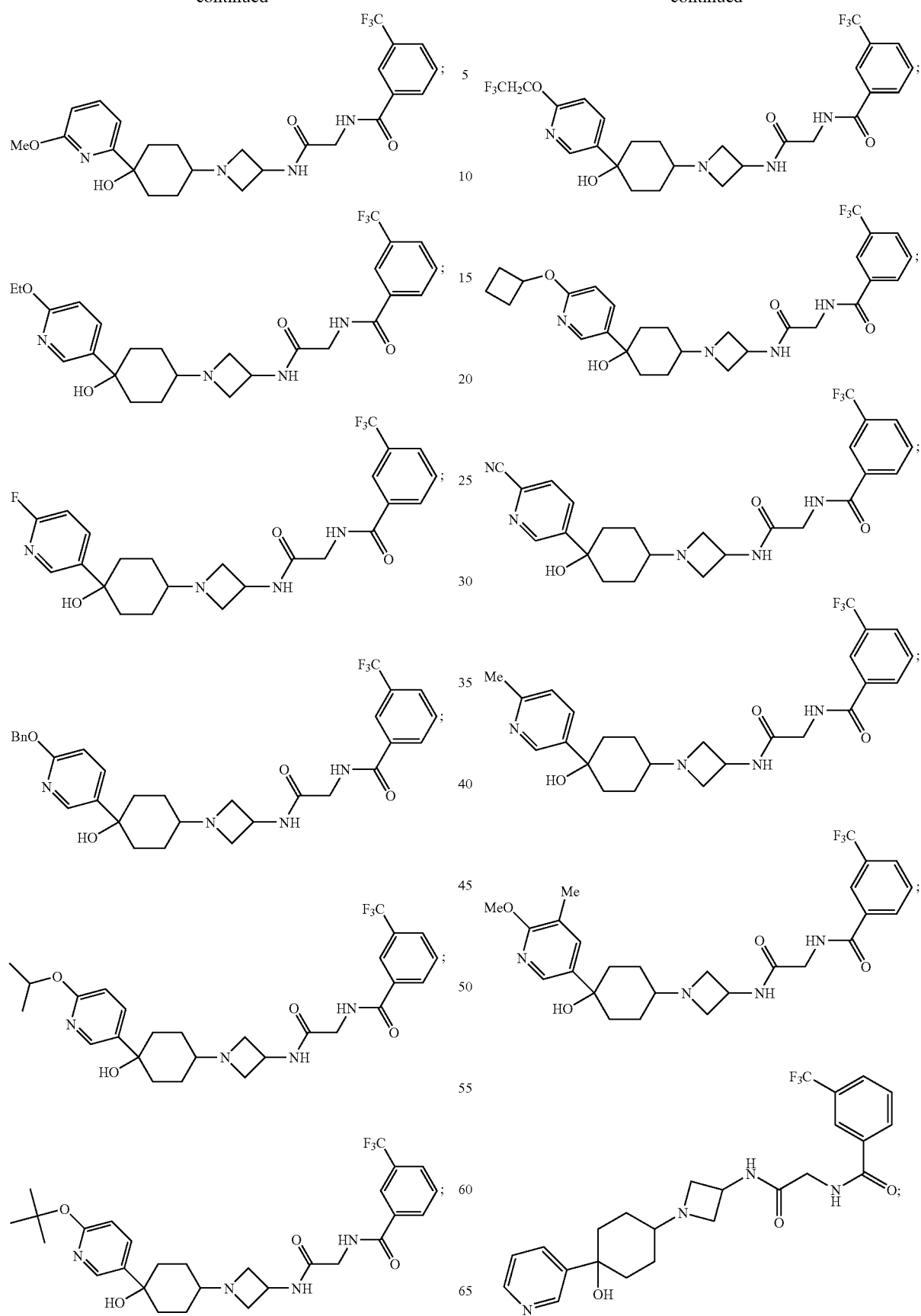

9
-continued
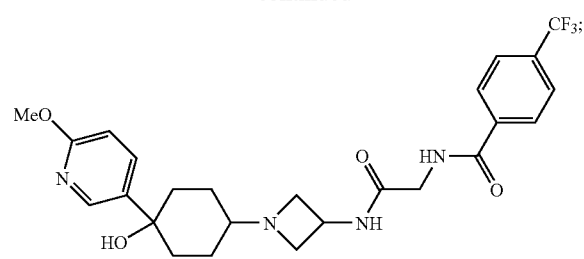
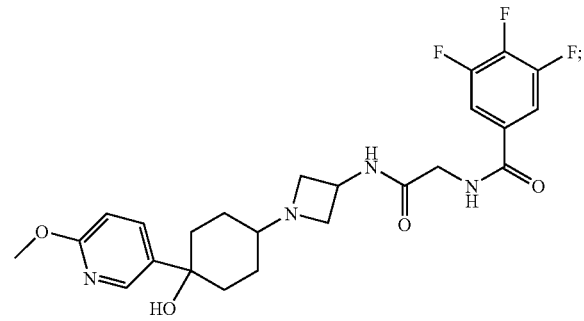
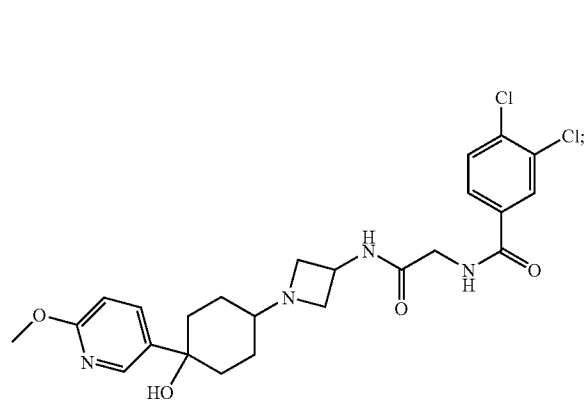
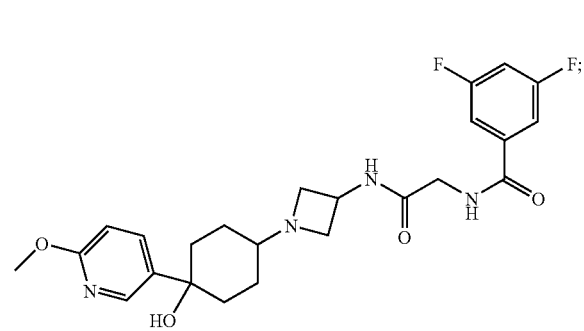
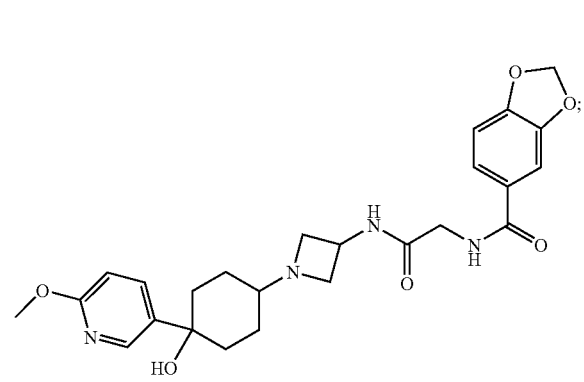
10
-continued
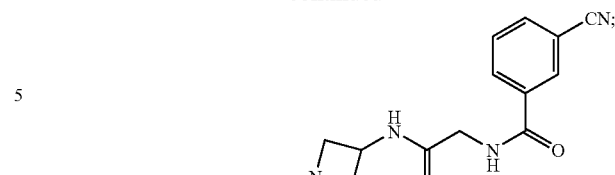
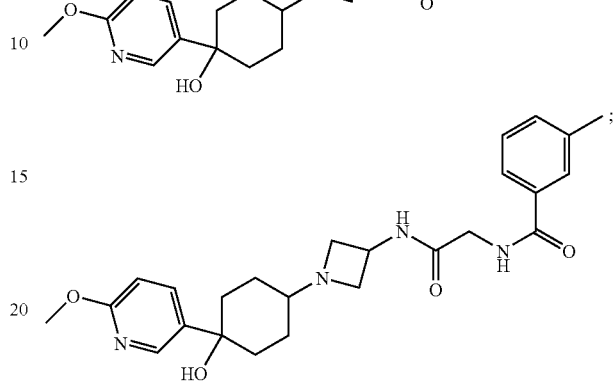
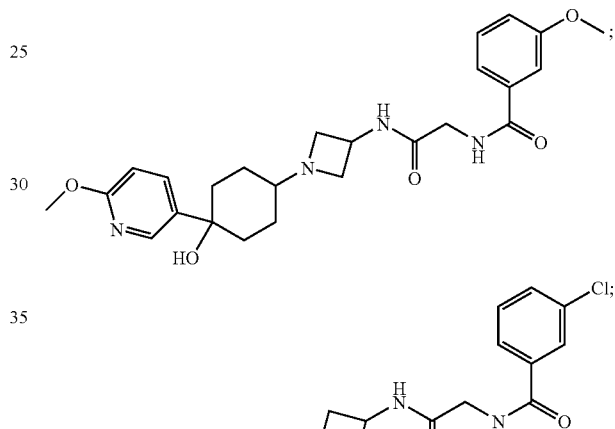
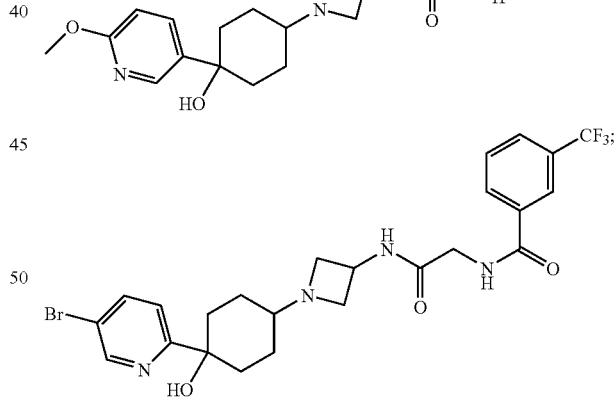
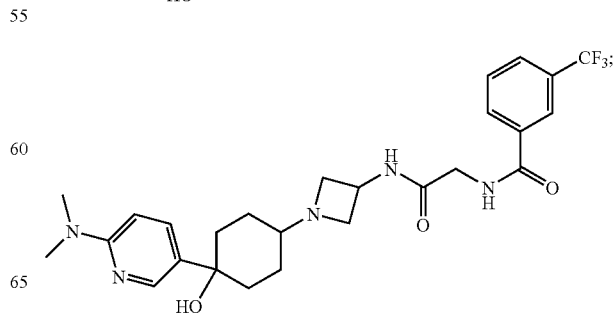

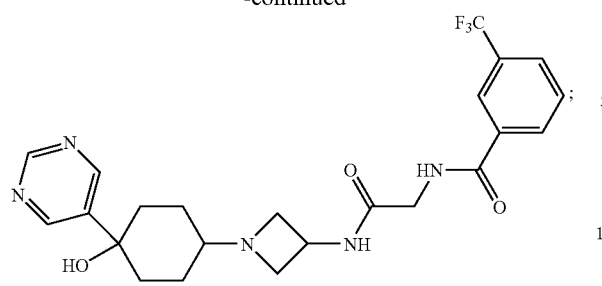
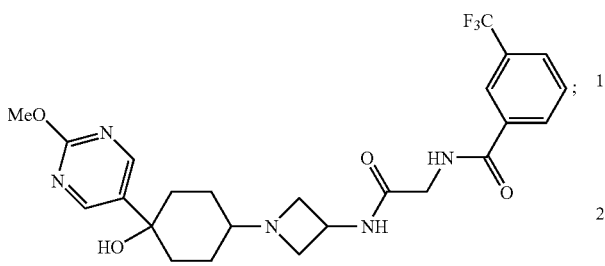
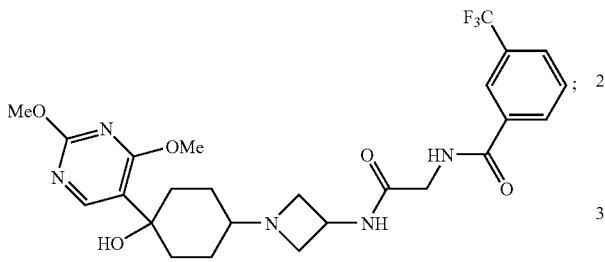
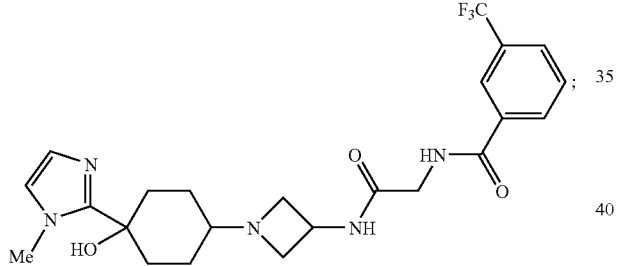
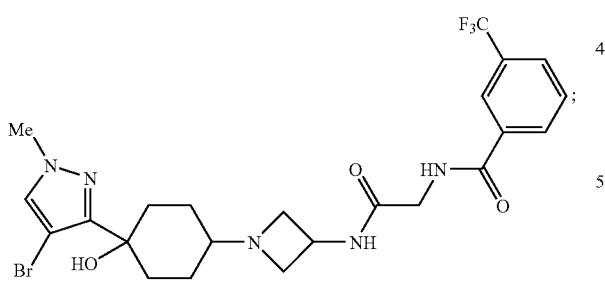
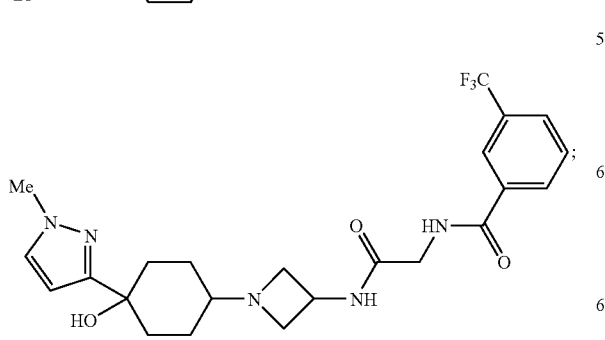
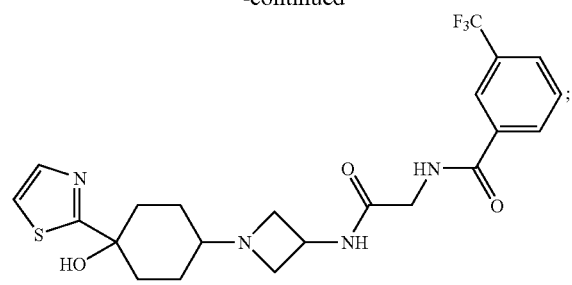
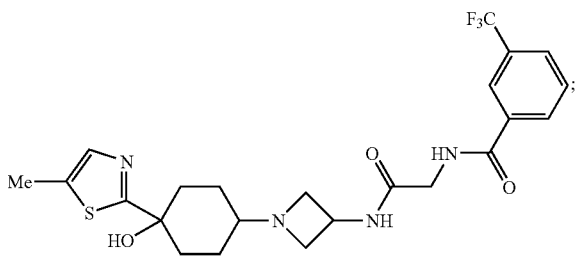
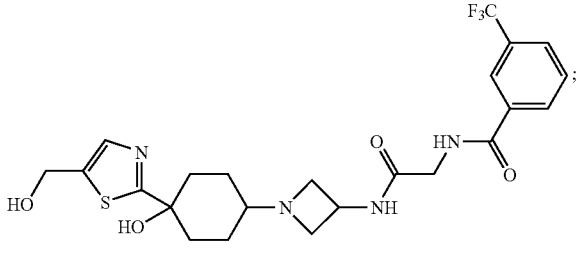
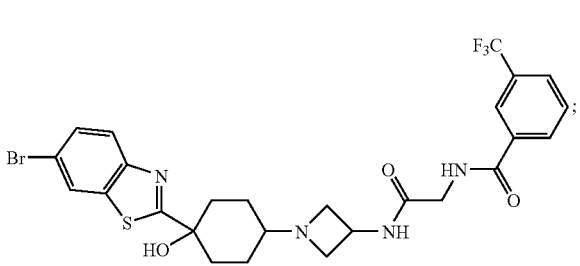
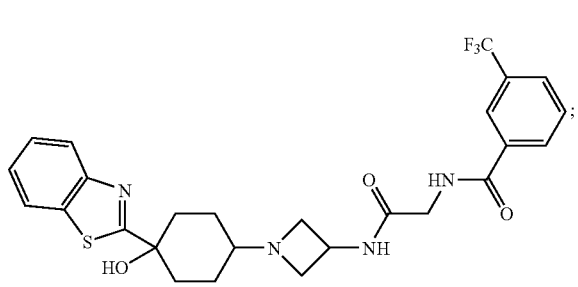
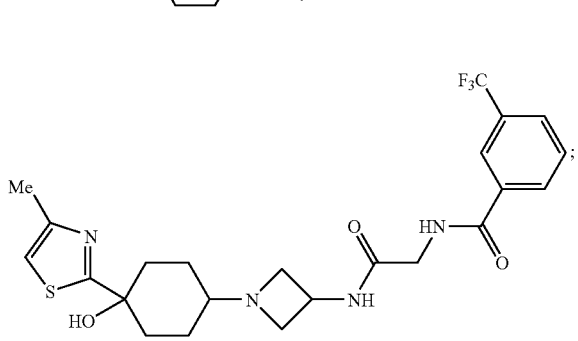

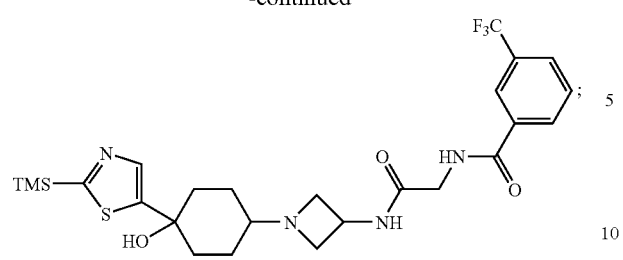
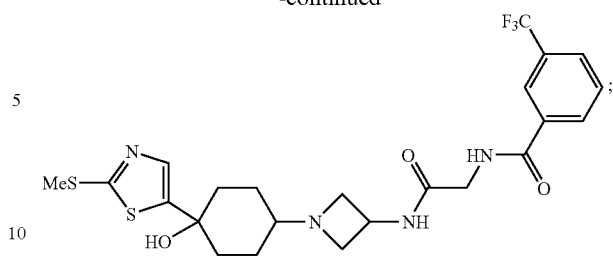
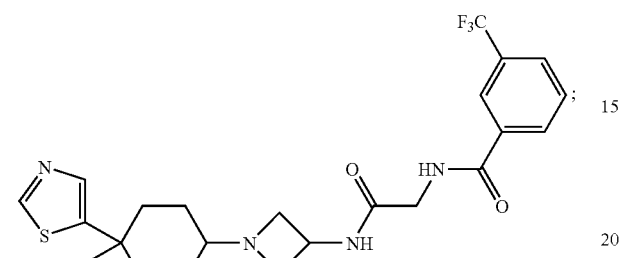
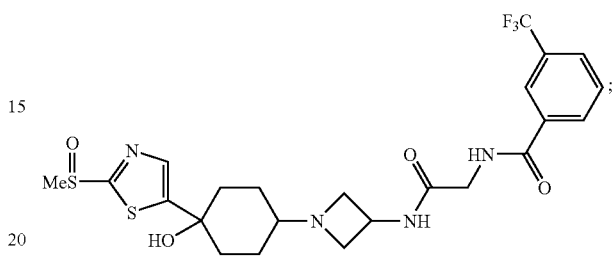
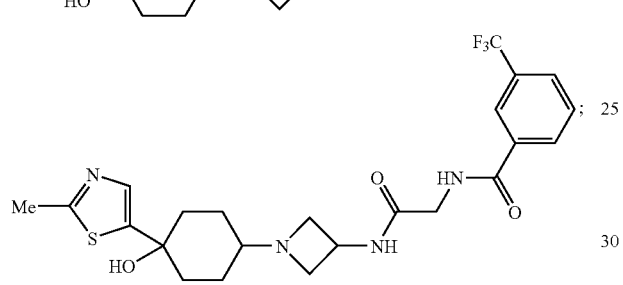
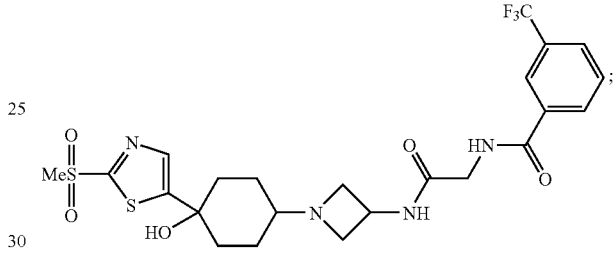
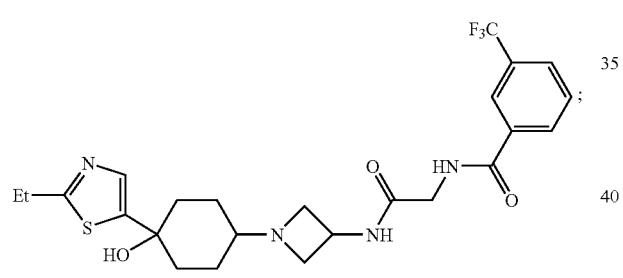
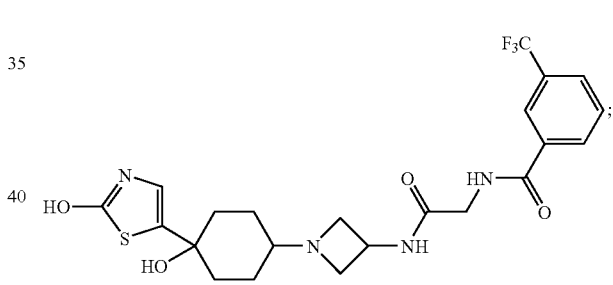
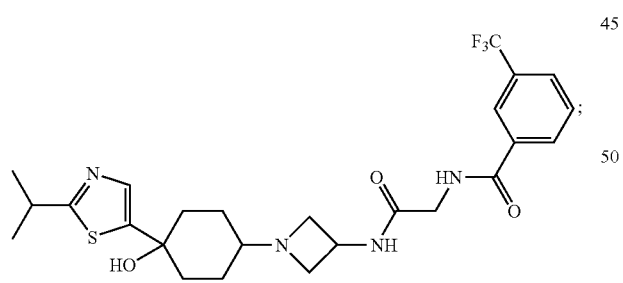
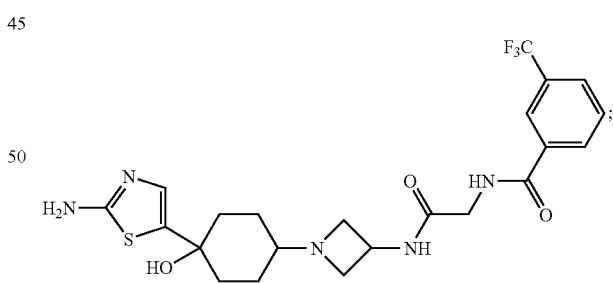
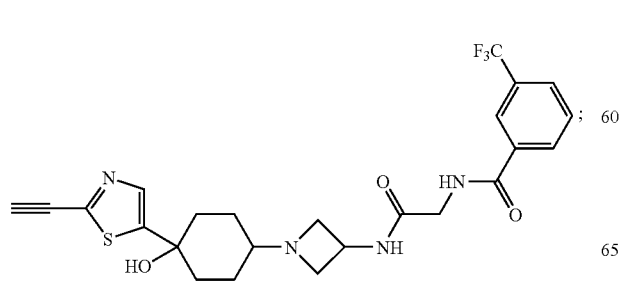
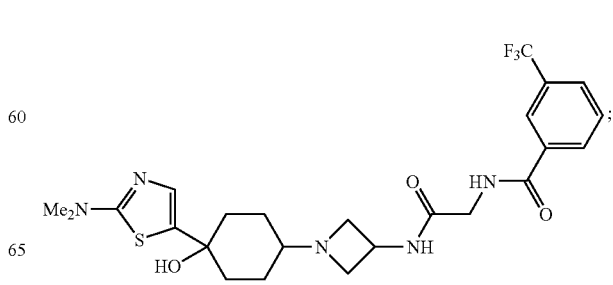

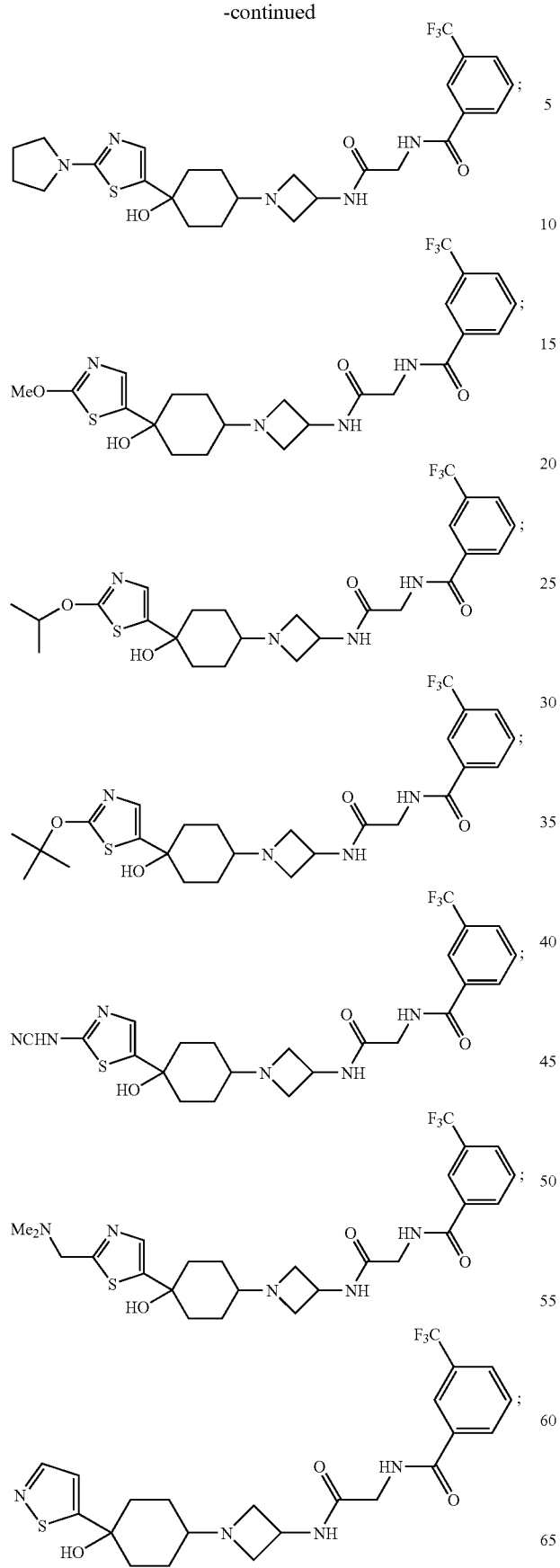
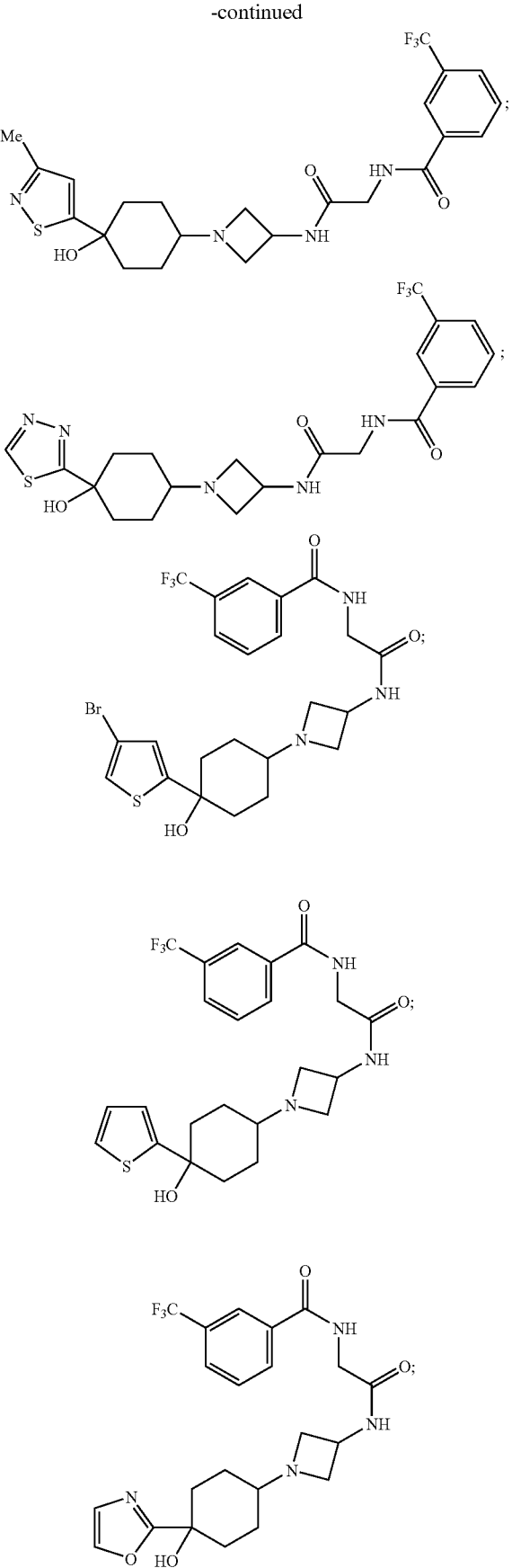

17
-continued
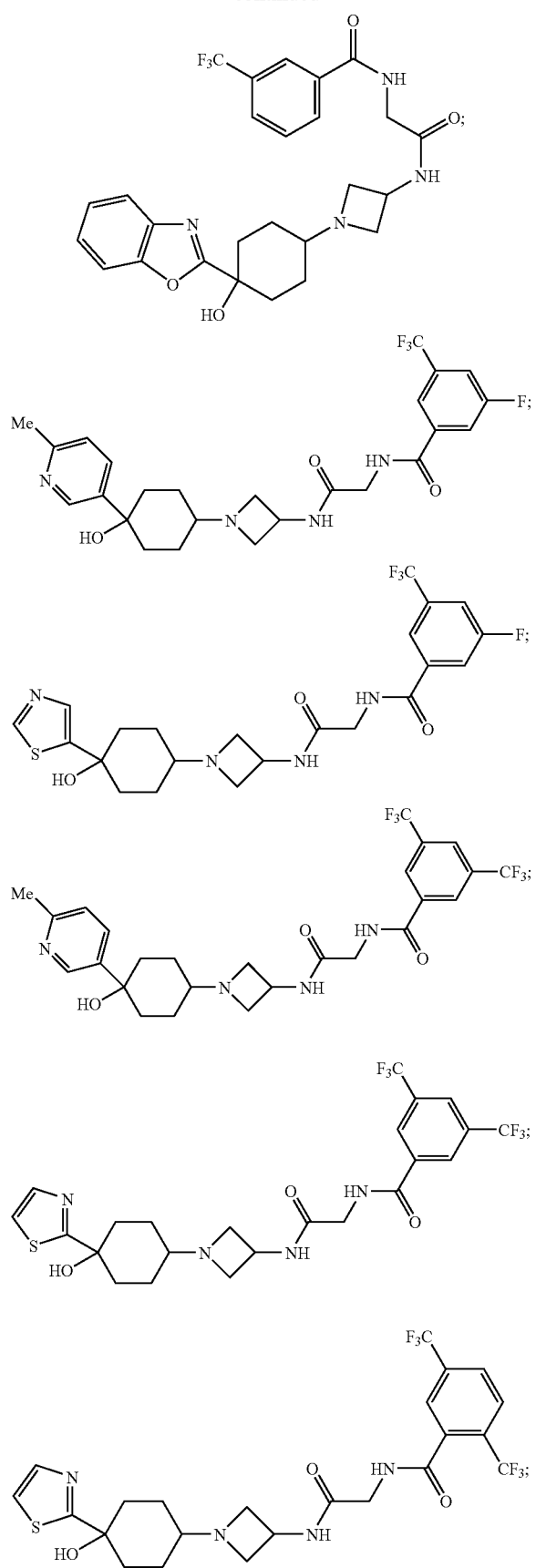
18
-continued
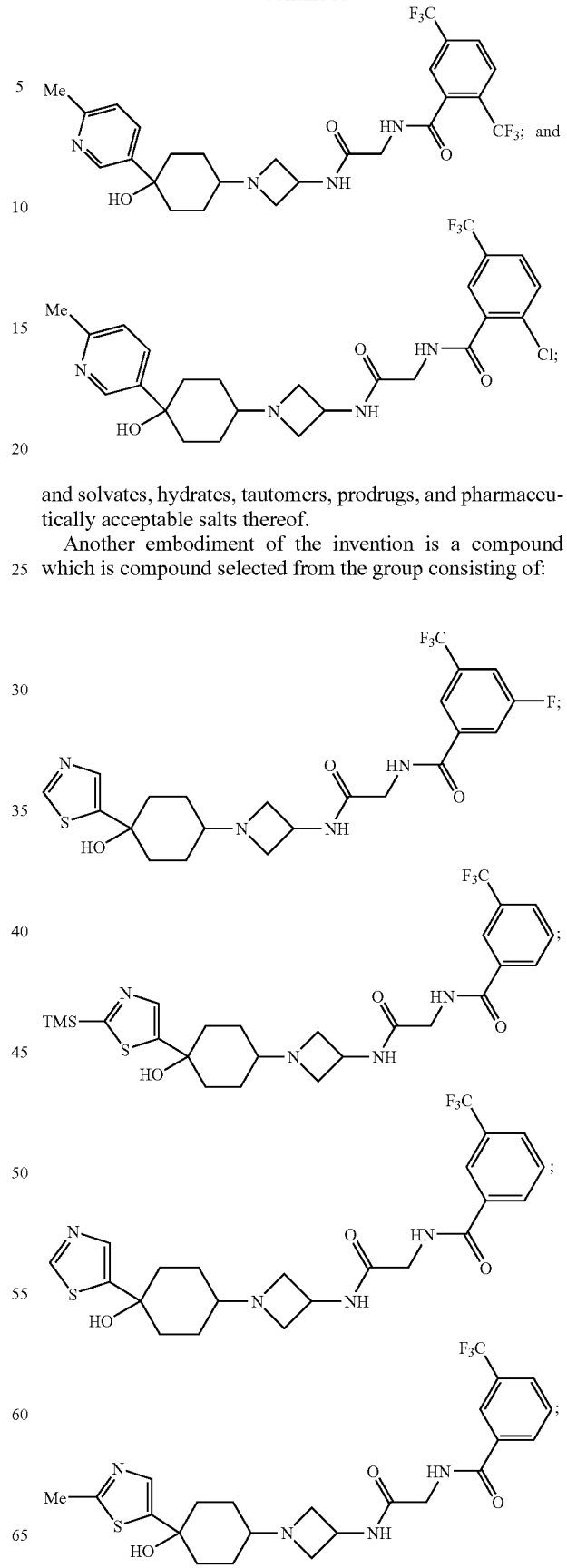
and solvates, hydrates, tautomers, prodrugs, and pharmaceutically acceptable salts thereof.
Another embodiment of the invention is a compound which is compound selected from the group consisting of:

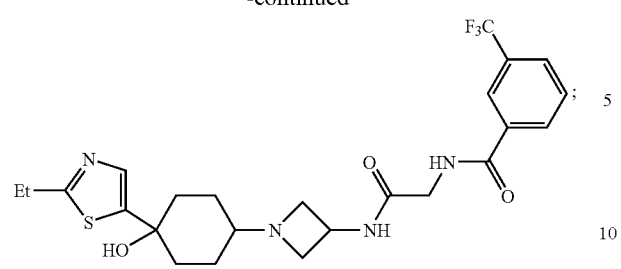
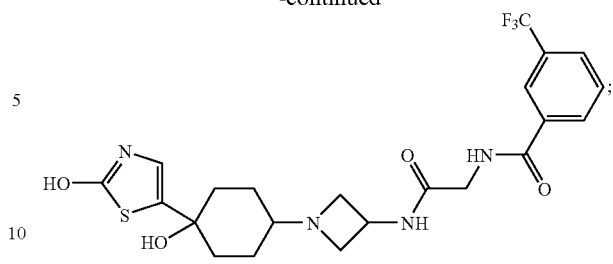
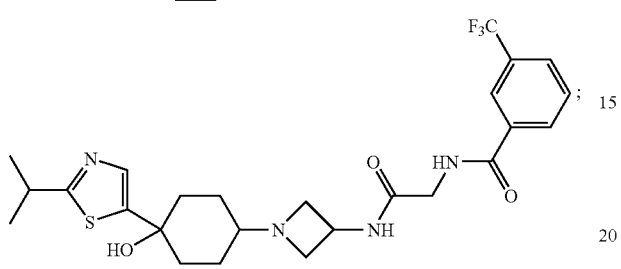
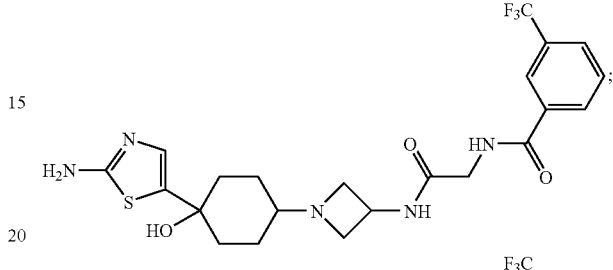
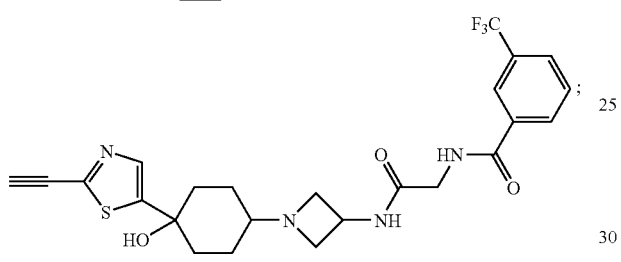
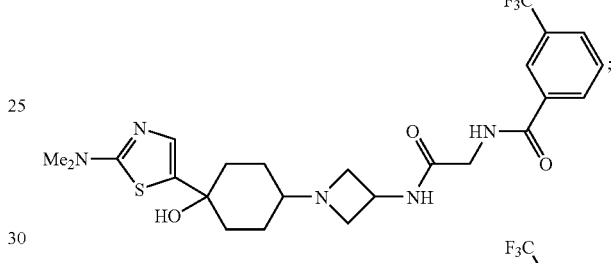
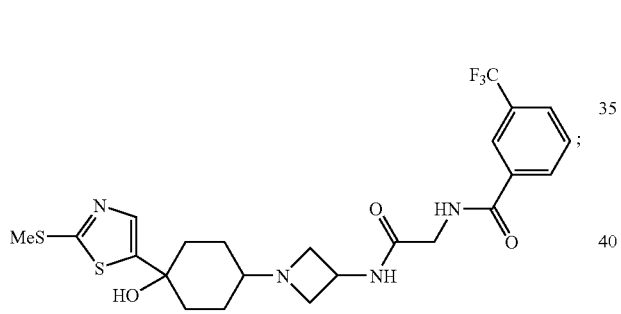
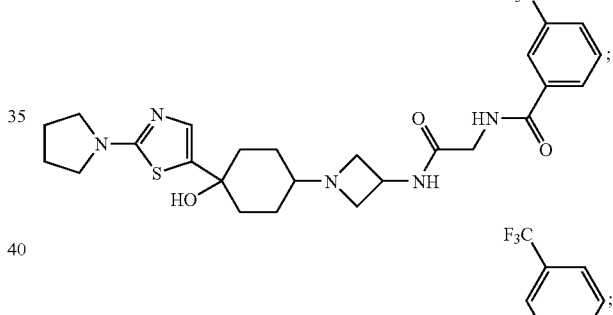
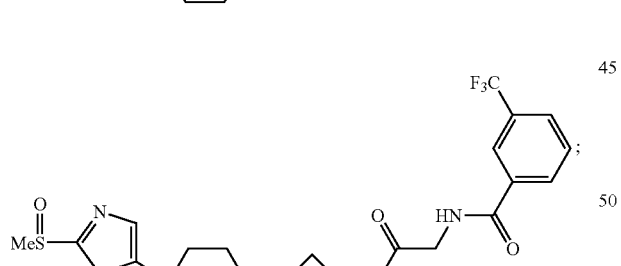
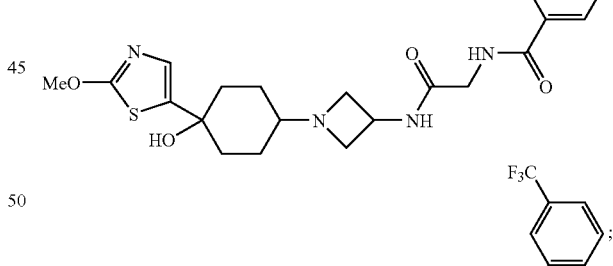
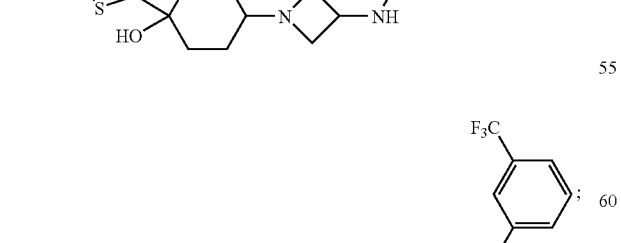
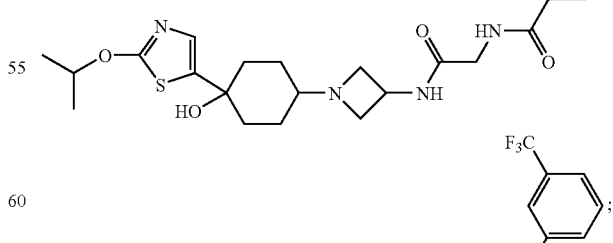
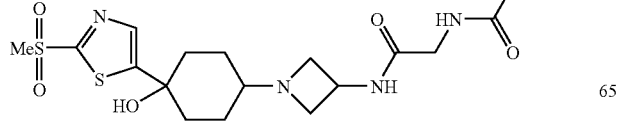
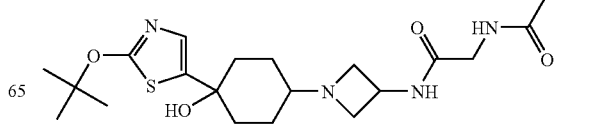

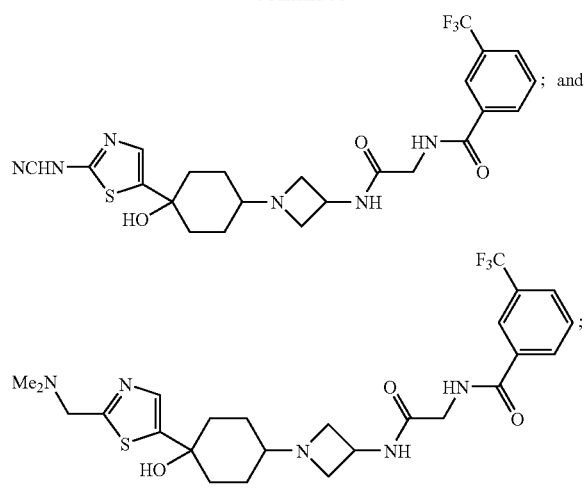
and solvates, hydrates, tautomers, prodrugs, and pharmaceutically acceptable salts thereof.
Another embodiment of the invention is a compound which is
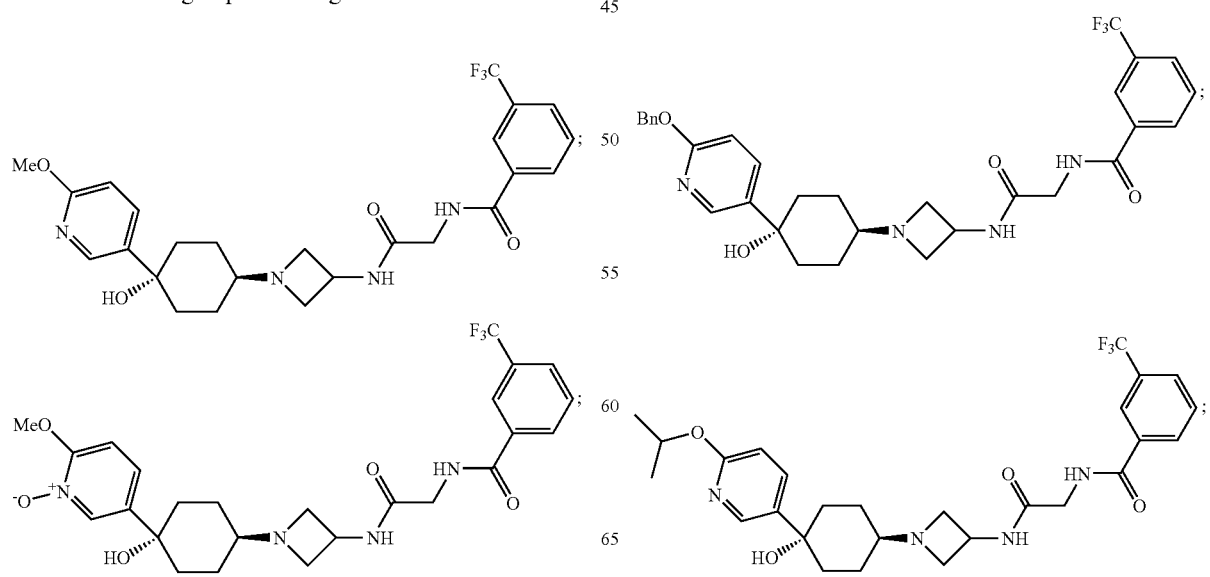
and solvates, hydrates, tautomers, prodrugs, and pharmaceutically acceptable salts thereof.
Another embodiment of the invention is a compound selected from the group consisting of:
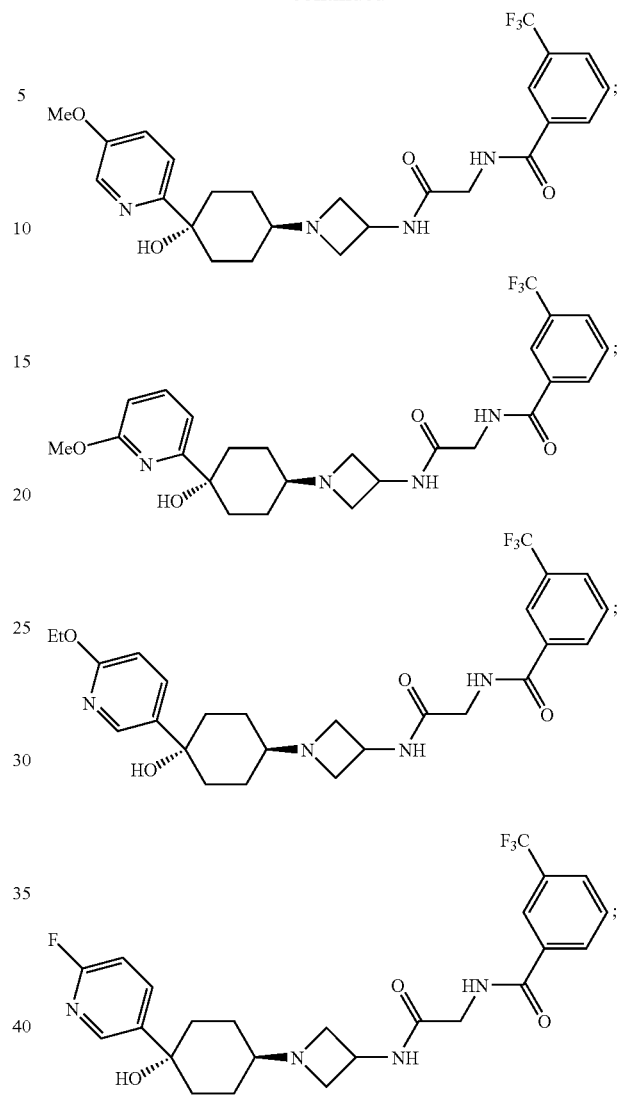

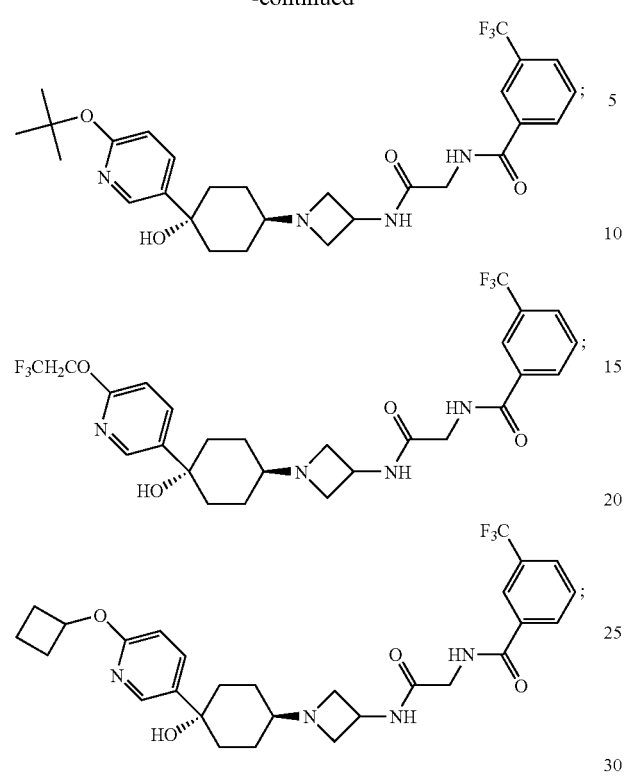
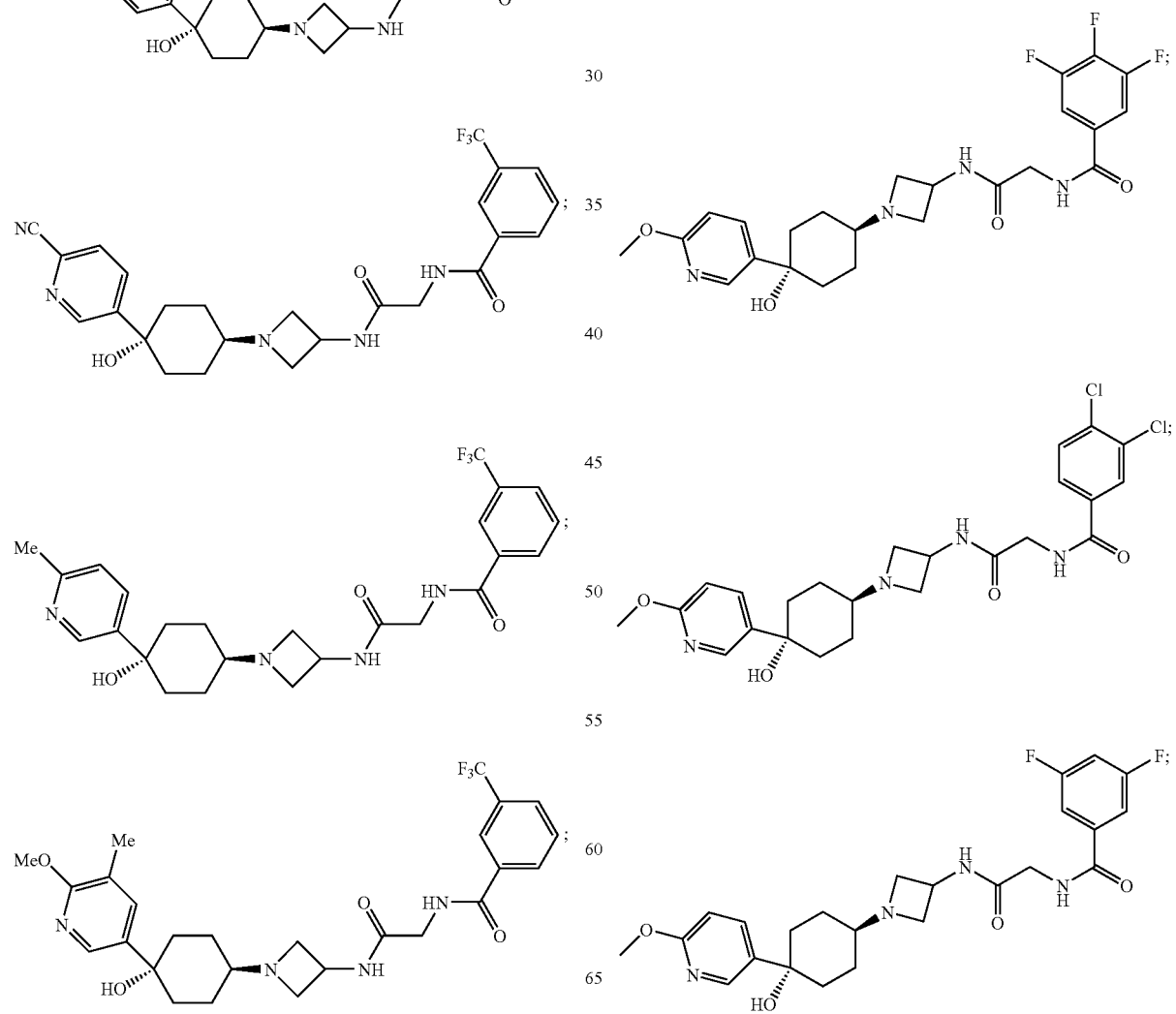

25
-continued
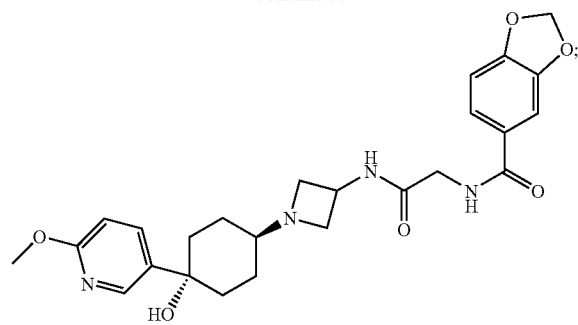
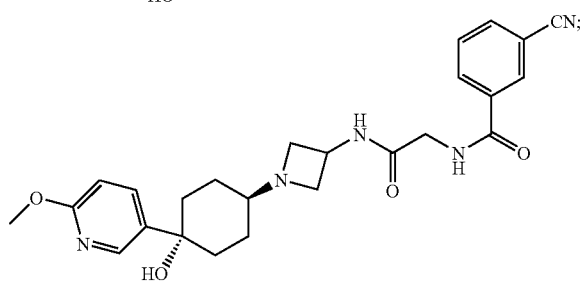
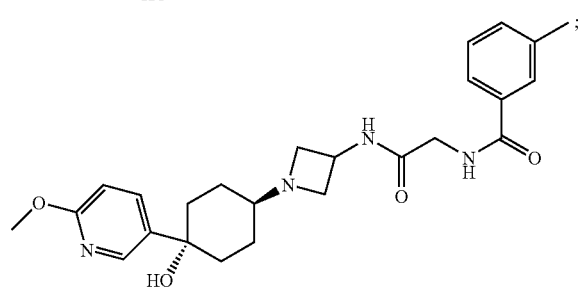
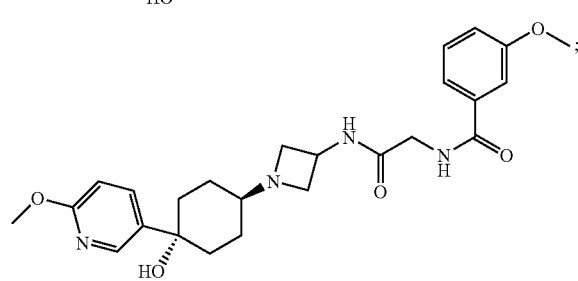
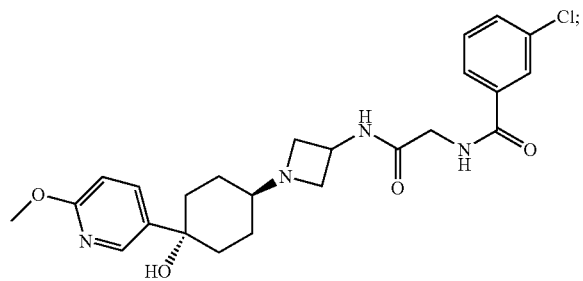
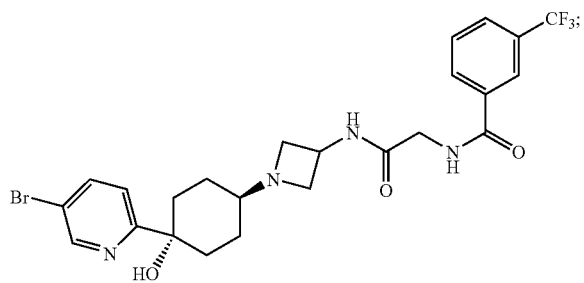
26
-continued
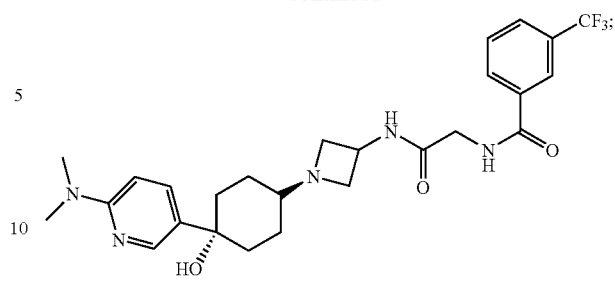
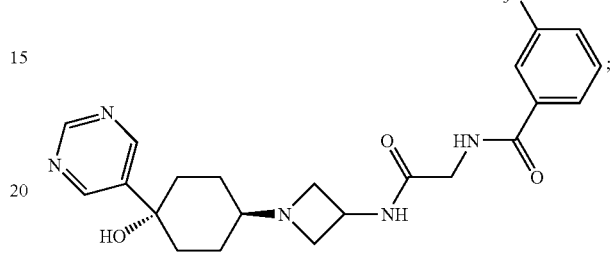
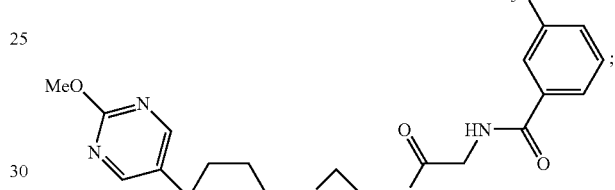
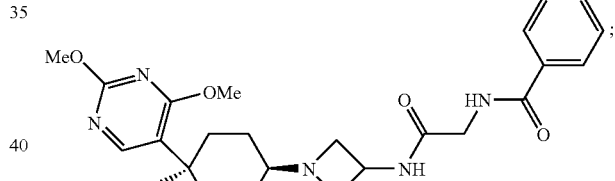
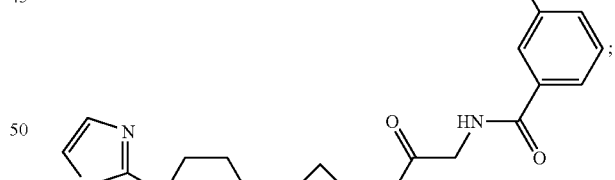
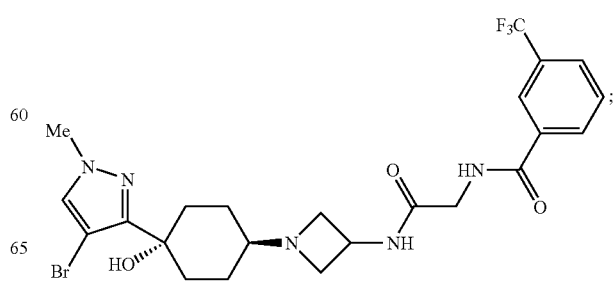

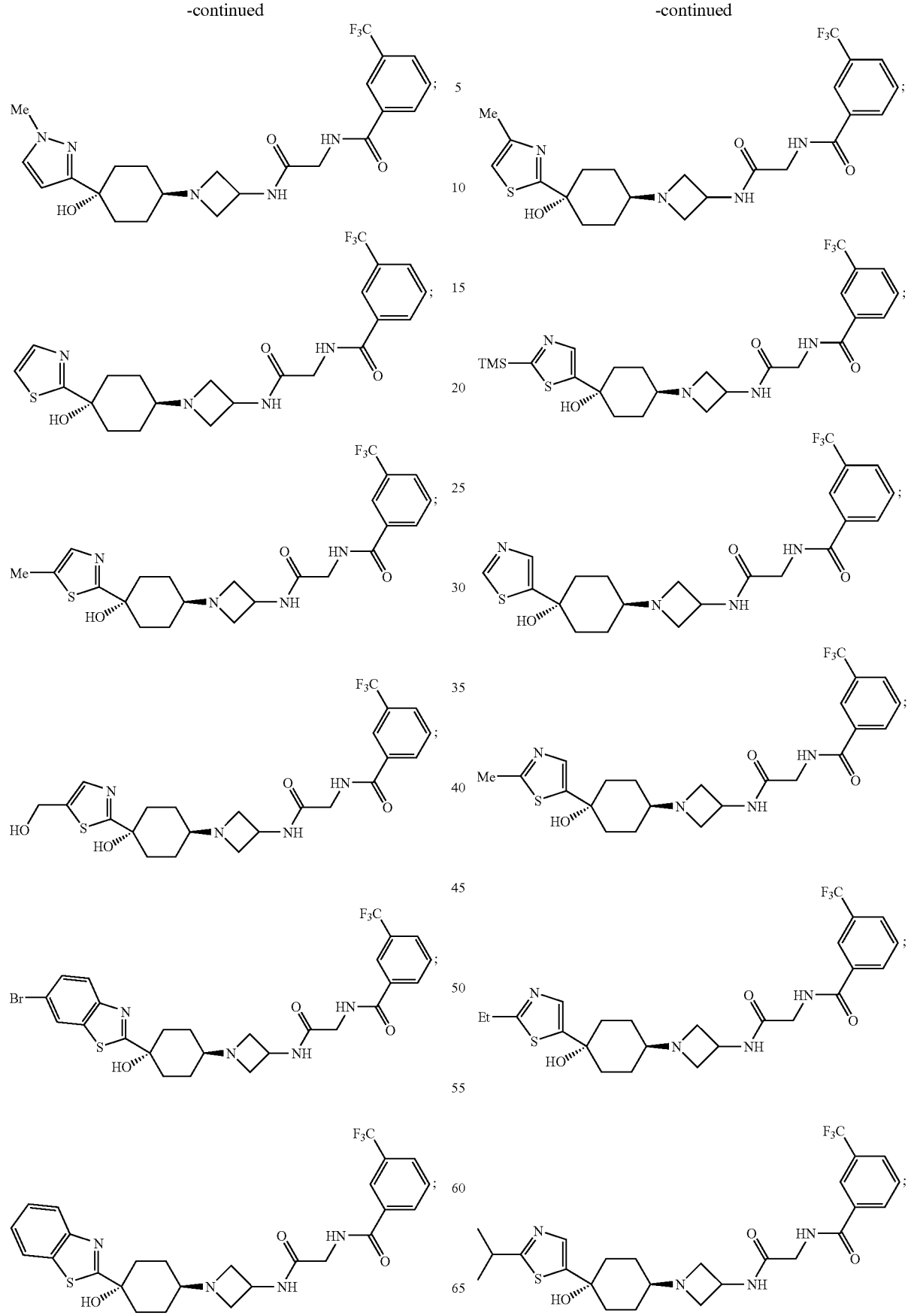

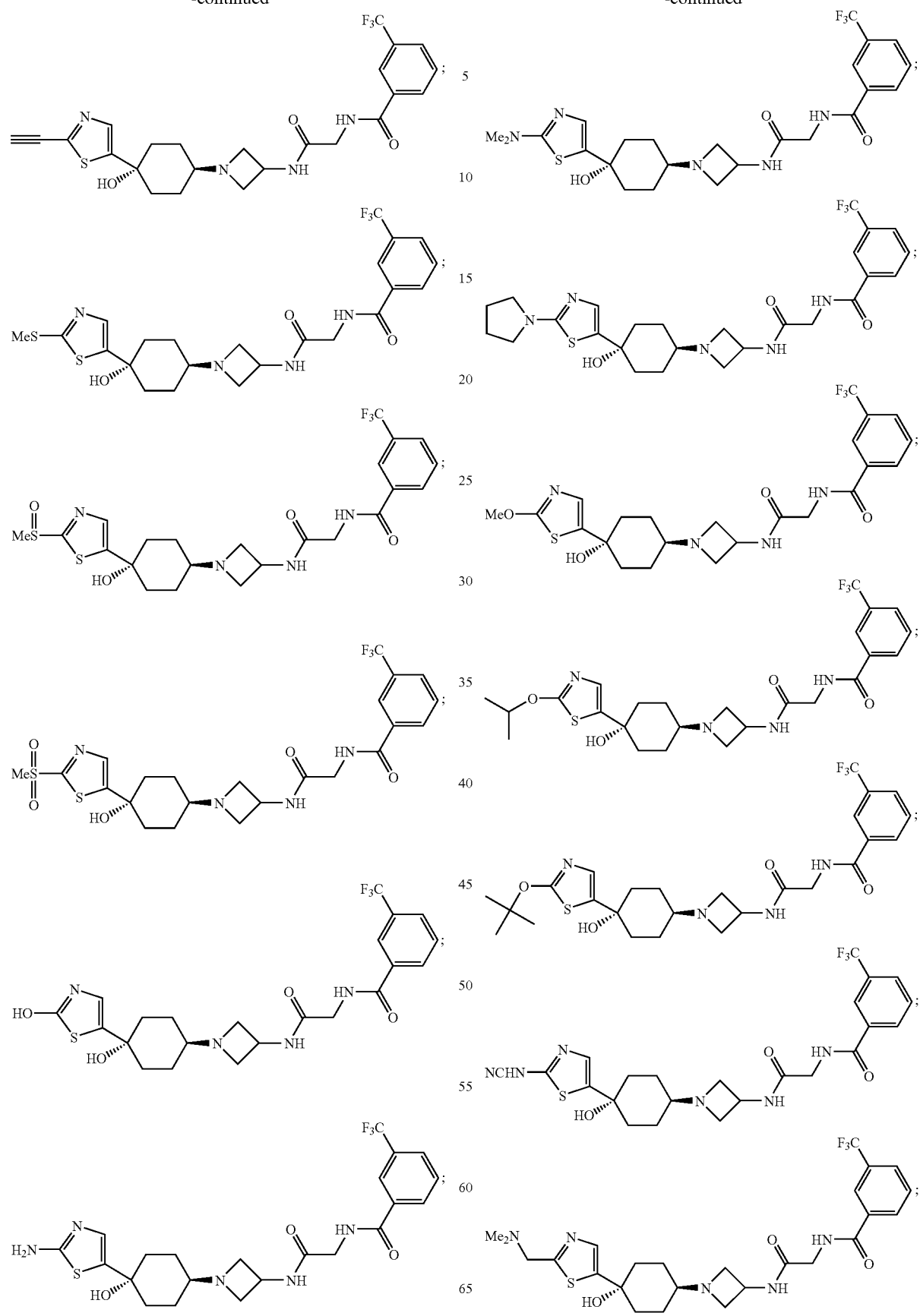

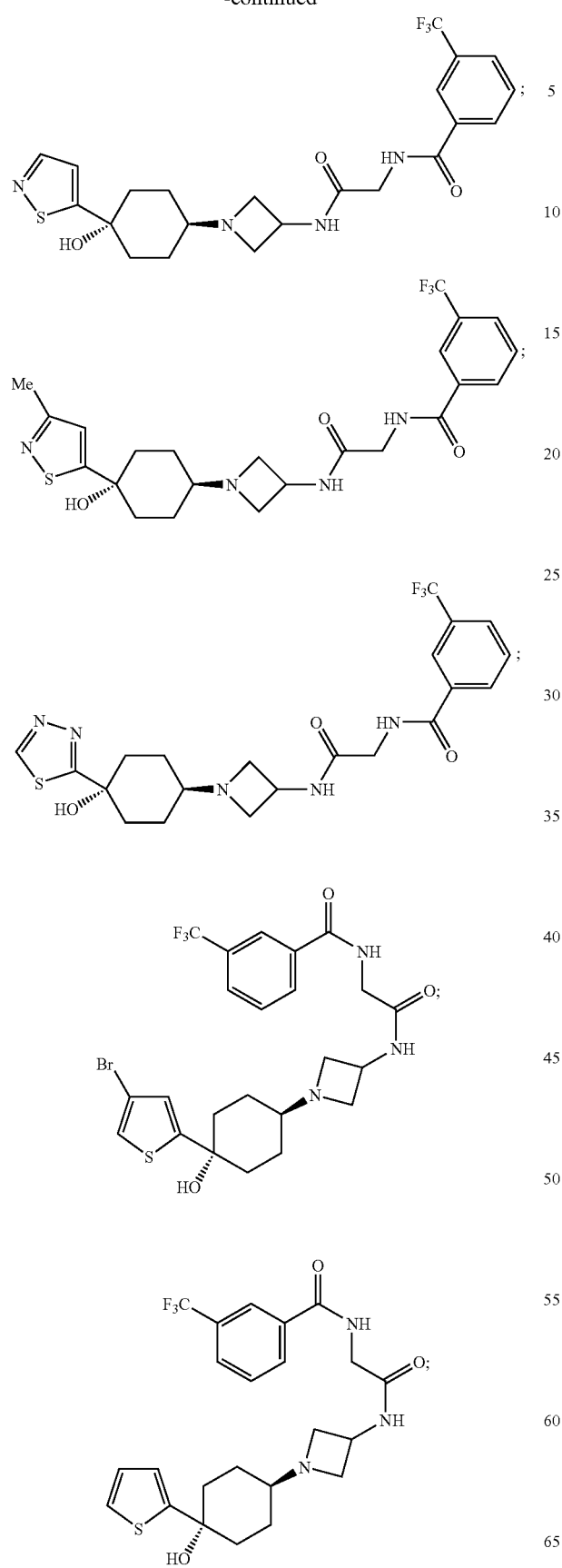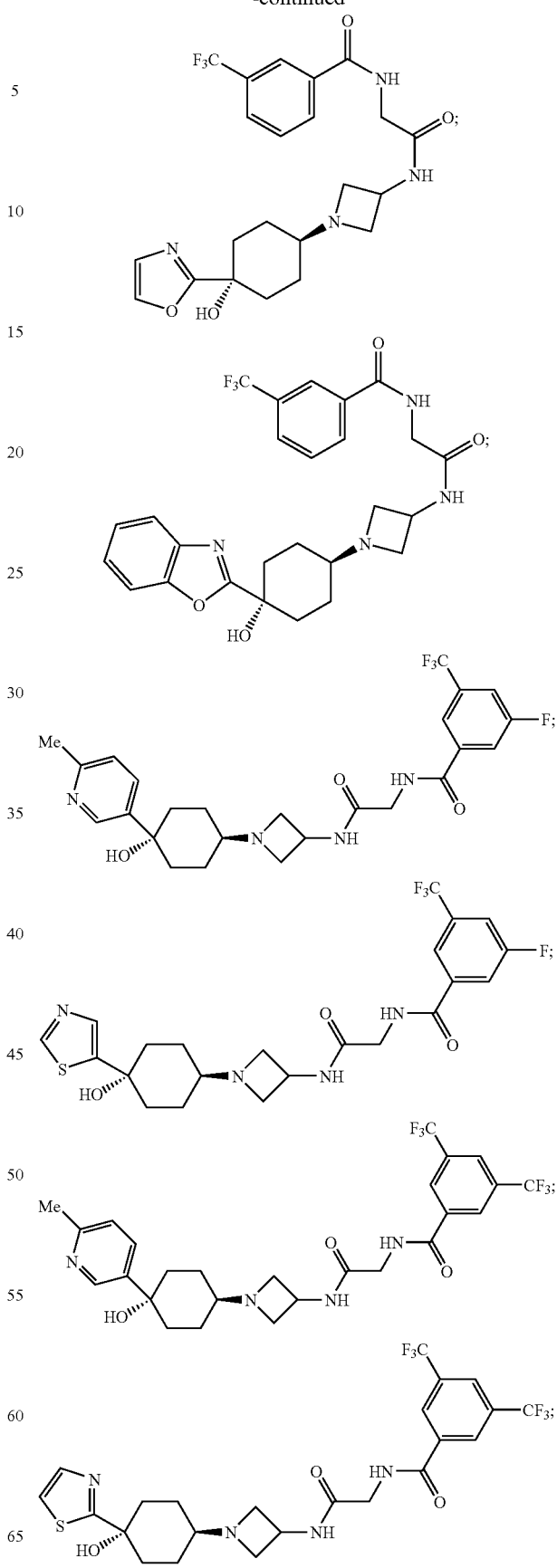

-continued

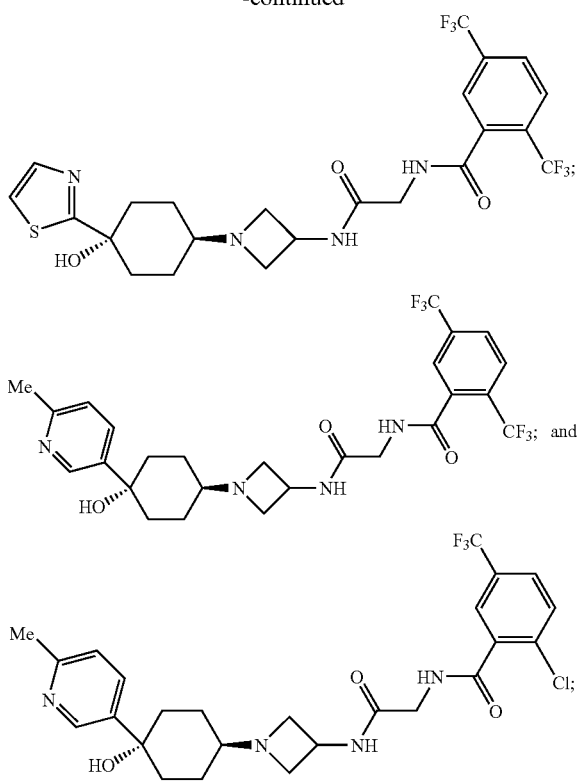

and solvates, hydrates, tautomers, prodrugs, and pharmaceutically acceptable salts thereof.

Another embodiment of the invention is the compound:

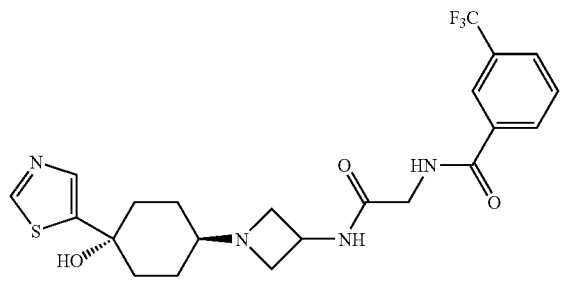 [SMILES: O=C(CNC(=O)c1cccc(C(F)(F)F)c1)NC1CN([C@H]2CC[C@@](O)(c3cncs3)CC2)C1]

and solvates, hydrates, tautomers, prodrugs, and pharmaceutically acceptable salts thereof.

Another embodiment is the compound of the formula

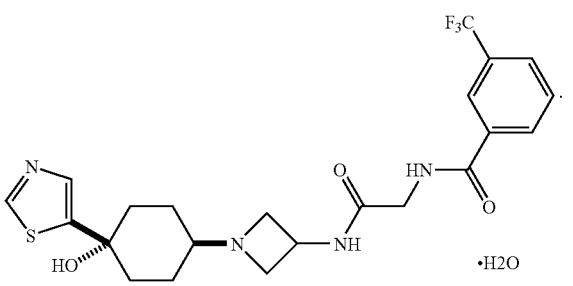

In another embodiment of the invention is a crystalline compound of the formula

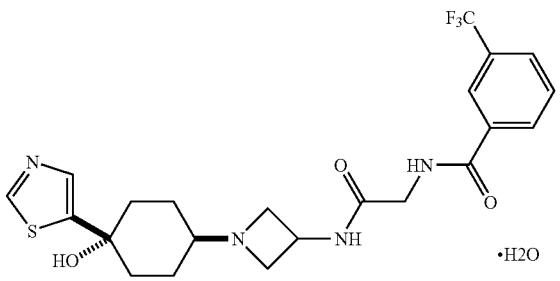

having the following XRPD °2Θ peaks:

| Position [°2Θ] |
| --- |
| 7.0 |
| 7.4 |
| 9.3 |
| 11.0 |
| 12.6 |
| 14.3 |
| 14.4 |
| 14.8 |
| 15.3 |
| 17.1 |
| 17.4 |
| 18.3 |
| 18.7 |
| 19.2 |
| 19.7 |
| 21.3 |
| 21.8 |
| 22.2 |
| 22.9 |
| 23.5 |
| 23.9 |
| 24.5 |
| 24.7 |
| 25.3 |
| 26.3 |
| 28.2 |
| 28.8 |
| 29.5 |

Another embodiment of the invention is a pharmaceutical composition, comprising a compound of Formula (I) or (Ia) and a pharmaceutically acceptable carrier.

Another embodiment of the invention is a pharmaceutical composition, comprising a compound listed in the Examples section of this specification and a pharmaceutically acceptable carrier.

The present invention also provides a method for preventing, treating or ameliorating a CCR2 mediated syndrome, disorder or disease comprising administering to a subject in need thereof a therapeutically effective amount of a compound of Formula (I) or (Ia) or a form, composition or medicament thereof. Examples of CCR2 mediated disorders include, but are not limited to, chronic obstructive pulmonary disorder (COPD), ophthalmic disorders, uveitis, atherosclerosis, rheumatoid arthritis, psoriasis, psoriatic arthritis, atopic dermatitis, multiple sclerosis, Crohn's Disease, ulcerative colitis, nephritis, organ allograft rejection, fibroid lung, renal insufficiency, type-I diabetes, type II diabetes, diabetic complications, diabetic nephropathy, diabetic retinopathy, diabetic retinitis, diabetic microangiopathy, overweight, obesity, obesity-associated insulin resistance, metabolic syndrome, tuberculosis, sarcoidosis, invasive staphyloccocia, inflammation after cataract surgery, allergic rhinitis, allergic conjunctivitis, chronic urticaria, asthma, allergic asthma, periodontal diseases, periodonitis, gingivitis, gum disease, diastolic cardiomyopathies, cardiac infarction, myocarditis, chronic heart failure, angiostenosis, restenosis, reperfusion disorders, aortic abdominal aneurism, glomerulonephritis, solid tumors and cancers, chronic lymphocytic leukemia, chronic myelocytic leukemia, multiple myeloma, malignant myeloma, Hodgkin's disease, carcinomas of the bladder, breast, cervix, colon, lung, prostate, or stomach, and chronic neuroinflammatory disorders including, but not limited to, Alzheimer's disease, ischemic stroke, spinal cord injury, nerve crush injury and traumatic brain injury. In an embodiment of the present invention, the CCR2 mediated syndrome, disorder or disease is an inflammatory syndrome, disorder or disease.

The present invention also provides a method for preventing, treating or ameliorating a CCR2 mediated inflammatory syndrome, disorder or disease wherein the syndrome, disorder or disease is associated with elevated MCP-1 expression or MCP-1 overexpression, or is an inflammatory condition that accompanies syndromes, disorders or diseases associated with elevated MCP-1 expression or MCP-1 overexpression comprising administering to a subject in need thereof a therapeutically effective amount of a compound of Formula (I) or (Ia) or a form, composition or medicament thereof.

The present invention also provides a method of preventing, treating or ameliorating a syndrome, disorder or disease, wherein said syndrome, disorder or disease is selected from the group consisting of: chronic obstructive pulmonary disorder (COPD), ophthalmic disorders, uveitis, atherosclerosis, rheumatoid arthritis, psoriasis, psoriatic arthritis, atopic dermatitis, multiple sclerosis, Crohn's Disease, ulcerative colitis, nephritis, organ allograft rejection, fibroid lung, renal insufficiency, type-I diabetes, type II diabetes, diabetic complications, diabetic nephropathy, diabetic retinopathy, diabetic retinitis, diabetic microangiopathy, overweight, obesity, obesity-associated insulin resistance, metabolic syndrome, tuberculosis, sarcoidosis, invasive staphyloccocia, inflammation after cataract surgery, allergic rhinitis, allergic conjunctivitis, chronic urticaria, asthma, allergic asthma, periodontal diseases, periodonitis, gingivitis, gum disease, diastolic cardiomyopathies, cardiac infarction, myocarditis, chronic heart failure, angiostenosis, restenosis, reperfusion disorders, aortic abdominal aneurism, glomerulonephritis, solid tumors and cancers, chronic lymphocytic leukemia, chronic myelocytic leukemia, multiple myeloma, malignant myeloma, Hodgkin's disease, carcinomas of the bladder, breast, cervix, colon, lung, prostate, or stomach, and chronic neuroinflammatory disorders including, but not limited to, Alzheimer's disease, ischemic stroke, spinal cord injury, nerve crush injury and traumatic brain injury comprising administering to a subject in need thereof a therapeutically effective amount of a compound of Formula (I) or (Ia) or a form, composition or medicament thereof.

In another embodiment is a method of preventing, treating or ameliorating a syndrome, disorder or disease, wherein said syndrome, disorder or disease is selected from the group consisting of: type I diabetes, type II diabetes, diabetic complications, diabetic nephropathy, diabetic retinopathy, diabetic retinitis, diabetic microangiopathy, obesity, obesity-associated insulin resistance, metabolic syndrome, asthma, and allergic asthma, comprising administering to a subject in need thereof a therapeutically effective amount of a compound of formula (I) or (Ia) or a form, composition or medicament thereof.

Another embodiment is a method of treating a disorder selected from the group consisting of type II diabetes, obesity and asthma comprising administering to a subject in need thereof a therapeutically effective amount of a compound of formula (I) or (Ia) or a form, composition or medicament thereof.

In one embodiment, the present invention provides a method of treating or ameliorating a syndrome, disorder or disease, wherein said syndrome, disorder or disease is selected from the group consisting of: ophthalmic disorders, rheumatoid arthritis, psoriasis, psoriatic arthritis, atopic dermatitis, chronic obstructive pulmonary disease, allergic rhinitis, asthma, allergic asthma, and periodontal diseases comprising administering to a subject in need thereof a therapeutically effective amount of a compound of Formula (I) or (Ia) or a form, composition or medicament thereof.

The invention also relates to methods of inhibiting CCR2 activity in a mammal by administration of an effective amount of at least one compound of Formula (I) or (Ia).

In another embodiment, the invention relates to a product made by the process of any of Examples from Example 1 to Example 72.

In another embodiment, the invention relates to a compound of claim 1, which is the less polar isomer of any of Examples #1-72.

In another embodiment, the invention relates to a compound of claim 1, which is the less polar isomer of Example #40.

In another embodiment, the invention relates to the use of hCCR2 knock-in mice to identify antagonists of CCR2 for use in the treatment of asthma.

In another embodiment, the invention relates to the use of hCCR2 knock-in mice to identify antagonists of CCR2 for use in the treatment of obesity.

In another embodiment, the invention relates to the use of hCCR2 knock-in mice to identify antagonists of CCR2 as described in an example selected from Example 78, Example 79 and Example 80.

The invention also provides a process for the preparation of a compound of formula (I) as herein described, comprising reacting a compound of Formula (V)

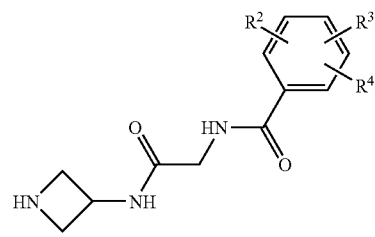

with a compound of Formula (VI)

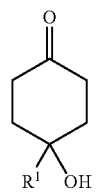

in the presence of a reducing agent to provide the compound of formula (I). The invention also includes a product made by this process.

In an embodiment is a process for the preparation of a compound of formula (I) as herein described, comprising reacting a compound of Formula (VI)

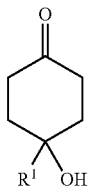

with

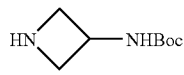

in the presence of a reducing agent to provide the compound of formula (I). In another embodiment is a product made by this process.

DEFINITIONS

The term "alkyl" refers to both linear and branched chain radicals of up to 12 carbon atoms, preferably up to 6 carbon atoms, unless otherwise indicated, and includes, but is not limited to, methyl, ethyl, propyl, isopropyl, butyl, isobutyl, sec-butyl, tert-butyl, pentyl, isopentyl, hexyl, isohexyl, heptyl, octyl, 2,2,4-trimethylpentyl, nonyl, decyl, undecyl and dodecyl.

The term "$C_{(a-b)}$" (where a and b are integers referring to a designated number of carbon atoms) refers to an alkyl, alkenyl, alkynyl, alkoxy or cycloalkyl radical or to the alkyl portion of a radical in which alkyl appears as the prefix root containing from a to b carbon atoms inclusive. For example, $C_{(1-4)}$ denotes a radical containing 1, 2, 3 or 4 carbon atoms.

The term "cycloalkyl" refers to a saturated or partially unsaturated monocyclic or bicyclic hydrocarbon ring radical derived by the removal of one hydrogen atom from a single ring carbon atom. Typical cycloalkyl radicals include cyclopropyl, cyclobutyl, cyclopentyl, cyclopentenyl, cyclohexyl, cyclohexenyl, cycloheptyl and cyclooctyl. Additional examples include $C_{(3-8)}$cycloalkyl, $C_{(5-8)}$cycloalkyl, $C_{(3-12)}$cycloalkyl, $C_{(3-20)}$cycloalkyl, decahydronaphthalenyl, and 2,3,4,5,6,7-hexahydro-1H-indenyl.

The term "oxo" refers to the functional group

The term "heterocyclyl" refers to a saturated or partially unsaturated monocyclic ring radical derived by the removal of one hydrogen atom from a single carbon or nitrogen ring atom. Said ring comprises 3, 4, 5 or 6 ring carbon atoms plus 1, 2, or 3 heteroatoms. Suitable heteroatoms include nitrogen, oxygen, and sulfur. Typical heterocyclyl radicals include, but are not limited to, 2H-pyrrole, 2-pyrrolinyl, 3-pyrrolinyl, pyrrolidinyl, 1,3-dioxolanyl, 2-imidazolinyl (also referred to as 4,5-dihydro-1H-imidazolyl), imidazolidinyl, 2-pyrazolinyl, pyrazolidinyl, tetrazolyl, piperidinyl, 1,4-dioxanyl, morpholinyl, 1,4-dithianyl, thiomorpholinyl, piperazinyl, azepanyl, hexahydro-1,4-diazepinyl and the like.

The term "heteroaromatic" or "heteroaryl" refers to 5- to 7-membered mono- or 8- to 10-membered bicyclic aromatic ring systems, containing from one to four heteroatoms selected from N, O, or S where the nitrogen and sulfur atoms can exist in any allowed oxidation state. Examples include, but are not limited to, benzimidazolyl, benzothiazolyl, benzothienyl, benzoxazolyl, furyl, imidazolyl, isothiazolyl, isoxazolyl, oxazolyl, pyrazinyl, pyrazolyl, pyridyl, pyrimidinyl, pyrrolyl, quinolinyl, thiazolyl and thienyl.

The term "heteroatom" refers to a nitrogen atom, an oxygen atom or a sulfur atom wherein the nitrogen and sulfur atoms can exist in any allowed oxidation states.

For use in medicines, the salts of the compounds of this invention refer to non-toxic "pharmaceutically acceptable salts." FDA approved pharmaceutically acceptable salt forms (Ref International J. Pharm. 1986, 33, 201-217; J. Pharm. Sci., 1977, January, 66(1), p1) include pharmaceutically acceptable acidic/anionic or basic/cationic salts.

Throughout this specification, compounds are described as being separated, usually by silica gel column, although preporatory thin layer chromatography, or high or low pressure liquid choromatography may also be used. It is generally accepted that when eluting compounds through a silica gel-type separation medium, that the least polar compounds elute before the more polar compounds. Therefore, the term "less polar isomer", refers to the isomer that will elute first from a silica gel type separation medium. By X-ray Crystallography, "less polar isomer" is determined as "cis" isomer, which relates "cis" relationship between the aryl or heteroaryl rings and the azetidine rings on the cyclohexyl ring systems. Correspondingly, "more polar isomer" refers to "trans" isomer.

Abbreviations

Herein and throughout this application, the following abbreviations may be used.

| | |
|---|---|
| BOC or Boc | tert-butyloxycarbonyl |
| Bu | butyl |
| DCC | dicyclohexylcarbodiimide |
| DCM | dicholomethane |
| DMF | dimethylformamide |
| EDCI | 1-ethyl-3-(3'-dimethylaminopropyl)carbodiimide |
| Et | ethyl |
| EtOAc | ethyl acetate |
| HOBt | hydroxybenzotriazole |
| IPA | isopropyl alcohol |
| Me | methyl |
| Ms | mesylate |
| M.S. | molecular seives |
| OAc | acetate |
| OXONE | registered trademark of Dupont, the active ingredient of which is potassium monopersulfate ($KHSO_5$) |
| $PdCl_2$(dppf) | [1,1'-bis(diphenylphosphino)ferrocene]dichloropalladium(II) |
| $PPh_3$ | triphenylphosphine |
| iPr | isopropyl |
| PyBrop | bromo-tris-pyrrolidinophosphonium hexafluorophosphate |
| TBAF | tetrabutylammonium fluoride |
| TEA | triethylamine |
| TFA | trifluoroacetic acid |
| THF | tetrahydrofuran |
| Ts | tosylate |

Pharmaceutically acceptable acidic/anionic salts include, and are not limited to acetate, benzenesulfonate, benzoate, bicarbonate, bitartrate, bromide, calcium edetate, camsylate, carbonate, chloride, citrate, dihydrochloride, edetate, edisylate, estolate, esylate, fumarate, glyceptate, gluconate, glutamate, glycollylarsanilate, hexylresorcinate, hydrabamine, hydrobromide, hydrochloride, hydroxynaphthoate, iodide, isethionate, lactate, lactobionate, malate, maleate, mandelate, mesylate, methylbromide, methylnitrate, methylsulfate, mucate, napsylate, nitrate, pamoate, pantothenate, phosphate/diphosphate, polygalacturonate, salicylate, stearate, subacetate, succinate, sulfate, tannate, tartrate, teoclate, tosylate and triethiodide. Organic or inorganic acids also include, and are not limited to, hydriodic, perchloric, sulfuric, phosphoric, propionic, glycolic, methanesulfonic, hydroxyethanesulfonic, oxalic, 2-naphthalenesulfonic, p-toluenesulfonic, cyclohexanesulfamic, saccharinic or trifluoroacetic acid.

Pharmaceutically acceptable basic/cationic salts include, and are not limited to aluminum, 2-amino-2-hydroxymethyl-propane-1,3-diol (also known as tris(hydroxymethyl)aminomethane, tromethane or "TRIS"), ammonia, benzathine, t-butylamine, calcium, calcium gluconate, calcium hydroxide, chloroprocaine, choline, choline bicarbonate, choline chloride, cyclohexylamine, diethanolamine, ethylenediamine, lithium, LiOMe, L-lysine, magnesium, meglumine, $NH_3$, $NH_4OH$, N-methyl-D-glucamine, piperidine, potassium, potassium-t-butoxide, potassium hydroxide (aqueous), procaine, quinine, sodium, sodium carbonate, sodium-2-ethylhexanoate (SEH), sodium hydroxide, triethanolamine or zinc.

Methods of Use

The present invention is directed to a method for preventing, treating or ameliorating a CCR2 mediated syndrome, disorder or disease comprising administering to a subject in need thereof an effective amount of a compound of Formula (I) or a form, composition or medicament thereof.

Examples of a CCR2 mediated syndrome, disorder or disease for which the compounds of Formula (I) are useful include chronic obstructive pulmonary disorder (COPD), ophthalmic disorders, uveitis, atherosclerosis, rheumatoid arthritis, psoriasis, psoriatic arthritis, atopic dermatitis, multiple sclerosis, Crohn's Disease, ulcerative colitis, nephritis, organ allograft rejection, fibroid lung, renal insufficiency, type-I diabetes, type II diabetes, diabetic complications, diabetic nephropathy, diabetic retinopathy, diabetic retinitis, diabetic microangiopathy, overweight, obesity, obesity-associated insulin resistance, metabolic syndrome, tuberculosis, chronic obstructive pulmonary disease, sarcoidosis, invasive staphyloccocia, inflammation after cataract surgery, allergic rhinitis, allergic conjunctivitis, chronic urticaria, asthma, allergic asthma, periodontal diseases, periodonitis, gingivitis, gum disease, diastolic cardiomyopathies, cardiac infarction, myocarditis, chronic heart failure, angiostenosis, restenosis, reperfusion disorders, aortic abdominal aneurism, multiple sclerosis, glomerulonephritis, solid tumors and cancers, chronic lymphocytic leukemia, chronic myelocytic leukemia, multiple myeloma, malignant myeloma, Hodgkin's disease, carcinomas of the bladder, breast, cervix, colon, lung, prostate, or stomach, and chronic neuroinflammatory disorders including, but not limited to, Alzheimer's disease, ischemic stroke, spinal cord injury, nerve crush injury and traumatic brain injury.

The term "administering" with respect to the methods of the invention, means a method for therapeutically or prophylactically preventing, treating or ameliorating a syndrome, disorder or disease as described herein by using a compound of Formula (I) or a form, composition or medicament thereof. Such methods include administering an effective amount of said compound, compound form, composition or medicament at different times during the course of a therapy or concurrently in a combination form. The methods of the invention are to be understood as embracing all known therapeutic treatment regimens.

The term "subject" refers to a patient, which may be animal, typically a mammal, typically a human, which has been the object of treatment, observation or experiment. In one aspect of the invention, the subject is at risk of (or susceptible to) developing a syndrome, disorder or disease that is associated with elevated MCP-1 expression or MCP-1 overexpression, or a patient with an inflammatory condition that accompanies syndromes, disorders or diseases associated with elevated MCP-1 expression or MCP-1 overexpression.

The term "therapeutically effective amount" means that amount of active compound or pharmaceutical agent that elicits the biological or medicinal response in a tissue system, animal or human, that is being sought by a researcher, veterinarian, medical doctor, or other clinician, which includes preventing, treating or ameliorating the symptoms of a syndrome, disorder or disease being treated.

The term "uveitis" generically refers to any inflammatory disease involving the eye. Uveitis can be divided into clinically distinct subtypes based on the part of the eye in which the inflammation is present (percentages correspond to patients known to fit these categories): anterior (51%), intermediate (13%), posterior (20%), or panuveitis (16%) and, according to the course of the disease, as either acute (16%), recurring (26%), or chronic (58%). Those with anterior uveitis (•19%) eventually develop irreparable vision damage despite aggressive treatment such as unilateral blindness (9%), bilateral blindness (2%), or unilateral or bilateral vision impairment (8%). Most cases of uveitis are idiopathic, but known causes include infection (e.g., toxoplasmosis, cytomegalovirus, and the like) or development as a component of a systemic inflammatory and/or autoimmune disorder (e.g., juvenile RA, HLA-B27 associated spondyloarthropathies, sarcoidosis, and the like). (HLA-B27: Human Leukocyte Antigen B*27—is a class I surface antigen encoded by the B locus in the major histocompatibility complex (MHC) on chromosome 6 and presents micobial antigens to T cells. HLA-B27 is strongly associated with a certain set of autoimmune diseases referred to as the seronegative spondyloarthropathies.)

When employed as CCR2 inhibitors, the compounds of the invention may be administered in an effective amount within the dosage range of about 0.5 mg to about 10 g, preferably between about 0.5 mg to about 5 g, in single or divided daily doses. The dosage administered will be affected by factors such as the route of administration, the health, weight and age of the recipient, the frequency of the treatment and the presence of concurrent and unrelated treatments.

It is also apparent to one skilled in the art that the therapeutically effective dose for compounds of the present invention or a pharmaceutical composition thereof will vary according to the desired effect. Therefore, optimal dosages to be administered may be readily determined by one skilled in the art and will vary with the particular compound used, the mode of administration, the strength of the preparation, and the advancement of the disease condition. In addition, factors associated with the particular subject being treated, including subject age, weight, diet and time of administration, will result in the need to adjust the dose to an appropriate therapeutic level. The above dosages are thus exemplary of the average case. There can, of course, be individual instances where higher or lower dosage ranges are merited, and such are within the scope of this invention.

The compounds of Formula (I) and/or (Ia) may be formulated into pharmaceutical compositions comprising any known pharmaceutically acceptable carriers. Exemplary carriers include, but are not limited to, any suitable solvents, dispersion media, coatings, antibacterial and antifungal agents and isotonic agents. Exemplary excipients that may also be components of the formulation include fillers, binders, disintegrating agents and lubricants.

The pharmaceutically-acceptable salts of the compounds of Formula (I) and/or (Ia) include the conventional non-toxic salts or the quaternary ammonium salts which are formed from inorganic or organic acids or bases. Examples of such acid addition salts include acetate, adipate, benzoate, benzenesulfonate, citrate, camphorate, dodecylsulfate, hydrochloride, hydrobromide, lactate, maleate, methanesulfonate, nitrate, oxalate, pivalate, propionate, succinate, sulfate and tartrate. Base salts include ammonium salts, alkali metal salts such as sodium and potassium salts, alkaline earth metal salts such as calcium and magnesium salts, salts with organic bases such as dicyclohexylamino salts and salts with amino acids such as arginine. Also, the basic nitrogen-containing groups may be quaternized with, for example, alkyl halides.

The pharmaceutical compositions of the invention may be administered by any means that accomplish their intended purpose. Examples include administration by parenteral, subcutaneous, intravenous, intramuscular, intraperitoneal, transdermal, buccal or ocular routes. Alternatively or concurrently, administration may be by the oral route. Suitable formulations for parenteral administration include aqueous solutions of the active compounds in water-soluble form, for example, water-soluble salts, acidic solutions, alkaline solutions, dextrose-water solutions, isotonic carbohydrate solutions and cyclodextrin inclusion complexes.

The present invention also encompasses a method of making a pharmaceutical composition comprising mixing a pharmaceutically acceptable carrier with any of the compounds of the present invention. Additionally, the present invention includes pharmaceutical compositions made by mixing a pharmaceutically acceptable carrier with any of the compounds of the present invention. As used herein, the term "composition" is intended to encompass a product comprising the specified ingredients in the specified amounts, as well as any product which results, directly or indirectly, from combinations of the specified ingredients in the specified amounts.

Polymorphs and Solvates

Furthermore, the compounds of the present invention may have one or more polymorph or amorphous crystalline forms and as such are intended to be included in the scope of the invention. In addition, the compounds may form solvates, for example with water (i.e., hydrates) or common organic solvents. As used herein, the term "solvate" means a physical association of the compounds of the present invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. The term "solvate" is intended to encompass both solution-phase and isolatable solvates. Non-limiting examples of suitable solvates include ethanolates, methanolates, and the like.

It is intended that the present invention include within its scope polymorphs and solvates of the compounds of the present invention. Thus, in the methods of treatment of the present invention, the term "administering" shall encompass the means for treating, ameliorating or preventing a syndrome, disorder or disease described herein with the compounds of the present invention or a polymorph or solvate thereof, which would obviously be included within the scope of the invention albeit not specifically disclosed.

In another embodiment, the invention relates to a compound as described in the Examples or Formula (I) or Formula (Ia) for use as a medicament, in particular, for use as a medicament for treating a CCR2 mediated syndrome disorder or disease.

In another embodiment, the invention relates to the use of a compound as described in the Examples of Formula (I) or Formula (Ia) for the preparation of a medicament for the treatment of a disease associated with an elevated or inappropriate CCR2 activity.

The present invention includes within its scope prodrugs of the compounds of this invention. In general, such prodrugs will be functional derivatives of the compounds which are readily convertible in vivo into the required compound. Thus, in the methods of treatment of the present invention, the term "administering" shall encompass the treatment of the various disorders described with the compound specifically disclosed or with a compound which may not be specifically disclosed, but which converts to the specified compound in vivo after administration to the patient. Conventional procedures for the selection and preparation of suitable prodrug derivatives are described, for example, in "Design of Prodrugs", Ed. H. Bundgaard, Elsevier, 1985.

Where the compounds according to this invention have at least one chiral center, they may accordingly exist as enantiomers. Where the compounds possess two or more chiral centers, they may additionally exist as diastereomers. It is to be understood that all such isomers and mixtures thereof are encompassed within the scope of the present invention.

Where the processes for the preparation of the compounds according to the invention give rise to mixture of stereoisomers, these isomers may be separated by conventional techniques such as preparative chromatography. The compounds may be prepared in racemic form, or individual enantiomers may be prepared either by enantiospecific synthesis or by resolution. The compounds may, for example, be resolved into their component enantiomers by standard techniques, such as the formation of diastereomeric pairs by salt formation with an optically active acid, such as (−)-di-p-toluoyl-D-tartaric acid and/or (+)-di-p-toluoyl-L-tartaric acid followed by fractional crystallization and regeneration of the free base. The compounds may also be resolved by formation of diastereomeric esters or amides, followed by chromatographic separation and removal of the chiral auxiliary. Alternatively, the compounds may be resolved using a chiral HPLC column.

During any of the processes for preparation of the compounds of the present invention, it may be necessary and/or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973; and T. W. Greene & P. G. M. Wuts, *Protective Groups in Organic Synthesis*, John Wiley & Sons, 1991. The protecting groups may be removed at a convenient subsequent stage using methods known from the art.

GENERAL REACTION SCHEME

Representative compounds of the present invention can be synthesized in accordance with the general synthetic methods described below. Compounds of Formula (I) can be prepared by methods known to those who are skilled in the art. The following reaction schemes are only meant to represent examples of the invention and are in no way meant to be a limit of the invention.

Compounds of Formula (I) may be prepared according to the processes outlined in Scheme 1.

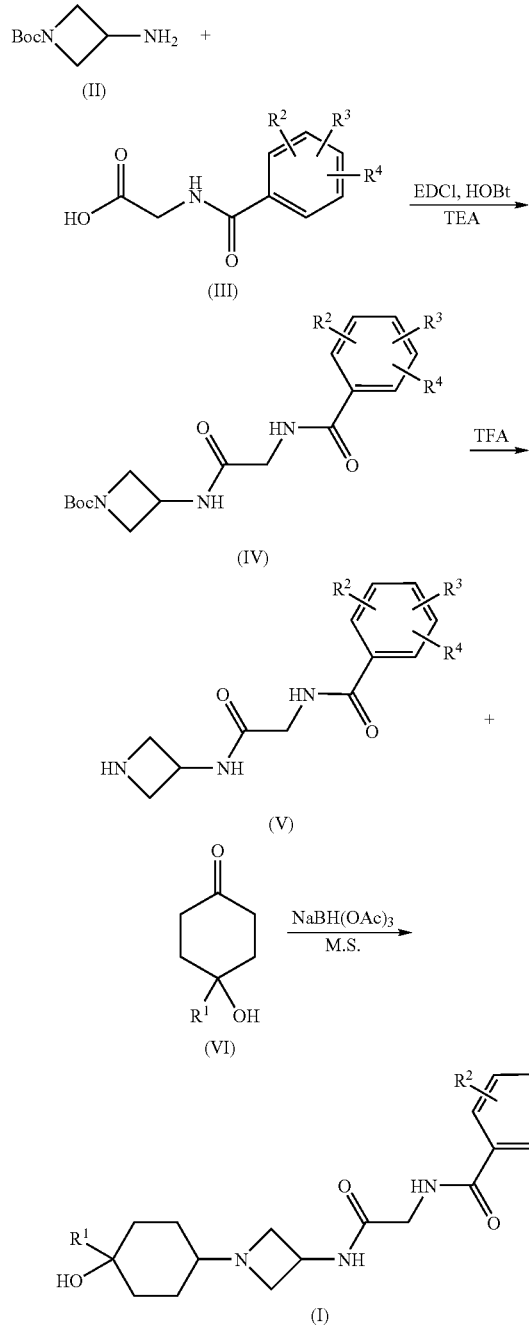

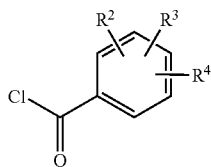

for benzoyl chloride, in the presence of a coupling reagent such as EDCl/HOBt, PyBrop, or DCC, in an organic solvent such as THF, dichloromethane or 1,2-dichloroethane, at a temperature in the range of about 0° C. to about 25° C., to yield the corresponding amide (IV).

Amide (IV) is treated with an acid such as 1N HCl, 1N $H_2SO_4$ or trifluoroacetic acid in an organic solvent such as diethyl ether, THF, dichloromethane or dioxane, at a temperature in the range of about 0° C. to about 25° C. to yield amine (V).

Amine (V) is reacted with a suitably substituted ketone (VI), in the presence of a reducing reagent such as $NaBH_4$, $NaBH(CN)_3$ or $NaBH(OAc)_3$, in an organic base such as triethylamine, diethylpropylamine or N-methylmorpholine with or without molecule sieves, in an organic solvent such as dichloromethane, 1,2-dichloroethane or THF, at a temperature in the range of 0° C. to about 25° C., to yield the corresponding azetidine (I).

Alternatively, compounds of Formula (I) may be prepared according to the processes outlined in Scheme 2.

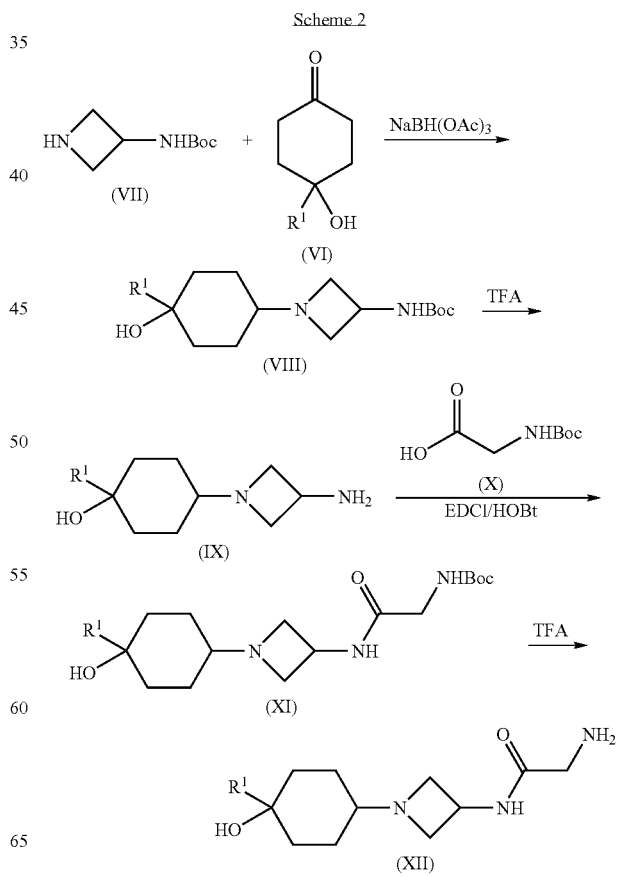

Scheme 1 illustrates a synthetic route leading to compounds of Formula (I). Commercially available azetidine (II) is reacted with acid (III), wherein (III) is prepared according to the procedure described by Ingersoll, A. W. et. al., Organic Syntheses 1932, XII, 40-2 substituting commercially available -continued

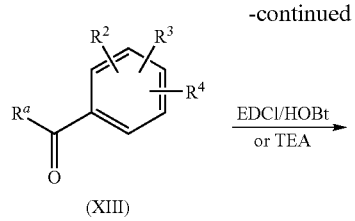

(XIII)

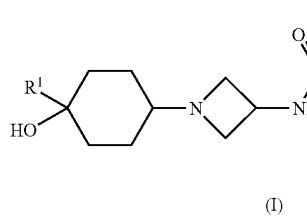

(I)

wherein $R^a$ is OH, or Cl

Commercially available azetidine (VII) is reacted with a suitably substituted ketone (VI), in the presence of a reducing reagent such as $NaBH_4$, $NaBH(CN)_3$ or $NaBH(OAc)_3$, in an organic base such as triethylamine, diethylpropylamine or N-methylmorpholine, with or without molecule sieves, in an organic solvent such as dichloromethane, 1,2-dichloroethane or THF at a temperature in the range of 0° C. to about 25° C., to yield the corresponding azetidine (VIII).

Azetidine (VIII) is treated with 1N HCl, 1N $H_2SO_4$ or trifluoroacetic acid in an organic solvent such as diethyl ether, THF, dioxane or dichloromethane, at a temperature in the range of about 0° C. to about 25° C., to yield the corresponding amine (IX).

Amine (IX) is reacted with acid (X), in the presence of a coupling reagent such as EDCl/HOBt, PyBrop or DCC, in an organic solvent such as THF, dichloromethane or 1,2-dichloroethane, at a temperature in the range of about 0° C. to about 25° C., to yield the corresponding azetidine (XI).

Azetidine (XI) is treated with 1N HCl or $H_2SO_4$ or trifluoroacetic acid, in an organic solvent such as diethyl ether, THF or dioxane, at a temperature in the range of about 0° C. to about 25° C., to yield the corresponding amine (XII).

Amine (XII) is reacted with acid (XIII). When $R^a$ is OH, the reaction is performed in the presence of a coupling reagent such as EDCl/HOBt, PyBrop or DCC, in an organic solvent such as THF, dichloromethaneor 1,2-dichloroethane, at a temperature in the range of about 0° C. to about 25° C. When $R^a$ is Cl, the reaction is performed in the presence of an organic base such triethylamine, diethylpropylamine or N-methylmorpholine, in an organic solvent such as THF, dichloromethane or 1,2-dichloroethane, at a temperature in the range of about 0° C. to about 25° C., to yield the corresponding azetidine (I).

Compounds of Formula (I) may be derived from ketone (VI). Preparation of (VI) is outlined in Scheme 3.

Scheme 3

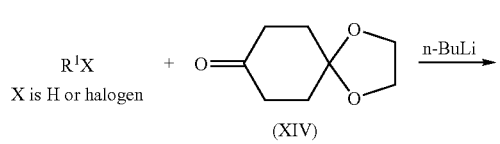

(XIV)

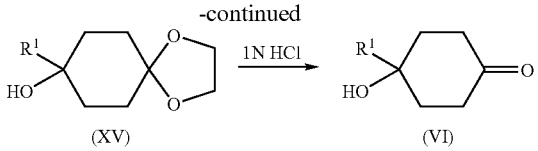

Commercially available aryl halide or aryl alkane $R^1X$ (where $R^1$ is as defined in Formula (I)) is reacted with commercially available ketone (XIV) in the presence of organometalic agent such as n-BuLi, i-PrMgBr or i-PrMgCl, in an organic solvent such as ether, THF or dioxane, at a temperature in the range of about −78° C. to about 0° C., to yield the corresponding ketal (XV).

Ketal (XV) is treated with an acid such as 1N HCl or 1N $H_2SO_4$ in an organic solvent such as acetone, acetonitrile or THF, at a temperature in the range of about 0° C. to about 25° C., to yield the corresponding ketone (VI).

EXAMPLES

Representative compounds of the present invention can be synthesized in accordance with the general synthetic methods described below. Compounds of Formula (I) can be prepared by methods known to those who are skilled in the art. The following examples are only meant to represent examples of the invention and are in no way meant to be a limit of the invention.

Example 1

N-({1-[4-Hydroxy-4-(6-methoxy-pyridin-3-yl)-cyclohexyl]-azetidin-3-ylcarbamoyl}-methyl)-3-trifluoromethyl-benzamide Step A: 8-(6-Methoxy-pyridin-3-yl)-1,4-dioxa-spiro[4.5]decan-8-ol

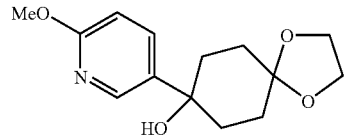

A solution of 5-bromo-2-methoxy-pyridine (Aldrich, 5.0 g, 26.6 mmol) in THF or ether (30 mL) at −78° C. was treated with n-BuLi (2.5 M in hexanes, 12 mL, 30 mmol) dropped slowly over 10 min. The reaction was stirred for an additional 20 min. at −78° C. A solution of 1,4-dioxa-spiro[4.5]decan-8-one (Aldrich, 4.37 g, 28 mmol) in THF (10 mL) was slowly dropped into the reaction. After addition, the reaction was stirred for an additional 2 hours at −78° C. The reaction was then quenched with water and warmed to room temperature. The solvent was removed in vacuo and the residue was partitioned between ethyl acetate and water. The organic layer was washed with brine, dried over anhydrous $Na_2SO_4$, filtered and concentrated to give a yellow solid, which was then purified by silica gel column on a CombiFlash® system (Teledyne Isco, Inc, Lincoln, Nebr.) using hexanes and ethyl acetate (from 10% ethyl acetate to 100% ethyl acetate) to afford the title compound as a yellow solid.

$^1$H NMR (400 MHz, CDCl$_3$) δ 8.28 (s, 1H), 7.75 (d, J=7.5 Hz, 1H), 6.72 (d, J=7.5 Hz, 1H), 3.95 (m, 4H), 2.35 (s, br, 1H), 2.10 (m, 1H), 1.85 (m, 2H), 1.65 (m, 2H).

Step B:
4-Hydroxy-4-(6-methoxy-pyridin-3-yl)-cyclohexanone

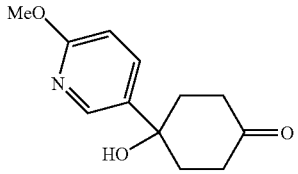 [SMILES: COc1ccc(C2(O)CCC(=O)CC2)cn1]

8-(6-Methoxy-pyridin-3-yl)-1,4-dioxa-spiro[4.5]decan-8-ol (4.00 g, 15.7 mmol) as prepared in the previous step was treated with 1N HCl (~16 mL) in acetone (20 mL) at room temperature for 4 hours. The reaction was neutralized with saturated NaHCO$_3$ solution and the solvent was removed. The residue was partitioned between ethyl acetate and water. The organic layer was washed with brine, dried over anhydrous Na$_2$SO$_4$, filtered and concentrated to give a yellow solid, which was then purified by silica gel column on a CombiFlash® system using hexanes and ethyl acetate (from 10% ethyl acetate to 100% ethyl acetate) to afford the title compound as a pale yellow solid.

$^1$H NMR (400 MHz, CDCl$_3$) δ 8.30 (s, 1H), 7.75 (d, J=7.0 Hz, 1H), 6.75 (d, J=6.5 Hz, 1H), 3.90 (s, 4H), 2.91 (m, 2H), 2.35 (d, J=6.8 Hz, 2H), 2.22 (m, 4H).

Step C: 3-[2-(3-Trifluoromethyl-benzoylamino)-acetylamino]-azetidine-1-carboxylic acid tent-butyl ester

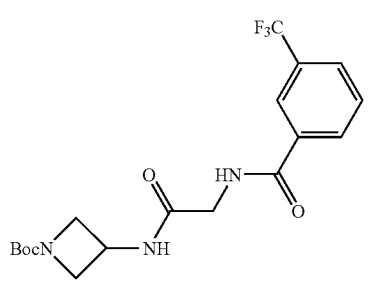 [SMILES: CC(C)(C)OC(=O)N1CC(NC(=O)CNC(=O)c2cccc(C(F)(F)F)c2)C1]

3-Amino-azetidine-1-carboxylic acid tert-butyl ester (AstaTech, 1.2 g, 6.97 mmol) and (3-trifluoromethyl-benzoylamino)-acetic acid (Bionet Building Blocks, 1.57 g, 6.36 mmol) were treated with EDCI (Aldrich, 1.57 g, 6.36 mmol), HOBT (Aldrich, 1.22 g, 6.36 mmol) in DCM (10 mL) at room temperature for 4 hours. The reaction solution was partitioned between DCM and water. The organic layer was washed with brine, dried over anhydrous Na$_2$SO$_4$, filtered and concentrated to give a yellow oil, and purified by silica gel column on a CombiFlash® system using hexanes and ethyl acetate (from 10% ethyl acetate to 100% ethyl acetate) to afford the title compound as a white solid.

$^1$H NMR (400 MHz, CDCl$_3$) δ 8.10 (s, 1H), 8.02 (d, J=6.6 Hz, 1H), 7.80 (d, J=6.8 Hz, 1H), 7.56 (t, J=6.5 Hz, 1H), 4.61 (m, 1H), 4.25 (t, J=7.2 Hz, 2H), 4.18 (d, J=5.5 Hz, 2H), 3.82 (t, J=7.5 Hz, 2H), 1.41 (s, 9H).

Step D: N-(Azetidin-3-ylcarbamoylmethyl)-3-trifluoromethyl-benzamide free base, HCl and TFA salt

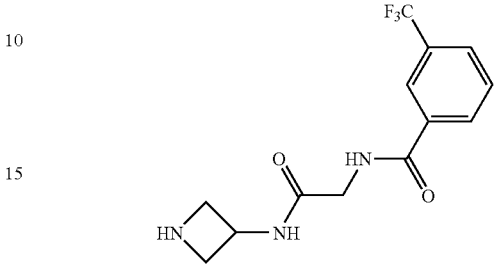

3-[2-(3-Trifluoromethyl-benzoylamino)-acetylamino]-azetidine-1-carboxylic acid tert-butyl ester (7.5 g, 18.7 mmol), as prepared in the previous step, was dissolved in 4N HCl in dioxane (5 mL) and MeOH (20 mL) at room temperature. The reaction was stirred for another 4 hours. The solvent was removed and the residue was dried to give the title compound as a HCl salt (yellow foam).

3-[2-(3-Trifluoromethyl-benzoylamino)-acetylamino]-azetidine-1-carboxylic acid tert-butyl ester (2.10 g, 5.24 mmol) was dissolved in 1:1 TFA and DCM mixed solution (10 mL) at room temperature. The reaction was stirred for another 2 hours. The solvent was removed and the residue was dried to give the title compound as a TFA salt containing extra TFA (colorless oil).

The free base was obtained by treating the salt in MeOH with solid Na$_2$CO$_3$ overnight. The solid was filtered and residue was dried to give the title compound for analytical characterization. The HCl or TFA salt was general used for the further reactions.

$^1$H NMR (400 MHz, CDCl$_3$) δ 8.10 (s, 1H), 8.05 (d, J=6.0 Hz, 1H), 7.78 (d, J=6.2 Hz, 1H), 7.55 (m, 2H), 4.78 (m, 1H), 4.15 (d, J=3.2 Hz, 2H), 3.95 (t, J=7.0 Hz, 2H), 3.52 (t, J=7.0 Hz, 2H).

Step E: N-({1-[4-Hydroxy-4-(6-methoxy-pyridin-3-yl)-cyclohexyl]-azetidin-3-ylcarbamoyl}-methyl)-3-trifluoromethyl-benzamide

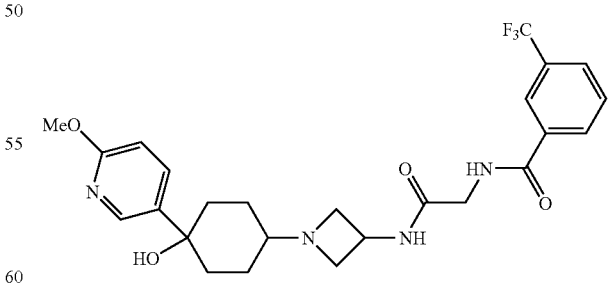

4-Hydroxy-4-(6-methoxy-pyridin-3-yl)-cyclohexanone, as prepared in Step B of this example, (300 mg, 1.36 mmol) and N-(azetidin-3-ylcarbamoylmethyl)-3-trifluoromethyl-benzamide HCl salt, as prepared in Step D of this example, (460 mg, 1.36 mmol) in DCM (5 mL) were treated with TEA (1 mL, 7.12 mmol) for 10 min followed by NaBH(OAc)$_3$ (860 mg, 4.07 mmol) for another 4 hours at room temperature. The reaction was quenched with saturated sodium bicarbonate. The organic layer was separated and the aqueous layer was extracted 3 times with chloroform and IPA "cocktail" (~3:1, v/v). The combined organic layer was dried over anhydrous Na$_2$SO$_4$, filtered and concentrated to give the crude product, which was then purified by a CombiFlash® system using ethyl acetate and 7N NH$_3$ in MeOH as eluent (from pure ethyl acetate to 5% 7N NH$_3$ in MeOH in ethyl acetate) to afford two title compounds as white solids: a less polar isomer, and a more polar isomer.

1a: less polar isomer from silica gel column, $^1$H NMR (400 MHz, CDCl$_3$) δ 8.28 (s, 1H), 8.11 (s, 1H), 8.05 (d, J=5.8 Hz, 1H), 7.78 (d, J=6.5 Hz, 1H), 7.70 (d, J=6.5 Hz, 1H), 7.57 (t, J=6.8 Hz, 1H), 6.70 (d, J=6.5 Hz, 1H), 4.51 (m, 1H), 4.20 (d, J=3.2 Hz, 2H), 3.88 (s, 3H), 3.65 (t, J=6.0 Hz, 2H), 2.92 (t, J=5.8 Hz, 2H), 2.20 (m, 2H), 1.85 (m, 2H), 1.56 (m, 2H), 1.45 (m, 2H).

1b: more polar isomer from silica gel column $^1$H NMR (400 MHz, CDCl$_3$) δ 8.25 (s, 1H), 8.10 (s, 1H), 8.05 (d, J=6.5 Hz, 1H), 7.80 (d, J=6.4 Hz, 1H), 7.71 (d, J=6.5 Hz, 1H), 7.62 (d, J=6.5 Hz, 1H), 7.60 (t, J=6.8 Hz, 1H), 7.37 (d, J=6.2 Hz, 1H), 6.70 (d, J=6.8 Hz, 1H), 4.55 (m, 1H), 4.20 (d, J=3.5 hz, 2H), 3.65 (t, J=6.5 Hz, 2H), 3.08 (t, J=6.5 Hz, 2H), 1.85~1.50 (m, 8H).

Example 2

N-({1-[4-Hydroxy-4-(6-methoxy-1-oxy-pyridin-3-yl)-cyclohexyl]-azetidin-3-ylcarbamoyl}-methyl)-3-trifluoromethyl-benzamide

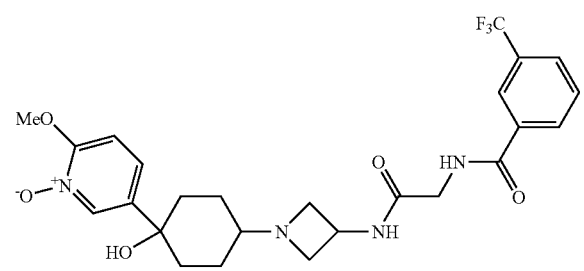

N-({1-[4-Hydroxy-4-(6-methoxy-pyridin-3-yl)-cyclohexyl]-azetidin-3-ylcarbamoyl}-methyl)-3-trifluoromethyl-benzamide (less polar isomer, 1a, 150 mg, 0.30 mmol) in DCM (5 mL) was treated with mCPBA (Aldrich, 62 mg, 0.36 mmol) at 0° C. for 2 hours. The reaction was partitioned between DCM and diluted NaHSO$_3$ solution. The aqueous layer was extracted three times with chloroform and IPA "cocktail" (~3:1, v/v). The combined organic layer was dried over anhydrous Na$_2$SO$_4$, filtered and concentrated to give the crude product, which was re-crystallized from IPA to give the title compound as a white solid.

$^1$H NMR (400 MHz, CDCl$_3$) δ 8.25 (s, 1H), 8.15 (s, 1H), 8.05 (d, J=6.8 Hz, 1H), 7.90 (d, J=7.0 Hz, 1H), 7.70 (d, J=6.5 Hz, 1H), 7.40 (t, J=6.5 Hz, 1H), 7.20 (d, J=6.4 Hz, 1H), 6.75 (d, J=6.4 Hz, 1H), 4.75 (m, 1H), 4.55 (m, 1H), 4.20 (m, 1H), 3.80 (t, J=7.0 Hz, 2H), 2.55 (t, J=6.5 Hz, 2H), 1.95~1.75 (m, 8H). ESI-MS (m/z): Calcd. For C$_{25}$H$_{29}$F$_3$N$_4$O$_5$, 522; found: 523 (M+H).

Example 3

N-({1-[4-Hydroxy-4-(5-methoxy-pyridin-2-yl)-cyclohexyl]-azetidin-3-ylcarbamoyl}-methyl)-3-trifluoromethyl-benzamide Step A: 8-(5-Methoxy-pyridin-2-yl)-1,4-dioxa-spiro[4.5]decan-8-ol

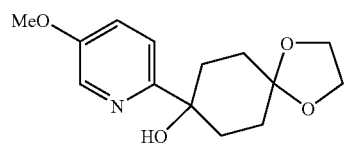 [SMILES: COc1ccc(C2(O)CCC3(CC2)OCCO3)nc1]

The title compound was prepared as a white solid from 2-bromo-5-methoxy-pyridine (Aldrich) and 1,4-dioxa-spiro[4.5]decan-8-one in ether using the procedure described in Step A of Example 1.

$^1$H NMR (400 MHz, CDCl$_3$) δ 8.33 (s, 1H), 8.11 (s, 1H), 7.40 (s, 1H), 4.01 (s, 4H), 3.87 (s, 3H), 2.18 (m, 4H), 1.85 (m, 2H), 1.70 (m, 2H).

Step B: 4-Hydroxy-4-(5-methoxy-pyridin-2-yl)-cyclohexanone

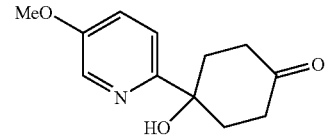

The title compound was prepared as a white solid from 8-(5-methoxy-pyridin-2-yl)-1,4-dioxa-spiro[4.5]decan-8-ol as prepared in the previous step using the procedure described in Step B of Example 1.

$^1$H NMR (400 MHz, CDCl$_3$) δ 8.28 (s, 1H), 8.12 (s, 1H), 7.41 9s, 1H), 3.90 (s, 3H), 3.0 (m, 2H), 2.38 (d, J=6.8 Hz, 2H), 2.25 (m, 4H).

Step C: N-({1-[4-Hydroxy-4-(5-methoxy-pyridin-2-yl)-cyclohexyl]-azetidin-3-ylcarbamoyl}-methyl)-3-trifluoromethyl-benzamide

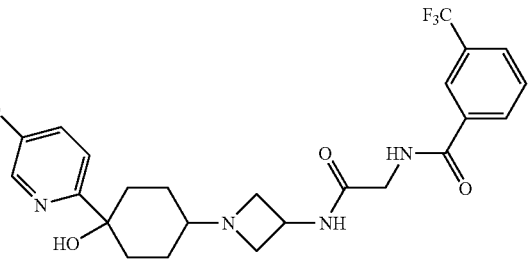

The title compounds were prepared as white solids from the reductive amination of 4-hydroxy-4-(5-methoxy-pyridin-2-yl)-cyclohexanone, as prepared in the previous step, and N-(azetidin-3-ylcarbamoylmethyl)-3-trifluoromethyl-benzamide using the procedure described in Step E of Example 1.

3a: less polar isomer from silica gel column.

$^1$H NMR (400 MHz, CDCl$_3$) δ 8.25 (s, 1H), 8.14 (s, 1H), 8.10 (s, 1H), 8.02 (d, J=6.5 Hz, 1H), 7.72 (d, J=7.1 Hz, 1H), 7.52 (t, J=6.8 Hz, 1H), 7.40 (s, 1H), 4.50 (m, 1H), 4.18 (d, J=3.0 Hz, 2H), 3.55 (t, J=6.0 Hz, 2H), 2.85 (t, J=6.0 Hz, 2H), 2.31 (s, br, 1H), 2.15 (t, J=9.0 Hz, 2H), 1.85 (m, 2H), 1.45 (m, 4H).

3b: more polar isomer from silica gel column $^1$H NMR (400 MHz, CDCl$_3$) δ 8.31 (s, 1H), 8.23 (d, J=6.8 Hz, 2H), 8.05 (d, J=6.7 Hz, 1H), 7.78 (m, 2H), 7.55 (m, 2H), 7.44 (s, 1H), 4.55 (m, 1H), 4.15 (d, J=3.0 Hz, 2H), 3.65 (t, J=7.0 Hz, 2H0, 3.10 (d, J=5.8 Hz, 2H), 2.15 (s, br, 1H), 1.9~1.55 (m, 8H).

Example 4

N-({1-[4-Hydroxy-4-(6-methoxy-pyridin-2-yl)-cyclohexyl]-azetidin-3-ylcarbamoyl}-methyl)-3-trifluoromethyl-benzamide Step A: 8-(6-Methoxy-pyridin-2-yl)-1,4-dioxa-spiro[4.5]decan-8-ol

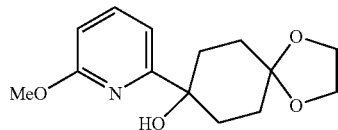 [SMILES: COc1cccc(C2(O)CCC3(CC2)OCCO3)n1]

The title compound was prepared as a white solid from 2-bromo-6-methoxy-pyridine (Aldrich) in ether using the procedure described in Step A of Example 1.

$^1$H NMR (400 MHz, CDCl$_3$) δ 7.60 (t, J=7.2 Hz, 1H), 6.98 (d, J=6.5 Hz, 1H), 6.62 (d, J=6.8 Hz, 1H), 4.00 (s, 3H), 3.95 (m, 4H), 2.05 (m, 4H), 1.90 (m, 2H), 1.75 (m, 2H).

Step B:
4-Hydroxy-4-(6-methoxy-pyridin-2-yl)-cyclohexanone

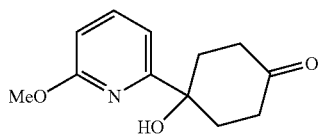 [SMILES: COc1cccc(C2(O)CCC(=O)CC2)n1]

The title compound was prepared as a white solid from 8-(6-methoxy-pyridin-2-yl)-1,4-dioxa-spiro[4.5]decan-8-ol as prepared in the previous step using the procedure described in Step B of Example 1.

$^1$H NMR (400 MHz, CDCl$_3$) δ 7.67 (t, J=6.8 Hz, 1H), 6.98 9d, J=7.0 Hz, 1H), 6.69 (d, J=6.8 Hz, 1H), 3.95 (s, 3H), 2.95 (m, 2H), 2.35 (m, 2H), 2.20 (m, 4H).

Step C: N-({1-[4-Hydroxy-4-(6-methoxy-pyridin-2-yl)-cyclohexyl]-azetidin-3-ylcarbamoyl}-methyl)-3-trifluoromethyl-benzamide

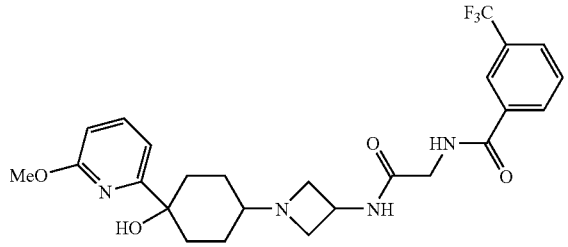 [SMILES: COc1cccc(C2(O)CCC(N3CC(NC(=O)CNC(=O)c4cccc(C(F)(F)F)c4)C3)CC2)n1]

The title compounds were prepared as white solids from reductive amination of 4-hydroxy-4-(6-methoxy-pyridin-2-yl)-cyclohexanone, as prepared in the previous step, and N-(azetidin-3-ylcarbamoylmethyl)-3-trifluoromethyl-benzamide using the procedure described in Step E of Example 1.

4a: less polar isomer from silica gel column.

$^1$H NMR (400 MHz, CDCl$_3$) δ 8.15 (s, 1H), 8.02 9d, J=5.0 Hz, 1H), 7.75 (d, J=6.0 Hz, 1H), 7.55 (m, 1H), 7.41 (m, 1H), 7.02 (d, J=6.6 Hz, 1H), 6.62 (d, J=6.8 Hz, 1H), 4.54 (m, 1H), 4.18 (d, J=3.5 Hz, 2H), 3.62 (t, J=6.8 Hz, 2H), 2.95 (t, J=6.5 Hz, 2H), 2.10 (m, 2H), 1.90 (m, 2H), 1.52 (m, 2H), 1.45 (M, 2H).

4b: more polar isomer from silica gel column $^1$H NMR (400 MHz, CDCl$_3$) δ 8.15 (s, 1H), 8.08 (d, J=5.0 Hz, 1H), 7.85 (t, J=4.5 Hz, 1H), 7.80 (d, J=6.5 Hz, 1H), 7.60 (m, 2H), 6.90 (d, J=6.6 Hz, 1H), 6.62 (d, J=6.8 Hz, 1H), 4.52 (m, 1H), 4.20 (d, J=5.8 Hz, 2H), 3.65 (t, J=6.4 Hz, 1H), 3.05 (t=6.6 Hz, 2H), 1.85~1.48 (m, 8H).

Example 5

N-({1-[4-(6-Ethoxy-pyridin-3-yl)-4-hydroxy-cyclohexyl]-azetidin-3-ylcarbamoyl}-methyl)-3-trifluoromethyl-benzamide Step A: 8-(6-Ethoxy-pyridin-3-yl)-1,4-dioxa-spiro[4.5]decan-8-ol

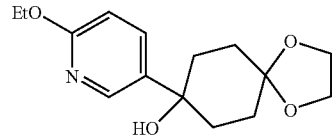 [SMILES: CCOc1ccc(C2(O)CCC3(CC2)OCCO3)cn1]

The title compound was prepared as a white solid from 5-bromo-ethoxy-pyridine (Aldrich) and 1,4-dioxa-spiro[4.5]decan-8-one in ether using the procedure described in Step A of Example 1.

$^1$H NMR (400 MHz, CDCl$_3$) δ 8.25 (s, 1H), 7.70 (d, J=7.0 Hz, 1H), 6.75 (d, J=7.0 Hz, 1H), 4.32 (q, J=7.1 Hz, 2H), 4.02 (m, 4H), 2.10 (m, 4H), 1.85 (d, J=7.5 Hz, 2H), 1.70 (d, J=7.7 Hz, 2H), 1.48 (t, J=7.3 Hz, 3H).

Step B:
4-(6-Ethoxy-pyridin-3-yl)-4-hydroxy-cyclohexanone

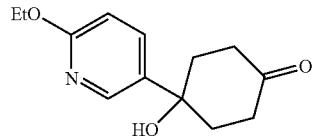 [SMILES: CCOc1ccc(C2(O)CCC(=O)CC2)cn1]

The title compound was prepared as a white solid from 8-(6-ethoxy-pyridin-3-yl)-1,4-dioxa-spiro[4.5]decan-8-ol as prepared in the previous step using the procedure described in Step B of Example 1.

ESI-MS (m/z): Calcd. For $C_{13}H_{17}NO_3$, 235; found: 236 (M+H).

Step C: N-({1-[4-(6-Ethoxy-pyridin-3-yl)-4-hydroxy-cyclohexyl]-azetidin-3-ylcarbamoyl}-methyl)-3-trifluoromethyl-benzamide

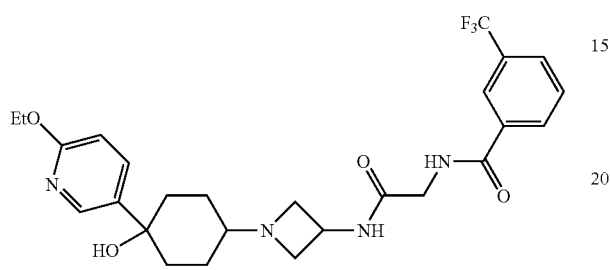

The title compounds were prepared as white solids from reductive amination of 4-(6-ethoxy-pyridin-3-yl)-4-hydroxy-cyclohexanone, as prepared in the previous step, and N-(azetidin-3-ylcarbamoylmethyl)-3-trifluoromethyl-benzamide using the procedure described in Step E of Example 1.

5a: less polar isomer from silica gel column,
$^1$H NMR (400 MHz, CDCl$_3$) δ 8.29 (s, 1H), 8.15 (s, 1H), 8.08 (m, 2H), 7.80 (m, 2H), 7.62 (m, 2H), 6.75 (d, J=6.5 Hz, 1H), 4.53 (m, 1H), 4.35 (q, J=7.8 Hz, 2H), 4.22 (d, J=6.1 Hz, 2H), 3.75 (t, J=6.5 Hz, 2H), 2.95 (t, J=6.5 Hz, 2H), 2.40 (m, 2H), 2.26 (m, 2H), 1.92 (m, 2H), 1.65 (m, 2H), 1.48 (t, J=7.5 Hz, 3H).

5b: less polar isomer from silica gel column
$^1$H NMR (400 MHz, CDCl$_3$) δ 8.25 (s, 1H), 8.15 9s, 1H), 8.04 (d, J=6.2 Hz, 1H), 7.85 (t, J=5.5 Hz, 1H), 7.72 (d, J=6.7 Hz, 1H), 7.70 (t, J=6.4 Hz, 1H), 6.68 (d, J=7.0 Hz, 1H), 6.10 (s, br, 1H), 5.72 (s, br, 1H), 4.51 (m, 1H), 4.30 (q, J=7.8 Hz, 2H), 4.18 (d, J=3.5 Hz, 2H), 3.62 (t, J=6.9 Hz, 2H), 3.10 (t, J=6.5 Hz, 2H), 1.85 (m, 2H), 1.70 (m, 4H), 1.55 (m, 2H), 1.38 (t, J=8.0 Hz, 3H).

Example 6

N-({1-[4-(6-Fluoro-pyridin-3-yl)-4-hydroxy-cyclohexyl]-azetidin-3-ylcarbamoyl}-methyl)-3-trifluoromethyl-benzamide Step A: 8-(6-Fluoro-pyridin-3-yl)-1,4-dioxa-spiro[4.5]decan-8-ol

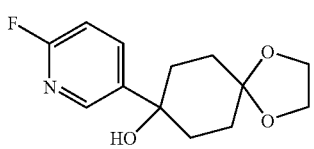 [SMILES: OC1(c2ccc(F)nc2)CCC2(CC1)OCCO2]

The title compound was prepared as a white solid from 5-bromo-2-fluoro-pyridine (Aldrich) and 1,4-dioxa-spiro[4.5]decan-8-one in ether using the procedure described in Step A of Example 1.

$^1$H NMR (400 MHz, CDCl$_3$) δ 8.35 (s, 1H), 7.98 (dd, J=9.0, 6.5 Hz, 1H), 6.90 (d, J=6.5 Hz, 1H), 4.01 (m, 4H), 2.10 (m, 4H), 1.85 (d, J=7.8 Hz, 2H), 0.70 (d, J=7.8 Hz, 2H).

Step B: 4-(6-Fluoro-pyridin-3-yl)-4-hydroxy-cyclohexanone

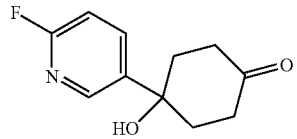 [SMILES: O=C1CCC(O)(c2ccc(F)nc2)CC1]

The title compound was prepared as a white solid from 8-(6-fluoro-pyridin-3-yl)-1,4-dioxa-spiro[4.5]decan-8-ol as prepared in the previous step using the procedure described in Step B of Example 1.

$^1$H NMR (400 MHz, CDCl$_3$) δ 8.40 (s, 1H), 8.00 (dd, J=8.2, 6.5 Hz, 1H), 6.98 (d, J=6.5 Hz, 1H), 2.95 (m, 2H), 2.50 (m, 2H), 2.32 (m 4H).

Step C: N-({1-[4-(6-Fluoro-pyridin-3-yl)-4-hydroxy-cyclohexyl]-azetidin-3-ylcarbamoyl}-methyl)-3-trifluoromethyl-benzamide

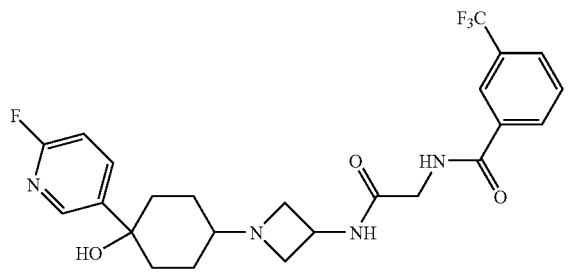 [SMILES: O=C(CNC(=O)c1cccc(C(F)(F)F)c1)NC1CN(C2CCC(O)(c3ccc(F)nc3)CC2)C1]

The title compounds were prepared as white solids from reductive amination of 4-(6-fluoro-pyridin-3-yl)-4-hydroxy-cyclohexanone, as prepared in the previous step, and N-(azetidin-3-ylcarbamoylmethyl)-3-trifluoromethyl-benzamide using the procedure described in Step E of Example 1.

6a: less polar isomer from silica gel column
$^1$H NMR (400 MHz, CDCl$_3$) δ 8.35 (s, 1H), 8.15 (s, 1H), 8.05 (d, J=6.4 Hz, 1H), 7.96 (t, J=6.8 Hz, 1H), 7.74 (d, J=6.5 Hz, 1H), 7.55 (t, J=7.2 Hz, 1H), 7.50 (m, 1H), 6.90 (d, J=6.7 Hz, 1H), 4.53 (m, 1H), 4.15 (d, J=3.5 Hz, 2H), 3.60 (t, J=6.7 Hz, 2H), 2.88 (t, J=6.8 Hz, 2H), 2.20 (m, 2H), 1.85 (m, 2H), 1.65 (m, 4H).

6b: more polar isomer from silica gel column,
8.32 (s, 1H), 8.10 (d, J=6.0 Hz, 1H), 8.01 (d, J=6.2 Hz, 1H), 7.95 (m, 1H), 7.72 (d, J=6.2 Hz, 1H), 7.50 (t, J=6.5 Hz, 1H), 6.85 (d, J=6.6 Hz, 1H), 4.50 (m, 1H), 4.15 (s, br, 2H), 3.70 (t, J=6.5 Hz, 2H), 3.10 (t, J=5.5 Hz, 2H), 1.90~1.50 (m, 8H).

Example 7

N-({1-[4-(6-Benzyloxy-pyridin-3-yl)-4-hydroxy-cyclohexyl]-azetidin-3-ylcarbamoyl}-methyl)-3-trifluoromethyl-benzamide Step A: 8-(6-Benzyloxy-pyridin-3-yl)-1,4-dioxa-spiro[4.5]decan-8-ol

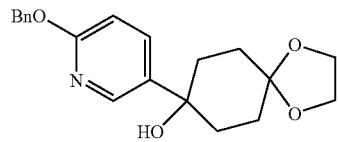 [SMILES: OC1(c2ccc(OCc3ccccc3)nc2)CCC2(CC1)OCCO2]

The title compound was prepared as a white solid from 5-bromo-2-benzyloxy-pyridine (Alfa Aesar) and 1,4-dioxa-spiro[4.5]decan-8-one in ether using the procedure described in Step A of Example 1.

$^1$H NMR (400 MHz, CDCl$_3$) δ 7.55 (d, J=7.0 Hz, 1H), 7.40 (m, 5H), 7.33 (m, 1H), 6.42 (d, J=6.8 Hz, 1H), 5.10 (s, 2H), 4.05 (m, 4H), 2.05 (m, 4H), 1.80 (m, 2H), 1.55 (m, 2H).

Step B: 4-(6-Benzyloxy-pyridin-3-yl)-4-hydroxy-cyclohexanone

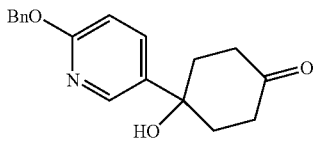 [SMILES: O=C1CCC(O)(c2ccc(OCc3ccccc3)nc2)CC1]

The title compound was prepared as a white solid from 8-(6-benzyloxy-pyridin-3-yl)-1,4-dioxa-spiro[4.5]decan-8-ol, as prepared in the previous step, using the procedure described in Step B of Example 1.

$^1$H NMR (400 MHz, CDCl$_3$) δ 7.45 (d, J=6.5 Hz, 1H), 7.30 (m, 5H), 7.33 (m, 1H), 6.52 (d, J=6.6 Hz, 1H), 5.10 (s, 2H), 2.90 (m, 2H), 2.30 (m, 2H), 2.05 (m, 4H).

Step C: N-({1-[4-(6-Benzyloxy-pyridin-3-yl)-4-hydroxy-cyclohexyl]-azetidin-3-ylcarbamoyl}-methyl)-3-trifluoromethyl-benzamide

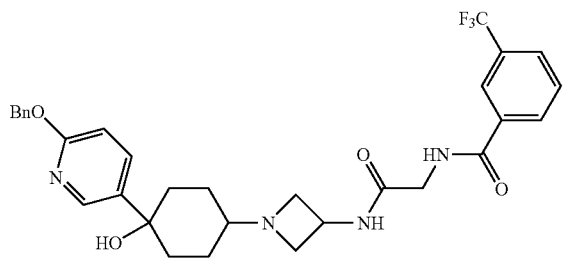 [SMILES: O=C(CNC(=O)c1cccc(C(F)(F)F)c1)NC1CN(C2CCC(O)(c3ccc(OCc4ccccc4)nc3)CC2)C1]

The title compounds were prepared as white solids from reductive amination of 4-(6-benzyloxy-pyridin-3-yl)-4-hydroxy-cyclohexanone, as prepared in the previous step, and N-(azetidin-3-ylcarbamoylmethyl)-3-trifluoromethyl-benzamide using the procedure described in Step E of Example 1.

7a: less polar isomer from silica gel column $^1$H NMR (400 MHz, CDCl$_3$) δ 8.15 (s, 1H), 8.01 (d, J=6.1 Hz, 1H), 7.80 (d, J=6.5 Hz, 1H), 7.62 (t, J=6.8 Hz, 1H), 7.35 (m, 5H), 6.55 (d, J=7.0 Hz, 1H), 5.15 (s, 2H), 4.52 (m, 1H), 4.15 (d, J=4.0 Hz, 2H), 3.60 (t, J=7.0 Hz, 2H), 2.90 (t, J=6.8 Hz, 2H), 2.30 (s, br, 1H), 2.05 (m, 1H), 1.75 (m, 4H), 1.45 (m, 2H).

7b: more polar isomer from silica gel column $^1$H NMR (400 MHz, CDCl$_3$) δ 8.15 (s, 1H), 8.00 (d, J=6.5 Hz, 1H), 7.78 (d, J=6.6 Hz, 1H), 7.60 (t, J=6.6 Hz, 1H), 7.35 (m, 1H), 6.60 (d, J=6.8 Hz, 1H), 4.50 (m, 1H), 4.20 (d, J=4.0 Hz, 2H), 3.65 (t, J=7.0 Hz, 2H), 3.10 (t, J=7.0 Hz, 2H), 2.30 (s, 1H), 2.02 (m, 2H), 1.90~1.65 (6H).

Example 8

N-({1-[4-Hydroxy-4-(6-isopropoxy-pyridin-3-yl)-cyclohexyl]-azetidin-3-ylcarbamoyl}-methyl)-3-trifluoromethyl-benzamide

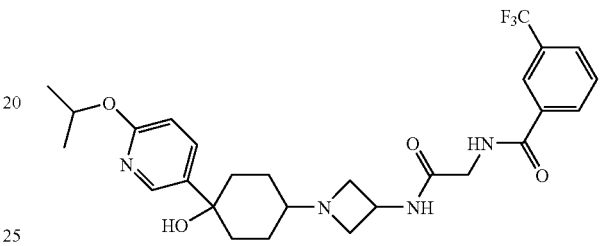

NaH (95%, 51 mg, 2 mmol) was added into IPA (4 mL) at 0° C. slowly until bubble disappeared. To this solution was added N-({1-[4-(6-fluoro-pyridin-3-yl)-4-hydroxy-cyclohexyl]-azetidin-3-ylcarbamoyl}-methyl)-3-trifluoromethyl-benzamide (6a, 200 mg, 0.40 mmol) in DMF (1 mL). After addition, the reaction was heated for another 2 hours at 80° C. The reaction solution was quenched with MeOH and partitioned between DCM and water. The organic layer was separated and the aqueous layer was extracted 3 times with chloroform and IPA "cocktail" (~3:1, v/v). The combined organic layer was dried over anhydrous Na$_2$SO$_4$, filtered and concentrated to give the crude product, which was then purified by a CombiFlash® system using ethyl acetate and 7N NH$_3$ in MeOH as eluent (from pure ethyl acetate to 5% 7N NH$_3$ in MeOH in ethyl acetate) to afford the title compound as a white solid.

$^1$H NMR (400 MHz, CDCl$_3$) δ 8.25 (s, 1H), 8.15 (s, 1H), 8.05 (d, J=6.8 Hz, 1H), 7.75 (d, J=6.8 Hz, 1H), 7.70 (d, J=6.8 Hz, 1H), 7.52 (t, J=6.5 Hz, 1H), 6.68 (d, J=6.0 Hz, 1H), 5.20 (m, 1H), 4.62 (m, 1H), 4.15 (d, J=4.0 Hz, 2H), 3.60 (t, J=7.0 Hz, 2H), 3.05 (s., br, 2H), 2.30 (s, 1H), 2.20 (m, 2H), 2.05 (m, 2H), 1.65 (m, 2H), 1.52 (m, 2H), 1.31 (d, J=6.0 Hz, 6H).

Example 9

N-({1-[4-(6-tert-Butoxy-pyridin-3-yl)-4-hydroxy-cyclohexyl]-azetidin-3-ylcarbamoyl}-methyl)-3-trifluoromethyl-benzamide

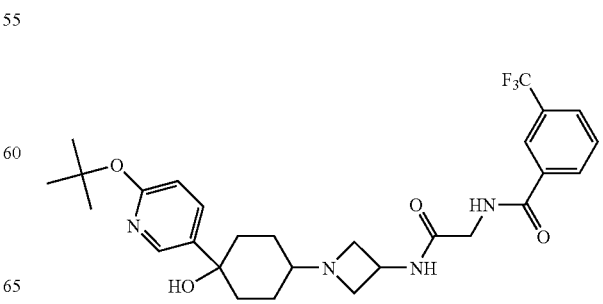

The title compound was prepared as a white solid from N-({1-[4-(6-fluoro-pyridin-3-yl)-4-hydroxy-cyclohexyl]-azetidin-3-ylcarbamoyl}-methyl)-3-trifluoromethyl-benzamide 6a and t-BuOK using the procedure described in Example 8.

$^1$H NMR (400 MHz, CDCl$_3$) δ 8.25 (s, 1H), 8.10 (s, 1H), 8.00 (d, J=6.5 Hz, 1H), 7.80 (d, J=6.5 Hz, 1H), 7.61 (d, J=6.6 Hz, 1H), 7.52 (t, J=5.5 Hz, 1H), 7.35 (m, 1H), 6.88 (m, 1H), 6.60 (d, J=6.8 Hz, 1H), 4.52 (m, 1H), 4.15 (d, J=4.0 Hz, 2H), 3.65 (t, J=7.0 Hz, 2H), 2.95 (t, J=7.0 Hz, 2H), 2.30 (s, 1H), 2.21 (m, 1H), 1.80 (m, 6H), 1.52 (s, 9H), 1.35 (m, 2H).

Example 10

N-[(1-{4-Hydroxy-4-[6-(2,2,2-trifluoro-ethoxy)-pyridin-3-yl]-cyclohexyl}-azetidin-3-ylcarbamoyl)-methyl]-3-trifluoromethyl-benzamide

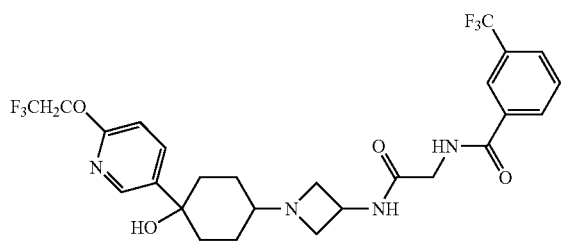

The title compound was prepared as a white solid from N-({1-[4-(6-fluoro-pyridin-3-yl)-4-hydroxy-cyclohexyl]-azetidin-3-ylcarbamoyl}-methyl)-3-trifluoromethyl-benzamide 6a and CF$_3$CH$_2$OH (Sigma) using the procedure described in Example 8.

$^1$H NMR (400 MHz, CDCl$_3$) δ 8.28 (s, 1H), 8.15 (s, 1H), 8.05 (d, J=6.4 Hz, 1H), 7.78 (d, J=6.6 Hz, 1H), 7.70 (t, J=6.6 Hz, 1H), 7.65 (m, 1H), 7.55 (t, J=5.8 Hz, 2H), 6.70 (d, J=6.8 Hz, 1H), 4.75 (q, J=8.5 Hz, 2H), 4.55 (m, 1H), 4.15 (d, J=4.0 Hz, 2H), 3.62 (t, J=6.0 Hz, 2H), 2.95 (t, J=7.0 Hz, 2H), 2.30 (s, 1H), 1.85 (m, 4H), 1.55 (m, 2H), 1.45 (m, 2H).

Example 11

N-({1-[4-(6-Cyclobutoxy-pyridin-3-yl)-4-hydroxy-cyclohexyl]-azetidin-3-ylcarbamoyl}-methyl)-3-trifluoromethyl-benzamide

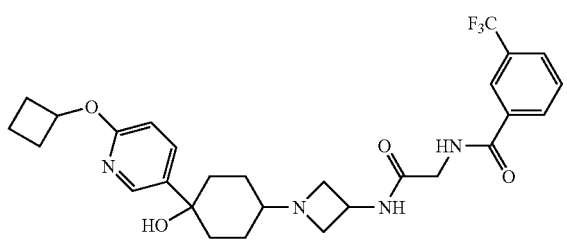 [SMILES: O=C(CNC(=O)c1cccc(C(F)(F)F)c1)NC1CN(C2CCC(O)(c3ccc(OC4CCC4)nc3)CC2)C1]

The title compound was prepared as a white solid from N-({1-[4-(6-fluoro-pyridin-3-yl)-4-hydroxy-cyclohexyl]-azetidin-3-ylcarbamoyl}-methyl)-3-trifluoromethyl-benzamide 6a and cyclobutanol (Aldrich) using the procedure described in Example 8.

$^1$H NMR (400 MHz, CDCl$_3$) δ 8.25 (s, 1H), 8.10 (s, 1H), 8.01 (d, J=6.5 Hz, 1H), 7.75 (d, J=6.6 Hz, 1H), 7.70 (d, J=6.8 Hz, 1H), 7.55 (t, J=6.6 Hz, 1H), 7.25 (m, 1H), 6.65 (d, J=6.0 Hz, 1H), 5.10 (m, 1H), 4.50 (m, 1H), 4.10 (d, J=4.0 Hz, 2H), 3.60 (t, J=7.0 Hz, 2H), 2.90 (t, J=7.0 Hz, 2H), 2.40 (m, 1H), 2.37 (m, 4H), 2.15 (m, 2H), 2.10 (m, 2H), 1.83 (m, 2H), 1.80~1.45 (4H).

Example 12

N-({1-[4-(6-Cyano-pyridin-3-yl)-4-hydroxy-cyclohexyl]-azetidin-3-ylcarbamoyl}-methyl)-3-trifluoromethyl-benzamide

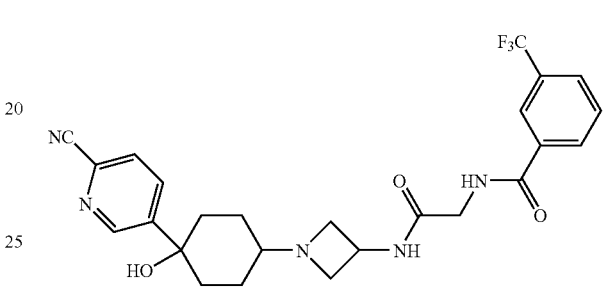

N-({1-[4-(6-fluoro-pyridin-3-yl)-4-hydroxy-cyclohexyl]-azetidin-3-ylcarbamoyl}-methyl)-3-trifluoromethyl-benzamide 6a (70 mg, 0.14 mmol), KCN (Aldrich, 46 mg, 0.70 mmol) and 18-crown-6 (Aldrich, 190 mg, 0.70 mmol) in DMF (1 mL) were heated to 150° C. in a sealed tube overnight. The reaction solution was loaded on a silica gel column with a CombiFlash® system using ethyl acetate and 7N NH$_3$ in MeOH as eluent (from pure ethyl acetate to 5% 7N NH$_3$ in MeOH in ethyl acetate) to afford the title compound as a white solid.

$^1$H NMR (400 MHz, CDCl$_3$) δ 8.35 (s, 1H), 8.15 (s, 1H), 8.01 (d, J=6.0 Hz, 1H), 7.80 (d, J=6.5 Hz, 1H), 7.61 (t, J=6.8 Hz, 1H), 7.35 (s, br, 1H), 7.88 (d, J=6.2 Hz, 1H), 4.52 (m, 1H), 4.18 (d, J=3.0 Hz, 2H), 3.62 (t, J=7.0 Hz, 2H), 2.90 (t, J=6.8 Hz, 2H), 2.32 (s, 1H), 2.20 (m, 2H), 1.80 (4H), 1.55 (m, 2H).

Example 13

N-({1-[4-Hydroxy-4-(6-methyl-pyridin-3-yl)-cyclohexyl]-azetidin-3-ylcarbamoyl}-methyl)-3-trifluoromethyl-benzamide Step A: 8-(6-Methyl-pyridin-3-yl)-1,4-dioxa-spiro[4.5]decan-8-ol

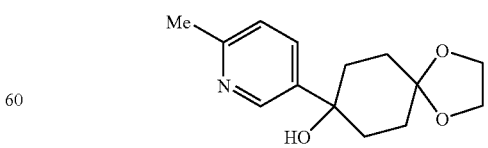

The title compound was prepared as a white solid from 5-bromo-2-methyl-pyridine (Acros Organics) and 1,4-dioxa-spiro[4.5]decan-8-one in ether using the procedure described in Step A of Example 1.

¹H NMR (400 MHz, CDCl₃) δ 8.45 (s, 1H), 7.75 (d, J=7.2 Hz, 1H), 7.10 (d, J=7.0 Hz, 1H), 4.02 (s, 4H), 2.45 (s, 3H), 2.10 (m, 4H), 1.90 (d, J=9.0 Hz, 2H), 1.72 (d, J=8.5 Hz, 2H).

Step B: 4-Hydroxy-4-(6-methyl-pyridin-3-yl)-cyclohexanone

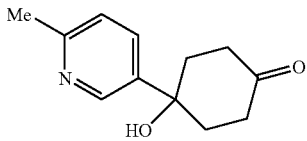 [SMILES: Cc1ccc(C2(O)CCC(=O)CC2)cn1]

The title compound was prepared as a white solid from 8-(6-methyl-pyridin-3-yl)-1,4-dioxa-spiro[4.5]decan-8-ol, as prepared in the previous step, using the procedure described in Step B of Example 1.

¹H NMR (400 MHz, CDCl₃) δ 8.65 (s, 1H), 7.81 (d, J=6.5 Hz, 1H), 7.20 9d, J=6.5 Hz, 1H), 3.10 (m, 2H), 2.61 (s, 3H), 2.42 (m, 2H), 2.28 (m, 4H).

Step C: N-({1-[4-Hydroxy-4-(6-methyl-pyridin-3-yl)-cyclohexyl]-azetidin-3-ylcarbamoyl}-methyl)-3-trifluoromethyl-benzamide

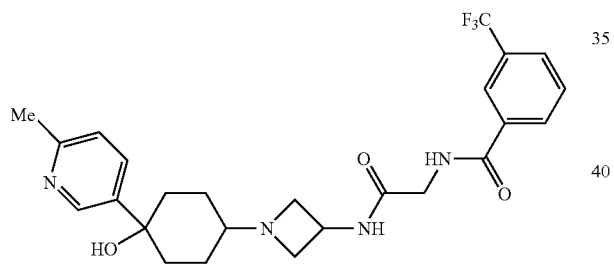

The title compounds were prepared as white solids from reductive amination of 4-hydroxy-4-(6-methyl-pyridin-3-yl)-cyclohexanone, as prepared in the previous step, and N-(azetidin-3-ylcarbamoylmethyl)-3-trifluoromethyl-benzamide using the procedure described in Step E of Example 1.

13a: less polar isomer from silica gel column,

¹H NMR (400 MHz, CDCl₃) δ 8.61 (s, 1H), 8.15 (s, 1H), 8.02 (d, J=7.0 Hz, 1H), 7.70 (m, 2H), 7.68 (m, 1H), 7.55 (d, J=6.5 Hz, 1H), 7.70 (s, 1H), 7.10 (d, J=6.8 Hz, 1H), 4.52 (m, 1H), 4.10 (d, J=6.0 Hz, 2H), 3.62 (t, J=7.5 Hz, 2H), 2.98 (t, J=7.8 Hz, 2H), 2.50 (s, 3H), 2.25 (m, 2H), 1.85 (m, 2H), 1.55 (m, 4H).

13b: more polar isomer from silica gel column

¹H NMR (400 MHz, CDCl₃) δ 8.60 (s, 1H), 8.18 (s, 1H), 8.10 (d, J=6.5 Hz, 1H), 7.80 (d, J=6.8 Hz, 1H), 7.76 (d, J=6.5 Hz, 1H), 7.60 (t, J=7.2 Hz, 1H), 7.45 (m, 1H), 7.12 (d, J=6.8 Hz, 1H), 4.62 (m, 1H), 4.17 (d, J=5.8 Hz, 2H), 3.38 (br, s, 2H), 2.75 (m, 4H), 1.85 (m, 2H), 1.70 (m, 2H).

Example 14

N-({1-[4-Hydroxy-4-(6-methoxy-5-methyl-pyridin-3-yl)-cyclohexyl]-azetidin-3-ylcarbamoyl}-methyl)-3-trifluoromethyl-benzamide Step A: 8-(6-Methoxy-5-methyl-pyridin-3-yl)-1,4-dioxa-spiro[4.5]decan-8-ol

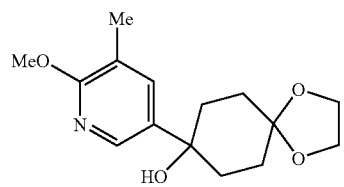 [SMILES: COc1ncc(C2(O)CCC3(CC2)OCCO3)cc1C]

The title compound was prepared as a white solid from 5-bromo-2-methoxy-3-methyl-pyridine (Alfa Aesar) and 1,4-dioxa-spiro[4.5]decan-8-one in ether using the procedure described in Step A of Example 1.

¹H NMR (400 MHz, CDCl₃) δ 7.50 (s, 1H), 3.98 (m, 4H), 3.92 (s, 3H), 2.20 (s, 3H), 2.10 (m, 4H), 1.85 (m, 2H), 1.78 (m, 2H).

Step B: 4-Hydroxy-4-(6-methoxy-5-methyl-pyridin-3-yl)-cyclohexanone

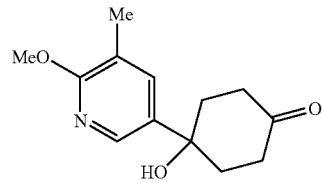

The title compound was prepared as a white solid from 8-(6-methoxy-5-methyl-pyridin-3-yl)-1,4-dioxa-spiro[4.5]decan-8-ol, as prepared in the previous step, using the procedure described in Step B of Example 1.

¹H NMR (400 MHz, CDCl₃) δ 7.50 (s, 1H), 3.90 (s, 3H), 2.25 (s, 3H), 2.70 (m, 2H), 2.35 (m, 2H), 2.20 (m, 4H).

Step C: N-({1-[4-Hydroxy-4-(6-methoxy-5-methyl-pyridin-3-yl)-cyclohexyl]-azetidin-3-ylcarbamoyl}-methyl)-3-trifluoromethyl-benzamide

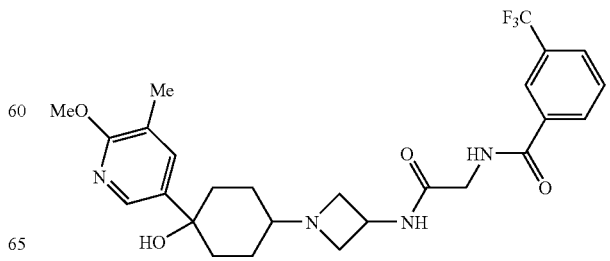

The title compounds were prepared as white solids from reductive amination of 4-hydroxy-4-(6-methoxy-5-methyl-pyridin-3-yl)-cyclohexanone, as prepared in the previous step, and N-(azetidin-3-ylcarbamoylmethyl)-3-trifluoromethyl-benzamide using the procedure described in Step E of Example 1.

14a: less polar isomer from silica gel column,
¹H NMR (400 MHz, CDCl₃) δ 8.10 (s, 1H), 8.02 (d, J=6.5 Hz, 1H), 7.80 (d, J=6.6 Hz, 1H), 7.55 (t, J=6.6 Hz, 1H), 7.60 (s, 1H), 6.72 (d, J=6.4 Hz, 1H), 4.50 (m, 1H), 4.18 (d, J=4.3 Hz, 2H), 3.60 (t, J=6.8 Hz, 2H), 2.90 (t, J=6.5 Hz, 2H), 2.20 (m, 2H), 1.85 (m, 2H), 1.62 (m, 2H), 1.43 (m, 2H).

14b: more polar isomer from silica gel column
¹H NMR (400 MHz, CDCl₃) δ 8.15 (s, 1H), 8.05 (d, J=6.6 Hz, 1H), 7.78 (d, J=6.5 Hz, 1H), 7.58 (t, J=6.7 Hz, 1H), 7.55 (s, 1H), 6.95 (d, J=6.6 Hz, 1H), 4.55 (m, 1H), 4.20 (d, J=3.5 Hz, 2H), 3.66 (t, J=7.5 Hz, 2H), 3.10 (t, J=7.5 Hz, 2H), 1.90~1.68 (m, 6H), 1.60 (m, 2H).

Example 15

N-{[1-(4-Hydroxy-4-pyridin-3-yl-cyclohexyl)-azetidin-3-ylcarbamoyl]-methyl}-3-trifluoromethyl-benzamide Step A:
8-Pyridin-3-yl-1,4-dioxa-spiro[4.5]decan-8-ol

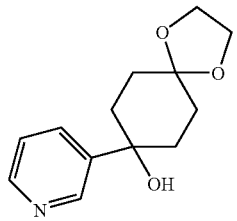 [SMILES: OC1(c2cccnc2)CCC2(CC1)OCCO2]

The title compound was prepared as yellow solid from 3-bromopyridine (Aldrich) in ether using the procedure described in Step A of Example 1.
¹H NMR (CHLOROFORM-d) δ: 8.67 (d, J=1.8 Hz, 1H), 8.30 (d, J=4.8 Hz, 1H), 7.86 (d, J=9.6 Hz, 1H), 7.22 (dd, J=8.1, 4.8 Hz, 1H), 3.97 (s, 4H), 2.00-2.22 (m, 4H), 1.77-1.88 (m, 2H), 1.67 (d, J=10.4 Hz, 2H).

Step B: 4-Hydroxy-4-pyridin-3-yl-cyclohexanone

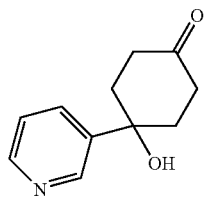 [SMILES: O=C1CCC(O)(c2cccnc2)CC1]

The title compound was prepared from 8-pyridin-3-yl-1,4-dioxa-spiro[4.5]decan-8-ol, as prepared in the previous step, usingdecan-8-ol, as prepared in the previous step, using the procedure described in Step B of Example 1.
¹H NMR (MeOH) δ: 8.98 (s, 1H), 8.80 (d, J=6.1 Hz, 2H), 8.12 (t, J=6.9 Hz, 1H), 1.96-2.12 (m, 2H), 1.82-1.96 (m, 2H), 1.80 (br. s., 2H), 1.60-1.76 (m, 2H).

Step C: N-{[1-(4-Hydroxy-4-pyridin-3-yl-cyclohexyl)-azetidin-3-ylcarbamoyl]-methyl}-3-trifluoromethyl-benzamide

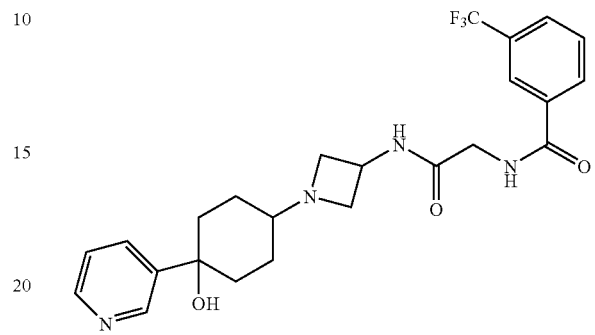

The title compound was prepared as yellow solid using the procedure described in Step E of Example 1 from reductive amination of 4-Hydroxy-4-pyridin-3-yl-cyclohexanone, as prepared in the previous step, and N-(azetidin-3-ylcarbamoylmethyl)-3-trifluoromethyl-benzamide.
¹H NMR (CHLOROFORM-d) δ: 8.65-8.94 (m, 1H), 8.33-8.58 (m, 1H), 8.12 (s, 1H), 8.01 (d, J=6.3 Hz, 1H), 7.70-7.91 (m, 2H), 7.58 (t, J=7.7 Hz, 1H), 7.25 (br. s., 1H), 4.54 (t, J=6.1 Hz, 2H), 4.16 (br s, 1H), 3.51-3.72 (m, 2H), 3.00-3.14 (m, 2H), 2.92 (t, J=6.6 Hz, 1H), 2.06-2.32 (m, 2H), 1.79-1.98 (m, 2H), 1.51 (br. s., 2H), 1.25 (s, 2H).

Example 16

N-({1-[4-Hydroxy-4-(6-methoxy-pyridin-3-yl)-cyclohexyl]-azetidin-3-ylcarbamoyl}-methyl)-4-trifluoromethyl-benzamide Step A: {1-[4-Hydroxy-4-(6-methoxy-pyridin-3-yl)-cyclohexyl]-azetidin-3-yl}-carbamic acid tent-butyl ester

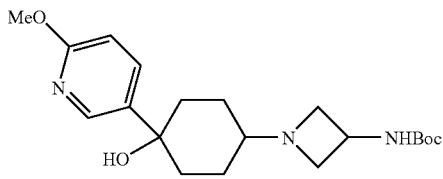 [SMILES: COc1ccc(C2(O)CCC(N3CC(NC(=O)OC(C)(C)C)C3)CC2)cn1]

The title compounds were prepared as white solids from reductive amination of 4-hydroxy-4-(6-methoxy-pyridin-3-yl)-cyclohexanone (as described in Example 1, Step B) and azetidin-3-yl-carbamic acid tert-butyl ester (BetaPharm) using the procedure described in Step E of Example 1.

Less polar isomer from silica gel column
¹H NMR (400 MHz, CDCl₃) δ 8.28 (s, 1H), 7.72 (d, J=6.4 Hz, 1H), 6.75 (d, J=6.4 Hz, 1H), 4.95 (s, br, 1H), 4.25 (m, 1H), 3.90 (s, 3H), 3.55 (t, J=6.1 Hz, 2H), 2.75 (s, br, 3H), 2.20 (m, 2H), 1.82 (m, 2H), 1.65 (m, 2H), 1.42 (s, 9H), 1.35 (m, 2H).

More polar isomer from silica gel column
¹H NMR (400 MHz, CDCl₃) δ 8.25 (s, 1H), 7.70 (d, J=6.5 Hz, 1H), 4.90 (s, br, 1H), 4.30 (s, br, 1H), 3.92 9s, 3H), 3.65 (t, J=3.5 Hz, 2H), 2.89 (s, br, 2H), 2.05 (m, 1H), 2.9~2.69 (m, 6H), 1.55 (m, 2H), 1.45 (s, 9H).

Step B: 4-(3-Amino-azetidin-1-yl)-1-(6-methoxy-pyridin-3-yl)-cyclohexanol TFA salt

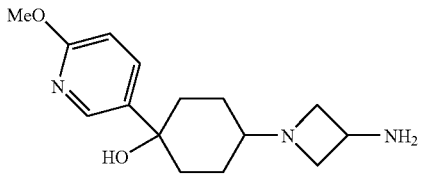 [SMILES: COc1ccc(C2(O)CCC(N3CC(N)C3)CC2)cn1]

{1-[4-Hydroxy-4-(6-methoxy-pyridin-3-yl)-cyclohexyl]-azetidin-3-yl}-carbamic acid tert-butyl ester (less polar isomer from Step A, 5.50 g, 14.6 mmol) in DCM (10 mL) and TFA (10 mL) at room temperature was stirred for 2 hours. The solvent was removed and dried under vacuum to give the title compound as colorless oil.

ESI-MS (m/z): Calcd. For $C_{15}H_{23}N_3O_2$, 277; found: 278 (M+H).

Step C: ({1-[4-Hydroxy-4-(6-methoxy-pyridin-3-yl)-cyclohexyl]-azetidin-3-ylcarbamoyl}-methyl)-carbamic acid tent-butyl ester

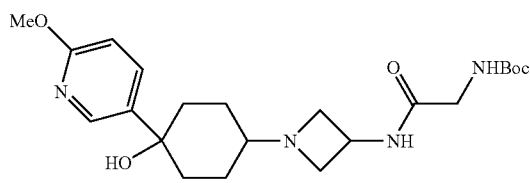 [SMILES: COc1ccc(C2(O)CCC(N3CC(NC(=O)CNC(=O)OC(C)(C)C)C3)CC2)cn1]

4-(3-Amino-azetidin-1-yl)-1-(6-methoxy-pyridin-3-yl)-cyclohexanol TFA salt (~4.2 g, 15.1 mmol), tert-butoxycarbonylamino-acetic acid (Sigma, 2.70 g, 15.1 mmol) and TEA (4.20 mL, 30 mmol) were dissolved in DCM (30 mL) at room temperature. The mixture was then treated with EDCI (Aldrich, 3.05 g, 16 mmol) and HOBT (Aldrich, 2.16 g, 16 mmol). And the reaction was stirred at room temperature for additional 6 hours. The reaction solution was partitioned between DCM and water. The organic layer was washed with brine, dried over anhydrous $Na_2SO_4$, filtered and concentrated to give the crude product, which was then purified by CombiFlash® system DCM and MeOH MeOH as eluent (from pure DCM to 10% MeOH in DCM) to afford the title compound as a white solid.

$^1$H NMR (400 MHz, CDCl$_3$) δ 7.68 (d, J=6.5 Hz, 1H), 7.55 (t, J=6.8 Hz, 1H), 6.64 (d, J=6.5 Hz, 1H), 5.21 (s, br, 1H), 4.50 (m, 1H), 4.00 (t, J=3.2 Hz, 2H), 3.60 (t, J=6.5 Hz, 2H), 2.95 (t, J=6.5 Hz, 2H), 2.60 (s, br, 1H), 2.33 (m, 1H), 1.92 (m, 2H), 1.72 (m, 2H), 1.58 (m, 2H), 1.50 (m, 2H), 1.47 (s, 9H)

Step D: 2-Amino-N-{1-[4-hydroxy-4-(6-methoxy-pyridin-3-yl)-cyclohexyl]-azetidin-3-yl}-acetamide TFA salt

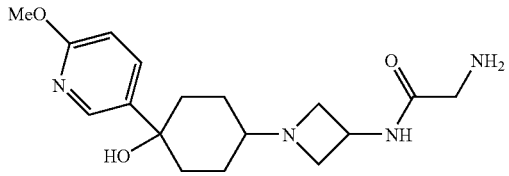 [SMILES: COc1ccc(C2(O)CCC(N3CC(NC(=O)CN)C3)CC2)cn1]

The title compound was prepared from ({1-[4-hydroxy-4-(6-methoxy-pyridin-3-yl)-cyclohexyl]-azetidin-3-ylcarbamoyl}-methyl)-carbamic acid tert-butyl ester by de-protection of N-Boc group using the procedure described in Step B of this Example.

ESI-MS (m/z): Calcd. For $C_{17}H_{26}N_4O_3$, 334; found: 335 (M+H).

Step E: N-({1-[4-Hydroxy-4-(6-methoxy-pyridin-3-yl)-cyclohexyl]-azetidin-3-ylcarbamoyl}-methyl)-4-trifluoromethyl-benzamide

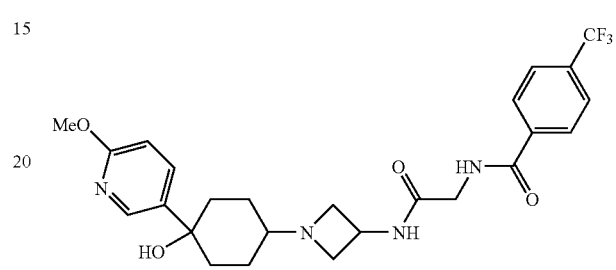

The title compound was prepared from 2-amino-N-{1-[4-hydroxy-4-(6-methoxy-pyridin-3-yl)-cyclohexyl]-azetidin-3-yl}-acetamide, as prepared in the previous step, and 4-trifluorobenzoic (Aldrich) acid by EDCI coupling using the procedure described in Step C of this Example.

$^1$H NMR (400 MHz, CDCl$_3$) δ 8.30 (s, 1H), 7.95 (d, J=7.0 Hz, 2H), 7.72 (d, J=6.8 Hz, 3H), 7.10 (m, 1H), 6.75 (d, J=6.4 Hz, 1H), 6.40 (m, 1H), 4.51 (m, 1H), 4.15 (d, J=3.0 Hz, 2H), 3.95 (s, 3H), 3.62 (t, J=6.8 Hz, 2H), 2.90 (t, J=6.6 Hz, 2H), 2.35 (m, 1H), 2.20 (m, 1H), 1.80 (m, 2H), 1.65 (m, 4H), 1.52 (m, 2H).

Example 17

3,4,5-Trifluoro-N-({1-[4-hydroxy-4-(6-methoxy-pyridin-3-yl)-cyclohexyl]-azetidin-3-ylcarbamoyl}-methyl)-benzamide

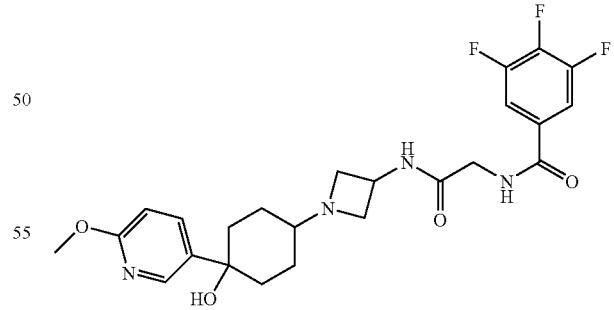

The title compound was prepared from 2-amino-N-{1-[4-hydroxy-4-(6-methoxy-pyridin-3-yl)-cyclohexyl]-azetidin-3-yl}-acetamide, as prepared in Step D of Example 16, and 3,4,5-trifluorobenzoic acid by EDCI coupling using the procedure described in Step C of Example 16.

$^1$H NMR (MeOH) δ: 8.26 (d, J=2.5 Hz, 1H), 7.82 (dd, J=8.7, 2.7 Hz, 1H), 7.54-7.69 (m, 2H), 6.76 (d, J=8.8 Hz, 1H), 4.45 (m, 1H), 4.12 (q, J=7.2 Hz, 2H), 4.01-4.10 (m, 2H), 3.91

(s, 3H), 3.64 (t, J=7.8 Hz, 2H), 3.27-3.38 (m, 4H), 2.91-3.02 (m, 2H), 2.36 (t, J=3.4 Hz, 2H).

Example 18

3,4-Dichloro-N-({1-[4-hydroxy-4-(6-methoxy-pyridin-3-yl)-cyclohexyl]-azetidin-3-ylcarbamoyl}-methyl)-benzamide

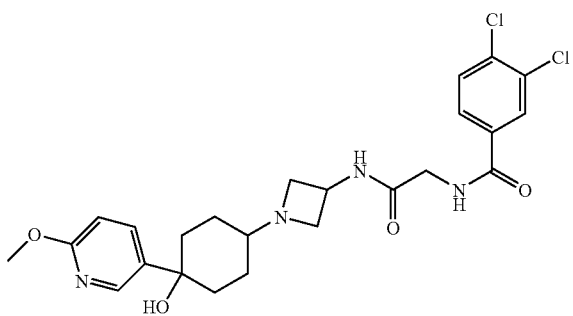 [SMILES: COc1ccc(C2(O)CCC(N3CC(NC(=O)CNC(=O)c4ccc(Cl)c(Cl)c4)C3)CC2)cn1]

A solution containing 2-amino-N-{1-[4-hydroxy-4-(6-methoxy-pyridin-3-yl)-cyclohexyl]-azetidin-3-yl}-acetamide, as prepared in Step D of Example 16, (60 mg, 0.13 mmol), 3,4-dichloro benzoyl chloride (Aldrich, 27 mg, 0.13 mmol) and Et$_3$N (76 uL, 0.54 mmol) in DCM (4 mL) was stirred at room temperature for 1 hour followed by aqueous workup with sat NaHCO$_3$ and DCM. The organic layer was dried (Na$_2$SO$_4$) and concentrated in vacuo followed by column chromatography purification (5% NH$_3$ in MeOH mixed with EtOAc) resulting in the title compound as a white solid.
$^1$H NMR (MeOH) δ: 8.26 (d, J=2.8 Hz, 1H), 7.99 (d, J=2.3 Hz, 1H), 7.77 (dd, J=8.7, 2.7 Hz, 1H), 7.70 (dd, J=8.5, 2.1 Hz, 1H), 7.53 (d, J=8.3 Hz, 1H), 6.73 (d, J=9.3 Hz, 1H), 4.46 (t, J=6.4 Hz, 2H), 4.00 (br. s., 1H), 3.91 (s, 3H), 3.59 (t, J=7.5 Hz, 2H), 2.94 (t, J=6.1 Hz, 2H), 2.33 (br. s., 1H), 2.12-2.24 (m, 2H), 1.74-1.90 (m, 2H), 1.55-1.65 (m, 2H), 1.33-1.43 (m, 2H).

Example 19

3,5-Difluoro-N-({1-[4-hydroxy-4-(6-methoxy-pyridin-3-yl)-cyclohexyl]-azetidin-3-ylcarbamoyl}-methyl)-benzamide

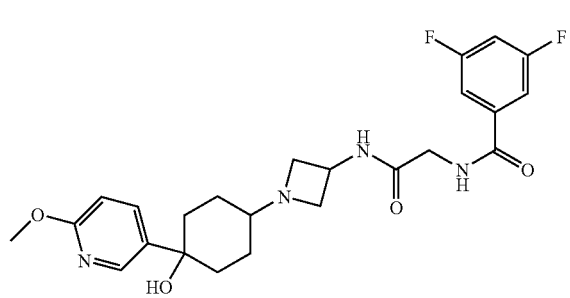 [SMILES: COc1ccc(C2(O)CCC(N3CC(NC(=O)CNC(=O)c4cc(F)cc(F)c4)C3)CC2)cn1]

The title compound was prepared as yellow solid from coupling of 2-amino-N-{1-[4-hydroxy-4-(6-methoxy-pyridin-3-yl)-cyclohexyl]-azetidin-3-yl}-acetamide, as prepared in Step D of Example 16, and 3,5-difluorobenzoyl chloride using the procedure described in Example 18.

$^1$H NMR (CHLOROFORM-d) δ: 8.30 (d, J=2.5 Hz, 1H), 7.73 (dd, J=8.7, 2.7 Hz, 1H), 7.37 (dd, J=7.7, 2.1 Hz, 2H), 6.89-7.06 (m, 1H), 6.72 (d, J=8.6 Hz, 1H), 4.41-4.60 (m, 1H), 4.10-4.14 (m, 2H), 3.92 (s, 3H), 3.62 (t, J=7.1 Hz, 2H), 2.34 (br. s., 1H), 2.12-2.25 (m, 2H), 1.77-1.90 (m, 2H), 1.67 (d, J=8.8 Hz, 2H), 1.49-1.61 (m, 4H).

Example 20

Benzo[1,3]dioxole-5-carboxylic acid ({1-[4-hydroxy-4-(6-methoxy-pyridin-3-yl)-cyclohexyl]-azetidin-3-ylcarbamoyl}-methyl)-amide

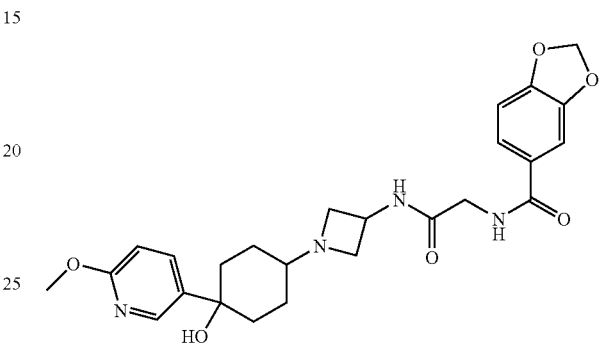

The title compound was prepared as yellow solid from coupling of 2-amino-N-{1-[4-hydroxy-4-(6-methoxy-pyridin-3-yl)-cyclohexyl]-azetidin-3-yl}-acetamide, as prepared in Step D of Example 16, and piperonoyl chloride (Aldrich) using the procedure described in Example 18.
$^1$H NMR (CHLOROFORM-d) δ6: 8.30 (d, J=2.5 Hz, 1H), 7.72 (dd, J=8.8, 2.5 Hz, 1H), 7.29-7.43 (m, 1H), 6.91-7.11 (m, 1H), 6.83 (d, J=8.1 Hz, 1H), 6.71 (d, J=8.6 Hz, 1H), 5.96-6.09 (m, 2H), 4.39-4.58 (m, 1H), 4.12 (d, J=5.1 Hz, 2H), 3.91 (s, 3H), 3.62 (t, J=6.8 Hz, 2H), 2.88 (br. s., 2H), 2.55 (br s., 1H), 2.32 (br. s., 2H), 2.10-2.25 (m, 4H), 1.73-1.91 (m, 2H).

Example 21

3-Cyano-N-({1-[4-hydroxy-4-(6-methoxy-pyridin-3-yl)-cyclohexyl]-azetidin-3-ylcarbamoyl}-methyl)-benzamide

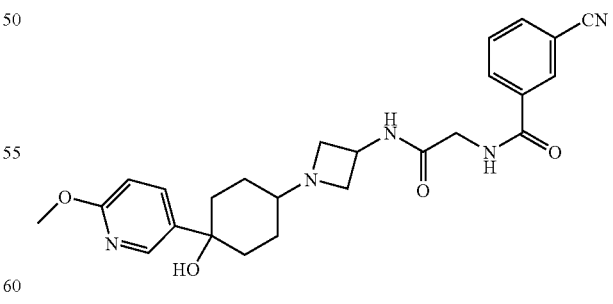

The title compound was prepared as yellow solid from 2-amino-N-{1-[4-hydroxy-4-(6-methoxy-pyridin-3-yl)-cyclohexyl]-azetidin-3-yl}-acetamide, as prepared in Step D of Example 16, and 3-cyanobenzoic acid (Aldrich) by EDCI coupling using the procedure described in Step C of Example 16.

$^1$H NMR (CHLOROFORM-d) δ: 8.28 (d, J=2.3 Hz, 1H), 8.16 (t, J=1.5 Hz, 1H), 8.07 (d, J=7.8 Hz, 1H), 7.79 (d, J=6.6 Hz, 1H), 7.56 (t, J=7.8 Hz, 1H), 7.12 (d, J=7.6 Hz, 1H), 6.70 (d, J=8.6 Hz, 1H), 4.43-4.60 (m, 1H), 4.14 (d, J=5.6 Hz, 2H), 3.59 (t, J=7.3 Hz, 2H), 3.30 (br s., 3H), 2.88 (t, J=6.8 Hz, 2H), 2.29 (t, J=3.4 Hz, 1H), 2.10-2.21 (m, 2H), 1.76-1.90 (m, 2H), 1.54 (d, J=12.4 Hz, 2H), 1.39 (d, J=13.1 Hz, 2H).

Example 22

N-({1-[4-Hydroxy-4-(6-methoxy-pyridin-3-yl)-cyclohexyl]-azetidin-3-ylcarbamoyl}-methyl)-3-methyl-benzamide

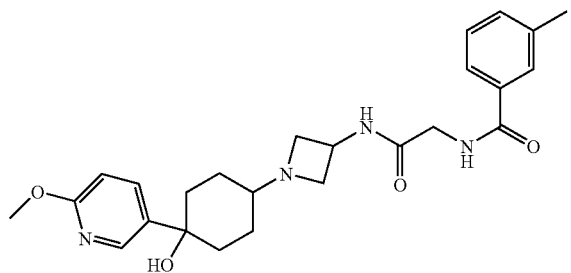

The title compound was prepared as yellow solid from 2-amino-N-{1-[4-hydroxy-4-(6-methoxy-pyridin-3-yl)-cyclohexyl]-azetidin-3-yl}-acetamide, as prepared in Step D of Example 16, and 3-methylbenzoic acid (Aldrich) by EDCI coupling using the procedure described in Step C of Example 16.

$^1$H NMR (CHLOROFORM-d) δ: 8.29 (d, J=2.0 Hz, 1H), 7.71 (dd, J=8.7, 2.7 Hz, 1H), 7.29-7.42 (m, 2H), 7.03-7.12 (m, 2H), 6.70 (d, J=9.3 Hz, 1H), 4.41-4.59 (m, 1H), 4.14 (d, J=5.1 Hz, 2H), 3.91 (s, 3H), 3.52-3.63 (m, 2H), 2.86 (t, J=7.1 Hz, 2H), 2.83 (s, 3H), 2.51 (br s., 1H), 2.27 (t, J=3.4 Hz, 2H), 2.12-2.21 (m, 4H), 1.85 (br. S., 2H).

Example 23

N-({1-[4-Hydroxy-4-(6-methoxy-pyridin-3-yl)-cyclohexyl]-azetidin-3-ylcarbamoyl}-methyl)-3-methoxy-benzamide

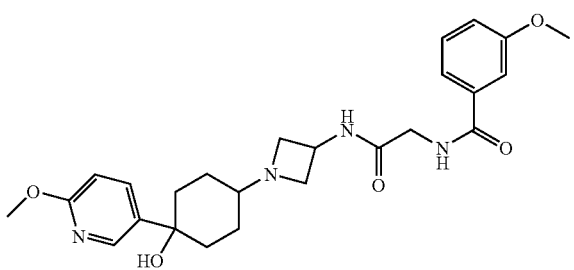

The title compound was prepared as yellow solid from 2-amino-N-{1-[4-hydroxy-4-(6-methoxy-pyridin-3-yl)-cyclohexyl]-azetidin-3-yl}-acetamide, as prepared in Step D of Example 16, and 3-methoxylbenzoic acid (Aldrich) by EDCI coupling using the procedure described in Step C of Example 16.

$^1$H NMR (CHLOROFORM-d) δ: 8.29 (s, 1H), 7.71 (dd, J=8.7, 2.7 Hz, 1H), 7.32-7.43 (m, 2H), 7.02-7.11 (m, 2H), 6.63-6.76 (m, 1H), 4.43-4.58 (m, 1H), 4.14 (d, J=5.1 Hz, 2H), 3.91 (s, 3H), 3.83 (s, 3H), 3.59 (t, J=7.3 Hz, 2H), 3.45-3.40 (m, 2H), 2.86 (t, J=7.1 Hz, 2H), 2.51 (br s., 1H), 1.85 (br. s., 4H), 1.53 (d, J=13.6 Hz, 2H).

Example 24

3-Chloro-N-({1-[4-hydroxy-4-(6-methoxy-pyridin-3-yl)-cyclohexyl]-azetidin-3-ylcarbamoyl}-methyl)-benzamide

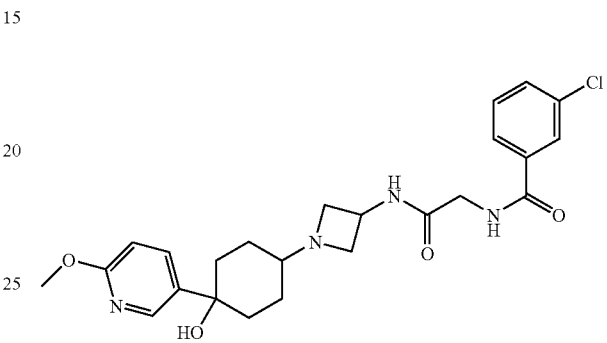

The title compound was prepared as yellow solid from 2-amino-N-{1-[4-hydroxy-4-(6-methoxy-pyridin-3-yl)-cyclohexyl]-azetidin-3-yl}-acetamide, as prepared in Step D of Example 16, and m-chlorobenzoic (Aldrich) acid by EDCI coupling using the procedure described in Step C of Example 16.

$^1$H NMR (CHLOROFORM-d) δ: 8.29 (s, 1H), 7.85 (s, 1H), 7.71 (d, J=9.6 Hz, 1H), 7.49 (d, J=7.3 Hz, 1H), 7.44 (t, J=4.8 Hz, 1H), 7.31-7.40 (m, 1H), 6.70 (d, J=8.8 Hz, 1H), 4.49 (s, 1H), 4.14 (d, J=11.9 Hz, 2H), 3.92 (br. s., 3H), 3.55-3.64 (m, 2H), 3.02-2.95 (m, 2H), 2.86 (t, J=6.9 Hz, 2H), 2.52 (br s., 1H), 2.28 (br. s., 2H), 1.87-1.99 (m, 2H), 1.74-1.86 (m, 2H).

Example 25

N-({1-[4-(5-Bromo-pyridin-2-yl)-4-hydroxy-cyclohexyl]-azetidin-3-ylcarbamoyl}-methyl)-3-trifluoromethyl-benzamide Step A: 8-(5-Bromo-pyridin-2-yl)-1,4-dioxa-spiro[4.5]decan-8-ol

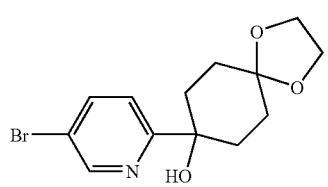 [SMILES: OC1(c2ccc(Br)cn2)CCC2(CC1)OCCO2]

The title compound was prepared as a white solid from 2,5-dibromo-pyridine (Aldrich) and 1,4-dioxa-spiro[4.5]decan-8-one in ether using the procedure described in Step A of Example 1.

¹H NMR (CHLOROFORM-d) δ: 7.52-7.60 (m, 1H), 7.35-7.42 (m, 2H), 4.01 (s, 4H), 1.98-2.26 (m, 4H), 1.74 (t, J=12.8 Hz, 4H).

Step B:
4-(5-Bromo-pyridin-2-yl)-4-hydroxy-cyclohexanone

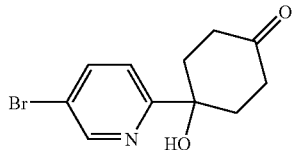 [SMILES: O=C1CCC(O)(c2ccc(Br)cn2)CC1]

The title compound was prepared as a white solid from 8-(5-bromo-pyridin-2-yl)-1,4-dioxa-spiro[4.5]decan-8-ol, as prepared in the previous step, using the procedure described in Step B of Example 1.

¹H NMR (CHLOROFORM-d) δ: 7.53 (t, J=7.7 Hz, 1H), 7.37 (d, J=7.8 Hz, 1H), 7.23-7.30 (m, 1H), 2.90 (td, J=14.1, 6.3 Hz, 2H), 2.27-2.41 (m, 2H), 2.12-2.25 (m, 2H), 1.98-2.09 (m, 2H).

Step C: N-({1-[4-(5-Bromo-pyridin-2-yl)-4-hydroxy-cyclohexyl]-azetidin-3-ylcarbamoyl}-methyl)-3-trifluoromethyl-benzamide

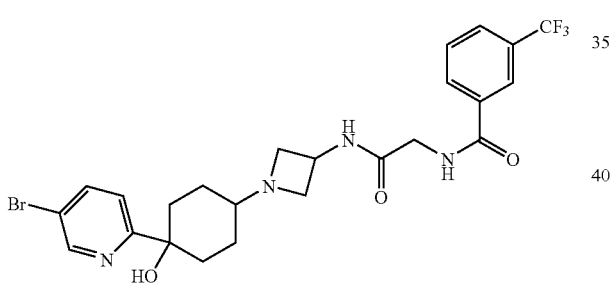

The title compounds were prepared as white solids from reductive amination of 4-(5-bromo-pyridin-2-yl)-4-hydroxy-cyclohexanone, as prepared in the previous step, and N-(azetidin-3-ylcarbamoylmethyl)-3-trifluoromethyl-benzamide using the procedure described in Step E of Example 1.

25a: less polar isomer from silica gel column,

¹H NMR (CHLOROFORM-d) δ: 8.06 (s, 1H), 7.96 (d, J=7.8 Hz, 1H), 7.71 (d, J=7.8 Hz, 1H), 7.47 (d, J=7.8 Hz, 2H), 7.37 (d, J=7.6 Hz, 1H), 7.30 (d, J=7.8 Hz, 1H), 4.12 (d, J=5.1 Hz, 1H), 3.55 (t, J=7.2 Hz, 2H), 3.45 (t, J=7.0 Hz, 2H), 2.86 (br. s, 2H), 2.29 (br. s., 1H), 2.05 (td, J=12.9, 3.8 Hz, 2H), 1.74-1.88 (m, 2H), 1.43 (d, J=16.9 Hz, 2H), 1.35 (d, J=12.4 Hz, 2H).

25b: more polar isomer from silica gel column

¹H NMR (CHLOROFORM-d) δ: 8.06 (s, 1H), 7.97 (d, J=7.8 Hz, 1H), 7.72 (d, J=7.8 Hz, 1H), 7.44-7.57 (m, 2H), 7.37 (t, J=4.5 Hz, 1H), 7.09 (d, J=7.8 Hz, 1H), 4.42-4.56 (m, 1H), 4.12 (d, J=4.8 Hz, 2H), 3.58 (t, J=7.6 Hz, 2H), 2.96-3.05 (m, 2H), 2.51 (br s., 1H), 2.01-2.12 (m, 2H), 1.73 (br. s., 2H), 1.58-1.70 (m, 2H), 1.44-1.57 (m, 2H).

Example 26

N-({1-[4-(6-Dimethylamino-pyridin-3-yl)-4-hydroxy-cyclohexyl]-azetidin-3-ylcarbamoyl}-methyl)-3-trifluoromethyl-benzamide Step A: 8-(6-Dimethylamino-pyridin-3-yl)-1,4-dioxa-spiro[4.5]decan-8-ol

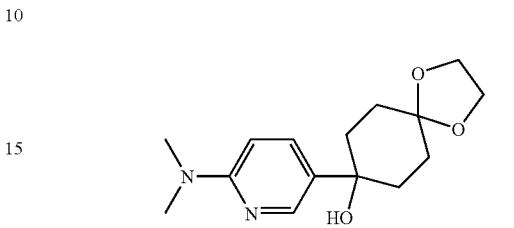

The title compound was prepared as a white solid from 5-bromo-2-dimethylamino-pyridine (Indofine) and 1,4-dioxa-spiro[4.5]decan-8-one in ether using the procedure described in Step A of Example 1.

¹H NMR (CHLOROFORM-d) δ: 8.27 (d, J=2.8 Hz, 1H), 7.59 (dd, J=9.0, 2.7 Hz, 1H), 6.49 (d, J=8.8 Hz, 1H), 3.86-4.03 (m, 4H), 3.07 (s, 6H), 2.07 (dd, J=8.7, 2.7 Hz, 4H), 1.77-1.93 (m, 2H), 1.60-1.73 (m, 2H).

Step B: 4-(6-Dimethylamino-pyridin-3-yl)-4-hydroxy-cyclohexanone

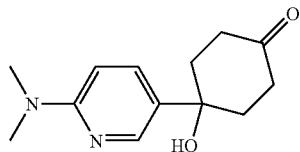 [SMILES: CN(C)c1ccc(C2(O)CCC(=O)CC2)cn1]

The title compound was prepared as a white solid from 8-(6-dimethylamino-pyridin-3-yl)-1,4-dioxa-spiro[4.5]decan-8-ol, as prepared in the previous step, using the procedure described in Step B of Example 1.

¹H NMR (CHLOROFORM-d) δ: 8.19 (d, J=2.8 Hz, 1H), 7.48-7.60 (m, 1H), 6.45 (d, J=8.3 Hz, 1H), 3.02 (s, 6H), 2.71-2.87 (m, 2H), 2.55 (t, J=6.9 Hz, 2H), 2.25 (d, J=13.6 Hz, 2H), 2.08-2.17 (m, 2H).

Step C: N-({1-[4-(6-Dimethylamino-pyridin-3-yl)-4-hydroxy-cyclohexyl]-azetidin-3-ylcarbamoyl}-methyl)-3-trifluoromethyl-benzamide

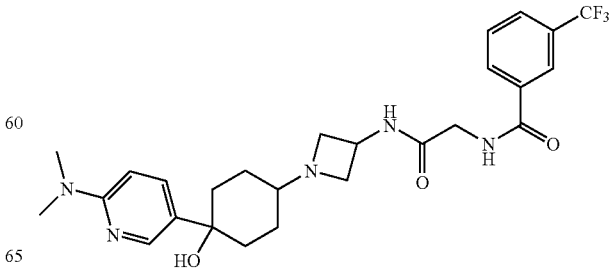

The title compounds were prepared as white solids from reductive amination of 4-(6-dimethylamino-pyridin-3-yl)-4-hydroxy-cyclohexanone, as prepared in the previous step, and N-(azetidin-3-ylcarbamoylmethyl)-3-trifluoromethyl-benzamide using the procedure described in Step E of Example 1.

¹H NMR (CHLOROFORM-d) δ: 8.25 (d, J=2.3 Hz, 1H), 8.07 (s, 1H), 7.97 (d, J=7.8 Hz, 1H), 7.70 (d, J=8.6 Hz, 1H), 7.59 (dd, J=8.8, 2.5 Hz, 1H), 7.46-7.54 (m, 2H), 4.46-4.57 (m, 1H), 4.09 (d, J=5.1 Hz, 2H), 3.61-3.71 (m, 2H), 3.21 (br. s., 6H), 2.44 (br s., 1H), 2.11-2.23 (m, 2H), 1.75-1.86 (m, 2H), 1.65 (d, J=6.3 Hz, 4H), 1.52 (d, J=14.9 Hz, 2H).

Example 27

N-{[1-(4-Hydroxy-4-pyrimidin-5-yl-cyclohexyl)-azetidin-3-ylcarbamoyl]-methyl}-3-trifluoromethyl-benzamide Step A:
8-Pyrimidin-5-yl-1,4-dioxa-spiro[4.5]decan-8-ol

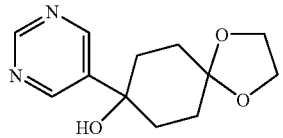 [SMILES: OC1(c2cncnc2)CCC2(CC1)OCCO2]

The title compound was prepared as a white solid from 5-bromo-pyrimidine (Aldrich) in ether using the procedure described in Step A of Example 1.

¹H NMR (400 MHz, CDCl₃) δ 9.40 (s, 1H), 8.90 (s, 2H), 1.95 (m, 2H), 1.75 (m, 4H), 1.50 (m, 2H).

Step B: 4-Hydroxy-4-pyrimidin-5-yl-cyclohexanone

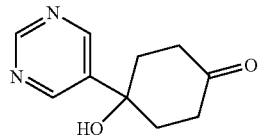 [SMILES: O=C1CCC(O)(c2cncnc2)CC1]

The title compound was prepared as a white solid from 8-pyrimidin-5-yl-1,4-dioxa-spiro[4.5]decan-8-ol, as prepared in the previous step, using the procedure described in Step B of Example 1.

¹H NMR (400 MHz, CDCl₃) δ 9.20 (s, 1H), 8.90 (s, 2H), 2.60 (m, 2H), 2.20 (m, 4H), 2.15 (m, 2H).

Step C: N-{[1-(4-Hydroxy-4-pyrimidin-5-yl-cyclohexyl)-azetidin-3-ylcarbamoyl]-methyl}-3-trifluoromethyl-benzamide

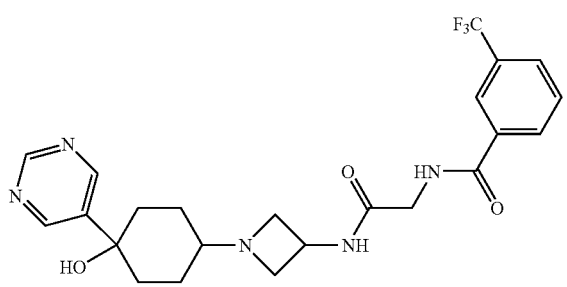 [SMILES: O=C(CNC(=O)c1cccc(C(F)(F)F)c1)NC1CN(C2CCC(O)(c3cncnc3)CC2)C1]

The title compounds were prepared as white solids from reductive amination of 4-hydroxy-4-pyrimidin-5-yl-cyclohexanone, as prepared in the previous step, and N-(azetidin-3-ylcarbamoylmethyl)-3-trifluoromethyl-benzamide using the procedure described in Step E of Example 1.

27a: less polar isomer from silica gel column,

¹H NMR (400 MHz, CDCl₃) δ 9.10 (s, 1H), 8.90 (s, 2H), 8.15 (s, 1H), 8.00 (d, J=7.0 Hz, 1H), 7.75 (d, J=6.6 Hz, 1H), 7.62 (t, J=6.6 Hz, 1H), 4.52 (m, 1H), 4.15 (d, J=3.4 Hz, 2H), 3.60 (t, J=6.2 Hz, 2H), 2.96 (t, J=6.5 Hz, 2H), 2.40 (s, br, 1H), 2.19 (m 2H), 1.85 (m, 2H), 1.55 (m, 4H).

27b: more polar isomer from silica gel column

¹H NMR (400 MHz, CDCl₃) δ 9.11 (s, 1H), 8.88 (s, 2H), 8.16 (s, 1H), 8.05 (d, J=6.1 Hz, 1H), 7.82 (d, J=6.2 Hz, 1H), 7.75 (m, 1H), 7.60 (m, 1H), 4.58 (m, 1H), 4.20 (d, J=3.2 Hz, 2H), 3.65 (t, J=6.0 Hz, 2H), 3.12 (t, J=6.0 Hz, 2H), 2.20 (m, 2H), 1.90~1.69 (m, 4H), 1.55 (m, 2H).

Example 28

N-({1-[4-Hydroxy-4-(2-methoxy-pyrimidin-5-yl)-cyclohexyl]-azetidin-3-ylcarbamoyl}-methyl)-3-trifluoromethyl-benzamide Step A: 8-(2-Methoxy-pyrimidin-5-yl)-1,4-dioxa-spiro[4.5]decan-8-ol

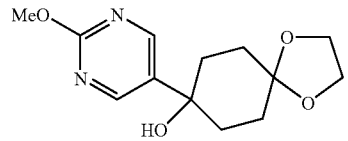

The title compound was prepared as a white solid from 5-bromo-2-methoxy-pyrimidine (Aldrich) and 1,4-dioxa-spiro[4.5]decan-8-one in ether using the procedure described in Step A of Example 1.

¹H NMR (400 MHz, CDCl₃) δ 8.51 (s, 2H), 4.05 (s, 4H), 3.75 (s, 3H), 2.01 (m, 2H), 1.83 (m 2H), 1.70 (m, 2H), 1.52 (m, 2H).

Step B: 4-Hydroxy-4-(2-methoxy-pyrimidin-5-yl)-cyclohexanone

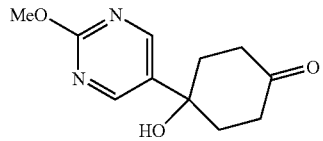

The title compound was prepared as a white solid from 8-(2-methoxy-pyrimidin-5-yl)-1,4-dioxa-spiro[4.5]decan-8-ol, as prepared in the previous step, using the procedure described in Step B of Example 1.

¹H NMR (400 MHz, CDCl₃) δ 8.70 (s, 2H), 3.75 (s, 3H), 2.85 (m, 2H), 2.34 (m, 2H), 2.20 (m, 2H), 1.95 (m, 2H).

Step C: N-({1-[4-Hydroxy-4-(2-methoxy-pyrimidin-5-yl)-cyclohexyl]-azetidin-3-ylcarbamoyl}-methyl)-3-trifluoromethyl-benzamide

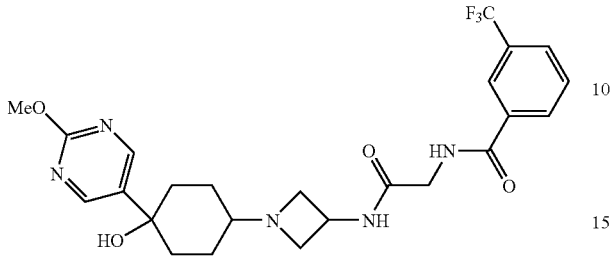

The title compounds were prepared as white solids from reductive amination of 4-hydroxy-4-(2-methoxy-pyrimidin-5-yl)-cyclohexanone, as prepared in the previous step, and N-(azetidin-3-ylcarbamoylmethyl)-3-trifluoromethyl-benzamide using the procedure described in Step E of Example 1.

28a: less polar isomer from silica gel column,
$^1$H NMR (400 MHz, CDCl$_3$) δ 8.70 (s, 2H), 8.10 (s, 1H), 8.05 (d, J=6.5 Hz, 1H), 7.80 (d, J=6.6 Hz, 1H), 7.73 (t, J=6.5 Hz, 1H), 4.60 (m, 1H), 4.15 (d, J=3.0 Hz, 2H), 3.70 (t, J=5.6 Hz, 2H), 3.06 (t, J=3.5 Hz, 2H), 2.20 (m, 2H), 1.70~1.45 (m, 6H).

28b: less polar isomer from silica gel column
$^1$H NMR (400 MHz, CDCl$_3$) δ 8.60 (s, 2H), 8.15 (s, 1H), 8.02 (d, J=6.6 Hz, 1H), 7.80 (d, J=6.8 Hz, 1H), 7.60 (t, J=6.5 Hz, 1H), 7.45 (m, 1H), 4.55 (m, 1H), 4.15 (d, J=3.6 Hz, 2H), 3.60 (t, J=6.0 Hz, 2H), 3.10 (t, J=6.0 Hz, 2H), 1.96 (m, 2H), 1.75 (m, 4H), 1.64 (m, 2H).

Example 29

N-({1-[4-(2,4-Dimethoxy-pyrimidin-5-yl)-4-hydroxy-cyclohexyl]-azetidin-3-ylcarbamoyl}-methyl)-3-trifluoromethyl-benzamide Step A: 8-(2,4-Dimethoxy-pyrimidin-5-yl)-1,4-dioxa-spiro[4.5]decan-8-ol

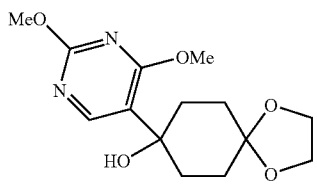 [SMILES: COc1ncc(C2(O)CCC3(CC2)OCCO3)c(OC)n1]

The title compound was prepared as a white solid from 5-bromo-2,4-dimethoxy-pyrimidine (Aldrich) and 1,4-dioxa-spiro[4.5]decan-8-one in ether using the procedure described in Step A of Example 1.

$^1$H NMR (400 MHz, CDCl$_3$) δ 8.21 (s, 1H), 4.10 (s, 3H), 4.00 (s, 3H), 3.98 (m, 4H), 2.11 (m, 2H), 2.02 (m, 4H), 1.76 (m, 2H).

Step B: 4-(2,4-Dimethoxy-pyrimidin-5-yl)-4-hydroxy-cyclohexanone

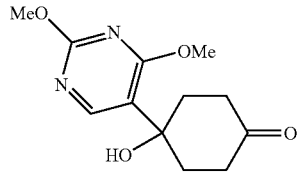 [SMILES: COc1ncc(C2(O)CCC(=O)CC2)c(OC)n1]

The title compound was prepared as a white solid from 8-(2,4-dimethoxy-pyrimidin-5-yl)-1,4-dioxa-spiro[4.5]decan-8-ol, as prepared in the previous step, using the procedure described in Step B of Example 1.
ESI-MS (m/z): Calcd. For C$_{12}$H$_{16}$N$_2$O$_4$, 252; found: 253 (M+H).

Step C: N-({1-[4-(2,4-Dimethoxy-pyrimidin-5-yl)-4-hydroxy-cyclohexyl]-azetidin-3-ylcarbamoyl}-methyl)-3-trifluoromethyl-benzamide

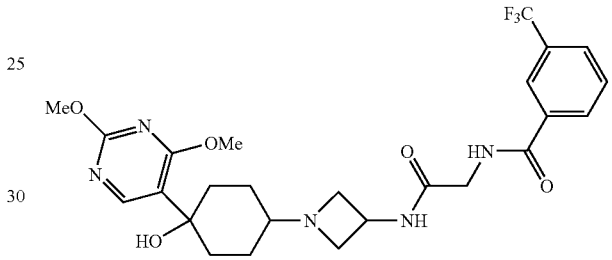

The title compounds were prepared as white solids from reductive amination of 4-(2,4-dimethoxy-pyrimidin-5-yl)-4-hydroxy-cyclohexanone, as prepared in the previous step, and N-(azetidin-3-ylcarbamoylmethyl)-3-trifluoromethyl-benzamide using the procedure described in Step E of Example 1.

29a: less polar isomer from silica gel column,
$^1$H NMR (400 MHz, d$_4$-MeOH) δ 8.28 (s, 1H), 8.21 (s, 1H), 8.16 (d, J=6.2 Hz, 1H), 7.85 (d, J=7.0 Hz, 1H), 7.70 (t, J=6.5 Hz, 1H), 4.46 (m, 1H), 4.08 (s, 2H), 4.01 (s, 3H), 3.69 (t, J=7.0 Hz, 2H), 3.32 (s, 3H), 3.02 (t, J=7.2 Hz, 2H), 2.5 (m, 2H), 2.31 (s, br, 1H), 1.90 (m, 2H), 1.55 (m, 2H), 1.35 (m, 2H).

29b: more polar isomer from silica gel column
$^1$H NMR (400 MHz, d$_4$-MeOH) δ 8.38 (s, 1H), 8.30 (s, 1H), 8.21 (d, J=6.5 Hz, 1H), 7.95 (d, J=6.0 Hz, 1H), 7.78 (t, J=6.5 Hz, 1H), 4.75 (m, 1H), 4.45 (t, J=6.8 Hz, 2H), 4.32 (t, J=6.8 Hz, 2H), 4.12 (s, 2H), 4.01 (s, 3H), 3.50 (s, 3H), 2.35 (m, 1H), 2.31 (m, 2H), 1.95 (m, 2H), 1.85 (m, 4H).

Example 30

N-({1-[4-Hydroxy-4-(1-methyl-1H-imidazol-2-yl)-cyclohexyl]-azetidin-3-ylcarbamoyl}-methyl)-3-trifluoromethyl-benzamide Step A: 8-(1-Methyl-1H-imidazol-2-yl)-1,4-dioxa-spiro[4.5]decan-8-ol

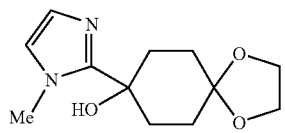

The title compound was prepared as a white solid from 2-bromo-1-methyl-1H-imidazole (Aldrich) and 1,4-dioxa-spiro[4.5]decan-8-one in THF using the procedure described in Step A of Example 1.

¹H NMR (400 MHz, CDCl₃) δ 6.78 (d, J=3.0 Hz, 2H), 3.95 (m, 4H), 3.90 (s, 3H), 2.30 (m, 2H), 2.11 (m, 2H), 2.0 (d, J=8.5 Hz, 2H), 1.72 (d, J=8.8 Hz, 2H).

Step B: 4-Hydroxy-4-(1-methyl-1H-imidazol-2-yl)-cyclohexanone

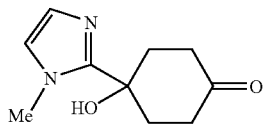

The title compound was prepared as a white solid from 8-(1-methyl-1H-imidazol-2-yl)-1,4-dioxa-spiro[4.5]decan-8-ol, as prepared in the previous step, using the procedure described in Step B of Example 1.

¹H NMR (400 MHz, CDCl₃) δ 6.80 (s, 2H), 3.85 (s, 3H), 2.78 (m, 2H), 2.40 (m, 4H), 2.25 (m, 2H).

Step C: N-({1-[4-Hydroxy-4-(1-methyl-1H-imidazol-2-yl)-cyclohexyl]-azetidin-3-ylcarbamoyl}-methyl)-3-trifluoromethyl-benzamide

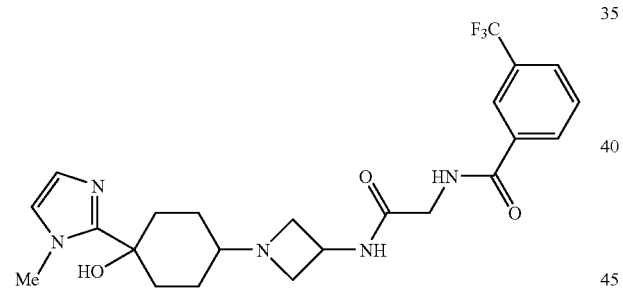

The title compounds were prepared as white solids from reductive amination of 4-hydroxy-4-(1-methyl-1H-imidazol-2-yl)-cyclohexanone, as prepared in the previous step, and N-(azetidin-3-ylcarbamoylmethyl)-3-trifluoromethyl-benzamide using the procedure described in Step E of Example 1.

30a: less polar isomer from silica gel column,

¹H NMR (400 MHz, d₄-MeOH) δ 8.15 (s, 1H), 8.06 (d, J=6.5 Hz, 1H), 7.80 (d, J=6.4 Hz, 1H), 7.65 (t, J=6.5 Hz, 1H), 6.93 (d, J=4.5 Hz, 1H), 6.75 (d, J=4.0 Hz, 1H), 4.34 (m, 1H), 3.98 (s, 2H), 3.79 (s, 3H), 3.65 (t, J=6.0 Hz, 2H), 3.04 (t, J=6.0 Hz, 2H), 2.35 (m, 1H), 2.30 (m, 2H), 1.85 (m, 2H), 1.65 (m, 2H), 1.30 (m, 2H).

30b: more polar isomer from silica gel column

¹H NMR (400 MHz, d₄-MeOH) δ 8.14 (s, 1H), 8.06 (d, J=6.0 Hz, 1H), 7.78 (d, J=6.2 Hz, 1H), 7.58 (t, J=6.5 Hz, 1H), 6.88 (s, 1H), 6.72 (s, 1H), 4.41 (m, 1H), 3.98 (s, 2H), 3.90 (t, J=6.0 Hz, 2H), 3.80 (s, 3H), 3.12 (s, 3H), 3.36 (t, J=6.0 Hz, 2H), 2.55 (m, 1H), 2.16 (m, 2H), 1.85 (m, 2H), 1.35 (m, 2H), 1.70 (m, 2H), 1.55 (m, 2H).

Example 31

N-({1-[4-(4-Bromo-1-methyl-1H-pyrazol-3-yl)-4-hydroxy-cyclohexyl]-azetidin-3-ylcarbamoyl}-methyl)-3-trifluoromethyl-benzamide Step A: 4-Bromo-1-methyl-1H-pyrazole

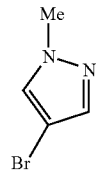

4-Bromo-1H-pyrazole (Aldrich, 5.0 g, 34 mmol) in DMF (10 mL) was treated with NaH (95%, 940 mg, 37.4 mmol) followed by MeI (2.28 mL, 34 mmol) at 0° C. The reaction was warmed to room temperature over 2 hours and quenched with MeOH. The solution was partitioned between ethyl acetate and water. The organic layer was washed with brine, dried over anhydrous Na₂SO₄, filtered and concentrated to give yellow solid, which was then purified by silica gel column on a CombiFlash® system using hexanes and ethyl acetate (from 10% ethyl acetate to 100% ethyl acetate) to afford the title compound as yellow solid.

¹H NMR (400 MHz, CDCl₃) δ 7.45 (s, 1H), 7.38 (s, 1H), 3.90 (s, 3H).

Step B: 8-(4-Bromo-1-methyl-1H-pyrazol-3-yl)-1,4-dioxa-spiro[4.5]decan-8-ol

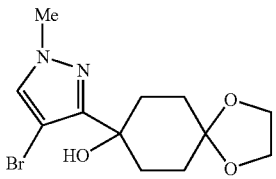

The title compound was prepared as a white solid from 4-bromo-1-methyl-1H-pyrazole, as prepared in the previous step, and 1,4-dioxa-spiro[4.5]decan-8-one in THF using the procedure described in Step A of Example 1.

¹H NMR (400 MHz, CDCl₃) δ 7.30 (s, 1H), 4.10 (s, 4H), 3.98 (s, 3H), 2.52 (t, J=7.5 Hz, 2H), 2.10 (t, J=7.2 Hz, 2H), 2.00 (d, J=7.1 Hz, 2H), 1.70 (d, J=6.8 Hz, 2H).

Step C: 4-(4-Bromo-1-methyl-1H-pyrazol-3-yl)-4-hydroxy-cyclohexanone

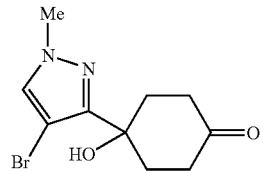

The title compound was prepared as a white solid from 8-(4-bromo-1-methyl-1H-pyrazol-3-yl)-1,4-dioxa-spiro[4.5]decan-8-ol, as prepared in the previous step, using the procedure described in Step B of Example 1.

¹H NMR (400 MHz, CDCl₃) δ 7.30 (s, 1H), 4.05 (s, 3H), 3.02 (s, 1H), 2.92 (t, J=8.0 Hz, 2H), 2.65 (t, J=8.0 Hz, 2H), 2.23 (m, 4H).

Step D: N-({1-[4-(4-Bromo-1-methyl-1H-pyrazol-3-yl)-4-hydroxy-cyclohexyl]-azetidin-3-ylcarbamoyl}-methyl)-3-trifluoromethyl-benzamide

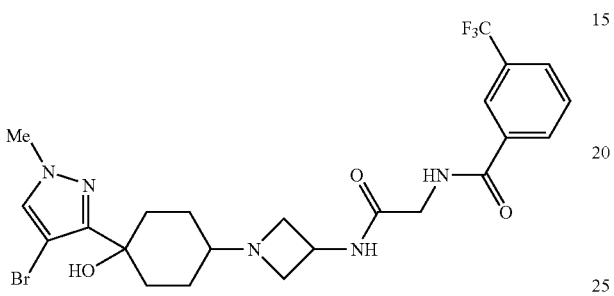

The title compounds were prepared as white solids from reductive amination of 4-(4-bromo-1-methyl-1H-pyrazol-3-yl)-4-hydroxy-cyclohexanone, as prepared in the previous step, and N-(azetidin-3-ylcarbamoylmethyl)-3-trifluoromethyl-benzamide using the procedure described in Step E of Example 1.

31a: less polar isomer from silica gel column,
¹H NMR (400 MHz, d₄-MeOH) δ 8.25 (s, 1H), 8.16 (d, J=6.5 Hz, 1H), 7.90 (d, J=6.4 Hz, 1H), 7.68 (t, J=6.5 Hz, 1H), 7.32 (s, 1H), 4.42 (m, 1H), 4.11 (s, 3H), 4.05 (s, 2H), 3.68 (t, J=6.0 Hz, 2H), 3.05 (t, J=6.0 Hz, 2H), 2.55 (m, 2H), 2.40 (m, 1H), 1.96 (m, 2H), 1.70 (m, 2H), 1.55 (m, 2H).

31b: more polar isomer from silica gel column
¹H NMR (400 MHz, d₄-MeOH) δ 8.24 (s, 1H), 8.20 (d, J=6.6 Hz, 1H), 7.88 (d, J=6.4 Hz, 1H), 7.70 (t, J=6.8 Hz, 1H), 7.35 (s, 1H), 4.50 (m, 1H), 4.15 (s, 3H), 4.06 (s, 2H), 3.75 (t, J=6.8 Hz, 2H), 3.12 (t, J=6.8 Hz, 2H), 2.35 (m, 3H), 1.95 (m, 2H), 1.75 (m, 2H), 1.60 (m, 2H).

Example 32

N-({1-[4-Hydroxy-4-(1-methyl-1H-pyrazol-3-yl)-cyclohexyl]-azetidin-3-ylcarbamoyl}-methyl)-3-trifluoromethyl-benzamide

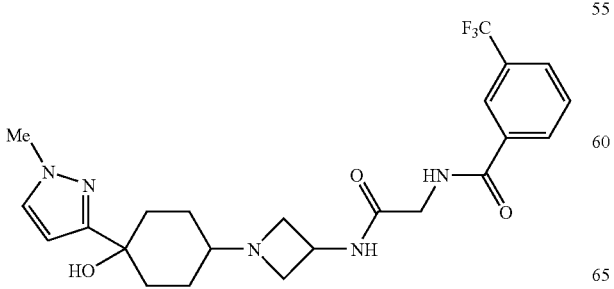

N-({1-[4-(4-Bromo-1-methyl-1H-pyrazol-3-yl)-4-hydroxy-cyclohexyl]-azetidin-3-ylcarbamoyl}-methyl)-3-trifluoromethyl-benzamide 31a (100 mg, 0.18 mmol) in MeOH (25 mL) was passed through a 10% Pd on C cartridge in a H-Cube® Continuous-flow Hydrogenation reactor (ThalesNano, Budapest, Hungary) under full hydrogen mode (flow rate 1 mL/min). The resulting solution was concentrated to give the title compound as a yellow solid.

¹H NMR (400 MHz, d₄-MeOH) δ 8.21 (s, 1H), 8.20 (d, J=6.5 Hz, 1H), 7.90 (d, J=6.5 Hz, 1H), 7.72 (t, J=6.5 Hz, 1H), 7.32 (s, 1H), 6.28 (s, 1H), 4.51 (m, 1H), 4.15 (s, 2H), 4.08 (s, 3H), 3.95 (t, J=6.0 Hz, 2H), 3.52 (t, J=6.0 Hz, 2H), 2.85 (m, 1H), 2.26 (m, 2H), 2.02 (m, 2H), 1.82 (m, 2H), 1.45 (m, 2H).

Example 33

N-{[1-(4-Hydroxy-4-thiazol-2-yl-cyclohexyl)-azetidin-3-ylcarbamoyl]-methyl}-3-trifluoromethyl-benzamide Step A:
8-Thiazol-2-yl-1,4-dioxa-spiro[4.5]decan-8-ol

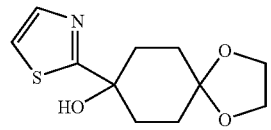 [SMILES: OC1(c2nccs2)CCC2(CC1)OCCO2]

A solution of n-BuLi (2.5 M in hexanes, 26 mL, 65 mmol) was dropped slowly into a solution of thiazole (Aldrich, 5.0 g, 59 mmol) in THF (50 mL) at −78° C. over 10 min. The reaction was stirred for additional 20 min. at −78° C. A solution of 1,4-dioxa-spiro[4.5]decan-8-one (9.36 g, 60 mmol) in THF (20 mL) was slowly dropped into the reaction. After addition, the reaction was stirred for additional 2 hours at −78° C. The reaction was then quenched with water solution and warmed to room temperature. The solvent was removed in vacuo and the residue was partitioned between ethyl acetate and water. The organic layer was washed with brine, dried over anhydrous Na₂SO₄, filtered and concentrated to give yellow solid, which was then purified by silica gel column on a CombiFlash® system using hexanes and ethyl acetate (from 10% ethyl acetate to 100% ethyl acetate) to afford the title compound as a white solid.

¹H NMR (400 MHz, CDCl₃) δ 7.70 (s, 1H), 7.28 (s, 1H), 4.01 (m, 4H), 3.30 (s, 1H), 2.35 (m, 2H), 2.23 (m, 2H), 2.05 (m, 2H), 1.85 (m, 2H).

Step B: 4-Hydroxy-4-thiazol-2-yl-cyclohexanone

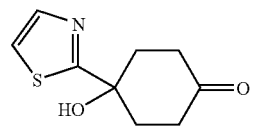 [SMILES: O=C1CCC(O)(c2nccs2)CC1]

The title compound was prepared as a white solid from de-protection of 8-thiazol-2-yl-1,4-dioxa-spiro[4.5]decan-8-ol, as prepared in the previous step, using the procedure described in Step B of Example 1.

¹H NMR (400 MHz, CDCl₃) δ 7.71 (s, 1H), 7.32 (s, 1H), 2.93 (m, 2H), 2.40 (m, 4H), 2.31 (m, 2H).

Step C: N-{[1-(4-Hydroxy-4-thiazol-2-yl-cyclo-hexyl)-azetidin-3-ylcarbamoyl]-methyl}-3-trifluoromethyl-benzamide

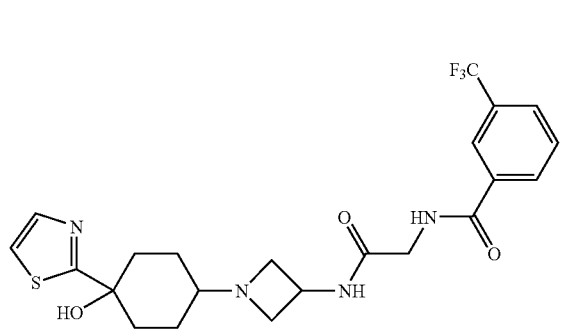

The title compounds were prepared as white solids from reductive amination of 4-hydroxy-4-thiazol-2-yl-cyclohexanone, as prepared in the previous step, and N-(azetidin-3-ylcarbamoylmethyl)-3-trifluoromethyl-benzamide using the procedure described in Step E of Example 1.

33a: less polar isomer from silica gel column, $^1$H NMR (400 MHz, CDCl$_3$) δ 8.15 (s, 1H), 8.02 (d, J=6.0 Hz, 1H), 7.75 (d, J=6.5 Hz, 1H), 7.70 (m, 1H), 7.65 (s, 1H), 7.55 (t, J=6.8 Hz, 1H), 7.43 (d, J=6.0 Hz, 1H), 7.22 (d, J=6.2 Hz, 1H), 4.48 (m, 1H), 4.18 (d, J=6.7 Hz, 2H), 3.51 (t, J=7.0 Hz, 2H), 2.98 (t, J=7.0 Hz, 2H), 2.30 (m, 2H), 1.81 (m, 2H), 1.68 (m, 2H), 1.48 (m, 2H).

33b: more polar isomer from silica gel column $^1$H NMR (400 MHz, CDCl$_3$) δ 8.10 (s, 1H), 8.02 (d, J=7.0 Hz, 1H), 7.75 (d, J=7.0 Hz, 1H), 7.70 (s, 1H), 7.55 (t, J=6.5 Hz, 1H), 7.32 (d, 4.5 Hz, 1H), 7.01 (d, J=4.0 Hz, 1H), 4.55 (m, 1H), 4.15 (d, J=7.8 Hz, 2H), 3.65 9t, J=7.5 Hz, 2H), 3.08 (t, J=7.5 Hz, 2H), 2.05 (m, 2H), 1.80 (m, 4H), 1.70 (m, 2H).

Example 34

N-({1-[4-Hydroxy-4-(5-methyl-thiazol-2-yl)-cyclohexyl]-azetidin-3-ylcarbamoyl}-methyl)-3-trifluoromethyl-benzamide Step A: 8-(5-Methyl-thiazol-2-yl)-1,4-dioxa-spiro[4.5]decan-8-ol

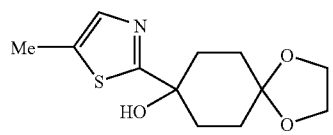 [SMILES: Cc1cnc(C2(O)CCC3(CC2)OCCO3)s1]

The title compound was prepared as a white solid from 5-methyl-thiazole using the procedure described in Step A of Example 33.

$^1$H NMR (400 MHz, CDCl$_3$) δ 7.32 (s, 1H), 4.01 (m, 4H), 2.45 (s, 3H), 2.20 (t, J=6.2 Hz, 2H), 2.02 (t, J=6.5 Hz, 2H), 1.98 (d, J=6.2 Hz, 2H), 1.70 (d, J=6.2 Hz, 2H).

Step B: 4-Hydroxy-4-(5-methyl-thiazol-2-yl)-cyclohexanone

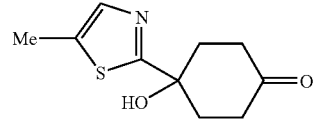

The title compound was prepared as a white solid from de-protection of 8-(5-methyl-thiazol-2-yl)-1,4-dioxa-spiro[4.5]decan-8-ol, as prepared in the previous step, using the procedure described in Step B of Example 1.

$^1$H NMR (400 MHz, CDCl$_3$) δ 7.30 (s, 1H), 2.90 (m, 2H), 2.52 (s, 3H), 2.45 (m, 4H), 2.33 (m, 2H).

Step C: N-({1-[4-Hydroxy-4-(5-methyl-thiazol-2-yl)-cyclohexyl]-azetidin-3-ylcarbamoyl}-methyl)-3-trifluoromethyl-benzamide

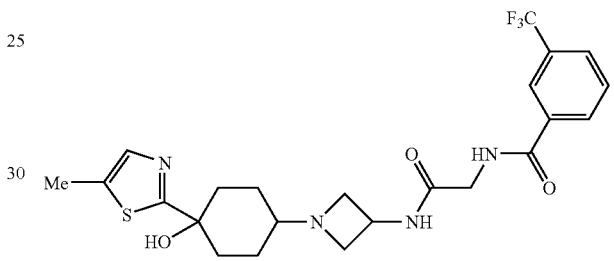

The title compounds were prepared as white solids from reductive amination of 4-hydroxy-4-(5-methyl-thiazol-2-yl)-cyclohexanone, as prepared in the previous step, and N-(azetidin-3-ylcarbamoylmethyl)-3-trifluoromethyl-benzamide using the procedure described in Step E of Example 1.

34a: less polar isomer from silica gel column, $^1$H NMR (400 MHz, d$_4$-MeOH) δ 8.21 (s, 1H), 8.15 (d, J=6.5 Hz, 1H), 7.82 (d, J=6.0 Hz, 1H), 7.65 (t, J=7.2 Hz, 1H), 4.40 (m, 1H), 3.55 (t, J=7.5 Hz, 2H), 3.30 (s, 3H), 2.98 (t, J=7.2 Hz, 2H), 2.30 (m, 2H), 1.80 (m, 2H), 1.65 (m, 2H), 1.42 (m, 2H).

34b: more polar isomer from silica gel column $^1$H NMR (400 MHz, CDCl$_3$) δ 8.15 (s, 1H), 8.06 (d, J=6.0 Hz, 1H), 7.78 (d, J=6.4 Hz 1H), 7.62 (t, J=6.5 Hz, 1H), 7.32 (s, 1H), 4.62 (m, 1H), 4.18 (d, J=4.5 Hz, 2H), 3.89 (t, J=6.8 Hz, 2H), 3.50 (s, br, 2H), 2.52 (s, br, 1H), 2.10~1.89 (m, 3H), 1.82~1.63 (m, 3H).

Example 35

N-({1-[4-Hydroxy-4-(5-hydroxymethyl-thiazol-2-yl)-cyclohexyl]-azetidin-3-ylcarbamoyl}-methyl)-3-trifluoromethyl-benzamide Step A:
5-(tert-Butyl-dimethyl-silanyloxymethyl)-thiazole

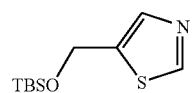

5-Oxymethyl-thiazole (3B Scientific, 5 g, 43 mmol) and imidazole (3.50 g, 52 mmol) in DMF (10 mL) were treated with TBSCl (6.48 g, 43 mmol) at −78° C. for 30 min. The reaction was quenched with MeOH and warmed to room temperature. The solution was partitioned between ether and water. The organic layer was washed with brine, dried over anhydrous $Na_2SO_4$, filtered and concentrated to give a yellow solid, and purified by silica gel column on a CombiFlash® system using hexanes and ethyl acetate (from 5% ethyl acetate to 30% ethyl acetate) to afford the title compound as a white solid.

ESI-MS (m/z): Calcd. For $C_{10}H_{19}NOSSi$, 229. Found: 230 (M+H).

Step B: 8-(5-Hydroxymethyl-thiazol-2-yl)-1,4-dioxa-spiro[4.5]decan-8-ol

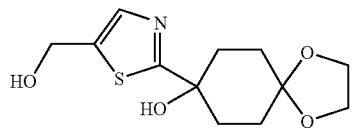

The title compound was prepared as a white solid from 5-(tert-butyl-dimethyl-silanyloxymethyl)-thiazole using the procedure described in Step A of Example 33 followed by TBAF work-up.

ESI-MS (m/z): Calcd. For $C_{12}H_{17}NO_4S$, 271. Found: 272 (M+H).

Step C: 4-Hydroxy-4-(5-hydroxymethyl-thiazol-2-yl)-cyclohexanone

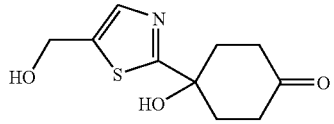

The title compound was prepared as a white solid from de-protection of 8-(5-hydroxymethyl-thiazol-2-yl)-1,4-dioxa-spiro[4.5]decan-8-ol, as prepared in the previous step, using the procedure described in Step B of Example 1.

$^1$H NMR (400 MHz, CDCl$_3$) δ 7.60 (s, 1H), 4.85 (s, 2H), 2.22 (m, 4H), 2.05 (m, 4H).

Step D: N-({1-[4-Hydroxy-4-(5-hydroxymethyl-thiazol-2-yl)-cyclohexyl]-azetidin-3-ylcarbamoyl}-methyl-3-trifluoromethyl-benzamide

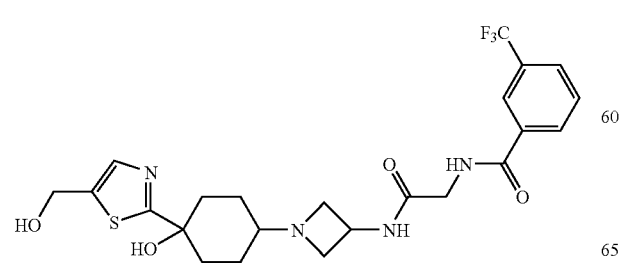

The title compounds were prepared as white solids from reductive amination of 4-hydroxy-4-(5-hydroxymethyl-thiazol-2-yl)-cyclohexanone, as prepared in the previous step, and N-(azetidin-3-ylcarbamoylmethyl)-3-trifluoromethyl-benzamide using the procedure described in Step E of Example 1.

35a: less polar isomer from silica gel column, $^1$H NMR (400 MHz, d$_4$-MeOH) δ 8.25 (s, 1H), 8.18 (d, J=6.5 Hz, 1H), 7.90 (d, J=6.5 Hz, 1H), 7.72 (d, J=6.6 Hz, 1H), 7.55 (s, 1H), 4.77 (s, 2H), 4.62 (m, 1H), 4.20 (t, J=6.5 Hz, 2H), 4.08 (d, J=3.5 Hz, 2H), 3.85 (m, J=6.1 Hz, 2H), 2.35 (m, 1H), 2.01 (m, 2H), 1.85 (m, 2H), 1.64 (m, 2H).

35b: more polar isomer from silica gel column $^1$H NMR (400 MHz, CDCl$_3$) δ 8.10 (s, 1H), 8.05 (d, J=6.5 Hz, 1H), 7.90 (m, 1H), 7.78 (d, J=6.6 Hz, 1H), 7.63 (t, J=6.6 Hz, 1H), 7.55 (s, 1H), 4.82 (s, 2H), 4.68 (m, 1H), 4.18 (d, J=3.5 Hz, 2H), 3.75 (m, J=6.5 Hz, 2H), 3.20 (m, J=6.1 Hz, 2H), 2.35 (m, 1H), 1.85 (m, 4H), 1.65 (m, 2H), 1.24 (m, 2H).

Example 36

N-({1-[4-(6-Bromo-benzothiazol-2-yl)-4-hydroxy-cyclohexyl]-azetidin-3-ylcarbamoyl}-methyl)-3-trifluoromethyl-benzamide Step A: 8-(6-Bromo-benzothiazol-2-yl)-1,4-dioxa-spiro[4.5]decan-8-ol

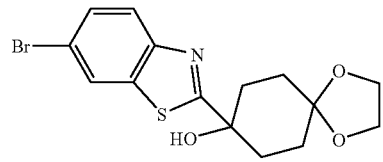 [SMILES: OC1(c2nc3ccc(Br)cc3s2)CCC2(CC1)OCCO2]

The title compound was prepared as a white solid from 6-bromo-benzothiazole (Aldrich) using the procedure described in Step A of Example 33.

$^1$H NMR (400 MHz, CDCl$_3$) δ 8.05 (s, 1H), 7.82 (d, J=6.1 Hz, 1H), 7.55 (d, J=6.1 Hz, 1H), 4.05 (s, 4H), 2.32 (m, 2H), 2.10 (m, 4H), 1.81 (m, 2H).

Step B: 4-(6-Bromo-benzothiazol-2-yl)-4-hydroxy-cyclohexanone

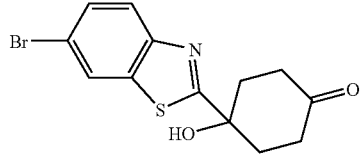

The title compound was prepared as a white solid from de-protection of 8-(6-bromo-benzothiazol-2-yl)-1,4-dioxa-spiro[4.5]decan-8-ol, as prepared in the previous step, using the procedure described in Step B of Example 1.

¹H NMR (400 MHz, CDCl₃) δ 8.02 (s, 1H), 7.80 (d, J=6.5 Hz, 1H), 7.58 (d, J=6.5 Hz, 1H), 2.91 (m, 2H), 2.55 (m, 4H), 2.32 (m, 2H).

Step C: N-({1-[4-(6-Bromo-benzothiazol-2-yl)-4-hydroxy-cyclohexyl]-azetidin-3-ylcarbamoyl}-methyl)-3-trifluoromethyl-benzamide

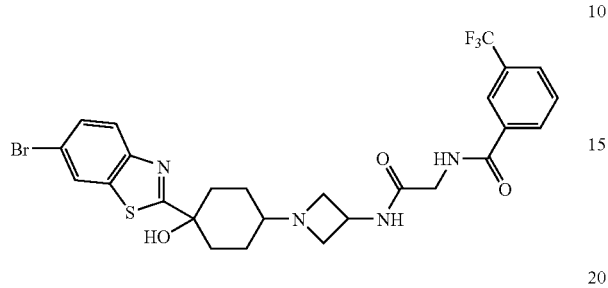

The title compounds were prepared as white solids from reductive amination of 4-(6-Bromo-benzothiazol-2-yl)-4-hydroxy-cyclohexanone, as prepared in the previous step, and N-(azetidin-3-ylcarbamoylmethyl)-3-trifluoromethyl-benzamide using the procedure described in Step E of Example 1.

36a: less polar isomer from silica gel column,
¹H NMR (400 MHz, CDCl₃) δ 8.12 (s, 1H), 8.02, 8.00 (s, 1H), 7.80 (d, J=6.5 Hz, 1H), 7.77 (d, J=6.2 Hz, 1H), 7.61 (m, 1H), 7.57 (m, 2H), 4.55 (m, 1H), 4.20 (s, 2H), 3.60 (t, J=6.5 Hz, 2H), 3.10 (t, J=6.4 Hz, 2H), 2.38 (m, 3H), 1.85 (m, 2H), 1.74 (m, 2H), 1.60 (m, 2H).

36b: more polar isomer from silica gel column
¹H NMR (400 MHz, CDCl₃) δ 8.10 (s, 1H), 8.02 (m, 2H), 7.80 (m, 2H), 7.65 (d, J=6.5 Hz, 1H), 7.60 (m, 1H), 7.45 (m, 1H), 4.58 (m, 1H), 4.20 (s, 2H), 3.65 (t, J=6.5 Hz, 2H), 3.02 (t, J=6.6 Hz, 2H), 2.23 (m, 1H), 2.10 (m, 4H), 1.80 (m, 2H), 1.65 (m, 2H).

Example 37

N-{[1-(4-Benzothiazol-2-yl-4-hydroxy-cyclohexyl)-azetidin-3-ylcarbamoyl]-methyl}-3-trifluoromethyl-benzamide

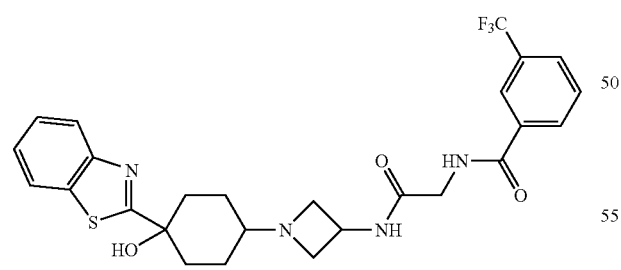

The title compounds were prepared as white solids from reductive de-bromination of N-({1-[4-(6-bromo-benzothiazol-2-yl)-4-hydroxy-cyclohexyl]-azetidin-3-ylcarbamoyl}-methyl)-3-trifluoromethyl-benzamide (less polar isomer, 36a) using the procedure described in Example 32.

¹H NMR (400 MHz, CDCl₃) δ 8.15 (s, 1H), 8.05 (d, J=6.6 Hz, 1H), 7.93 (d, J=6.4 Hz, 1H), 7.89 (d, J=6.0 Hz, 1H), 7.80 (d, J=6.7 Hz, 1H), 7.55 (t, J=6.2 Hz, 1H), 7.48 (t, J=6.4 Hz, 1H), 7.37 (t, J=6.1 Hz, 1H), 4.50 (m, 1H), 4.19 (d, J=3.2 Hz, 2H), 3.64 (t, J=6.8 Hz, 2H), 3.10 (s, 1H), 3.02 (t, J=6.7 Hz, 2H), 2.40 (m, 1H), 2.25 (m, 2H), 1.85 (m, 2H), 1.72 (m, 2H), 1.60 (m, 2H).

Example 38

N-({1-[4-Hydroxy-4-(4-methyl-thiazol-2-yl)-cyclohexyl]-azetidin-3-ylcarbamoyl}-methyl)-3-trifluoromethyl-benzamide Step A: 8-(4-Methyl-thiazol-2-yl)-1,4-dioxa-spiro[4.5]decan-8-ol

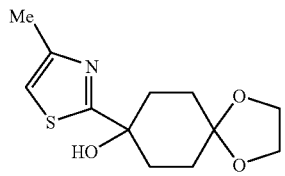

The title compound was prepared as a white solid from 4-methyl-thiazole (Aldrich) and 1,4-dioxa-spiro[4.5]decan-8-one using the procedure described in Step A of Example 33.
¹H NMR (400 MHz, CDCl₃) δ 6.80 (s, 1H), 3.98 (m, 4H), 2.41 (s, 3H), 2.22 (m, J=6.2 Hz, 2H), 2.08 (m, J=6.2 Hz, 2H), 1.95 (d, J=6.0 Hz, 2H), 1.72 (d, J=6.2 Hz, 2H).

Step B: 4-Hydroxy-4-(4-methyl-thiazol-2-yl)-cyclohexanone

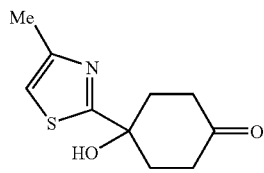 [SMILES: Cc1csc(C2(O)CCC(=O)CC2)n1]

The title compound was prepared as a white solid from de-protection of 8-(4-methyl-thiazol-2-yl)-1,4-dioxa-spiro[4.5]decan-8-ol, as prepared in the previous step, using the procedure described in Step B of Example 1.
¹H NMR (400 MHz, CDCl₃) δ 6.85 (s, 1H), 2.85 (m, 2H), 2.45 (s, 3H), 2.40 (m, 4H), 2.28 (m, 4H).

Step C: N-({1-[4-Hydroxy-4-(4-methyl-thiazol-2-yl)-cyclohexyl]-azetidin-3-ylcarbamoyl}-methyl)-3-trifluoromethyl-benzamide

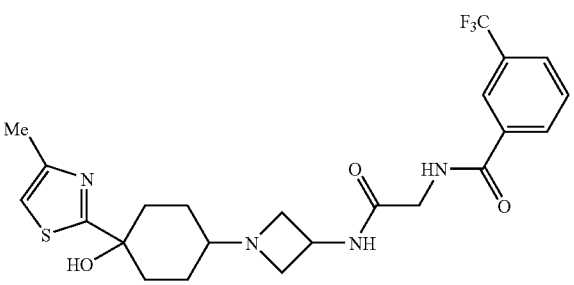 [SMILES: Cc1csc(C2(O)CCC(N3CC(NC(=O)CNC(=O)c4cccc(C(F)(F)F)c4)C3)CC2)n1]

The title compounds were prepared as white solids from reductive amination of 4-hydroxy-4-(4-methyl-thiazol-2-yl)-cyclohexanone, as prepared in the previous step, and N-(azetidin-3-ylcarbamoylmethyl)-3-trifluoromethyl-benzamide using the procedure described in Step E of Example 1.

38a: less polar isomer from silica gel column,
$^1$H NMR (400 MHz, d$_4$-MeOH) δ 8.15 (s, 1H), 8.08 (d, J=6.2 Hz, 1H), 7.81 (d, J=7.0 Hz, 1H), 7.63 (t, J=6.5 Hz, 1H), 6.92 (s, 1H), 4.38 (m, 1H), 4.00 (s, 2H), 3.55 (t, J=7.0 Hz, 2H), 2.92 (t, J=7.2 Hz, 2H), 2.35 (s, 3H), 2.25 (m, 2H), 1.72 (m, 2H), 1.58 (m, 2H), 1.43 (m, 2H).

38b: more polar isomer from silica gel column,
$^1$H NMR (400 MHz, d$_4$-MeOH) δ 8.18 (s, 1H), 8.10 (d, J=6.0 Hz, 1H), 7.82 (d, J=6.5 Hz, 1H), 7.62 (t, J=6.8 Hz, 1H), 6.90 (s, 1H), 4.45 (m, 1H), 4.02 (s, 2H), 3.70 (t, J=7.0 Hz, 2H), 3.15 (t, J=7.2 Hz, 2H), 2.32 (m, 3H), 2.30 (m, 1H), 1.98 (m, 2H), 1.85 (m, 2H), 1.70 (m, 2H), 1.48 (m, 2H).

Example 39

N-({1-[4-Hydroxy-4-(2-trimethylsilanyl-thiazol-5-yl)-cyclohexyl]-azetidin-3-ylcarbamoyl}-methyl)-3-trifluoromethyl-benzamide Step A: 8-(2-Trimethylsilanyl-thiazol-5-yl)-1,4-dioxa-spiro[4.5]decan-8-ol

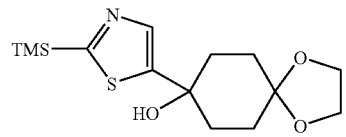 [SMILES: C[Si](C)(C)c1ncc(C2(O)CCC3(CC2)OCCO3)s1]

The title compound was prepared as a white solid from 2-trimethylsilanyl-thiazole (Fluka) and 1,4-dioxa-spiro[4.5]decan-8-one using the procedure described in Step A of Example 33.

ESI-MS (m/z): Calcd. For C$_{14}$H$_{23}$NO$_3$SSi, 313. Found: 314 (M+H).

Step B: 4-Hydroxy-4-(2-trimethylsilanyl-thiazol-5-yl)-cyclohexanone

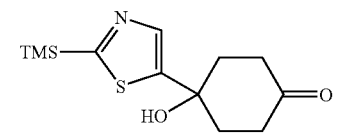 [SMILES: C[Si](C)(C)c1ncc(C2(O)CCC(=O)CC2)s1]

The title compound was prepared as a white solid from de-protection of 8-(2-trimethylsilanyl-thiazol-5-yl)-1,4-dioxa-spiro[4.5]decan-8-ol, as prepared in the previous step, using the procedure described in Step B of Example 1.

$^1$H NMR (400 MHz, CDCl$_3$) δ 7.68 (s, 1H), 3.98 (m, 4H), 2.20 (m, 2H), 2.04 (m, 2H), 1.95 (m, 2H), 1.75 (m, 2H), 0.29 (s, 9H).

Step C: N-({1-[4-Hydroxy-4-(2-trimethylsilanyl-thiazol-5-yl)-cyclohexyl]-azetidin-3-ylcarbamoyl}-methyl)-3-trifluoromethyl-benzamide

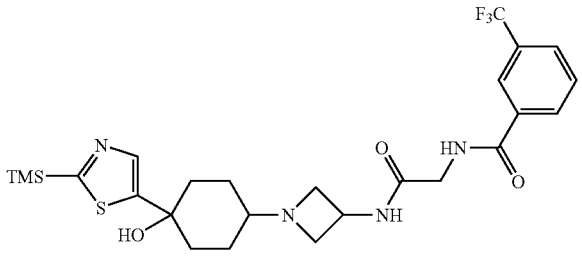

The title compounds were prepared as white solids from reductive amination of 4-hydroxy-4-(2-trimethylsilanyl-thiazol-5-yl)-cyclohexanone, as prepared in the previous step, and N-(azetidin-3-ylcarbamoylmethyl)-3-trifluoromethyl-benzamide using the procedure described in Step E of Example 1.

39a: less polar isomer from silica gel column,
$^1$H NMR (400 MHz, CDCl$_3$) δ 8.11 (s, 1H), 8.02 (d, J=6.6 Hz, 1H), 7.78 (d, J=6.6 Hz, 1H), 7.70 (s, 1H), 7.60 (t, J=6.9 Hz, 1H), 7.25 (br, s, 1H), 6.50 (s, br, 1H), 4.50 (m, 1H), 4.15 (d, J=4.5 Hz, 2H), 3.55 (t, J=7.0 Hz, 2H), 2.95 (t, J=7.1 Hz, 2H), 2.28 (m, 2H), 1.85~1.64 (m, 4H), 1.50 (m, 2H).

39b: more polar isomer from silica gel column
$^1$H NMR (400 MHz, CDCl$_3$) δ 8.10 (s, 1H), 8.02 (d, J=6.6 Hz, 1H), 7.80 (d, J=6.6 Hz, 1H), 7.68 (s, 1H), 7.58 (t, J=6.8 Hz, 1H), 7.24 (s, br, 1H), 6.72 (s, br, 1H), 4.55 (m, 1H), 4.18 (d, J=4.5 Hz, 2H), 3.65 (t, J=7.0 Hz, 2H), 3.00 (t, J=7.0 Hz, 2H), 2.20 (s, br, 1H), 1.98 (m, 2H), 1.75 (m, 2H), 1.66 (m, 2H), 1.45 (m, 2H), 0.32 (s, 9H).

Example 40

N-{[1-(4-Hydroxy-4-thiazol-5-yl-cyclohexyl)-azetidin-3-ylcarbamoyl]-methyl}-3-trifluoromethyl-benzamide Step A: 8-Thiazol-5-yl-1,4-dioxa-spiro[4.5]decan-8-ol

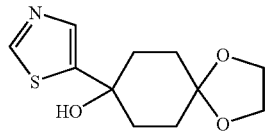 [SMILES: OC1(c2cncs2)CCC2(CC1)OCCO2]

A solution of 2-trimethylsilanyl-thiazole (Fluka, 5.0 g, 31.8 mmol) in THF (20 mL) at −78° C. was treated with n-BuLi (2.5 M in hexanes, 15.3 mL, 38.2 mmol) dropped slowly over 10 min. The reaction was stirred for an additional 20 min. at −78° C. A solution of 1,4-dioxa-spiro[4.5]decan-8-one (Aldrich, 6.0 g, 38 mmol) in THF (15 mL) was slowly dropped into the reaction. After addition, the reaction was stirred for an additional 2 hours at −78° C. The reaction was then quenched with water and warmed to room temperature.

The solvent was removed in vacuo and the residue was partitioned between ethyl acetate and water. The organic layer was washed with brine, dried over anhydrous Na$_2$SO$_4$, filtered and concentrated to give a yellow solid. To this solid in THF (20 mL) was added TBAF (1.0 N in THF, 30 mL) at room temperature. The reaction was stirred for 1 hour. The solvent was removed and the residue was partitioned between ethyl acetate and water. The organic layer was washed with brine, dried over anhydrous Na$_2$SO$_4$, filtered, concentrated and then purified by silica gel column on a CombiFlash® system using hexanes and ethyl acetate (from 10% ethyl acetate to 100% ethyl acetate) to afford the title compound as a white solid.

$^1$H NMR (400 MHz, CDCl$_3$) δ 8.65 (s, 1H), 7.72 (s, 1H), 4.01 (m, 4H), 2.20 (m, 2H), 2.08 (m, 4H), 1.69 (m, 2H).

Step B: 4-Hydroxy-4-thiazol-5-yl-cyclohexanone

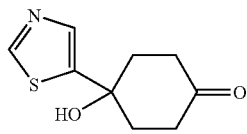

8-Thiazol-5-yl-1,4-dioxa-spiro[4.5]decan-8-ol (4.35 g, 18.0 mmol) as prepared in the previous step was treated with 1N HCl (~10 mL) in acetone (20 mL) at room temperature for 4 hours. The reaction was neutralized with saturated NaHCO$_3$ solution and the solvent was removed. The residue was partitioned between ethyl acetate and water. The organic layer was washed with brine, dried over anhydrous Na$_2$SO$_4$, filtered and concentrated to give a yellow solid, which was then purified by silica gel column on a CombiFlash® system using hexanes and ethyl acetate (from 10% ethyl acetate to 100% ethyl acetate) to afford the title compound as a pale yellow solid.

$^1$H NMR (400 MHz, CDCl$_3$) δ 8.70 (s, 1H), 7.73 (s, 1H), 2.96 (m, 2H), 2.35 (m, 4H), 2.23 (m, 2H).

Step C: N-{[1-(4-Hydroxy-4-thiazol-5-yl-cyclohexyl)-azetidin-3-ylcarbamoyl]-methyl}-3-trifluoromethyl-benzamide

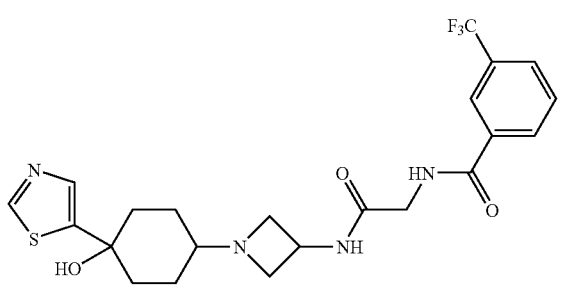

4-Hydroxy-4-thiazol-5-yl-cyclohexanone, as prepared in the previous step, (2.0 g, 10.1 mmol) and N-(azetidin-3-ylcarbamoylmethyl)-3-trifluoromethyl-benzamide, HCl salt (5.1 g, 15.0 mmol) as prepared in Step D of Example 1, in DCM (20 mL) was treated with TEA (2.8 mL, 20 mmol) for 10 min followed by NaBH(OAc)$_3$ (5.28 g, 25 mmol) for another 4 hours at room temperature. The reaction was quenched with saturated sodium bicarbonate. The organic layer was separated and the aqueous layer was extracted 3 times with chloroform and IPA "cocktail" (~3:1, v/v). The combined organic layer was dried over anhydrous Na$_2$SO$_4$, filtered and concentrated to give the crude product, which was then purified by a CombiFlash® system using ethyl acetate and 7N NH$_3$ in MeOH as eluent (from pure ethyl acetate to 5% 7N NH$_3$ in MeOH in ethyl acetate) to afford two title compounds as white solids: a less polar isomer and a more polar isomer.

40a: less polar isomer from silica gel column, $^1$H NMR (400 MHz, d$_4$-MeOH) δ 8.90 (s, 1H), 8.25 (s, 1H), 8.20 (d, J=6.3 Hz, 1H), 7.88 (d, J=6.5 Hz, 1H), 7.85 (s, 1H), 7.69 (t, J=6.5 Hz, 1H), 4.45 (m, 1H), 4.05 (s, 2H), 3.68 (t, J=7.0 Hz, 2H), 3.02 (t, J=7.0 Hz, 2H), 2.35 (s, br, 1H), 2.25 (m, 2H), 1.90 (m, 2H), 1.82 (m, 2H), 1.38 (m, 2H).

The stereochemistry of this compound was determined by X-ray crystallography to be "cis". As defined, "cis" is the relationship between thiazole and azetidine rings.

40b: more polar isomer from silica gel column $^1$H NMR (400 MHz, d$_4$-MeOH) δ 8.88 (s, 1H), 8.20 (s, 1H), 8.16 (d, J=6.5 Hz, 1H), 7.87 (d, J=6.5 Hz, 1H), 7.74 (s, 1H), 7.70 (t, J=6.5 Hz, 1H), 4.46 (m, 1H), 4.05 (s, 2H), 4.68 (t, J=7.0 Hz, 2H), 3.70 (t, J=7.2 Hz, 2H), 3.07 (t, J=7.0 Hz, 2H), 2.20 (m, 1H), 2.05 (m, 2H), 1.85 (t, J=7.8 Hz, 2H), 1.74 (m, 2H), 1.65 (m, 2H).

Step D: N-{[1-(4-Hydroxy-4-thiazol-5-yl-cyclohexyl)-azetidin-3-ylcarbamoyl]-methyl}-3-trifluoromethyl-benzamide hemisuccinate

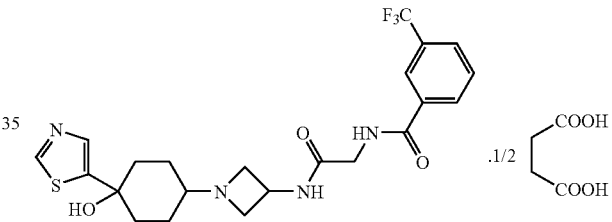

40a as prepared in the previous step (1.50 g, 3.14 mmol) and succinic acid (185 mg, 1.57 mmol) were dissolved in acetone (8 mL) and methanol (1 mL) until the solid disappeared. To this solution was added ether (100 mL). The white precipitate was then collected by filtration. The solid was washed with cold ether several times. The solid was then dried over vaccum to afford the title compound as a white solid.

LC-MS: LC, 99% pure; ESI-MS (m/z): Calcd. For C$_{22}$H$_{25}$F$_3$N$_4$O$_3$S, 482. Found: 483 (M+H).

Example 41

N-({1-[4-Hydroxy-4-(2-methyl-thiazol-5-yl)-cyclohexyl]-azetidin-3-ylcarbamoyl}-methyl)-3-trifluoromethyl-benzamide Step A: 8-(2-Methyl-thiazol-5-yl)-1,4-dioxa-spiro[4.5]decan-8-ol

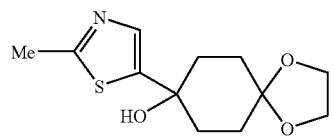 [SMILES: Cc1ncc(C2(O)CCC3(CC2)OCCO3)s1]

The title compound was prepared as a white solid from 2-methyl-thiazole (Aldrich) and 1,4-dioxa-spiro[4.5]decan-8-one using the procedure described in Step A of Example 33.

$^1$H NMR (400 MHz, CDCl$_3$) δ 7.30 (s, 1H), 3.98 (m, 4H), 2.42 (s, 3H), 2.20 (t, J=6.5 Hz, 2H), 2.10 (t, J=6.5 Hz, 2H), 2.00 (d, J=6.0 Hz, 2H), 1.72 (d, J=6.1 Hz, 2H).

Step B:
4-Hydroxy-4(-methyl-thiazol-5-yl)-cyclohexanone

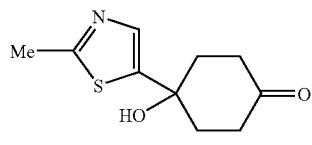

The title compound was prepared as a white solid from de-protection of 8-(2-methyl-thiazol-5-yl)-1,4-dioxa-spiro[4.5]decan-8-ol, as prepared in the previous step, using the procedure described in Step B of Example 1.

ESI-MS (m/z): Calcd. For C$_{10}$H$_{13}$NO$_2$S, 211. Found: 212 (M+H).

Step C: N-({1-[4-Hydroxy-4-(2-methyl-thiazol-5-yl)-cyclohexyl]-azetidin-3-ylcarbamoyl}-methyl)-3-trifluoromethyl-benzamide

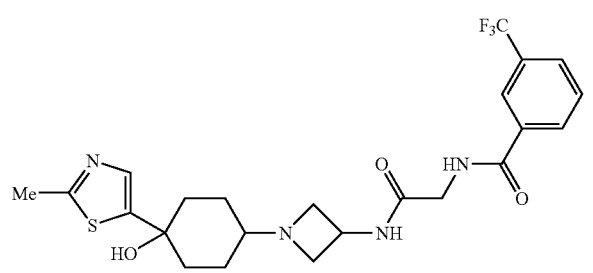

The title compounds were prepared as white solids from reductive amination of 4-hydroxy-4(-methyl-thiazol-5-yl)-cyclohexanone, as prepared in the previous step, and N-(azetidin-3-ylcarbamoylmethyl)-3-trifluoromethyl-benzamide using the procedure described in Step E of Example 1.

41a: less polar isomer from silica gel column, $^1$H NMR (400 MHz, d$_4$-MeOH) δ 8.25 (s, 1H), 8.18 (d, J=6.3 Hz, 1H), 7.85 (d, J=6.5 Hz, 1H), 7.69 (t, J=6.5 Hz, 1H), 7.49 (s, 1H), 4.42 (m, 1H), 4.05 (s, 2H), 3.75 (t, J=6.0 Hz, 2H), 3.02 (t, J=6.0 Hz, 2H), 2.68 (s, 3H), 2.32 (s, br, 1H), 2.25 (m, 2H), 1.90 (m, 2H), 1.82 (m, 2H), 1.32 (m, 2H).

41b: more polar isomer from silica gel column $^1$H NMR (400 MHz, d$_4$-MeOH) δ 8.18 (s, 1H), 8.06 (d, J=6.5 Hz, 1H), 7.79 (d, J=6.5 Hz, 1H), 7.62 (t, J=6.6 Hz, 1H), 7.32 (s, 1H), 4.55 (m, 1H), 4.35 (t, J=6.0 Hz, 2H), 4.20 (m, 2H), 4.00 (s, 2H), 2.95 (m, 1H), 2.52 (s, 3H), 2.02 (m, 2H), 2.25 (m, 2H), 1.90 (m, 2H), 1.82 (m, 2H), 1.75 (m, 2H), 1.65 (m, 2H).

Example 42

N-({1-[4-(2-Ethyl-thiazol-5-yl)-4-hydroxy-cyclohexyl]-azetidin-3-ylcarbamoyl}-methyl)-3-trifluoromethyl-benzamide Step A: 8-(2-Ethyl-thiazol-5-yl)-1,4-dioxa-spiro[4.5]decan-8-ol

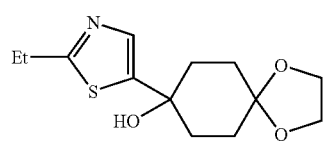

The title compound was prepared as a white solid from 2-ethyl-thiazole (Aldrich) and 1,4-dioxa-spiro[4.5]decan-8-one using the procedure described in Step A of Example 33.

$^1$H NMR (400 MHz, CDCl$_3$) δ 7.40 (s, 1H), 3.98 (m, 4H), 2.95 (q, J=6.8 Hz, 2H), 2.10 (m, 4H), 2.05 (m, 2H), 1.68 (d, J=6.0 Hz, 2H), 1.35 (t, J=6.8 Hz, 3H).

Step B:
4-Hydroxy-4-(2-ethyl-thiazol-5-yl)-cyclohexanone

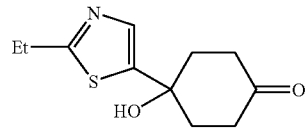 [SMILES: CCc1ncc(C2(O)CCC(=O)CC2)s1]

The title compound was prepared as a white solid from de-protection of 8-(2-ethyl-thiazol-5-yl)-1,4-dioxa-spiro[4.5]decan-8-ol, as prepared in the previous step, using the procedure described in Step B of Example 1.

$^1$H NMR (400 MHz, CDCl$_3$) δ 7.48 (s, 1H), 3.10 (m, 2H), 2.85 (q, J=6.0 Hz, 2H), 2.35 (m, 4H), 2.28 (m, 2H), 1.40 (t, J=6.0 Hz, 3H).

Step C: N-({1-[4-(2-Ethyl-thiazol-5-yl)-4-hydroxy-cyclohexyl]-azetidin-3-ylcarbamoyl}-methyl)-3-trifluoromethyl-benzamide

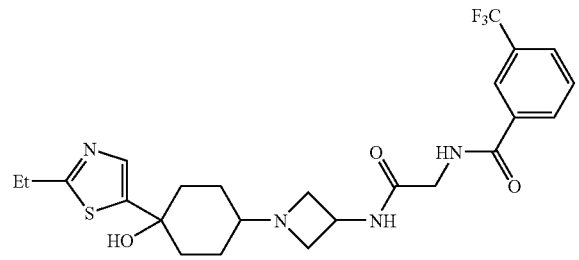 [SMILES: CCc1ncc(C2(O)CCC(N3CC(NC(=O)CNC(=O)c4cccc(C(F)(F)F)c4)C3)CC2)s1]

The title compounds were prepared as white solids from reductive amination of 4-hydroxy-4-(2-ethyl-thiazol-5-yl)- cyclohexanone, as prepared in the previous step, and N-(azetidin-3-ylcarbamoylmethyl)-3-trifluoromethyl-benzamide using the procedure described in Step E of Example 1.

42a: less polar isomer from silica gel column,
¹H NMR (400 MHz, d₄-MeOH) δ 8.16 (s, 1H), 8.08 (d, J=6.5 Hz, 1H), 7.80 (d, J=6.6 Hz, 1H), 7.64 (t, J=6.4 Hz, 1H), 7.49 (s, 1H), 4.38 (m, 1H), 3.98 (s, 2H), 3.58 (d, J=6.0 Hz, 2H), 2.95 (m, 4H), 2.30 (m, 1H), 2.15 (m, 2H), 1.80 (m, 2H), 1.65 (m, 2H), 1.32 (t, J=7.5 Hz, 3H), 1.28 (m, 2H).

42b: more polar isomer from silica gel column
¹H NMR (400 MHz, d₄-MeOH) δ 8.15 (s, 1H), 8.10 (d, J=6.8 Hz, 1H), 7.82 (d, J=6.4 Hz, 1H), 7.65 (t, J=6.5 Hz, 1H), 7.38 (s, 1H), 4.45 (m, 1H), 4.02 (s, 2H), 3.74 (t, J=6.0 Hz, 2H), 3.15 (t, J=7.0 Hz, 2H), 2.92 (q, J=7.2 Hz, 2H), 2.30 (m, 1H), 2.06 (m, 2H), 1.79 (m, 2H), 1.65 (m, 2H), 1.52 (m, 2H).

Example 43

N-({1-[4-Hydroxy-4-(2-isopropyl-thiazol-5-yl)-cyclohexyl]-azetidin-3-ylcarbamoyl}-methyl)-3-trifluoromethyl-benzamide Step A: 2-Isopropyl-thiazole

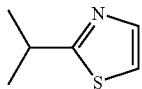

5-Isopropenyl-thiazole (TCI, 5 g, 40 mmol) in MeOH (20 mL) was charged with 5% Pd/C (Aldrich, ~2.0 g) and then loaded on a Parr Hydrogenation Shaker with 40 psi H₂ at room temperature for 2 hours. The catalyst was filtered off through a pad of Celite. The resulting solution was concentrated and passed quickly through a silica gel column with ethyl acetate to afford the title compound as a colorless oil.

ESI-MS (m/z): Calcd. For C₆H₉NS, 127. Found: 128 (M+H).

Step B: 8-(2-iso-Propyl-thiazol-5-yl)-1,4-dioxa-spiro[4.5]decan-8-ol

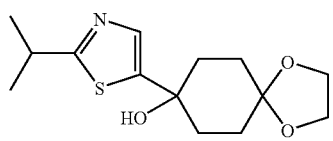 [SMILES: CC(C)c1ncc(C2(O)CCC3(CC2)OCCO3)s1]

The title compound was prepared as a white solid from 2-iso-propyl-thiazole and 1,4-dioxa-spiro[4.5]decan-8-one using the procedure described in Step A of Example 33.

ESI-MS (m/z): Calcd. For C₁₄H₂₁NO₃S, 283. Found: 284 (M+H).

Step C: 4-Hydroxy-4-(2-iso-Propyl-thiazol-5-yl)-cyclohexanone

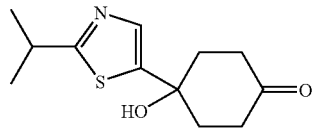 [SMILES: CC(C)c1ncc(C2(O)CCC(=O)CC2)s1]

The title compound was prepared as a white solid from de-protection of 8-(2-iso-propyl-thiazol-5-yl)-1,4-dioxa-spiro[4.5]decan-8-ol, as prepared in the previous step, using the procedure described in Step B of Example 1.
¹H NMR (400 MHz, CDCl₃) δ 7.47 (s, 1H), 3.25 (m, 1H), 2.85 (m, 2H), 2.40 (m, 4H), 2.28 (m, 2H), 1.38 (d, J=7.5 Hz, 6H).

Step D: N-({1-[4-Hydroxy-4-(2-isopropyl-thiazol-5-yl)-cyclohexyl]-azetidin-3-ylcarbamoyl}-methyl)-3-trifluoromethyl-benzamide

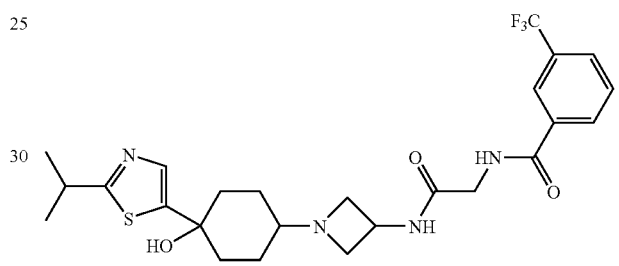

The title compounds were prepared as white solids from reductive amination of 4-hydroxy-4-(2-iso-Propyl-thiazol-5-yl)-cyclohexanone, as prepared in the previous step, and N-(azetidin-3-ylcarbamoylmethyl)-3-trifluoromethyl-benzamide using the procedure described in Step E of Example 1.

43a: less polar isomer from silica gel column,
¹H NMR (400 MHz, d₄-MeOH) δ 8.25 (s, 1H), 8.12 (d, J=6.5 Hz, 1H), 7.85 (d, J=6.6 Hz, 1H), 7.70 (t, J=6.4 Hz, 1H), 7.50 (s, 1H), 4.42 (m, 1H), 4.05 (s, 2H), 3.65 (d, J=6.0 Hz, 2H), 3.30 (m, 1H), 3.01 (t, J=6.0 Hz, 2H), 2.30 (m, 2H), 2.25 (m, 2H), 1.85 (m, 2H), 1.70 (m, 2H), 1.35 (d, J=7.5 Hz, 6H).

43b: more polar isomer from silica gel column
¹H NMR (400 MHz, d₄-MeOH) δ 8.25 (s, 1H), 8.15 (d, J=6.5 Hz, 1H), 7.90 (d, J=6.4 Hz, 1H), 7.75 (t, J=6.5 Hz, 1H), 7.48 (s, 1H), 4.55 (m, 1H), 4.12 (t, J=6.0 Hz, 2H), 4.05 (s, 2H), 3.72 (t, J=6.0 Hz, 2H), 2.85 (m, 1H), 2.06 (m, 2H), 1.85 (m, 4H), 1.65 (m, 2H).

Example 44

N-{1-[4-(2-Ethynyl-thiazol-5-yl)-4-hydroxy-cyclohexyl]-azetidin-3-ylcarbamoyl}-methyl)-3-trifluoromethyl-benzamide Step A: 2-Trimethylsilanylethynyl-thiazole

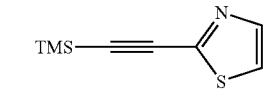

A solution of 2-Bromothiazole (Aldrich, 5.0 g, 30.5 mmol), ethynyl-trimethyl-silane (Aldrich, 3.0 g, 30.5 mmol), PdCl$_2$(PPh$_3$)$_2$ (Aldrich, 500 mg, 0.71 mmol) and CuI (Aldrich, 400 mg, 1.52 mmol) in THF (20 mL) was treated with TEA (5 mL) at room temperature for 20 min. The reaction was heated at 60 for 4 hours. The solid was filtered off through a pad of celite and the filtrate was concentrated to give yellow solid, which was then purified by silica gel column on a CombiFlash® system using hexanes and ethyl acetate (from 10% ethyl acetate to 100% ethyl acetate) to afford the title compound as yellow oil.

$^1$H NMR (400 MHz, CDCl$_3$) δ 7.80 (s, 1H), 7.31 (s, 1H), 0.28 (s, 9H).

Step B: 8-(2-Trimethylsilanylethynyl-thiazol-5-yl)-1,4-dioxa-spiro[4.5]decan-8-ol

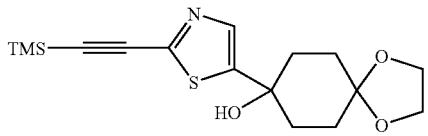 [SMILES: C[Si](C)(C)C#Cc1ncc(C2(O)CCC3(CC2)OCCO3)s1]

The title compound was prepared as a white solid from 2-trimethylsilanylethynyl-thiazole, as prepared in the previous step, and 1,4-dioxa-spiro[4.5]decan-8-one using the procedure described in Step A of Example 33.

ESI-MS (m/z): Calcd. For C$_{16}$H$_{23}$NO$_3$SSi, 337. Found: 338 (M+H).

Step C: 4-Hydroxy-4-(2-trimethylsilanylethynyl-thiazol-5-yl)-cyclohexanone

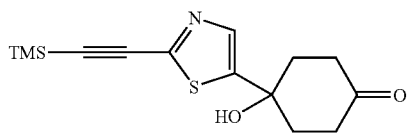

The title compound was prepared as a white solid from de-protection of 8-(2-trimethylsilanylethynyl-thiazol-5-yl)-1,4-dioxa-spiro[4.5]decan-8-ol, as prepared in the previous step, using the procedure described in Step B of Example 1.

ESI-MS (m/z): Calcd. For C$_{14}$H$_{19}$NO$_2$SSi, 293. Found: 294 (M+H).

Step D: N-({1-[4-(2-Ethynyl-thiazol-5-yl)-4-hydroxy-cyclohexyl]-azetidin-3-ylcarbamoyl}-methyl)-3-trifluoromethyl-benzamide

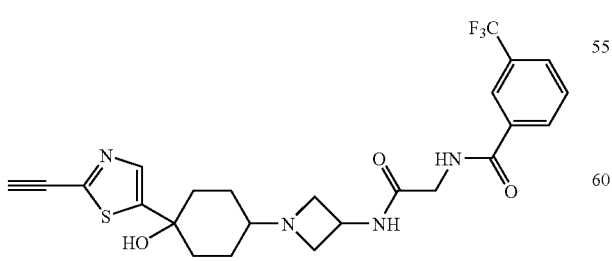

The title compounds were prepared as white solids from reductive amination of 4-hydroxy-4-(2-trimethylsilanylethynyl-thiazol-5-yl)-cyclohexanone, as prepared in the previous step, and N-(azetidin-3-ylcarbamoylmethyl)-3-trifluoromethyl-benzamide using the procedure described in Step E of Example 1 followed by TBAF work-up.

44a: less polar isomer from silica gel column, $^1$H NMR (400 MHz, d$_4$-MeOH) δ 8.11 (s, 1H), 8.05 (d, J=6.5 Hz, 1H), 7.78 (d, J=6.6 Hz, 1H), 7.55 (t, J=6.4 Hz, 1H), 7.50 (s, 1H), 4.32 (m, 1H), 3.98 (s, 2H), 3.65 (d, J=6.0 Hz, 2H), 2.90 (t, J=6.0 Hz, 2H), 2.85 (s, 1H), 2.20 (m, 1H), 2.02 (m, 2H), 1.85 (m, 2H), 1.50 (m, 2H), 1.25 (m, 2H).

44b: more polar isomer from silica gel column $^1$H NMR (400 MHz, d$_4$-MeOH) δ 8.22 (s, 1H), 8.15 (d, J=6.5 Hz, 1H), 7.90 (d, J=6.4 Hz, 1H), 7.75 (t, J=6.5 Hz, 1H), 7.70 (s, 1H), 4.45 (m, 1H), 4.05 (s, 2H), 3.72 (t, J=6.0 Hz, 2H), 3.05 (t, J=6.0 Hz, 2H), 3.00 (s, 1H), 2.25 (m, 1H), 2.16 (m, 2H), 1.85 (m, 2H), 1.65 (m, 2H), 152 (m, 2H).

Example 45

N-({1-[4-Hydroxy-4-(2-methylsulfanyl-thiazol-5-yl)-cyclohexyl]-azetidin-3-ylcarbamoyl}-methyl)-3-trifluoromethyl-benzamide Step A: 8-(2-Methylsulfanyl-thiazol-5-yl)-1,4-dioxa-spiro[4.5]decan-8-ol

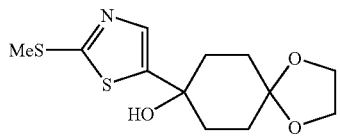 [SMILES: CSc1ncc(C2(O)CCC3(CC2)OCCO3)s1]

The title compound was prepared as a white solid from 2-methylsulfanyl-thiazole (Aldrich) and 1,4-dioxa-spiro[4.5]decan-8-one using the procedure described in Step A of Example 33.

$^1$H NMR (400 MHz, CDCl$_3$) δ 7.40 (s, 1H), 3.98 (m, 4H), 2.62 (s, 3H), 2.15~2.02 (m, 6H), 1.65 (m, 2H).

Step B: 8-(2-Methylsulfanyl-thiazol-5-yl)-1,4-dioxa-spiro[4.5]decan-8-ol

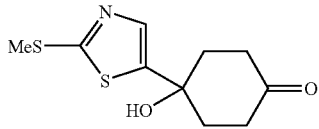

The title compound was prepared as a white solid from de-protection of 8-(2-methylsulfanyl-thiazol-5-yl)-1,4-dioxa-spiro[4.5]decan-8-ol, as prepared in the previous step, using the procedure described in Step B of Example 1.

ESI-MS (m/z): Calcd. For C$_{10}$H$_{13}$NO$_2$S$_2$, 243; found: 244 (M+H).

Step C: N-({1-[4-Hydroxy-4-(2-methylsulfanyl-thiazol-5-yl)-cyclohexyl]-azetidin-3-ylcarbamoyl}-methyl)-3-trifluoromethyl-benzamide

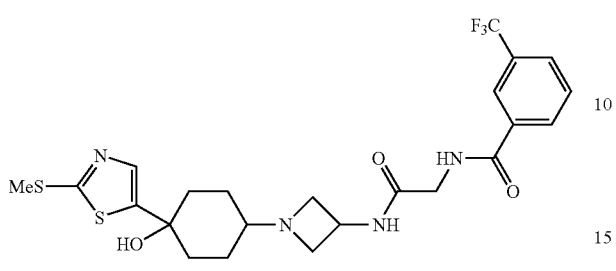

The title compounds were prepared as white solids from reductive amination of 8-(2-methylsulfanyl-thiazol-5-yl)-1,4-dioxa-spiro[4.5]decan-8-ol, as prepared in the previous step, and N-(azetidin-3-ylcarbamoylmethyl)-3-trifluoromethyl-benzamide using the procedure described in Step E of Example 1.

45a: less polar isomer from silica gel column,
$^1$H NMR (400 MHz, d$_4$-MeOH) δ 8.10 (s, 1H), 8.05 (d, J=6.5 Hz, 1H), 7.76 (d, J=6.6 Hz, 1H), 7.60 (t, J=6.6 Hz, 1H), 7.23 (s, 1H), 4.35 (m, 1H), 3.98 (d, J=3.5 Hz, 2H), 3.55 (t, J=6.5 Hz, 2H), 3.02 (t, J=6.1 Hz, 2H), 2.90 (m, 1H), 2.70 (s, 3H), 2.02 (m, 2H), 1.75 (m, 2H), 1.48 (m, 2H), 1.28 (m, 2H).

45b: more polar isomer from silica gel column
$^1$H NMR (400 MHz, CDCl$_3$) δ 8.15 (s, 1H), 8.02 (d, J=6.8 Hz, 1H), 7.80 (d, J=6.5 Hz, 1H), 7.62 (t, J=6.6 Hz, 1H), 7.40 (s, 1H), 4.52 (m, 1H), 4.18 (d, J=5.0 Hz, 2H), 3.65 (t, J=6.0 Hz, 2H), 3.11 (d, J=6.5 Hz, 2H), 2.85 (m, 1H), 2.80 (s, 3H), 2.10 (m, 2H), 1.75 (m, 2H), 1.62 (m, 2H), 1.42 (m, 2H).

Example 46

N-({1-[4-Hydroxy-4-(2-methanesulfinyl-thiazol-5-yl)-cyclohexyl]-azetidin-3-ylcarbamoyl}-methyl)-3-trifluoromethyl-benzamide

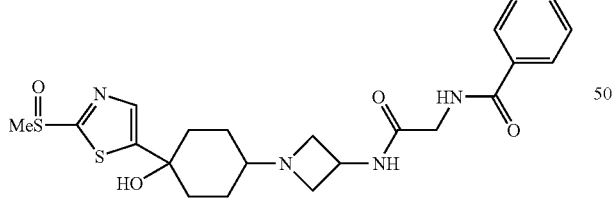

N-({1-[4-Hydroxy-4-(2-methylsulfanyl-thiazol-5-yl)-cyclohexyl]-azetidin-3-ylcarbamoyl}-methyl)-3-trifluoromethyl-benzamide (less polar isomer, 45a, 100 mg, 0.19 mmol) in MeOH (1 mL) and water (1 mL) was treated with OXONE (Aldrich, 230 mg, 0.38 mmol) at room temperature for 6 hours. The reaction mixture was partitioned between DCM and saturate NaHCO$_3$. The organic layer was separated and the aqueous layer was extracted 3 times with chloroform and IPA "cocktail" (~3:1, v/v). The combined organic layer was dried over anhydrous Na$_2$SO$_4$, filtered and concentrated to give the crude product, which was then purified by a CombiFlash® system using ethyl acetate and 7N NH$_3$ in MeOH as eluent (from pure ethyl acetate to 5% 7N NH$_3$ in MeOH in ethyl acetate) to afford the title compounds as a white solid.

$^1$H NMR (400 MHz, d$_4$-MeOH) δ 8.22 (s, 1H), 8.18 (d, J=6.5 Hz, 1H), 7.90 (s, 1H), 7.85 (d, J=6.6 Hz, 1H), 7.70 (t, J=6.4 Hz, 1H), 4.45 (m, 1H), 4.05 (s, 2H), 3.75 (d, J=6.0 Hz, 2H), 3.10 (t, J=6.0 Hz, 2H), 3.04 (s, 3H), 2.42 (m, 1H), 2.25 (m, 2H), 1.95 (m, 2H), 1.80 (m, 2H), 1.42 (m, 2H).

Example 47

N-({1-[4-Hydroxy-4-(2-methanesulfonyl-thiazol-5-yl)-cyclohexyl]-azetidin-3-ylcarbamoyl}-methyl)-3-trifluoromethyl-benzamide Step A: 4-Hydroxy-4-(2-methanesulfonyl-thiazol-5-yl)-cyclohexanone

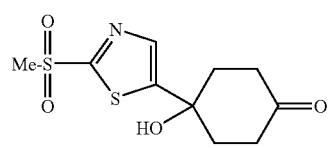

The title compound was prepared as a white solid from OXONE oxidation of 8-(2-methylsulfanyl-thiazol-5-yl)-1,4-dioxa-spiro[4.5]decan-8-ol, as prepared in Example 45 Step B, using the procedure described in Example 46.
$^1$H NMR (400 MHz, CDCl$_3$) δ 7.85 (s, 1H), 3.33 (s, 3H), 2.95 (m, 2H), 2.42 (m, 4H), 2.30 (m, 2H).

Step B: N-({1-[4-Hydroxy-4-(2-methanesulfonyl-thiazol-5-yl)-cyclohexyl]-azetidin-3-ylcarbamoyl}-methyl)-3-trifluoromethyl-benzamide

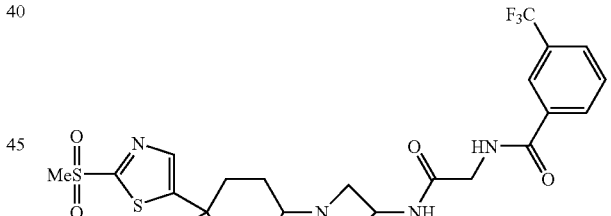

The title compounds were prepared as white solids from reductive amination of 4-hydroxy-4-(2-methanesulfonyl-thiazol-5-yl)-cyclohexanone, as prepared in the previous step, and N-(azetidin-3-ylcarbamoylmethyl)-3-trifluoromethyl-benzamide using the procedure described in Step E of Example 1.

47a: less polar isomer from silica gel column,
$^1$H NMR (400 MHz, CDCl$_3$) δ 8.10 (s, 1H), 8.05 (d, J=6.5 Hz, 1H), 7.85 (s, 1H), 7.78 (d, J=6.6 Hz, 1H), 7.63 (t, J=6.6 Hz, 1H), 7.45 (t, J=3.0 Hz, 1H), 7.01 (d, J=5.6 Hz, 1H), 4.65 (m, 1H), 4.15 (d, J=3.5 Hz, 2H), 3.60 (t, J=6.5 Hz, 2H), 3.35 (s, 3H), 2.98 (t, J=6.1 Hz, 2H), 2.35 (m, 1H), 2.22 (m, 2H), 1.87 (m, 2H), 1.79 (m, 2H), 1.46 (m, 2H).

47b: more polar isomer from silica gel column
$^1$H NMR (400 MHz, d$_4$-MeOH) δ 8.15 (s, 1H), 8.06 (d, J=6.8 Hz, 1H), 7.80 (d, J=6.5 Hz, 1H), 7.55 (t, J=6.6 Hz, 1H), 7.50 (s, 1H), 4.45 (m, 1H), 3.98 (s, 2H), 3.75 (t, J=6.0 Hz, 2H), 3.21 (d, J=6.5 Hz, 2H), 2.85 (m, 1H), 2.65 (m, 1H), 2.10 (m, 2H), 2.00 (m, 2H), 1.75 (m, 2H), 1.42 (m, 2H).

Example 48

N-({1-[4-Hydroxy-4-(2-hydroxy-thiazol-5-yl)-cyclohexyl]-azetidin-3-ylcarbamoyl}-methyl)-3-trifluoromethyl-benzamide

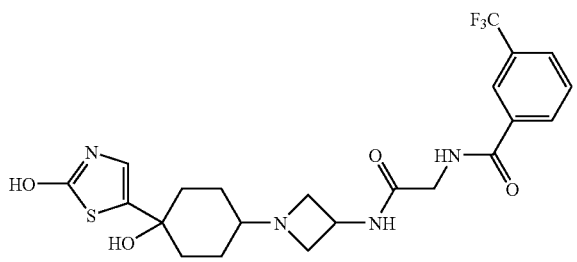

A solution of N-({1-[4-Hydroxy-4-(2-methanesulfonyl-thiazol-5-yl)-cyclohexyl]-azetidin-3-ylcarbamoyl}-methyl)-3-trifluoromethyl-benzamide (less polar isomer, 47a, 100 mg, 0.18 mmol) and LiOH hydrate (Aldrich, 15 mg, 0.36 mmol) in water (1 mL) and THF (1 mL) was heated to 60° C. in a sealed tube for 2 hours. The crude solution was directly purified by a CombiFlash® system using ethyl acetate and 7N NH$_3$ in MeOH as eluent (from pure ethyl acetate to 5% 7N NH$_3$ in MeOH in ethyl acetate) to afford the title compound as a white solid.

$^1$H NMR (400 MHz, d$_4$-MeOH) δ 8.11 (s, 1H), 8.05 (d, J=6.5 Hz, 1H), 7.80 (d, J=6.6 Hz, 1H), 7.62 (t, J=6.6 Hz, 1H), 6.60 (s, 1H), 4.45 (m, 1H), 4.05 (t, J=5.5 Hz, 2H), 3.95 (s, 2H), 3.65 (m, 2H), 2.98 (m, 1H), 2.35 (m, 2H), 2.22 (m, 1H), 1.97 (m, 2H), 1.59 (m, 2H), 1.50 (m, 1H), 1.25 (m, 1H).

Example 49

N-({1-[4-(2-Amino-thiazol-5-yl)-4-hydroxy-cyclohexyl]-azetidin-3-ylcarbamoyl}-methyl)-3-trifluoromethyl-benzamide Step A: [5-(8-Hydroxy-1,4-dioxa-spiro[4.5]dec-8-yl)-thiazol-2-yl]-carbamic acid tert-butyl ester

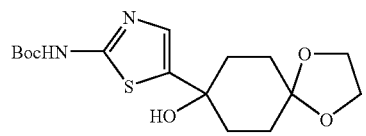 [SMILES: CC(C)(C)OC(=O)Nc1ncc(C2(O)CCC3(CC2)OCCO3)s1]

The title compound was prepared as a white solid from thiazol-2-yl-carbamic acid tert-butyl ester (prepared according to Das, B. et al. Tetrahedron Lett. 2006, 47, 7551-7556) and 1,4-dioxa-spiro[4.5]decan-8-one using the procedure described in Step A of Example 33.

ESI-MS (m/z): Calcd. For C$_{16}$H$_{24}$N$_2$O$_5$S, 356. Found: 357 (M+H).

Step B: [5-(1-Hydroxy-4-oxo-cyclohexyl)-thiazol-2-yl]-carbamic acid tert-butyl ester

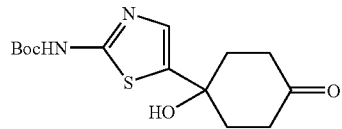

The title compound was prepared as a white solid from de-protection of [5-(8-hydroxy-1,4-dioxa-spiro[4.5]dec-8-yl)-thiazol-2-yl]-carbamic acid tert-butyl ester, as prepared in the previous step, using the procedure described in Step B of Example 1.

ESI-MS (m/z): Calcd. For C$_{14}$H$_{20}$N$_2$O$_4$S, 312. Found: 312 (M+H).

Step C: [5-(1-Hydroxy-4-{3-[2-(3-trifluoromethyl-benzoylamino)-acetylamino]-azetidin-1-yl}-cyclohexyl)-thiazol-2-yl]-carbamic acid tert-butyl ester

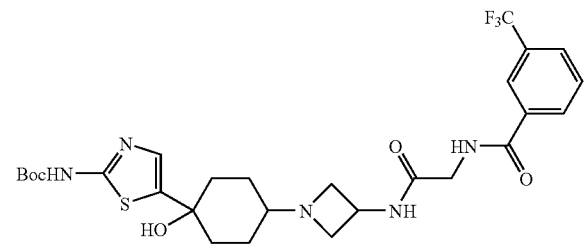 [SMILES: CC(C)(C)OC(=O)Nc1ncc(C2(O)CCC(N3CC(NC(=O)CNC(=O)c4cccc(C(F)(F)F)c4)C3)CC2)s1]

The title compounds were prepared as white solids from reductive amination of [5-(1-Hydroxy-4-oxo-cyclohexyl)-thiazol-2-yl]-carbamic acid tert-butyl ester, as prepared in the previous step, and N-(azetidin-3-ylcarbamoylmethyl)-3-trifluoromethyl-benzamide using the procedure described in Step E of Example 1.

$^1$H NMR (400 MHz, CDCl$_3$) δ 8.11 (s, 1H), 8.08 (d, J=6.5 Hz, 1H), 7.78 (d, J=6.6 Hz, 1H), 7.60 (t, J=6.6 Hz, 1H), 7.08 (s, 1H), 4.45 (m, 1H), 4.05 (s, 2H), 3.98 (m, 2H), 3.65 (t, J=5.6 Hz, 2H), 2.90 (m, 1H), 2.35 (m, 2H), 1.97 (m, 2H), 1.60 (m, 2H), 1.38 (s, 9H), 1.30 (m, 2H).

Step D: N-({1-[4-(2-Amino-thiazol-5-yl)-4-hydroxy-cyclohexyl]-azetidin-3-ylcarbamoyl}-methyl)-3-trifluoromethyl-benzamide

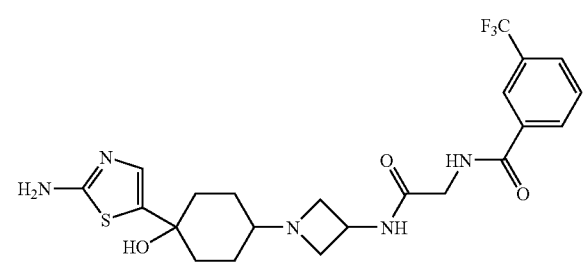 [SMILES: Nc1ncc(C2(O)CCC(N3CC(NC(=O)CNC(=O)c4cccc(C(F)(F)F)c4)C3)CC2)s1]

The title compound was prepared as colorless oil from TFA de-protection of [5-(1-hydroxy-4-{3-[2-(3-trifluoromethyl-benzoylamino)-acetylamino]-azetidin-1-yl}-cyclohexyl)-thiazol-2-yl]-carbamic acid tert-butyl ester, as prepared in the previous step, using the procedure described in Step B of Example 16.

ESI-MS (m/z): Calcd. For $C_{22}H_{26}F_3N_5O_3S$, 497. Found: 498 (M+H).

Example 50

N-({1-[4-(2-Dimethylamino-thiazol-5-yl)-4-hydroxy-cyclohexyl]-azetidin-3-ylcarbamoyl}-methyl)-3-trifluoromethyl-benzamide

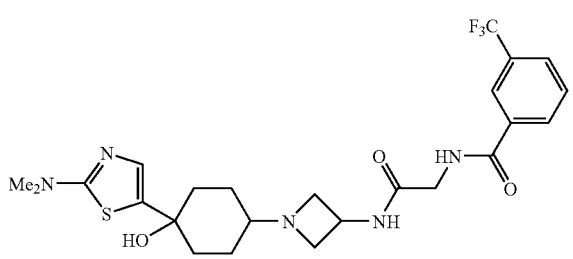 [SMILES: CN(C)c1ncc(C2(O)CCC(N3CC(NC(=O)CNC(=O)c4cccc(C(F)(F)F)c4)C3)CC2)s1]

A solution of N-({1-[4-Hydroxy-4-(2-methanesulfonyl-thiazol-5-yl)-cyclohexyl]-azetidin-3-ylcarbamoyl}-methyl)-3-trifluoromethyl-benzamide (less polar isomer, 47a, 100 mg, 0.18 mmol) and dimethylamine (Aldrich, 40% in water, 2 mL) in DMF (1 mL) was heated to 120° C. in a sealed tube overnight. The crude solution was directly purified by a CombiFlash® system using ethyl acetate and 7N $NH_3$ in MeOH as eluent (from pure ethyl acetate to 5% 7N $NH_3$ in MeOH in ethyl acetate) to afford the title compound as a white solid.

$^1$H NMR (400 MHz, $d_4$-MeOH) δ 8.25 (s, 1H), 8.18 (d, J=6.5 Hz, 1H), 7.88 (d, J=6.4 Hz, 1H), 7.75 (t, J=6.5 Hz, 1H), 7.05 (s, 1H), 4.51 (m, 1H), 4.25 (s, 2H), 4.10 (s, 2H), 3.72 (t, J=6.5 Hz, 2H), 3.15 (s, 6H), 3.05 (m, 2H), 2.38 (m, 1H), 2.20 (m, 2H), 1.95 (m, 2H), 1.55 (m, 2H), 1.32 (m, 2H).

Example 51

N-({1-[4-Hydroxy-4-(2-pyrrolidin-1-yl-thiazol-5-yl)-cyclohexyl]-azetidin-3-ylcarbamoyl}-methyl)-3-trifluoromethyl-benzamide

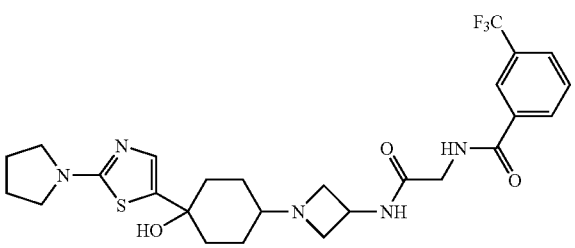 [SMILES: O=C(CNC(=O)c1cccc(C(F)(F)F)c1)NC1CN(C2CCC(O)(c3cnc(N4CCCC4)s3)CC2)C1]

The title compound was prepared as a white solid from N-({1-[4-hydroxy-4-(2-methanesulfonyl-thiazol-5-yl)-cyclohexyl]-azetidin-3-ylcarbamoyl}-methyl)-3-trifluoromethyl-benzamide (less polar isomer, 47a), and pyrrolidine (Aldrich) using the procedure described in Example 50.

$^1$H NMR (400 MHz, $d_4$-MeOH) δ 8.15 (s, 1H), 8.08 (d, J=4.5 Hz, 1H), 7.78 (d, J=6.6 Hz, 1H), 7.62 (t, J=6.6 Hz, 1H), 6.90 (d, J=5.2 Hz, 1H), 4.30 (m, 1H), 3.98 (s, 2H), 3.65 (m, 2H), 3.25 (m, 4H), 3.10 (m, 2H), 2.85 (m, 1H), 2.20 (m, 2H), 2.01 (m, 4H), 2.22 (m, 1H), 1.97 (m, 2H), 1.75 (m, 2H), 1.35 (m, 1H), 1.18 (m, 1H).

Example 52

N-({1-[4-Hydroxy-4-(2-methoxy-thiazol-5-yl)-cyclohexyl]-azetidin-3-ylcarbamoyl}-methyl)-3-trifluoromethyl-benzamide

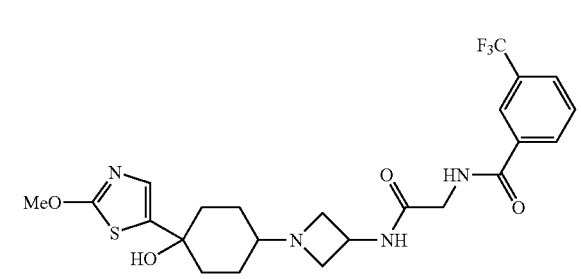

A solution of N-({1-[4-Hydroxy-4-(2-methanesulfonyl-thiazol-5-yl)-cyclohexyl]-azetidin-3-ylcarbamoyl}-methyl)-3-trifluoromethyl-benzamide (less polar isomer, 47a, 100 mg, 0.18 mmol) was treated with NaOMe (Aldrich, 0.5 M in MeOH, 1 mL) in DMF (1 mL) at 80° C. for 4 hours. The crude solution was directly purified by a CombiFlash® system using ethyl acetate and 7N $NH_3$ in MeOH as eluent (from pure ethyl acetate to 5% 7N $NH_3$ in MeOH in ethyl acetate) to afford the title compound as a white solid.

$^1$H NMR (400 MHz, $d_4$-MeOH) δ 8.10 (s, 1H), 8.05 (d, J=6.5 Hz, 1H), 7.72 (d, J=6.6 Hz, 1H), 7.60 (t, J=6.6 Hz, 1H), 6.92 (s, 1H), 4.35 (m, 1H), 3.92 (d, J=3.5 Hz, 2H), 3.90 (s, 3H), 3.45 (t, J=6.5 Hz, 2H), 2.85 (t, J=6.1 Hz, 2H), 2.30 (m, 1H), 2.12 (m, 2H), 1.77 (m, 2H), 1.60 (m, 2H), 1.28 (m, 2H).

Example 53

N-({1-[4-Hydroxy-4-(2-isopropoxy-thiazol-5-yl)-cyclohexyl]-azetidin-3-ylcarbamoyl}-methyl)-3-trifluoromethyl-benzamide

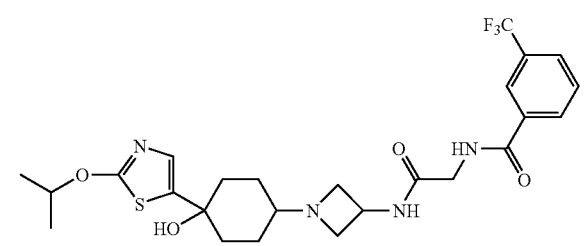 [SMILES: CC(C)Oc1ncc(C2(O)CCC(N3CC(NC(=O)CNC(=O)c4cccc(C(F)(F)F)c4)C3)CC2)s1]

The title compound was prepared as a white solid from N-({1-[4-hydroxy-4-(2-methanesulfonyl-thiazol-5-yl)-cyclohexyl]-azetidin-3-ylcarbamoyl}-methyl)-3-trifluoromethyl-benzamide (less polar isomer, 47a), and i-PrONa (prepared in situ from IPA and 95% NaH) using the procedure described in Example 52.

$^1$H NMR (400 MHz, $CDCl_3$) δ 8.12 (s, 1H), 8.03 (d, J=6.5 Hz, 1H), 7.81 (d, J=6.5 Hz, 1H), 7.58 (d, J=6.6 Hz, 1H), 7.35

(m, 1H), 7.25 (d, J=4.0 Hz, 1H), 5.12 (m, 1H), 4.55 (m, 1H), 4.15 (d, J=3.5 Hz, 2H), 3.60 (t, J=6.5 Hz, 2H), 3.02 (m, J=6.1 Hz, 2H), 2.25 (m, 1H), 2.15 (m, 2H), 2.00 (m, 2H), 1.85 (m, 4H), 1.41 (d, J=7.2 Hz, 6H), 1.35 (m, 2H).

Example 54

N-({1-[4-(2-tert-Butoxy-thiazol-5-yl)-4-hydroxy-cyclohexyl]-azetidin-3-ylcarbamoyl}-methyl)-3-trifluoromethyl-benzamide

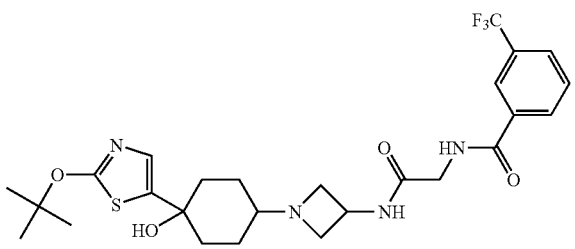 [SMILES: CC(C)(C)Oc1ncc(C2(O)CCC(N3CC(NC(=O)CNC(=O)c4cccc(C(F)(F)F)c4)C3)CC2)s1]

The title compound was prepared as a white solid from N-({1-[4-hydroxy-4-(2-methanesulfonyl-thiazol-5-yl)-cyclohexyl]-azetidin-3-ylcarbamoyl}-methyl)-3-trifluoromethyl-benzamide (less polar isomer, 47a), and t-BuOK (Aldrich, 1.0 N in THF) using the procedure described in Example 52.

ESI-MS (m/z): Calcd. For $C_{26}H_{33}F_3N_4O_4S$, 554. Found: 555 (M+H).

Example 55

N-({1-[4-(2-Cyanoamino-thiazol-5-yl)-4-hydroxy-cyclohexyl]-azetidin-3-ylcarbamoyl}-methyl)-3-trifluoromethyl-benzamide

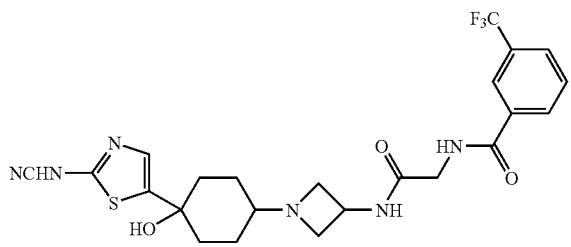

A solution of cyamide (Aldrich, 23 mg, 0.54 mmol) in DMF (1 mL) was treated with NaH (95%, 14 mg, 0.54 mmol) at 0° C. The reaction was warmed to room temperature over 10 min. To this solution was added N-({1-[4-hydroxy-4-(2-methanesulfonyl-thiazol-5-yl)-cyclohexyl]-azetidin-3-ylcarbamoyl}-methyl)-3-trifluoromethyl-benzamide (less polar isomer, 47a, 100 mg, 0.18 mmol) and the reaction was heated at 120° C. for 4 hours. The crude solution was directly purified by a CombiFlash® system using ethyl acetate and 7N $NH_3$ in MeOH as eluent (from pure ethyl acetate to 5% 7N $NH_3$ in MeOH in ethyl acetate) to afford the title compound as a white solid.

ESI-MS (m/z): Calcd. For $C_{23}H_{25}F_3N_6O_3S$, 522. Found: 523 (M+H).

Example 56

N-({1-[4-(2-Dimethylaminomethyl-thiazol-5-yl)-4-hydroxy-cyclohexyl]-azetidin-3-ylcarbamoyl}-methyl)-3-trifluoromethyl-benzamide Step A: Dimethyl-thiazol-2-ylmethyl-amine

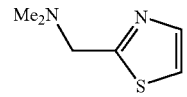

A solution of thiazole-2-carbaldehyde (Aldrich, 2.0 g, 17.7 mmol) in DCM (20 mL) was treated with dimethylamine (Aldrich, 40% in water, 3 mL) and molecular sieves (~1.0 g) followed by $NaBH(OAc)_3$ (4.2 g, 20 mmol). The reaction was stirred at room temperature overnight. The solvent was removed in vacuo and the residue was partitioned between ethyl acetate and water. The organic layer was washed with brine, dried over anhydrous $Na_2SO_4$, filtered and concentrated to give yellow solid, which was then purified by silica gel column on a CombiFlash® system using hexanes and ethyl acetate (from 10% ethyl acetate to 100% ethyl acetate) to afford the title compound as yellow solid.

$^1$H NMR (400 MHz, $CDCl_3$) δ 7.72 (s, 1H), 7.32 (s, 1H), 3.95 (s, 2H), 2.42 (s, 6H).

Step B: 8-(2-Dimethylaminomethyl-thiazol-5-yl)-1,4-dioxa-spiro[4.5]decan-8-ol

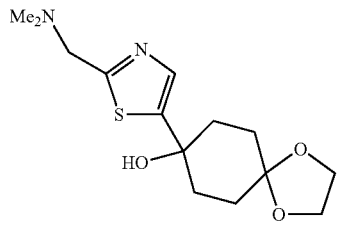 [SMILES: CN(C)Cc1ncc(C2(O)CCC3(CC2)OCCO3)s1]

The title compound was prepared as a white solid from dimethyl-thiazol-2-ylmethyl-amine, as prepared in the previous step, and 1,4-dioxa-spiro[4.5]decan-8-one in ether using the procedure described in Step A of Example 33.

ESI-MS (m/z): Calcd. For $C_{14}H_{22}N_2O_3S$, 298. Found: 299 (M+H).

Step C: 4-(2-Dimethylaminomethyl-thiazol-5-yl)-4-hydroxy-cyclohexanone

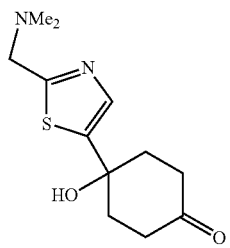 [SMILES: CN(C)Cc1ncc(C2(O)CCC(=O)CC2)s1]

The title compound was prepared as a white solid from de-protection of 8-(2-dimethylaminomethyl-thiazol-5-yl)-1,4-dioxa-spiro[4.5]decan-8-ol, as prepared in the previous step, using the procedure described in Step B of Example 1.

ESI-MS (m/z): Calcd. For $C_{12}H_{18}N_2O_2S$, 254. Found: 255 (M+H).

Step D: N-({1-[4-(2-Dimethylaminomethyl-thiazol-5-yl)-4-hydroxy-cyclohexyl]-azetidin-3-ylcarbamoyl}-methyl)-3-trifluoromethyl-benzamide

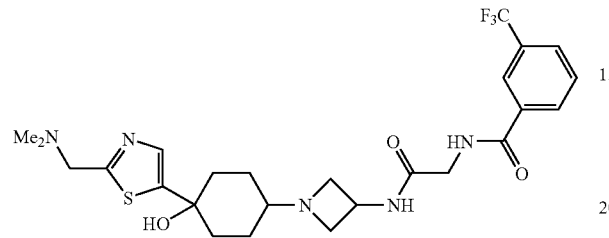

The title compounds were prepared as white solids from reductive amination of 4-(2-dimethylaminomethyl-thiazol-5-yl)-4-hydroxy-cyclohexanone, as prepared in the previous step, and N-(azetidin-3-ylcarbamoylmethyl)-3-trifluoromethyl-benzamide using the procedure described in Step E of Example 1.

$^1$H NMR (400 MHz, CDCl$_3$) δ 8.15 (s, 1H), 8.05 (d, J=6.6 Hz, 1H), 7.78 (d, J=6.4 Hz, 1H), 7.72 (t, J=4.0 Hz, 1H), 7.55 (t, J=6.2 Hz, 1H), 7.47 (s, 1H), 7.28 (d, J=6.4 Hz, 1H), 4.50 (m, 1H), 4.19 (d, J=3.2 Hz, 2H), 3.72 (s, 2H), 3.64 (t, J=6.8 Hz, 2H), 3.55 (s, 1H), 2.90 (t, J=6.7 Hz, 2H), 2.35 (s, 6H), 2.25 (m, 2H), 1.85 (m, 4H), 1.40 (m, 2H).

Example 57

N-{[1-(4-Hydroxy-4-isothiazol-5-yl-cyclohexyl)-azetidin-3-ylcarbamoyl]-methyl}-3-trifluoromethyl-benzamide Step A:
8-Isothiazol-5-yl-1,4-dioxa-spiro[4.5]decan-8-ol

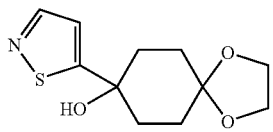 [SMILES: OC1(c2ccns2)CCC2(CC1)OCCO2]

The title compound was prepared as a white solid from isothiazole (Focus Synthesis) and 1,4-dioxa-spiro[4.5]decan-8-one using the procedure described in Step A of Example 33.

$^1$H NMR (400 MHz, CDCl$_3$) δ 8.35 (s, 1H), 7.12 (s, 1H), 4.05 (s, 4H), 2.40 (m, 2H), 2.05 (m, 2H), 1.78 (m, 2H), 1.56 (m, 2H).

Step B: 4-Hydroxy-4-isothiazol-5-yl-cyclohexanone

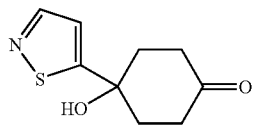

The title compound was prepared as a white solid from de-protection of 8-isothiazol-5-yl-1,4-dioxa-spiro[4.5]decan-8-ol, as prepared in the previous step, using the procedure described in Step B of Example 1.

$^1$H NMR (400 MHz, CDCl$_3$) δ 8.35 (s, 1H), 7.10 (s, 1H), 2.90 (m, 2H), 2.71 (s, 3H), 2.45 (m, 4H), 2.30 (m, 2H).

Step C: N-{[1-(4-Hydroxy-4-isothiazol-5-yl-cyclohexyl)-azetidin-3-ylcarbamoyl]-methyl}-3-trifluoromethyl-benzamide

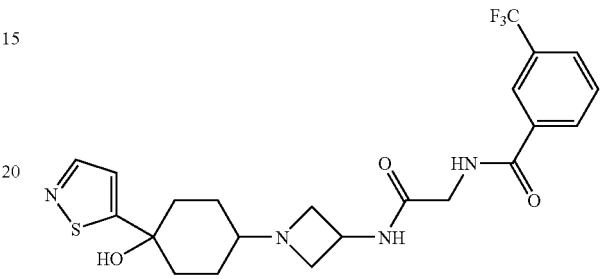

The title compounds were prepared as white solids from reductive amination of 4-hydroxy-4-isothiazol-5-yl-cyclohexanone, as prepared in the previous step, and N-(azetidin-3-ylcarbamoylmethyl)-3-trifluoromethyl-benzamide using the procedure described in Step E of Example 1.

57a: less polar isomer from silica gel column, prepared as hemi-succinate, $^1$H NMR (400 MHz, d$_4$-MeOH) δ 8.38 (s, 1H), 8.25 (s, 1H), 8.18 (d, J=6.5 Hz, 1H), 7.90 (d, J=6.6 Hz, 1H), 7.72 (t, J=6.6 Hz, 1H), 7.28 (s, 1H), 4.55 (m, 1H), 4.10 (s, 2H), 4.05 (t, J=7.5 Hz, 2H), 3.55 (t, J=7.5 Hz, 2H), 2.90 (m, 1H), 2.55 (s, 2H), 1.97 (m, 2H), 1.79 (m, 2H), 1.58 (m, 2H).

57b: more polar isomer from silica gel column $^1$H NMR (400 MHz, d$_4$-MeOH) δ 8.11 (s, 1H), 8.05 (d, J=6.5 Hz, 1H), 7.80 (d, J=6.6 Hz, 1H), 7.62 (t, J=6.6 Hz, 1H), 7.15 (s, 1H), 4.45 (m, 1H), 3.95 (s, 2H), 3.65 (t, J=7.0 Hz, 2H), 3.01 (t, J=6.5 Hz, 2H), 2.95 (m, 1H), 2.01 (m, 2H), 1.97 (m, 2H), 1.68 (m, 2H), 1.40 (m, 2H).

Example 58

N-({1-[4-Hydroxy-4-(3-methyl-isothiazol-5-yl)-cyclohexyl]-azetidin-3-ylcarbamoyl}-methyl)-3-trifluoromethyl-benzamide Step A: 8-(3-Methyl-isothiazol-5-yl)-1,4-dioxa-spiro[4.5]decan-8-ol

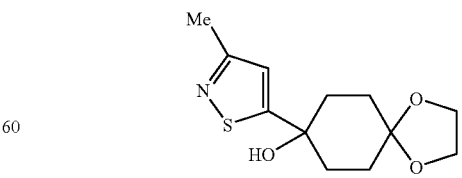

The title compound was prepared as a white solid from 3-methyl-isothiazole (Focus Synthesis) and 1,4-dioxa-spiro[4.5]decan-8-one in ether using the procedure described in Step A of Example 33.

ESI-MS (m/z): Calcd. For $C_{12}H_{17}NO_3S$, 255. Found: 256 (M+H)

Step B: 4-Hydroxy-4-(3-methyl-isothiazol-5-yl)-cyclohexanone

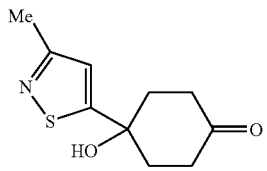 [SMILES: Cc1cc(C2(O)CCC(=O)CC2)sn1]

The title compound was prepared as a white solid from de-protection of 8-(3-methyl-isothiazol-5-yl)-1,4-dioxa-spiro[4.5]decan-8-ol, as prepared in the previous step, using the procedure described in Step B of Example 1.

$^1$H NMR (400 MHz, CDCl$_3$) δ 6.88 (s, 1H), 2.90 (m, 2H), 2.43 (s, 3H), 2.33 (m, 4H), 2.20 (m, 2H).

Step C: N-({1-[4-Hydroxy-4-(3-methyl-isothiazol-5-yl)-cyclohexyl]-azetidin-3-ylcarbamoyl}-methyl)-3-trifluoromethyl-benzamide

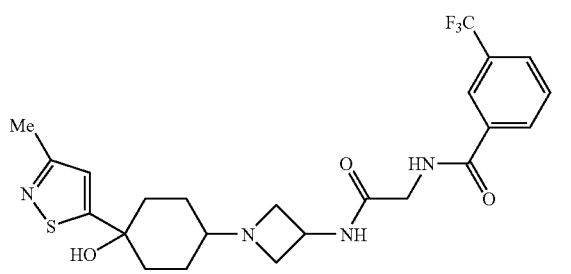 [SMILES: Cc1cc(C2(O)CCC(N3CC(NC(=O)CNC(=O)c4cccc(C(F)(F)F)c4)C3)CC2)sn1]

The title compounds were prepared as white solids from reductive amination of 4-hydroxy-4-(3-methyl-isothiazol-5-yl)-cyclohexanone, as prepared in the previous step, and N-(azetidin-3-ylcarbamoylmethyl)-3-trifluoromethyl-benzamide using the procedure described in Step E of Example 1.

58a: less polar isomer from silica gel column,
$^1$H NMR (400 MHz, CDCl$_3$) δ 8.14 (s, 1H), 8.02 (d, J=6.5 Hz, 1H), 7.71 (m, 2H), 7.50 (t, J=6.5 Hz, 1H), 6.92 (s, 1H), 4.50 (m, 1H), 4.15 (d, J=4.2 Hz, 2H), 3.65 (t, J=7.0 Hz, 2H), 3.10 (d, J=6.5 Hz, 2H), 2.42 (s, 3H), 2.35 (m, 1H), 2.20 (m, 1H), 2.11 (m, 2H), 1.85 (m, 2H), 1.70 (m, 2H), 1.42 (m, 2H).

58b: more polar isomer from silica gel column
$^1$H NMR (400 MHz, CDCl$_3$) δ 8.15 (s, 1H), 8.01 (d, J=6.7 Hz, 1H), 7.81 (s, 1H), 7.65 (m, 1H), 7.50 (t, J=6.5 Hz, 1H), 6.82 (s, 1H), 4.55 (m, 1H), 4.18 (d, J=4.0 Hz, 2H), 3.65 (t, J=7.0 Hz, 2H), 3.20 (d, J=6.5 Hz, 2H), 2.45 (s, 3H), 2.25 (m, 1H), 2.05 (m, 1H), 1.80 (m, 2H), 1.65 (m, 2H), 1.45 (m, 2H).

Example 59

N-{[1-(4-Hydroxy-4-[1,3,4]thiadiazol-2-yl-cyclohexyl)-azetidin-3-ylcarbamoyl]-methyl}-3-trifluoromethyl-benzamide Step A: 8-[1,3,4]Thiadiazol-2-yl-1,4-dioxa-spiro[4.5]decan-8-ol

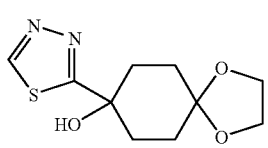 [SMILES: OC1(c2nncs2)CCC2(CC1)OCCO2]

The title compound was prepared as a white solid from [1,3,4]thiadiazole (3B Scientific) and 1,4-dioxa-spiro[4.5]decan-8-one using the procedure described in Step A of Example 33.

ESI-MS (m/z): Calcd. For $C_{10}H_{14}N_2O_3S$, 242. Found: 243 (M+H).

Step B: 4-Hydroxy-4-[1,3,4]thiadiazol-2-yl-cyclohexanone

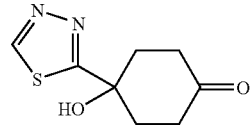 [SMILES: O=C1CCC(O)(c2nncs2)CC1]

The title compound was prepared as a white solid from de-protection of 8-[1,3,4]thiadiazol-2-yl-1,4-dioxa-spiro[4.5]decan-8-ol, as prepared in the previous step, using the procedure described in Step B of Example 1.

$^1$H NMR (400 MHz, CDCl$_3$) δ 9.15 (s, 1H), 2.70 (m, 2H), 2.52 (m, 2H), 2.35 (m, 4H).

Step C: N-{[1-(4-Hydroxy-4-[1,3,4]thiadiazol-2-yl-cyclohexyl)-azetidin-3-ylcarbamoyl-methyl}-3-trifluoromethyl-benzamide

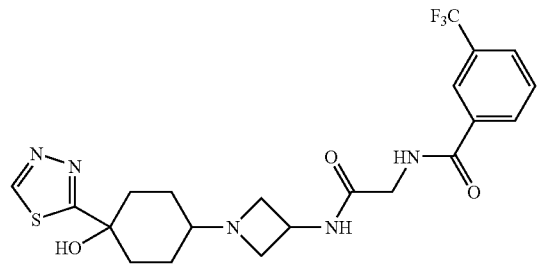

The title compounds were prepared as white solids from reductive amination of 4-hydroxy-4-[1,3,4]thiadiazol-2-yl-cyclohexanone, as prepared in the previous step, and N-(azetidin-3-ylcarbamoylmethyl)-3-trifluoromethyl-benzamide using the procedure described in Step E of Example 1.

$^1$H NMR (400 MHz, CDCl$_3$) δ 9.10 (s, 1H), 8.10 (s, 1H), 7.71 (d, J=5.8 Hz, 1H), 7.30 (d, J=6.5 Hz, 1H), 7.25 (t, J=5.6 Hz, 1H), 7.18 (s, 1H), 6.65 (m, 1H), 4.50 (m, 1H), 4.18 (d, J=4.2 Hz, 2H), 3.60 (t, J=7.0 Hz, 2H), 3.10 (d, J=6.5 Hz, 2H), 2.45 (m, 1H), 2.35 (m, 1H), 2.20 (m, 2H), 1.95 (m, 4H), 1.60 (m, 2H).

Example 60

N-({1-[4-(4-Bromo-thiophen-2-yl)-4-hydroxy-cyclohexyl]-azetidin-3-ylcarbamoyl}-methyl)-3-trifluoromethyl-benzamide Step A: 8-(4-Bromo-thiophen-2-yl)-1,4-dioxa-spiro[4.5]decan-8-ol

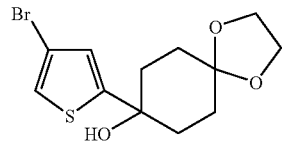 [SMILES: OC1(c2cc(Br)cs2)CCC2(CC1)OCCO2]

The title compound was prepared as a white solid from 2-bromothiophene (Aldrich) and 1,4-dioxa-spiro[4.5]decan-8-one using the procedure described in Step A of Example 33.

¹H NMR (MeOH) δ: 6.99 (s, 1H), 6.88-6.97 (m, 1H), 3.94-4.00 (m, 4H), 2.07-2.23 (m, 2H), 1.94-2.07 (m, 4H), 1.58-1.71 (m, 2H).

Step B:
4-(4-Bromo-thiophen-2-yl)-4-hydroxy-cyclohexanone

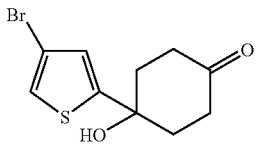 [SMILES: O=C1CCC(O)(c2cc(Br)cs2)CC1]

The title compound was prepared as a white solid from de-protection of 8-(4-bromo-thiophen-2-yl)-1,4-dioxa-spiro[4.5]decan-8-ol, as prepared in the previous step, using the procedure described in Step B of Example 1.

¹H NMR (MeOH) δ: 7.12-7.16 (m, 1H), 6.97 (d, J=3.0 Hz, 1H), 2.87-2.98 (m, 2H), 2.77-2.85 (m, 2H), 2.11-2.24 (m, 4H).

Step C: N-({1-[4-(4-Bromo-thiophen-2-yl)-4-hydroxy-cyclohexyl]-azetidin-3-ylcarbamoyl}-methyl)-3-trifluoromethyl-benzamide

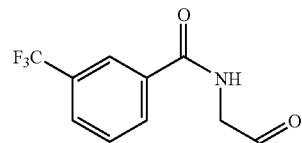

The title compound was prepared as a white solid from reductive amination of 4-(4-bromo-thiophen-2-yl)-4-hydroxy-cyclohexanone, as prepared in the previous step, and N-(azetidin-3-ylcarbamoylmethyl)-3-trifluoromethyl-benzamide using the procedure described in Step E of Example 1.

¹H NMR (MeOH) δ: 8.12 (s, 1H), 8.04 (d, J=7.8 Hz, 1H), 7.76 (d, J=7.8 Hz, 1H), 7.59 (t, J=7.8 Hz, 1H), 7.15 (d, J=5.3 Hz, 1H), 6.82 (d, J=5.3 Hz, 1H), 4.34 (t, J=6.8 Hz, 1H), 3.50-3.58 (m, 4H), 2.82 (t, J=7.5 Hz, 2H), 2.46-2.60 (m, 2H), 2.22 (t, J=3.4 Hz, 1H), 1.66-1.80 (m, 2H), 1.49 (d, J=13.6 Hz, 2H), 1.36 (dd, J=13.9, 4.5 Hz, 2H).

Example 61

N-{[1-(4-Hydroxy-4-thiophen-2-yl-cyclohexyl)-azetidin-3-ylcarbamoyl]-methyl}-3-trifluoromethyl-benzamide

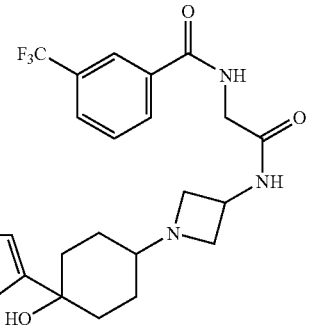

The title compound was prepared as a white solid from reductive de-bromination of N-({1-[4-(4-bromo-thiophen-2-yl)-4-hydroxy-cyclohexyl]-azetidin-3-ylcarbamoyl}-methyl)-3-trifluoromethyl-benzamide using the procedure described in Example 32.

¹H NMR (MeOH) δ: 8.12 (s, 1H), 8.06 (d, J=7.8 Hz, 1H), 7.77 (d, J=7.8 Hz, 1H), 7.60 (t, J=7.8 Hz, 1H), 7.22 (d, J=5.1 Hz, 1H), 6.96-7.07 (m, 1H), 6.82-6.90 (m, 1H), 4.43-4.57 (m, 1H), 4.14 (t, J=8.3 Hz, 2H), 3.96 (br s, 2H), 3.21 (d, J=1.8 Hz, 2H), 3.14 (br. s., 1H), 2.17-2.32 (m, 2H), 1.89-2.00 (m, 2H), 1.74 (t, J=13.4 Hz, 2H), 1.38 (d, J=9.3 Hz, 2H).

Example 62

N-{[1-(4-Hydroxy-4-oxazol-2-yl-cyclohexyl)-azetidin-3-ylcarbamoyl]-methyl}-3-trifluoromethyl-benzamide Step A: 4-Hydroxy-4-oxazol-2-yl-cyclohexanone

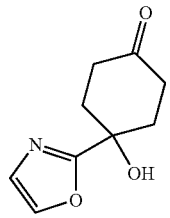 [SMILES: O=C1CCC(O)(c2ncco2)CC1]

The title compound was prepared using a modified procedure similar to Step A of Example 1.

Borane-THF (Aldrich, 1.0 M, 30.4 mL, 30.4 mmol) and oxazole (Aldrich, 2.0 mL, 30.41 mmol) in THF (20 mL) were pre-stirred at −78° C. for 1 hour before addition of n-butyl-lithium (2.5 M, 12.1 mL, 30.4 mmol) followed by 1,4-cyclohexanedione monoethylene acetal (5.2 g, 33.45 mmol). After maintaining the reaction at −78° C. for 4 hours, 1N HCl was added to the reaction and allowed to stir at RT o/n followed by aqueous work up with NaHCO₃ and EtOAc. The organic layer was dried (Na₂SO₄) and concentrated in vacuo and purified using column chromatography (0-100% EtOAc/Hexanes with NH₃ in MeOH).

¹H NMR (CHLOROFORM-d) δ: 7.66 (s, 1H), 7.09 (s, 1H), 2.76-2.98 (m, 2H), 2.19-2.48 (m, 4H), 1.86-2.15 (m, 2H).

Step B: N-{[1-(4-Hydroxy-4-oxazol-2-yl-cyclohexyl)-azetidin-3-ylcarbamoyl]-methyl}-3-trifluoromethyl-benzamide

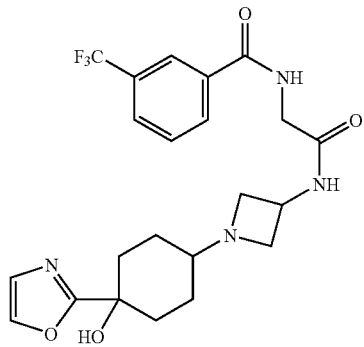 [SMILES: O=C(CNC(=O)c1cccc(C(F)(F)F)c1)NC1CN(C2CCC(O)(c3ncco3)CC2)C1]

The title compound was prepared as a white solid from reductive amination of 4-hydroxy-4-oxazol-2-yl-cyclohexanone, as prepared in the previous step, and N-(azetidin-3-ylcarbamoylmethyl)-3-trifluoromethyl-benzamide using the procedure described in Step E of Example 1.

¹H NMR (MeOH) δ: 8.20-8.32 (m, 1H), 8.10-8.20 (m, 1H), 7.87 (s, 1H), 7.90 (s, 1H), 7.71 (t, J=8.6 Hz, 1H), 7.07-7.22 (m, 1H), 4.43 (t, J=6.9 Hz, 1H), 3.71 (d, J=5.3 Hz, 2H), 3.54-3.65 (m, 2H), 3.01 (t, J=7.7 Hz, 2H), 2.76-2.96 (m, 1H), 2.52 (d, J=13.4 Hz, 2H), 2.21-2.33 (m, 2H), 2.07-2.18 (m, 2H), 1.76-1.92 (m, 2H).

Example 63

N-{[1-(4-Benzooxazol-2-yl-4-hydroxy-cyclohexyl)-azetidin-3-ylcarbamoyl]-methyl}-3-trifluoromethyl-benzamide Step A:
4-Benzooxazol-2-yl-4-hydroxy-cyclohexanone

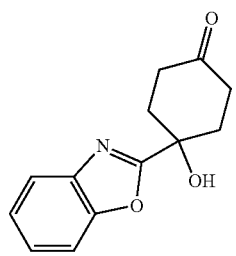 [SMILES: O=C1CCC(O)(c2nc3ccccc3o2)CC1]

The title compound was prepared from benzooxazole (Aldrich) using the procedure described in Example 61.

Step B: N-{[1-(4-Benzooxazol-2-yl-4-hydroxy-cyclohexyl)-azetidin-3-ylcarbamoyl]-methyl}-3-trifluoromethyl-benzamide

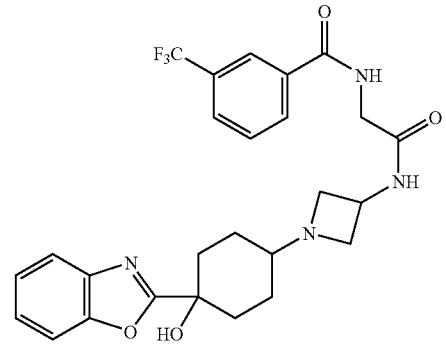 [SMILES: O=C(CNC(=O)c1cccc(C(F)(F)F)c1)NC1CN(C2CCC(O)(c3nc4ccccc4o3)CC2)C1]

The title compound was prepared as a white solid from reductive amination of 4-benzooxazol-2-yl-4-hydroxy-cyclohexanone, as prepared in the previous step, and N-(azetidin-3-ylcarbamoylmethyl)-3-trifluoromethyl-benzamide using the procedure described in Step E of Example 1.

¹H NMR (MeOH) δ: 8.23 (s, 1H), 8.15 (d, J=7.8 Hz, 1H), 7.88 (d, J=8.6 Hz, 1H), 7.65-7.76 (m, 2H), 7.58-7.65 (m, 1H), 7.33-7.48 (m, 2H), 4.42 (quin, J=7.0 Hz, 1H), 3.54-3.69 (m, 2H), 3.02 (t, J=7.6 Hz, 2H), 2.62 (d, J=13.4 Hz, 2H), 2.25-2.36 (m, 1H), 1.88 (d, J=13.6 Hz, 2H), 1.72-1.84 (m, 4H), 1.16-1.35 (m, 2H).

Example 64

3-Fluoro-N-({1-[4-hydroxy-4-(6-methyl-pyridin-3-yl)-cyclohexyl]-azetidin-3-ylcarbamoyl}-methyl)-5-trifluoromethyl-benzamide Step A: 3-[2-(3-trifluoromethyl-5-fluoro-benzoylamino)-acetylamino]-azetidine-1-carboxylic acid tert-butyl ester

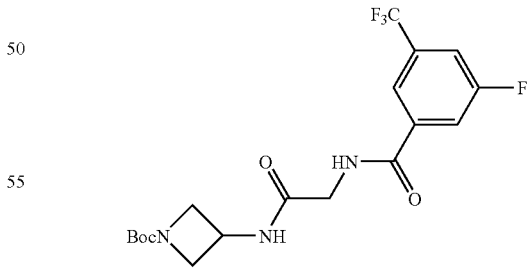

The title compounds were prepared as white solids from EDCI coupling between 3-amino-azetidine-1-carboxylic acid tert-butyl ester (AstaTech) and (5-fluoro-3-trifluoromethyl-benzoylamino)-acetic acid (prepared by the method similar to Ingersoll, A. W. et. al., Organic Syntheses 1932, XII, 40-2) using the procedure described in Step C of Example 1.

$^1$H NMR (400 MHz, CDCl$_3$) δ 8.05 (s, 1H), 7.89 (d, J=7.5 Hz, 1H), 7.41 (d, J=7.2 Hz, 1H), 4.55 (m, 1H), 4.28 (t, J=7.2 Hz, 2H), 4.15 (d, J=3.0 Hz, 2H), 3.80 (t, J=4.5 Hz, 2H), 1.45 (s, 9H).

Step B: N-(Azetidin-3-ylcarbamoylmethyl)-3-trifluoromethyl-5-fluoro-benzamide TFA salt

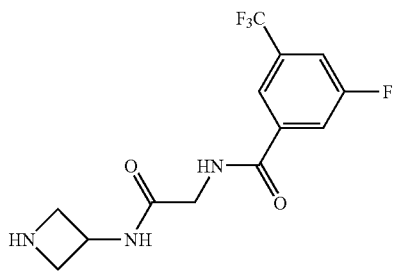 [SMILES: O=C(CNC(=O)c1cc(F)cc(C(F)(F)F)c1)NC1CNC1]

The title compound was prepared as colorless oil from TFA de-protection of 3-[2-(5-fluoro-3-trifluoromethyl-benzoylamino)-acetylamino]-azetidine-1-carboxylic acid tert-butylester, as prepared in the previous step, using the procedure described in Step D of Example 1.

ESI-MS (m/z): Calcd. For C$_{13}$H$_{13}$F$_4$N$_3$O$_2$, 319; found: 320 (M+H).

Step C: 3-Fluoro-N-({1-[4-hydroxy-4-(6-methyl-pyridin-3-yl)-cyclohexyl]-azetidin-3-ylcarbamoyl}-methyl)-5-trifluoromethyl-benzamide

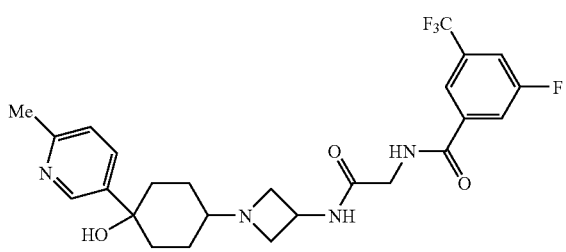 [SMILES: Cc1ccc(C2(O)CCC(N3CC(NC(=O)CNC(=O)c4cc(F)cc(C(F)(F)F)c4)C3)CC2)cn1]

The title compounds were prepared as white solids from reductive amination of 4-hydroxy-4-(6-methyl-pyridin-3-yl)-cyclohexanone, as prepared in Example 13 Step B, and N-(azetidin-3-ylcarbamoylmethyl)-3-trifluoromethyl-5-fluoro-benzamide, as prepared in the previous step, using the procedure described in Step E of Example 1.

64a: less polar isomer from silica gel column, $^1$H NMR (400 MHz, CDCl$_3$) δ 8.60 (s, 1H), 7.95 (s, 1H), 7.74 (m, 2H), 7.65 (d, J=6.6 Hz, 1H), 7.10 (d, J=6.4 Hz, 1H), 7.00 (m, 1H), 4.55 (m, 1H), 4.15 (d, J=5.5 Hz, 2H), 3.60 (d, J=6.8 Hz, 2H), 2.99 (t, J=6.8 Hz, 2H), 2.55 (s, 3H), 2.35 (m, 1H), 2.20 (m, 2H), 1.90 (m, 2H), 1.40 (m, 4H).

64b: more polar isomer from silica gel column $^1$H NMR (400 MHz, CDCl$_3$) δ 8.58 (s, 1H), 8.00 (s, br, 2H), 7.75 (s, 1H), 7.65 (m, 1H), 7.04 (d, J=4.5 Hz, 1H), 6.98 (m, 1H), 4.62 (m, 1H), 4.18 (d, J=4.5 Hz, 2H), 3.65 (d, J=6.6 Hz, 2H), 3.05 (t, J=6.6 Hz, 2H), 2.48 (s, 3H), 2.38 (m, 1H), 1.92 (m, 4H), 1.65 (m, 4H).

Example 65

3-Fluoro-N-{[1-(4-hydroxy-4-thiazol-5-yl-cyclohexyl)-azetidin-3-ylcarbamoyl]-methyl}-5-trifluoromethyl-benzamide

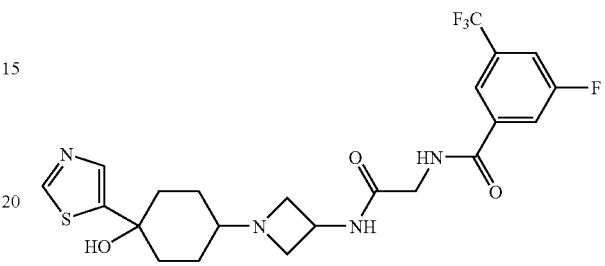

The title compounds were prepared as white solids from reductive amination of 4-hydroxy-4-thiazol-5-yl-cyclohexanone, as prepared in Example 40 Step B, and N-(azetidin-3-ylcarbamoylmethyl)-3-trifluoromethyl-5-fluoro-benzamide using the procedure described in Step E of Example 1.

$^1$H NMR (400 MHz, CDCl$_3$) δ 8.72 (s, 1H), 7.85 (s, 1H), 7.80 (s, 1H), 7.78 (d, J=6.5 Hz, 1H), 7.45 (d, J=7.5 Hz, 1H), 7.01 (s, 1H), 4.50 (m, 1H), 4.10 (s, 2H), 3.65 (m, J=6.5 Hz, 2H), 3.00 (m, J=6.1 Hz, 2H), 2.35 (m, 1H), 2.20 (m, 2H), 1.90 (m, 4H), 1.44 (m, 2H).

Example 66

N-({1-[4-Hydroxy-4-(6-methyl-pyridin-3-yl)-cyclohexyl]-azetidin-3-ylcarbamoyl}-methyl)-3,5-bis-trifluoromethyl-benzamide Step A: 3-[2-(3,5-Bis-trifluoromethyl-benzoylamino)-acetylamino]-azetidine-1-carboxylic acid tert-butyl ester

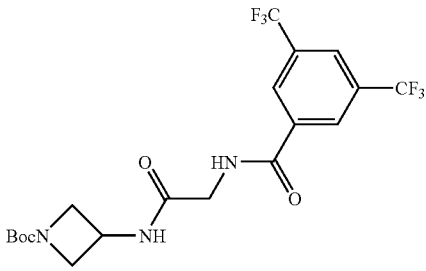 [SMILES: CC(C)(C)OC(=O)N1CC(NC(=O)CNC(=O)c2cc(C(F)(F)F)cc(C(F)(F)F)c2)C1]

The title compounds were prepared as white solids from EDCI coupling between 3-amino-azetidine-1-carboxylic acid tert-butyl ester and (3,5-bistrifluoromethyl-benzoylamino)-acetic acid (prepared by the method similar to Ingersoll, A. W. et. al., Organic Syntheses 1932, XII, 40-2) using the procedure described in Step C of Example 1.

ESI-MS (m/z): Calcd. For C$_{19}$H$_{21}$F$_6$N$_3$O$_4$, 469; found: 470 (M+H).

Step B: N-(Azetidin-3-ylcarbamoylmethyl)-3,5-bis-trifluoromethyl-benzamide TFA salt

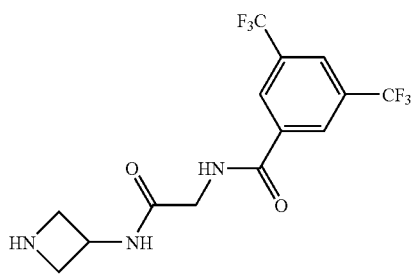 [SMILES: O=C(CNC(=O)c1cc(C(F)(F)F)cc(C(F)(F)F)c1)NC1CNC1]

The title compound was prepared as colorless oil from TFA de-protection of 3-[2-(3,5-bis-trifluoromethyl-benzoylamino)-acetylamino]-azetidine-1-carboxylic acid tert-butylester, as prepared in the previous step, using the procedure described in Step D of Example 1.

$^1$H NMR (400 MHz, CDCl$_3$) δ 8.28 (s, 2H), 8.05 (s, 1H), 4.63 (m, 1H), 4.40 (m, 2H), 2.15 (m, 2H), 3.88 (m, 2H).

Step D: N-({1-[4-Hydroxy-4-(6-methyl-pyridin-3-yl)-cyclohexyl]-azetidin-3-ylcarbamoyl}-methyl)-3,5-bis-trifluoromethyl-benzamide

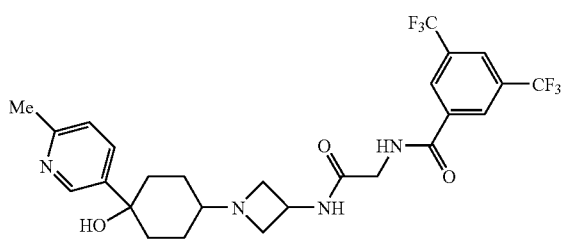 [SMILES: Cc1ccc(C2(O)CCC(N3CC(NC(=O)CNC(=O)c4cc(C(F)(F)F)cc(C(F)(F)F)c4)C3)CC2)cn1]

The title compounds were prepared as white solids from reductive amination of 4-hydroxy-4-(6-methyl-pyridin-3-yl)-cyclohexanone, as prepared in Example 13 Step B, and N-(azetidin-3-ylcarbamoylmethyl)-3,5-bis-trifluoromethyl-benzamide as prepared in the previous step, using the procedure described in Step E of Example 1.

66a: less polar isomer from silica gel column, $^1$H NMR (400 MHz, CDCl$_3$) δ 8.60 (s, 1H), 8.28 (s, 2H), 8.00 (s, 1H), 7.82 (m, 1H), 7.70 (d, J=6.6 Hz, 1H), 7.11 (d, J=6.4 Hz, 1H), 7.02 (m, 1H), 4.55 (m, 1H), 4.15 (d, J=5.5 Hz, 2H), 3.61 (d, J=6.8 Hz, 2H), 2.95 (t, J=6.8 Hz, 2H), 2.51 (s, 3H), 2.30 (m, 1H), 2.25 (m, 2H), 1.85 (m, 2H), 1.45 (m, 4H).

66b: more polar isomer from silica gel column $^1$H NMR (400 MHz, CDCl$_3$) δ 8.58 (s, 1H), 8.32 (s, br, 2H), 8.00 (s, 1H), 7.95 (m, 1H), 7.88 (m 1H), 7.70 (d, J=6.5 Hz, 1H), 7.11 (d, J=6.6 Hz, 1H), 4.62 (m, 1H), 4.18 (d, J=5.5 Hz, 2H), 3.75 (d, J=6.6 Hz, 2H), 3.35 (t, J=6.6 Hz, 2H), 2.48 (s, 3H), 2.38 (m, 1H), 1.92 (m, 4H), 1.65 (m, 2H).

Example 67

N-{[1-(4-Hydroxy-4-thiazol-2-yl-cyclohexyl)-azetidin-3-ylcarbamoyl]-methyl}-3,5-bis-trifluoromethyl-benzamide

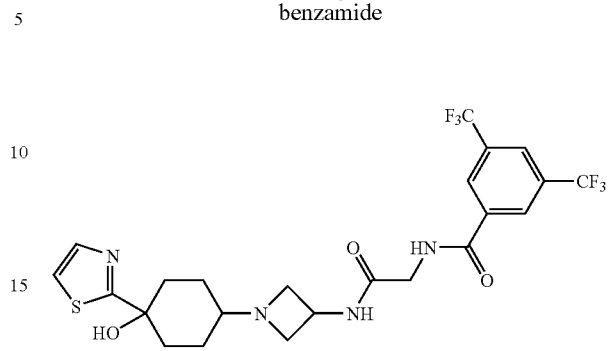

The title compounds were prepared as white solids from reductive amination of 4-hydroxy-4-thiazol-2-yl-cyclohexanone, as prepared in Example 40 Step B, and N-(azetidin-3-ylcarbamoylmethyl)-3,5-bis-trifluoromethyl-benzamide using the procedure described in Step E of Example 1.

67a: less polar isomer from silica gel column, $^1$H NMR (400 MHz, CDCl$_3$) δ 8.28 (s, 1H), 8.00 (s, 1H), 7.70 (d, J=6.6 Hz, 1H), 7.31 (d, J=6.4 Hz, 1H), 4.52 (m, 1H), 4.25 (d, J=5.0 Hz, 2H), 3.55 (d, J=6.0 Hz, 2H), 3.10 (t, J=6.0 Hz, 2H), 2.90 (m, 1H), 2.35 (m, 2H), 1.85 (m, 2H), 1.70 (m, 2H), 1.55 (m, 2H).

67b: more polar isomer from silica gel column $^1$H NMR (400 MHz, CDCl$_3$) δ 8.32 (s, br, 2H), 8.00 (s, 1H), 7.88 (m 1H), 7.70 (s, 1H), 7.41 (d, J=6.6 Hz, 1H), 4.58 (m, 1H), 4.15 (d, J=5.5 Hz, 2H), 3.65 (d, J=6.6 Hz, 2H), 3.20 (t, J=6.6 Hz, 2H), 2.30 (m, 1H), 2.05 (m, 4H), 1.82 (m, 2H), 1.65 (m, 2H).

Example 68

N-{[1-(4-Hydroxy-4-thiazol-2-yl-cyclohexyl)-azetidin-3-ylcarbamoyl]-methyl}-2,5-bis-trifluoromethyl-benzamide Step A: 3-[2-(2,5-Bis-trifluoromethyl-benzoylamino)-acetylamino]-azetidine-1-carboxylic acid tert-butyl ester

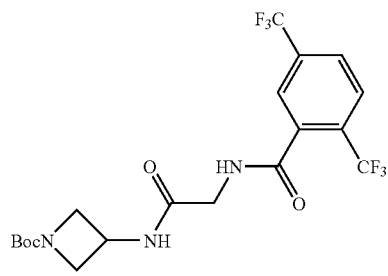 [SMILES: CC(C)(C)OC(=O)N1CC(NC(=O)CNC(=O)c2cc(C(F)(F)F)ccc2C(F)(F)F)C1]

The title compounds were prepared as white solids from EDCI coupling between 3-amino-azetidine-1-carboxylic acid tert-butyl ester and (2,5-bistrifluoromethyl-benzoylamino)-acetic acid (prepared by the method similar to Ingersoll, A. W. et. al., Organic Syntheses 1932, XII, 40-2) using the procedure described in Step C of Example 1.

ESI-MS (m/z): Calcd. For $C_{19}H_{21}F_6N_3O_4$, 469; found: 470 (M+H).

Step B: N-(Azetidin-3-ylcarbamoylmethyl)-2,5-bis-trifluoromethyl-benzamide TFA salt

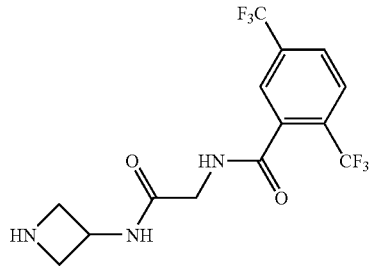 [SMILES: O=C(CNC(=O)c1cc(C(F)(F)F)ccc1C(F)(F)F)NC1CNC1]

The title compound was prepared as colorless oil from TFA de-protection of 3-[2-(2,5-bis-trifluoromethyl-benzoylamino)-acetylamino]-azetidine-1-carboxylic acid tert-butylester using the procedure described in Step D of Example 1.

$^1$H NMR (400 MHz, d$_4$-MeOH) δ 8.25 (s, 1H), 8.18 (d, J=7.0 Hz, 1H), 7.95 (d, J=7.5 Hz, 1H), 4.63 (m, 1H), 4.40 (dt, J=7.5, 5.0 Hz, 2H), 4.30 (dt, J=7.5, 4.5 Hz, 2H), 4.10 (s, 2H).

Step C: N-{[1-(4-Hydroxy-4-thiazol-2-yl-cyclohexyl)-azetidin-3-ylcarbamoyl]-methyl}-2,5-bis-trifluoromethyl-benzamide

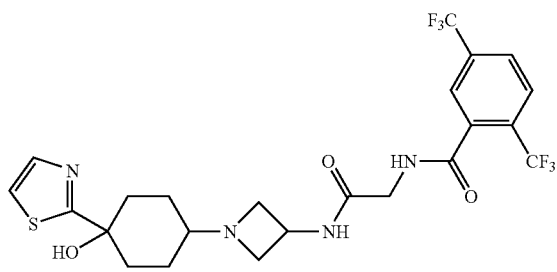 [SMILES: O=C(CNC(=O)c1cc(C(F)(F)F)ccc1C(F)(F)F)NC1CN(C2CCC(O)(c3nccs3)CC2)C1]

The title compound was prepared as white solids from reductive amination of 4-hydroxy-4-thiazol-2-yl-cyclohexanone, as prepared in Example 40 Step B, and N-(azetidin-3-ylcarbamoylmethyl)-2,5-bis-trifluoromethyl-benzamide using the procedure described in Step E of Example 1.

$^1$H NMR (400 MHz, d$_4$-MeOH) δ 8.20 (s, 1H), 7.75 (d, J=6.6 Hz, 1H), 7.63 (d, J=6.5 Hz, 1H), 7.44 (d, J=8.2 Hz, 1H), 7.35 9d, J=6.5 Hz, 1H), 4.55 (m, 1H), 4.10 (s, 2H), 3.91 (d, J=6.8 Hz, 2H), 3.20 (t, J=6.8 Hz, 2H), 2.45 (m, 1H), 2.30 (m, 1H), 2.05 (m, 4H), 1.85 (m, 2H), 1.45 (m, 2H).

Example 69

N-({1-[4-Hydroxy-4-(6-methyl-pyridin-3-yl)-cyclohexyl]-azetidin-3-ylcarbamoyl}-methyl)-2,5-bis-trifluoromethyl-benzamide

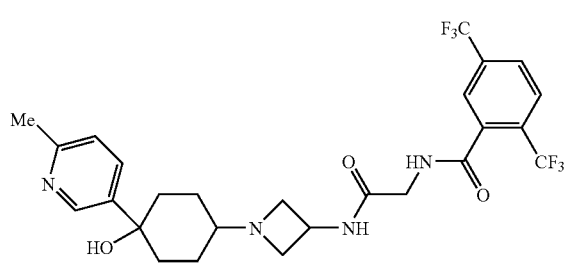 [SMILES: Cc1ccc(C2(O)CCC(N3CC(NC(=O)CNC(=O)c4cc(C(F)(F)F)ccc4C(F)(F)F)C3)CC2)cn1]

The title compounds were prepared as white solids from reductive amination of 4-hydroxy-4-(6-methyl-pyridin-3-yl)-cyclohexanone, as prepared in Example 13 Step B, and N-(azetidin-3-ylcarbamoylmethyl)-2,5-bis-trifluoromethyl-benzamide using the procedure described in Step E of Example 1.

69a: less polar isomer from silica gel column, $^1$H NMR (400 MHz, CDCl$_3$) δ 8.58 (s, 1H), 7.82 (m, 2H), 7.75 (d, J=6.6 Hz, 1H), 7.44 (m, 1H), 7.11 (d, J=6.4 Hz, 1H), 4.52 (m, 1H), 4.15 (d, J=5.5 Hz, 2H), 3.61 (d, J=6.8 Hz, 2H), 2.95 (t, J=6.8 Hz, 2H), 2.45 (s, 3H), 2.30 (m, 1H), 2.25 (m, 2H), 1.85 (m, 2H), 1.45 (m, 4H).

69b: more polar isomer from silica gel column $^1$H NMR (400 MHz, CDCl$_3$) δ 8.60 (s, 1H), 7.85 (m, 2H), 7.78 (d, J=6.5 Hz, 1H), 7.65 (d, J=6.5 Hz, 1H), 7.11 (d, J=6.6 Hz, 1H), 4.62 (m, 1H), 4.18 (d, J=5.5 Hz, 2H), 3.65 (d, J=6.6 Hz, 2H), 3.15 (t, J=6.6 Hz, 2H), 2.48 (s, 3H), 2.18 (m, 1H), 1.92 (m, 4H), 1.65 (m, 2H).

Example 70

2-Chloro-N-({1-[4-hydroxy-4-(6-methyl-pyridin-3-yl)-cyclohexyl]-azetidin-3-ylcarbamoyl}-methyl)-5-trifluoromethyl-benzamide Step A: 3-[2-(2-Chloro-5-trifluoromethyl-benzoylamino)-acetylamino]-azetidine-1-carboxylic acid tert-butylester

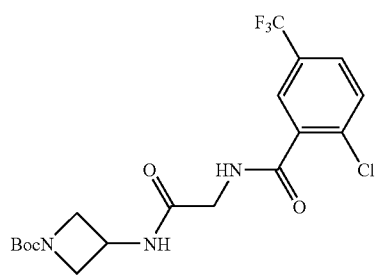 [SMILES: CC(C)(C)OC(=O)N1CC(NC(=O)CNC(=O)c2cc(C(F)(F)F)ccc2Cl)C1]

The title compounds were prepared as white solids from EDCI coupling between 3-amino-azetidine-1-carboxylic acid tert-butyl ester and (2-chloro-5-trifluoromethyl-benzoylamino)-acetic acid (prepared by the method similar to Ingersoll, A. W. et. al., Organic Syntheses 1932, XII, 40-2) using the procedure described in Step C of Example 1.

ESI-MS (m/z): Calcd. For C$_{18}$H$_{21}$ClF$_3$N$_3$O$_4$, 435; found: 436 (M+H).

Step B: N-(Azetidin-3-ylcarbamoylmethyl)-2-chloro-5-trifluoromethyl-benzamide TFA salt

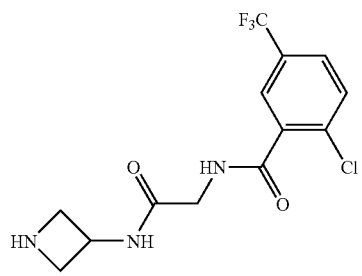 [SMILES: O=C(CNC(=O)c1cc(C(F)(F)F)ccc1Cl)NC1CNC1]

The title compound was prepared as colorless oil from TFA de-protection of 3-[2-(2-chloro-5-trifluoromethyl-benzoylamino)-acetylamino]-azetidine-1-carboxylic acid tert-butylester using the procedure described in Step D of Example 1.

$^1$H NMR (400 MHz, d$_4$-MeOH) δ 8.00 (s, 1H), 7.82 (d, J=6.0 Hz, 1H), 7.74 (d, J=6.5 Hz, 1H), 4.70 (m, 1H), 4.45 (dt, J=7.0, 4.5 Hz, 2H), 4.28 (dt, J=7.0, 4.5 Hz, 2H), 4.12 (s, 2H).

Step C: 2-Chloro-N-({1-[4-hydroxy-4-(6-methyl-pyridin-3-yl)-cyclohexyl]-azetidin-3-ylcarbamoyl}-methyl)-5-trifluoromethyl-benzamide

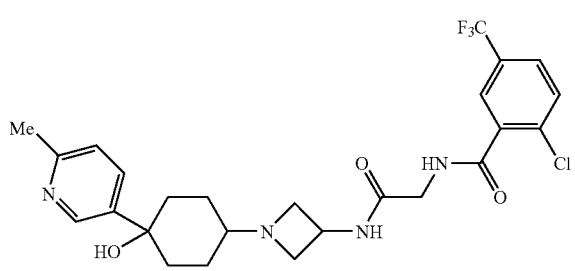 [SMILES: Cc1ccc(C2(O)CCC(N3CC(NC(=O)CNC(=O)c4cc(C(F)(F)F)ccc4Cl)C3)CC2)cn1]

The title compounds were prepared as white solids from reductive amination of 4-hydroxy-4-(6-methyl-pyridin-3-yl)-cyclohexanone, as prepared in Example 13 Step B, and N-(azetidin-3-ylcarbamoylmethyl)-2-chloro-5-trifluoromethyl-benzamide using the procedure described in Step E of Example 1.

70a: less polar isomer from silica gel column,
$^1$H NMR (400 MHz, CDCl$_3$) δ 8.60 (s, 1H), 7.90 (s, 1H), 7.75 (d, J=6.6 Hz, 1H), 7.61 (d, J=6.4 Hz, 2H), 7.52 (d, J=6.0 Hz, 1H), 7.35 (d, J=6.0 Hz, 1H), 7.2 (d, J=6.2 Hz, 1H), 5.70 (d, br, 2H), 4.55 (m, 1H), 4.15 (d, J=5.5 Hz, 2H), 3.60 (d, J=6.8 Hz, 2H), 2.95 (t, J=6.8 Hz, 2H), 2.51 (s, 3H), 2.30 (m, 1H), 2.25 (m, 2H), 1.85 (m, 2H), 1.45 (m, 4H).

70b: more polar isomer from silica gel column
$^1$H NMR (400 MHz, CDCl$_3$) δ 8.58 (s, 1H), 7.92 (s, 1H), 7.70 (d, J=6.2 Hz, 1H), 7.65 (d, J=6.0 Hz, 1H), 7.55 (d, J=6.5 Hz, 1H), 7.42 (m, 1H), 7.40 (d, J=6.5 Hz, 1H), 7.11 (d, J=6.6 Hz, 1H), 4.65 (m, 1H), 4.18 (d, J=5.5 Hz, 2H), 3.65 (d, J=6.6 Hz, 2H), 3.15 (t, J=6.6 Hz, 2H), 2.50 (s, 3H), 2.38 (m, 1H), 2.20 (m, 2H), 1.92 (m, 4H), 1.65 (m, 2H).

Example 71

N-[2-([1-[trans-4-Hydroxy-4-(1,3-thiazol-5-yl)cyclohexyl]-3-azetidinyl]amino)-2-oxoethyl]-3-(trifluoromethyl)benzamide, 40a (hemisuccinate and free-base monohydrate)

Step A: 2-(3-(trifluoromethyl)benzamido)acetic acid, 3

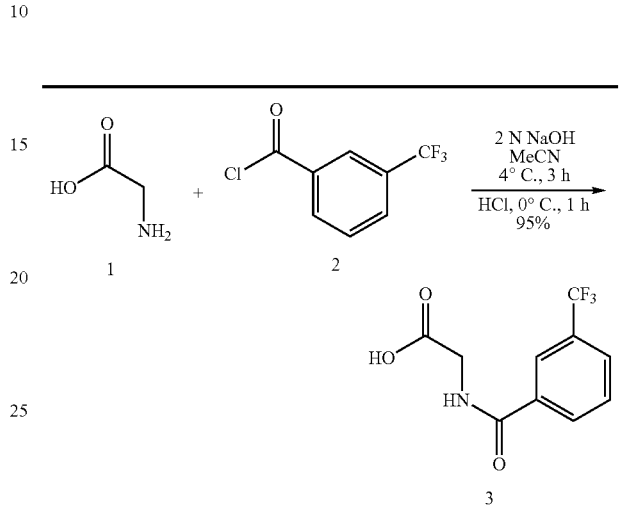

| compound/reagent name | Purity (%) | MW | d (g/mL) | eq. | mol | wt. or vol. |
|---|---|---|---|---|---|---|
| Glycine (1) | 99.00 | 75.07 | 1.00 | 1.00 | 4.19 | 320.0 g |
| 3-(Trifluoromethyl)benzoyl chloride (2) | 97.00 | 208.57 | 1.38 | 0.98 | 4.12 | 885.0 g |
| Acetonitrile | 99.0 | 41.05 | 0.78 | | 22.67 | 1.2 L |
| Sodium Hydroxide | 2.00 M | 40.00 | 1.04 | 2.53 | 10.62 | 5.31 L |
| Acetonitrile | 99.0 | 41.05 | 0.78 | | 14.17 | 0.75 L |

A 12-L 4-neck round bottom flask equipped with a thermocouple controller, mechanical stirrer, heating mantle, condenser and a nitrogen in/outlet adapter was charged with gycine (1, Alfa Aesar) (318 g; 4.19 mol), acetonitrile (1.2 L), and a solution of sodium hydroxide (5.31 L; 10.62 mo) and the mixture was cooled to 4° C. with stirring. A solution of 3-(trifluoromethyl)benzoyl chloride (2, Alfa Aesar) (885.0 g; 4.12 mol) (640 mL) in acetonitrile (0.75 L) (total 1.39 L) was added dropwise over 2 h while the internal temperature was maintained between 4-6° C., and the slightly orange-pinkish solution was stirred at 4° C. for an additional 30 min. The reaction was acidified to pH=3 with conc. 37% HCl solution (400 mL added over 30 min) at 0-6° C., and stirred for 1 h at 0° C. (until a slightly yellowish suspension resulted). The solid was collected by filtration, washed with cold (0° C.) deionized ("D.I") H$_2$O (300 mL×2), dried under air-suction for 2 h, and then placed in a drying oven at 60° C. under house vacuum (120 mmHg) for 20 h to afford pure 3 as an off-white solid. The filtrate was extracted with EtOAc (1 L×2), and the combined organic phases washed with brine (300 mL), and concentrated at 66° C. under house vacuum and then high vacuum (20 mmHg) to give crude product as an off-white waxy solid, which was triturated and sonicated with toluene (1 L) and stirred at 10° C. for 1 h. The resulting solid was collected by filtration, washed with hexanes (50 mL×2), dried in an vacuum oven at 50° C. under house vacuum to afford additional pure title compound, 3, as an off-white solid. The structure of 3 was confirmed with its ¹H-NMR.

Step B: 3-[2-(3-Trifluoromethyl-benzoylamino)-acetylamino]-azetidine-1-carboxylic acid tert-butyl ester, 5

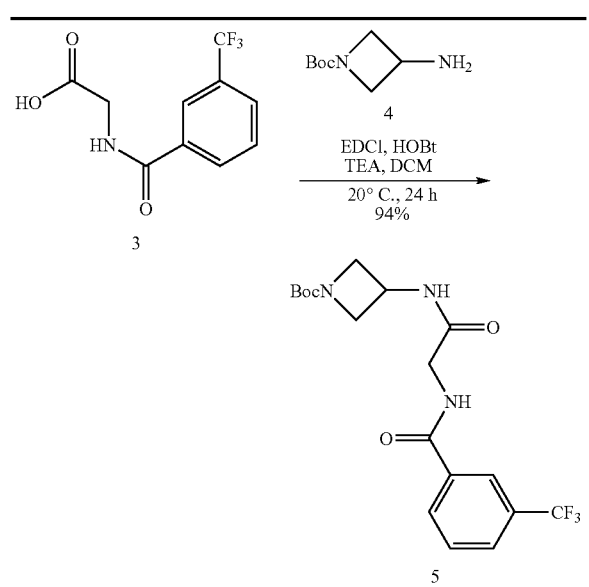

| compound/ reagent name | Purity (%) | MW | d (g/mL) | eq. | mol | wt. or vol. |
|---|---|---|---|---|---|---|
| 3 | 99.0 | 247.17 | 1.00 | 1.00 | 2.40 | 600.0 g |
| N-Boc-3-(amino)azetidine (4) | 98.00 | 172.23 | 1.38 | 1.06 | 2.55 | 448.0 g |
| HOBT | 98.00 | 135.13 | 1.00 | 0.117 | 0.28 | 37.7 g |
| EDCl | 99.00 | 191.70 | 1.02 | 1.42 | 3.41 | 660.0 g |
| Triethylamine | 99.0 | 101.19 | 0.73 | 1.30 | 3.13 | 0.44 L |
| Dichloromethane | 99.0 | 84.93 | 1.32 | | 135.91 | 8.8 L |

To a 22-L 4-neck round bottom flask equipped with a thermocouple controller, mechanical stirrer, heating mantle, condenser and a nitrogen inlet adapter was charged with acid 3 as prepared in the previous step (600 g; 2.40 mol), dichloromethane (8.8 L), TEA (440 mL; 3.13 mol), N-Boc-3-(amino)azetidine (4, CNH Technologies, Inc.) (448 g; 2.55 mol) and HOBT (37.7 g; 0.28 mol, AK Scientific), and the mixture was stirred at 20° C. for 5 min, EDCI (506 g; 2.64 mol; 1.1 eq., AK Scientific) was added as one portion. The mixture was stirred at 20° C. for an additional 6 h. More EDCI (120.0 g, 0.626 mol; 0.26 eq) was added and the reaction was stirred at 20° C. for 20 h. EDCI (33.3 g; 0.174 mol; 0.05 eq.) was added again at the 21st h and the reaction was stirred at 20° C. for an additional 4 h. The reaction was washed with saturated NaHCO₃ (4 L×2) (aqueous pH=9) and brine (3 L×2), and the separated organic phase was concentrated at 60° C. under house vacuum (120 mmHg) and then high vacuum (20 mmHg) to give crude 5 as a yellowish think syrup.

To a 22-L 4-neck round bottom flask equipped with a thermocouple controller, mechanical stirrer, heating mantle, condenser and a nitrogen inlet adapter was charged a warm solution (60° C.) of crude 5 in EtOAc (3.1 L) and the mixture was heated to 73° C. with stirring, while warm (60° C.) heptane (10.0 L) was added as five portions (2 L×5) over 30 min. The resulting slightly white turbid solution was stirred at 73° C. for 10 min. The heating mantle was removed and the mixture was gradually cooled to 20° C. over 3 h, and further to 10° C. in a water bath and stirred for 1 h. The solid was collected by filtration, washed with hexanes (300 mL×2), dried under air-suction and then placed in a drying oven at 50° C. under house vacuum for 20 h to afford pure title compound, 5, as an off-white crystalline solid. The structure of 5 was confirmed by ¹H-NMR.

Step C: N-(Azetidin-3-ylcarbamoylmethyl)-3-trifluoromethyl-benzamide sulfate salt, 6

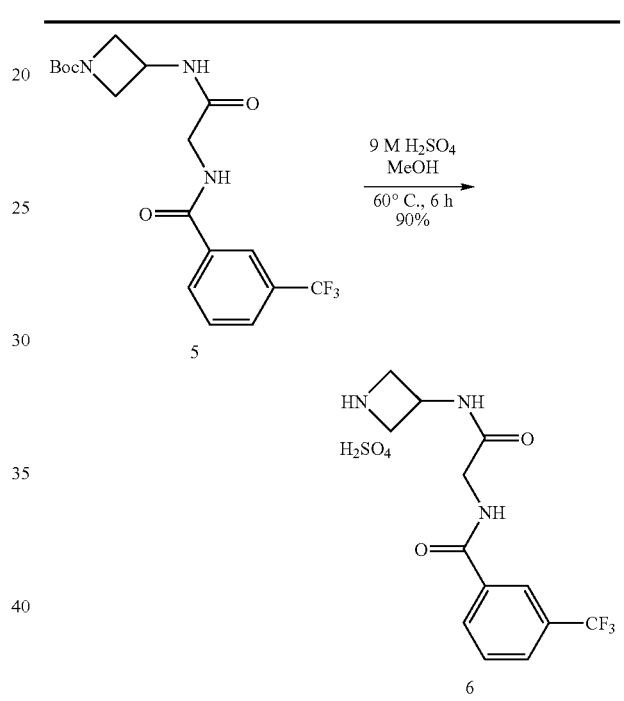

| compound/ reagent name | Purity (%) | MW | d (g/mL) | eq. | mol | wt. or vol. |
|---|---|---|---|---|---|---|
| 5 | 99.60 | 401.39 | 1.00 | 1.0 | 1.08 | 434.0 g |
| Sulfuric Acid | 48.0 (9.03 M) | 98.08 | 1.11 | 1.25 | 1.35 | 150 mL |
| Methanol | 99.0 | 32.04 | 0.79 | | 86.48 | 3.5 L |
| Sodium Bicarbonate | 99.0 | 84.01 | 2.17 | 4.63 | 5.00 | 420.0 g |

A 12-L 4-neck round bottom flask equipped with a thermocouple, a mechanical stirrer, a condenser, and a nitrogen inlet adapter was charged with Boc-protected intermediate 5 as prepared in the previous step (434 g; 1.08 mol) and methanol (3.5 L) and the solution was stirred at 20° C. under nitrogen. A solution of 9 M H₂SO₄ (140 mL; 1.26 mol) was added dropwise over 3 min, and then the mixture was warmed to 60° C. and stirred for 6 h. The reaction was cooled to 40° C. and NaHCO₃ (420 g; 5.00 mol) was added as one portion and stirred at 12-16° C. for 1 h. The white solid was removed by filtration and washed with MeOH (200 mL×3) and then discarded after being checked by HPLC. The filtrate (total about 4.0 L) was concentrated at 50° C. under high vacuum (20 mmHg) and chased with MeOH (1 L) once to afford crude title compound, 6, as an off-white foamy solid, which was kept at 0° C. in the dark under N₂ and used for futher reaction without additional purification. The structure of compound 6 was confirmed by ¹H-NMR.

Step D:
8-Thiazol-5-yl-1,4-dioxa-spiro[4.5]decan-8-ol, 9

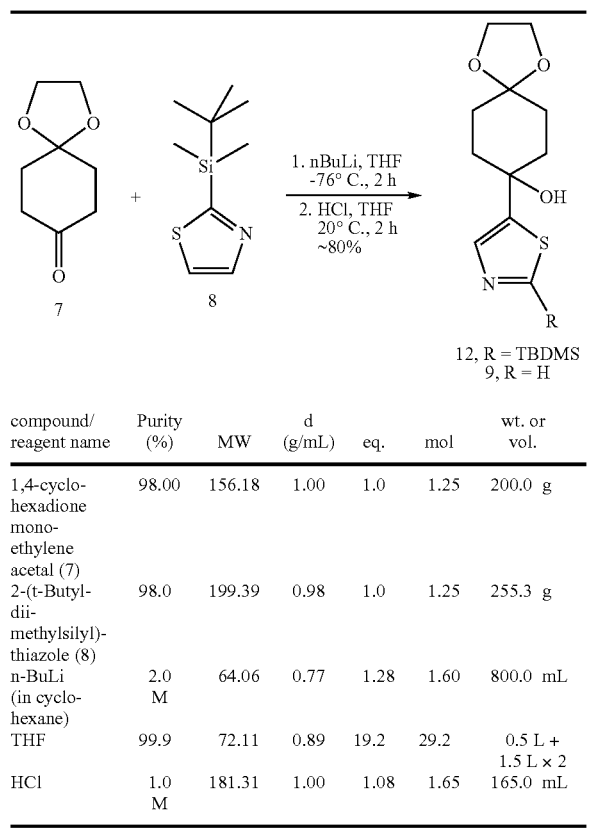

| compound/ reagent name | Purity (%) | MW | d (g/mL) | eq. | mol | wt. or vol. |
|---|---|---|---|---|---|---|
| 1,4-cyclo-hexadione mono-ethylene acetal (7) | 98.00 | 156.18 | 1.00 | 1.0 | 1.25 | 200.0 g |
| 2-(t-Butyl-dii-methylsilyl)-thiazole (8) | 98.0 | 199.39 | 0.98 | 1.0 | 1.25 | 255.3 g |
| n-BuLi (in cyclo-hexane) | 2.0 M | 64.06 | 0.77 | 1.28 | 1.60 | 800.0 mL |
| THF | 99.9 | 72.11 | 0.89 | 19.2 | 29.2 | 0.5 L + 1.5 L × 2 |
| HCl | 1.0 M | 181.31 | 1.00 | 1.08 | 1.65 | 165.0 mL |

A 12-L 4-neck round bottom flask equipped with a thermocouple, a mechanical stirrer, a pressure-equalization dropping funnel, a septum and a nitrogen inlet/outlet adapter was charged with THF (0.5 L) and cooled to −50° C. Butyl Lithium (800. mL, 1.60 mol. 2.0 M in cyclohexane) was added via a cannula under mild nitrogen pressure. A solution of 2-(t-butyldiimethylsilyl)thiazole (255.3 g, 1.25 mol, Synthonix) in THF (1.51 L) was added dropwise over 45 min while the internal temperature was maintained between −51° C. to −48° C. The resulting clear yellow-greenish solution was stirred at −50 to −53° C. for 30 min and then cooled to −73° C. A solution of 1,4-cyclohexadione monoethylene acetal (200.0 g; 1.25 mole, AK Scientific) in THF (1.5 L) was added dropwise over 50 min and the mixture was stirred at −76° C. for 2 h. The progress of the reaction was monitered by HPLC and LC-MS. The reaction was quenched with saturated NaHCO₃ (1.0 L), and then diluted with D.I H₂O (2.0 L) and EtOAc (3.5 L) with fast stirring. The dry-ice bath was replaced with a water bath and the mixture was stirred for 20 min. After phase separation, the aqueous was extracted with EtOAc (3 L), and the combined organic phase was washed with brine (800 mL) and then concentrated at 68° C. under hi-vac (20 mmHg) to afford crude intermediate 12 as a slightly brownish thick oil.

To a 2-L 3-neck round bottom flask was charged with a solution of the above crude 12 (472.7 g) in THF (2 L), 1.0 N HCl (165 mL, 0.165 mol) was added as one portion and the mixture was stirred at 28-24° C. for 2 h. The progress of the reaction was monitored by HPLC and LC-MS. The reaction was cooled to 0° C., the pH of the mixture was adjusted to 9-10 by addition of 1 N NaOH (220 mL), and then the solvent was concentrated at 60° C. under hi-vac (20 mmHg). The resulting material was dissolved in EtOAc (4 L) and washed with saturated NaHCO₃ (800 mL). After phase separation, solid NaCl was added to the aqueous phase, which was extracted with EtOAc (2 L) again. The organic phases were combined and concentrated at 68° C. under hi-vac (20 mmHg) to afford crude product, 9, as an off-white waxy solid. The crude 9 (352.4 g) was suspended in hexane (1.5 L) and then stirred at 20° C. with sonication for 20 min; the resulting white solid was collected by filtration, washed with hexane (300 mL×2), air-dried and then placed in a drying oven at 60° C. for 20 h to afford pure 9 as a white crystalline solid, which was used in next step without further purification. The structure of compound 9 was confirmed by ¹H NMR.

Step E: 4-Hydroxy-4-thiazol-5-yl-cyclohexanone, 10

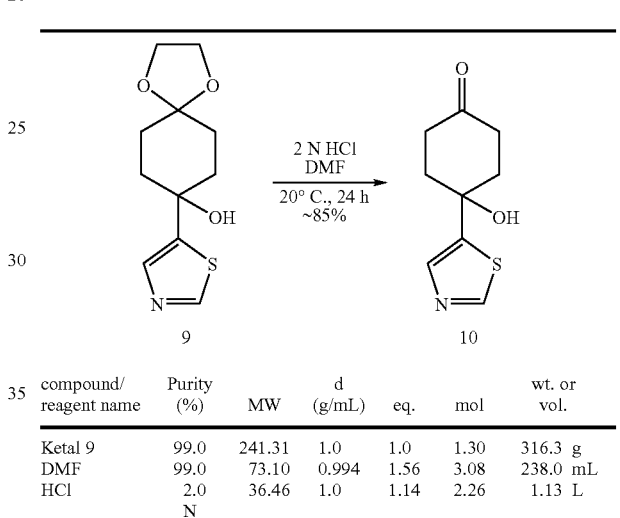

| compound/ reagent name | Purity (%) | MW | d (g/mL) | eq. | mol | wt. or vol. |
|---|---|---|---|---|---|---|
| Ketal 9 | 99.0 | 241.31 | 1.0 | 1.0 | 1.30 | 316.3 g |
| DMF | 99.0 | 73.10 | 0.994 | 1.56 | 3.08 | 238.0 mL |
| HCl | 2.0 N | 36.46 | 1.0 | 1.14 | 2.26 | 1.13 L |

A 5-L 4-neck round bottom flask equipped with a thermocouple, a mechanical stirrer, a condenser, and a nitrogen inlet/outlet adapter was charged with ketal 9 as prepared in the previous step (316.3 g, 1.30 mol) and DMF (238.0 mL) with stirring. A solution of 2 N HCl (1.13 L, 2.26 mol) was added over 2 min; the mixture was stirred at 26° C. for 5 min, warmed up to 60° C., and stirred for 3 h. The progress of the reaction was monitored by HPLC and LC-MS. The reaction was cooled to 0° C. in an ice-water bath, and the aqueous (pH=2~3) was adjusted to an alkaline (pH=10~11) by dropwise addition of 4 N NaOH solution with fast agitation. The resulting alkaline slurry was stirred at 0° C. for 1 h; the solid was collected by filtration, washed with cold water (100 mL), dried under air-suction for 1 h, and then placed in a vacuum drying oven under house vacuum (120 mmHg) at 50° C. for 48 h to afford the title compound, 10 as a beige crystalline solid.

The filtrate was saturated with solid NaCl and extracted with EtOAc (1 L×4). The combined extract was washed with brine (500 mL) and concentrated at 68° C. under hi-vac (20 mmHg) for 1 h to afford recovered impure 10 as orange waxy solid. This impure 10 was suspended in EtOAc/hexanes (100/200, mL/mL) at 66° C. with sonication and then stirred at 20 for 1 h. The brightly yellowish solid was collected by filtration, washed with hexane (50 mL×2), air-dried and then placed in a drying oven under house vacuum (120 mmHg) at 50° C. for 20 h to afford an additional amount of purer title compound, 10 as yellowish solid. The structure of compound 10 was confirmed by ¹H NMR.

Step F: N-[2-([1-[trans-4-Hydroxy-4-(1,3-thiazol-5-yl)cyclohexyl]-3-azetidinyl]-amino)-2-oxoethyl]-3-(trifluoromethyl)benzamide, 40a

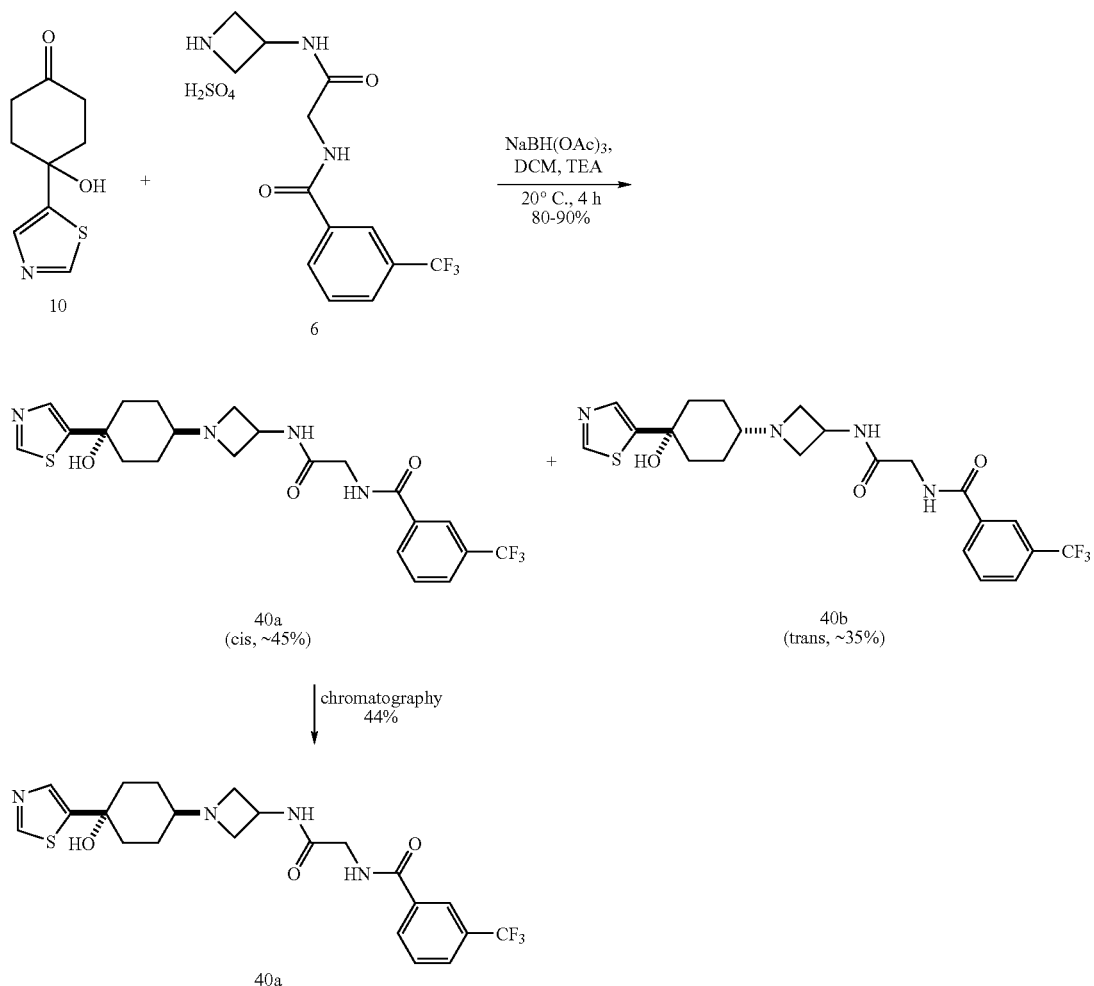

| compound/<br>reagent name | Purity<br>(%) | MW | d<br>(g/mL) | eq. | mol | wt. or<br>vol. |
|---|---|---|---|---|---|---|
| 6 ($H_2SO_4$ salt) | 90.0 | 301.10 | 1.00 | 1.03 | 0.87 | 291.04 g |
| Ketone 10 | 98.0 | 197.26 | 1.00 | 1.0 | 0.845 | 170.0 g |
| Sodium Triacetoxyboro-hydride (NaBH(OAc)$_3$) | 95.0 | 211.94 | 1.00 | 1.23 | 1.04 | 231.76 g |
| MeCN | 99.9 | 41.05 | 0.78 | | 92.1 | 4.82 L |

A 22-L 4-neck round bottom flask equipped with a thermocouple, a mechanical stirrer, a condenser, and a nitrogen inlet/outlet adapter was charged with 6 $H_2SO_4$ salt, as prepared in Step C of this example (291.04 g, 0.870 mol), MeCN (4.82 L) and ketone 10, as prepared in the previous step (170.0 g, 0.845 mol). The slightly yellowish suspension was stirred at 16° C. for 10 min and then treated with NaBH(OAc)$_3$ (231.76 g, 1.04 mol, Alfa Asear) was added over 5 min and the mixture was stirred at 28-20° C. for 2 h. The progress of the reaction was monitored by HPLC and LC-MS. A solution of saturated NaHCO$_3$ (2.5 L) was added to the reaction mixture followed by the addition of EtOAc (2.5 L), and the resulting mixture was stirred fast for 10 min. After phase separation, the aqueous (pH=8~9) was extracted with EtOAc (2.0 L), and the combined organic was washed with brine (2.0 L) and concentrated at 66° C. under high vacuum (20 mmHg) to afford a mixture of 40a and 40b as white foamy solid.

The above crude 40a/40b mixture was separated with Combi Flash® Companion® XL Preparative HPLC system using a Redi Sep® normal phase column (9×1.5 Kg), and eluted with 7 N NH$_3$ in MeOH/EtOAc (from 0%/100% to 6.5%/93.5% with flow rate=300 mL/min and monitored under UVmax=230 nm), to afford pure 40a free base as a white foamy solid. The structure of compound 40a was confirmed by $^1$H NMR.

Step G: N-[2-([1-[trans-4-Hydroxy-4-(1,3-thiazol-5-yl)cyclohexyl]-3-azetidinyl]amino)-2-oxoethyl]-3-(trifluoromethyl)benzamide hemisuccinate

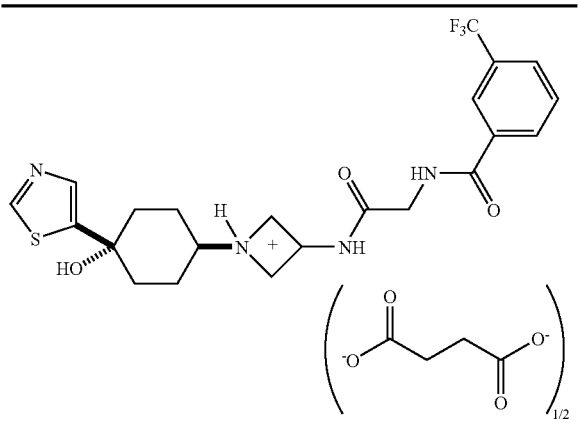

| compound/ reagent name | Purity (%) | MW | d (g/mL) | eq. | mol | wt. or vol. |
|---|---|---|---|---|---|---|
| 40a (free base) | 99.0 | 482.53 | 1.00 | 1.0 | 0.872 | 420.5 g |
| Succinic acid | 98.8 | 118.09 | 1.56 | 0.51 | 0.444 | 52.48 g |
| EtOAc | 99.0 | 88.11 | 0.90 | 19.7 | 17.2 | 1.682 L |
| EtOH | 99.99 | 46.07 | 0.79 | 8.29 | 7.22 | 0.425 L |

To a 4-neck 5-L round bottom flask equipped with a thermocouple, mechanical stirrer, an additional funnel, a condenser, and nitrogen inlet adapter was charged with the 40a free base (420.5 g, 0.872 mol) as prepared in the previous step, succinic acid (52.48 g; 0.444 mol) and EtOAc (1.682 L). The solution was warmed to 63° C. with stirring under nitrogen, and EtOH (0.421 L) was added with stirring until succinic acid was completely dissolved to become a clear solution. The solution was gradually cooled to 20° C. and stirred for 2 h; further cooled to 5° C. and stirred for an additional hour. The solid was collected by filtration and then placed in a vacuum oven at 65° C. for 72 h to afford the title compound as a white crystalline solid. The structure of the hemisuccinate salt of 40a was confirmed by $^1$H NMR.

Step H: Crystallization of 40a (free base monohydrate) from hemisuccinate N-[2-([1-[trans-4-Hydroxy-4-(1,3-thiazol-5-yl)cyclohexyl]-3-azetidinyl]amino)-2-oxoethyl]-3-(trifluoromethyl)benzamide monohydrate 40a

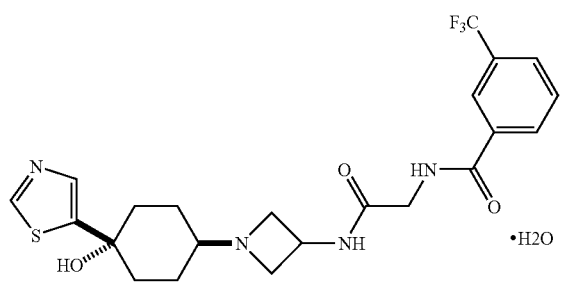

To a 125 mL Erlenmeyer flask equipped with a magnetic stir bar, a magnetic stir plate and 125 mL additional funnel was charged with the 40a hemisuccinate salt (2.53 g, 0.872 mol) as prepared in the previous step, and 12 mL of water. To the resulting solution, 0.2 N NaOH (58 mL) was added with stirring over the course of 4 h. The resulting suspension was stirred overnight. The solid was collected by filtration and dried under ambient laboratory conditions to afford the title compound as a white crystalline solid.

Step I: Crystallization of 40a (free base monohydrate) from free base N-[2-([1-[trans-4-Hydroxy-4-(1,3-thiazol-5-yl)cyclohexyl]-3-azetidinyl]amino)-2-oxoethyl]-3-(trifluoromethyl)benzamide monohydrate 40a To a 10 mL vial equipped with a magnetic stir bar, placed on a heating magnetic stir plate was charged with 10 mg of 40a free base as previously isolated in step F of this example, and 0.1 mL of methyl ethyl ketone. The resulting suspension was heated to reflux until the compound dissolved (a few minutes). The stir bar was removed and the solution was allowed to cool to ambient temperature. After one day, a crystalline material precipitated from solution. The supernatant was removed by pipet and the crystals were air dried under ambient laboratory conditions for 1 day to afford the title compound as a white crystalline solid.

Example 72

N-[2-([1-[trans-4-hydroxy-4-(1,3-thiazol-5-yl)cyclohexyl]-3-azetidinyl]amino)-2-oxoethyl]-3-(trifluoromethyl)benzamide monohydrate (40a freebase monohydrate)

Step A: N-[2-([1-[4-hydroxy-4-(1,3-thiazol-5-yl)cyclohexyl]-3-azetidinyl]amino)-2-oxoethyl]-3-(trifluoromethyl)benzamide

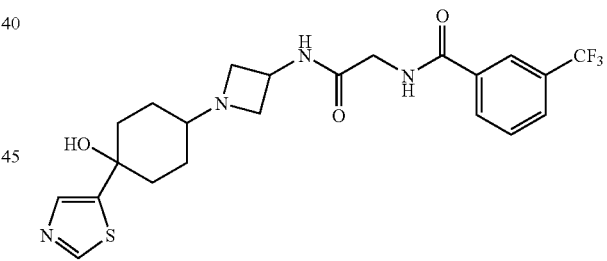

N-[2-(3-azetidinylamino)-2-oxoethyl]-3-(trifluoromethyl)benzamide (3.44 kg, 4.8 w/w % in 2-MeTHF, 0.548 mol) in 2-methyl tetrahydrofuran (2-MeTHF, 3.3 kg) was added to an inertisized reactor. 4-hydroxy-4-(1,3-thiazol-5-yl)cyclohexanone (108.1 g, 0.537 mol) was added. Pt/C 5% wet (213.8 g) was added. The reactor was rinsed three times with $N_2$, then rinsed three times with $H_2$ and stirred vigorous for 12 hours at 25° C. and 1 bar $H_2$. The catalyst was filtered and the mother liquor cooled to 15° C. 1N HCl (866 ml) was added to the mother liquor. Water (510 ml) was added and the mixture stirred for 30 minutes at 25° C. The layers were allowed to separate during 30 minutes and the organic layer was removed. 607 ml of isopropyl acetate (iPrOAc) was added to the water layer and stirred for 10 minutes. The layers were allowed to separate and the organic layer was removed. iPrOAc (607 ml) was added to the water layer and stirred for 10 minutes; the layers were allowed to separate and the organic layer was removed. 790 ml of iPrOAc was added to the water layer. Then, NaOH 50% (75.10 g) was added. The mixture was heated to 55° C., stirred for 30 minutes at 55° C., cooled to 25° C. over 2 hours and stirred for 3 hours at 25° C. The precipitate was filtered, washed with 152 ml iPrOAc and then washed three times with 152 ml water. The precipitate was dried for 20 hours at 40° C. under vacuum and $N_2$ atmosphere to afford the title compound.

Step B: N-[2-([1-[trans-4-hydroxy-4-(1,3-thiazol-5-yl)cyclohexyl]-3-azetidinyl]amino)-2-oxoethyl]-3-(trifluoromethyl)benzamide monohydrate

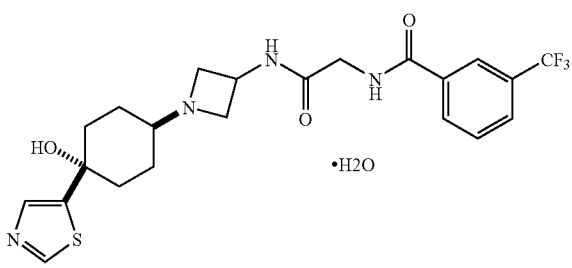

Solution 1 was prepared as follows: 3000 ml methyl isobutyl ketone (MIK) and 8.17 ml water were added to a 4-neck flask and stirred for 30 minutes. N-[2-([1-[trans-4-hydroxy-4-(1,3-thiazol-5-yl)cyclohexyl]-3-azetidinyl]amino)-2-oxoethyl]-3-(trifluoromethyl)benzamide (394 g), as prepared in the previous step, and 1500 ml of solution 1 were added to a 4-neck flask and heated to 80° C. The insoluble matter was filtered off, washed with 80 ml of solution 1 and the filtrate added to the reaction mixture. Solution 1 was distilled under atmospheric pressure to provide 790 ml and this 790 ml of solution 1 was added to the reaction mixture. The reaction mixture was cooled with stirring to 0° C. A precipitate crystallized from the reaction mixture. The precipitate was filtered, washed with MIK (2×130 ml) and dried for 20 hours at 40° C. under vacuum and $N_2$ atmosphere to provide crude title compound as a white solid.

Recrystallization. MIK (37.6 ml) and water (4 ml) were added to a reactor and stirred for 30 minutes at 25° C. The layers were allowed to separate during 30 minutes and the water layer was removed. Crude N-[2-([1-[trans-4-hydroxy-4-(1,3-thiazol-5-yl)cyclohexyl]-3-azetidinyl]amino)-2-oxoethyl]-3-(trifluoromethyl)benzamide hydrate (10 g) was added and the reaction heated to reflux and stirred for 10 minutes. The reaction mixture was cooled to 94° C. at a rate of 0.5° C./min and stirred for 10 minutes. The reaction mixture was cooled with a linear cooling curve over 11 hours to 0° C. and stirred for 2 hours at 0° C. to provide a precipitate. The precipitate was filtered, washed twice with 4 ml of MIK and dried for 20 hours at 30° C. under vacuum and $N_2$ atmosphere to provide the title compound, N-[2-([1-[trans-4-hydroxy-4-(1,3-thiazol-5-yl)cyclohexyl]-3-azetidinyl]amino)-2-oxoethyl]-3-(trifluoromethyl)benzamide hydrate, as a white solid.

Example 73

Powder X-Ray Diffraction Data for N-[2-([1-[trans-4-hydroxy-4-(1,3-thiazol-5-yl)cyclohexyl]-3-azetidinyl]amino)-2-oxoethyl]-3-(trifluoromethyl)benzamide monohydrate (40a freebase monohydrate)

In order to minimize the possible effects of preferred orientation, a sample of 40a (free base monohydrate) was moderately triturated using an agate mortar and pestle to reduce particle size. The 40a (free base monohydrate) was analyzed both untreated and ground. The diffraction patterns were compared to verify that no change had occurred in the crystal form due to grinding.

Analysis was performed using a Philips X'Pert Pro MPD diffractometer (PANalytical B.V., Almelo, the Netherlands). Each sample was backloaded and analyzed in a 16 mm sample holder. Using the X-Celerator detector (PANalytical B.V., Almelo, the Netherlands), each sample was scanned from 3 to 35° 2θ at a step size of 0.0165° 2θ and a time per step of 10.16 seconds. The effective scan speed was 0.2067°/s. Instrument voltage and current settings of 45 kV and 40 mA were employed.

Figure 2:
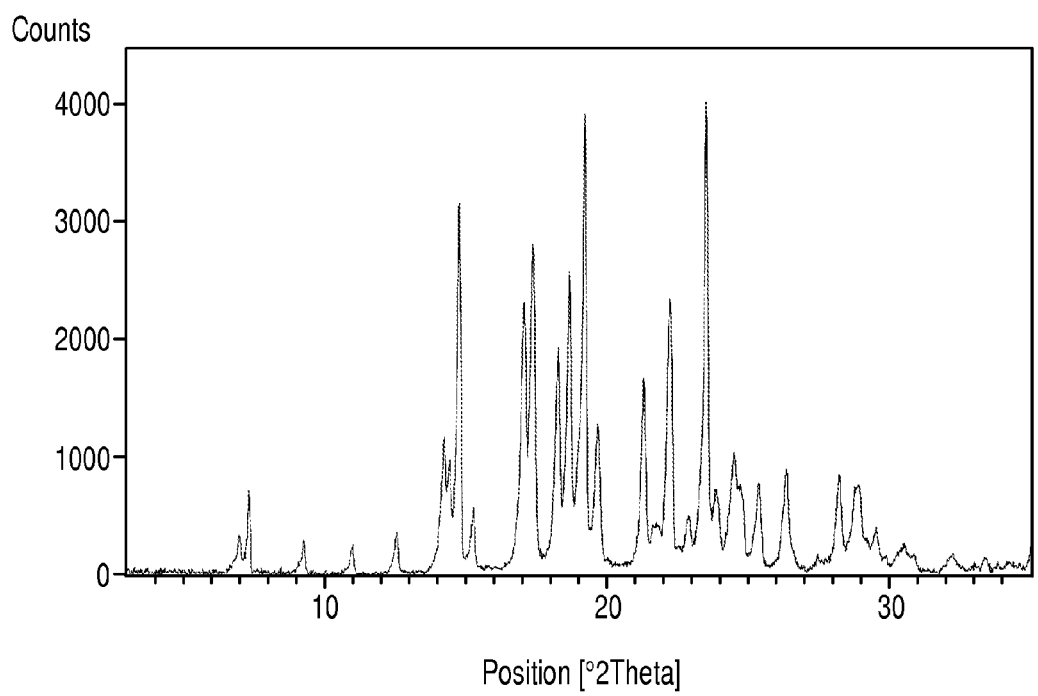
FIG. 2 is an X-ray powder diffraction pattern of the ground sample of compound 40a (freebase monohydrate) expressed in terms of ° 2θ.

A comparison of the diffraction patterns of the untreated and ground samples is presented in FIG. 1. The data showed that significant preferred orientation occurred for the untreated sample as evidenced by the intense peaks at ca. 7.4, 14.8 and 22.3° 2θ. This preferred orientation was significantly reduced by grinding. A separate display of the diffraction pattern of the ground sample is presented in FIG. 2. A tabulation of the corresponding d-spacings and °2θ values for the diffraction peaks of the ground sample of 40a (freebase monohydrate) with relative intensities >5% are presented in Table 1.

TABLE 1

| D-Spacings and °2θ Values of the Diffraction Peaks of JNJ-41443532-ZAF, Batch 32641161 JNJ-41443532-ZAF, Batch 32641161 | |
|---|---|
| Position [°2θ] | d-spacing [Å] |
| 7.0 | 12.6 |
| 7.4 | 12.0 |
| 9.3 | 9.50 |
| 11.0 | 8.02 |
| 12.6 | 7.04 |
| 14.3 | 6.21 |
| 14.4 | 6.13 |
| 14.8 | 5.99 |
| 15.3 | 5.80 |
| 17.1 | 5.20 |
| 17.4 | 5.10 |
| 18.3 | 4.85 |
| 18.7 | 4.75 |
| 19.2 | 4.62 |
| 19.7 | 4.51 |
| 21.3 | 4.17 |
| 21.8 | 4.08 |
| 22.2 | 4.00 |
| 22.9 | 3.89 |
| 23.5 | 3.79 |
| 23.9 | 3.73 |
| 24.5 | 3.64 |
| 24.7 | 3.60 |
| 25.3 | 3.51 |
| 26.3 | 3.39 |
| 28.2 | 3.17 |
| 28.8 | 3.10 |
| 29.5 | 3.03 |

Example 74

In Vitro Biological Data

Compounds of the invention were subjected to various representative biological tests. The results of these tests are intended to illustrate the invention in a non-limiting fashion.

MCP-1 Receptor Binding Assay in THP-1 Cells

Human monocytic cell line THP-1 cells were obtained from American Type Culture Collection (Manassas, Va., USA). The THP-1 cells were grown in RPMI-1640 (RPMI: Roswell Park Memorial Institute Medium-cell culture growth media) supplemented with 10% fetal bovine serum in a humidified 5% $CO_2$ atmosphere at 37° C. The cell density was maintained between $0.5 \times 10^6$ cells/mL.

THP-1 (cells were incubated with 0.5 nM $^{125}I$ labeled MCP-1 (Perkin-Elmer Life Sciences, Inc. Boston, Mass.) in the presence of varying concentrations of either unlabeled MCP-1 (R & D Systems, Minneapolis, Minn.) or test compound for 2 hours at 30° C. in a 96 well plate. Cells were then harvested onto a filter plate, dried, and 20 μL of Microscint 20 was added to each well. Plates were counted in a TopCount NXT, Microplate Scintillation & Luminescence Counter (Perkin-Elmer Life Sciences, Inc. Boston, Mass.). Blank values (buffer only) were subtracted from all values and drug treated values were compared to vehicle treated values. 1 μM cold MCP-1 was used for nonspecific binding.

Table 2 lists $IC_{50}$ values for inhibition of MCP-1 binding to CCR2 obtained for test compounds of the invention. Where an $IC_{50}$ value was not obtained for a particular compound, the percent inhibition is provided at a test concentration of 25 μM.

TABLE 2

Inhibition of MCP-1 Binding $IC_{50}$

| Example | CCR2 Binding (nM) |
|---|---|
| 1a | 44 |
| 2 | 290 |
| 3a | 210 |
| 4a | 71 |
| 5a | 18 |
| 6a | 190 |
| 7a | 1,900 |
| 8 | 26 |
| 9 | 49 |
| 10 | 17 |
| 11 | 28 |
| 12 | 170 |
| 13a | 45 |
| 14a | 215 |
| 15 | 190 |
| 16 | 6,450 |
| 17 | 6,400 |
| 18 | 120 |
| 19 | 4,300 |
| 20 | 6,900 |
| 21 | 7,500 |
| 22 | 2,300 |
| 23 | 14,500 |
| 24 | 1,600 |
| 25a | 3,100 |
| 26 | 300 |
| 27a | 650 |
| 28a | 1,100 |
| 29a | 24,000 |
| 30a | 5300 |
| 31a | 440 |
| 32 | 2,700 |
| 33a | 62 |
| 34a | 51 |
| 35a | 240 |
| 36a | 3.8 |
| 37 | 110 |
| 38a | 370 |
| 39a | 13 |
| 40a | 37 |
| 41a | 200 |
| 42a | 78 |
| 43a | 57 |
| 44a | 340 |
| 45a | 41 |
| 46 | 660 |
| 47a | 260 |
| 48 | 560 |
| 49 | 260 |
| 50 | 560 |
| 51 | 3,300 |
| 52 | 73 |
| 53 | 4.0 |
| 54 | 280 |
| 55 | 1,200 |
| 56 | 310 |
| 57a | 36 |
| 58a | 90 |
| 59 | 790 |
| 60 | 230 |
| 61 | 100 |
| 62 | 950 |
| 63 | 1,000 |
| 64a | 37 |
| 65 | 70 |
| 66a | 330 |
| 67a | 370 |
| 68 | 500 |
| 69a | 240 |
| 70a | 590 |

Example 75

Animals

Mouse CCR2 knock-out/human CCR2 knock-in mice were generated using targeted 129Sv/Evbrd embryonic stem cell clones injected into C57BL/6 mice. Expression of the hCCR2 transcript was confirmed by quantitative reverse transcription-polymerase chain reaction performed on spleen and blood total RNA from homozygous hCCR2 knock-in mice. Backcrossing into C57BL/6 genetic background continued to the eighth generation. Transgenic mice were housed in a specific-pathogen-free, temperature-controlled facility that maintained a 12-hour light/12-hour dark cycle. Mice had free access to water and food. Experimental procedures were carried out in accordance with institutional standards for animal care and were approved by the institute's animal care and use committee.

Example 76

Murine in Vivo Cell Migration Assay

Animals were orally dosed with vehicle or CCR2 antagonists at 3, 10 and 30 mg/kg bid. Animals underwent anesthesia and laparotomy. A distal loop of small bowel (5 cm in length) was gently eventrated onto moist sterile gauze. Synthetic human MCP-1 (1 mg/100 ml sterile PBS) or PBS alone was administered drop-wise onto the serosa of the eventrated loop. A suture knot was placed into the mesentery to mark the terminus of the treated area. Twenty-four hours later, the animal was sacrificed and the segment of bowel plus the adjacent region was removed. The tissue was opened along the mesenteric border, pinned flat and the mucosa removed. The remaining muscle layer was fixed briefly in 100% EtOH and then stained using Hanker-Yates reagent to detect myeloperoxidase-containing immune cells. At 10 mpk, P.O. bid, a compound is deemed efficacious if the inhibition of cell migration reaches 30% compared with vehicle-treated animals. The compound of Example 40 was found to be efficacious in blocking cell migration.

Example 77

Thiolycollate-Induced Peritonitis in Mice

Animals were orally dosed with vehicle or CCR2 antagonists at 3, 10, 30 and 100 mg/kg bid). One hour later, the animals were intraperiponeally injected with sterile thioglycollate (25 mL/kg, ip, Sigma) for induction of peritonitis. Animals were orally treated twice daily with vehicle or CCR2 antagonists. At 72-hour time point, perinoteal cavities were lavaged with 10 mL of sterile saline. Total cell counts in the peritoneal lavage fluid were performed using a microscope and cell differentiation was performed using cytospin analysis after Giemsa staining (Hema Tek 2000). Percent inhibition of the thioglycollate-induced peritonitis was calculated by comparing the change in number of leukocytes of CCR2 antagonist treated mice to the vehicle-treated mice. At 10 mpk, p.o. bid, the compound of Example 40 was shown to have >50% inhibition of thioglycollate-induced peritonitis.

Example 78

MCP-1-Induced Monocyte Recruitment to Airway of Mice

Animals were orally treated with vehicle or CCR2 antagonists at 3, 10, and 30 mg/kg po bid). One hour later, the animals were intranasally dosed with 4 μg of MCP-1 in sterile saline. The animals were orally treated twice daily with vehicle or CCR2 antagonists. After 48 h, mice were euthanized by intraperitoneal injection of anesthesia solution (Sleepaway-Sodium pentobarbital). Whole bronchoalveolar lavage (BAL) was performed using 1.4 ml of ice-cold PBS containing 3 mM EDTA. Total cell counts in the BAL lavage fluid were performed using a microscope and cell differentiation was performed using cytospin analysis after Giemsa staining (Hema Tek 2000). Percent inhibition was calculated by comparing the change in number of total leukocyte counts (including monocytes/macrophages and lymphocytes) of compound-treated mice to the vehicle-treated mice. Compounds are deemed efficacious if percent inhibition reaches 30%. At 10 mpk, p.o. bid, the compound of Example 40 was shown to have >50% inhibition.

Example 79

High-Fat Diet Induced Obesity and Insulin Resistance in Mice

Obesity was induced by a high-fat diet that derived approximately 60% calories from lipids (D-12492; Research Diets Inc.) in animals for 10-24 weeks at age of 7 weeks. Prior to age 7 weeks, animals were fed a standard pellet diet, in which 5% of calories were provided as fat. Obese animals were randomized by body weight and fat mass. The obese animals were orally treated with vehicle or CCR2 antagonists at 3, 10 and 30 mg/kg, po bid. Body weight and food intake and fasting blood glucose levels were monitored. Body mass was determined by a NMR analyzer (Burker MiniSpec). Insulin tolerance test was carried out in animals that were fasted for 3 hours. After an intraperitoneal bolus injection of recombinant human insulin (1.5 U/kg), blood glucose concentrations were measured using a Glucometer before and 15, 30, 45, 60, 90 and 120 minutes after injection. Glucose tolerance tests were performed after an overnight (17-hour) fast. Blood glucose concentrations were measured before and after 15, 30, 60, 90, 120 minutes after an oral dose of glucose dissolved in water (1 g/kg). Energy expenditure analysis was monitored by a complete laboratory animal monitor system. After 40 days treatment with vehicle or CCR2 antagonists, the animals were sacrificed by $CO_2$ asphyxiation. Percent of weight loss was calculated by comparing the body weight changes of the compound-treated mice with the vehicle-treated mice. At 10 mpk, p.o. bid, the compound of Example 40 was shown to reduce body weight >8%.

Example 80

Mouse Model of Allergic Asthma

Animals were sensitized by intraperitoneal injection of 10 μg chicken egg albumin (OVA) absorbed to 1 mg Imject® in 100 μL phosphate-buffered saline (PBS) on days 0 and 5. Control animals received PBS ip. OVA-immunized animals were challenged by inhalation of 0.5% OVA aerosol for 10 minutes by an ultrasonic nebulizer on days 12, 16 and 20. Control animals were challenged with PBS in similar fashion. The OVA-sensitized animals received vehicle (0.5% Methocel) or CCR2 antagonists orally at 3, 10, 30 mg/kg twice daily from days 9-20 and once daily on day 21, 2 hours before sacrifice. Dexamethason (5 mg/kg) and Montelukast (1 mg/kg) were given orally once a day. On day 21, 2 hours post the last dose of CCR2 compounds, bronchial reactivity to aerosolized methacholine was measured using a Buxco whole body plethysmograpgh. On day 21, the animals were sacrificed. Bronchoalveolar lavage fluid was collected (1 mL) and total cells counted. The numbers of eosinophils, lymphocytes, monocytes and neutrophils were determined using cytospin analysis after Giemsa staining (Hema Tek 2000). Percent inhibition of total BAL leukocyte count (and eosinophil count) was calculated by comparing the compound-treated mice with vehicle-treated mice. Compounds are deemed efficacious if the inhibition reaches 30%. At 10 mpk, p.o. bid, the compound of Example 40 was shown to be efficacious in reduction of cell count.

While the foregoing specification teaches the principles of the present invention, with examples provided for the purpose of illustration, it will be understood that the practice of the invention encompasses all of the usual variations, adaptations and/or modifications as come within the scope of the following claims and their equivalents.

We claim:

1. A compound of Formula (I)

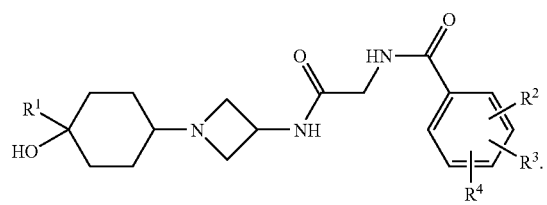

Formula (I)

wherein:
R¹ is

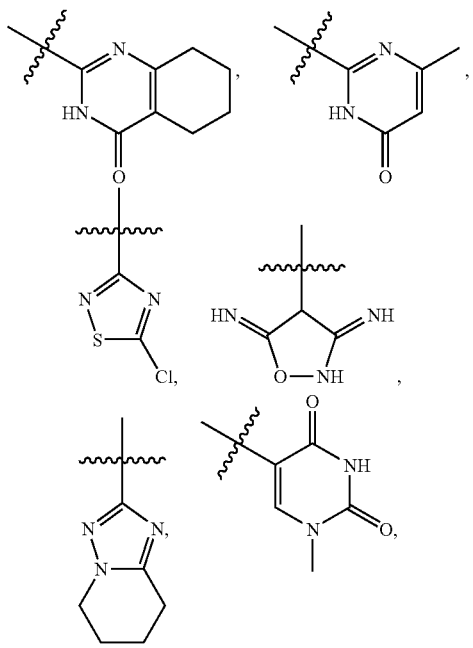

pyridyl, pyridyl-N-oxide, 1H-pyridin-2-onyl, indolyl, pyrazinyl, 3-H-thiazol-2-onyl, pyrimidyl, benzooxazolyl, oxazolyl, thiazolyl, isothiazolyl, pyrazolyl, imidazolyl, thiophenyl, furyl, [1,2,4]oxadiazolyl or [1,3,4]thiadiazolyl; wherein said pyridyl, pyridyl-N-oxide, pyrimidyl, pyrazolyl, imidazolyl, thiophenyl, or thiazolyl is optionally substituted with one substituent selected from the group consisting of $OC_{(1-4)}$alkyl, $OC_{(3-6)}$cycloalkyl, $OCH_2CF_3$, $OCH_2Ph$, F, CN, $CH_2CN$, $C_{(1-4)}$alkyl, $CH_2CF_3$, $N(C_{(1-4)}alkyl)_2$, $C_{(1-4)}$alkylOH, $Si(CH_3)_3$, —C≡CH, $SCH_3$, $S(O)CH_3$, $SO_2CH_3$, pyrrolidinyl, OH, $NH_2$, NHCN, $CO_2H$, $CONH_2$, $NHCO_2C_{(1-4)}$alkyl, $N(SO_2CH_3)_2$, $NHSO_2CH_3$, $NHC(O)CF_3$, $NHC_{(1-4)}$alkyl, $NHCO_2H$, $NHCO_2C_{(1-4)}$alkyl, $NHCOC_{(1-4)}$alkyl, $NHCONH_2$, $NHCONHC_{(1-4)}$alkyl, and Br; or said pyridyl may be substituted with one $OCH_3$ group and one $CH_3$; or wherein said pyrimidyl is optionally substituted with one $N(C_{(1-4)}alkyl)_2$ group or one or two $OCH_3$ groups; or wherein said thiazolyl is optionally substituted on two adjacent carbon atoms to form fused bicyclic system benzothiazol-2-yl, or wherein said benzothiazol-2-yl is optionally substituted with Br or $OCH_3$; or wherein said 1H-pyridin-2-onyl is optionally substituted with one substituent selected from the group consisting of $CH_2CN$, $C_{(1-4)}$alkyl, $CH_2CF_3$, and $CH_2CH_2OH$, or said 1H-pyridin-2-onyl may be optionally substituted with up to 2 methyl groups; or wherein said [1,2,4]oxadiazolyl is optionally substituted on any carbon atom with $CCl_3$, or pyrrolidinyl, or alternatively both hydrogens on said carbon atom of said [1,2,4]oxadiazolyl may be replaced by an oxo group;

R² is $C_{(1-4)}$alkyl, $NH_2$, $NO_2$, $NHCH_2CH_2OH$, $N(C_{(1-4)}alkyl)_2$, $N(SO_2CH_3)_2$, CN, F, Cl, Br, $CF_3$, $C_{(3-6)}$cycloalkyl, heterocyclyl, $OCF_3$, $OCF_2H$, $CF_2H$, or $OC_{(1-4)}$alkyl;

R³ is H, F, Cl, $CF_3$, or $OC_{(1-4)}$alkyl; alternatively, R² and R³ may be taken together with their attached phenyl to form a benzo[1,3]dioxolyl, 2,3-dihydro-benzofuranyl, or 2,3-dihydro-benzo[1,4]dioxinyl group;

R⁴ is H, $OC_{(1-4)}$alkyl, or F;

and hydrates, tautomers, and pharmaceutically acceptable salts thereof.

2. A compound claim 1 wherein:
R¹ is

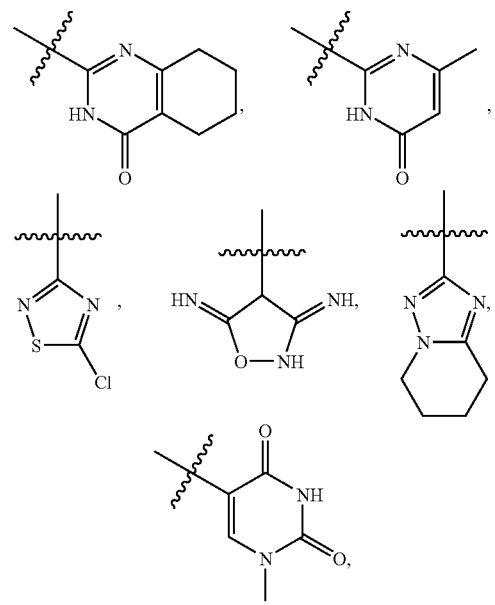

pyridyl, pyridyl-N-oxide, 1H-pyridin-2-onyl, indolyl, pyrazinyl, 3-H-thiazol-2-onyl, pyrimidyl, methyl substituted imidazolyl, methyl substituted pyrazolyl optionally substituted with Br, thiophenyl optionally substituted with Br, benzooxazolyl, oxazolyl, thiazolyl, isothiazolyl, [1,2,4]oxadiazolyl or [1,3,4]thiadiazolyl; wherein said pyridyl, pyridyl-N-oxide, or thiazolyl is optionally substituted with one substituent selected from the group consisting of $OC_{(1-4)}$alkyl, $OC_{(3-6)}$cycloalkyl, $OCH_2CF_3$, $OCH_2Ph$, F, CN, $CH_2CN$, $C_{(1-4)}$alkyl, $CH_2CF_3$, $N(C_{(1-4)}alkyl)_2$, $C_{(1-4)}$alkylOH, $Si(CH_3)_3$, —C≡CH, $SCH_3$, $S(O)CH_3$, $SO_2CH_3$, pyrrolidinyl, OH, $NH_2$, NHCN, $CO_2H$, $CONH_2$, $NHCO_2C_{(1-4)}$alkyl, $N(SO_2CH_3)_2$, $NHSO_2CH_3$, $NHC(O)CH_3$, $NHC(O)CF_3$, $NHC_{(1-4)}$alkyl, and Br; or said pyridyl may be substituted with one $OCH_3$ group and one $CH_3$; wherein said pyrimidyl is optionally substituted with one $N(C_{(1-4)}alkyl)_2$ group or one or two $OCH_3$ groups; wherein said thiazolyl is optionally substituted on two adjacent carbon atoms to form fused bicyclic system benzothiazol-2-yl, wherein said benzothiazol-2-yl is optionally substituted with Br or $OCH_3$; wherein said 1H-pyridin-2-onyl is optionally substituted with one substituent selected from the group consisting of $CH_2CN$, $C_{(1-4)}$alkyl, $CH_2CF_3$, and $CH_2CH_2OH$, or said 1H-pyridin-2-onyl may be optionally substituted with up to 2 methyl groups; wherein said [1,2,4]oxadiazolyl is optionally substituted on any carbon atom with $CCl_3$, or pyrrolidinyl, or alternatively both hydrogens on said carbon atom of said [1,2,4]oxadiazolyl may be replaced by an oxo group;

R² is C(1-4)alkyl, NH₂, NO₂, NHCH₂CH₂OH, N(C(1-4)alkyl)₂, N(SO₂CH₃)₂, CN, F, Cl, Br, CF₃, pyrrolidinyl, OCF₃, OCF₂H, CF₂H, or OC(1-4)alkyl;

R³ is H, F, Cl, CF₃, or OC(1-4)alkyl; alternatively, R² and R³ may be taken together with their attached phenyl to form a benzo[1,3]dioxolyl group;

R⁴ is H, OCH₃, or F;

and hydrates, tautomers, and pharmaceutically acceptable salts thereof.

3. A compound claim 2 wherein:

R¹ is pyridyl, pyridyl-N-oxide, pyrimidyl, methyl substituted imidazolyl, methyl substituted pyrazolyl optionally substituted with Br, thiophenyl optionally substituted with Br, benzooxazolyl, oxazolyl, thiazolyl, isothiazolyl, or [1,3,4]thiadiazolyl; wherein said pyridyl, pyridyl-N-oxide, or thiazolyl is optionally substituted with one substituent selected from the group consisting of OC(1-4)alkyl, OC(3-6)cycloalkyl, OCH₂CF₃, OCH₂Ph, F, CN, C(1-4)alkyl, N(C(1-4)alkyl)₂, C(1-4)alkylOH, Si(CH₃)₃, —C≡CH, SCH₃, S(O)CH₃, SO₂CH₃, pyrrolidinyl, OH, NH₂, NHCN, and Br; or said pyridyl may be substituted with one OCH₃ group and one CH₃; wherein said pyrimidyl is optionally substituted with one N(C(1-4)alkyl)₂ group or one or two OCH₃ groups; wherein said thiazolyl is optionally substituted on two adjacent carbon atoms to form fused bicyclic system benzothiazol-2-yl, wherein said benzothiazol-2-yl is optionally substituted with Br or OCH₃;

R² is NH₂, NO₂, NHCH₂CH₂OH, N(CH₃)₂, N(SO₂CH₃)₂, CN, F, Cl, Br, CF₃, pyrrolidinyl, or OCH₃;

R³ is H, F, Cl, CF₃, or OCH₃; alternatively, R² and R³ may be taken together with their attached phenyl to form a benzo[1,3]dioxolyl group;

R⁴ is H, or F;

and hydrates, tautomers, and pharmaceutically acceptable salts thereof.

4. A compound claim 3 wherein:

R¹ is pyridyl, pyridyl-N-oxide, pyrimidyl, methyl substituted imidazolyl, methyl substituted pyrazolyl optionally substituted with Br, thiophenyl optionally substituted with Br, benzooxazolyl, oxazolyl, thiazolyl, isothiazolyl, or [1,3,4]thiadiazolyl; wherein said pyridyl or pyridyl-N-oxide is optionally substituted with one substituent selected from the group consisting of OC(1-4)alkyl, OC(3-6)cycloalkyl, OCH₂CF₃, OCH₂Ph, F, CN, C(1-4)alkyl, N(C(1-4)alkyl)₂, and Br; or said pyridyl may be substituted with one OCH₃ group and one CH₃; wherein said pyrimidyl is optionally substituted with one N(C(1-4)alkyl)₂ group or one or two OCH₃ groups; wherein said thiazolyl is optionally substituted with C(1-4)alkyl, CH₂OH, Si(CH₃)₃, —C≡CH, SCH₃, S(O)CH₃, SO₂CH₃, OH, NH₂, N(C(1-4)alkyl)₂, pyrrolidinyl, OC(1-4)alkyl, NHCN, or said thiazolyl may be substituted on two adjacent carbon atoms to form fused bicyclic system benzothiazol-2-yl, wherein said benzothiazol-2-yl is optionally substituted with Br;

and hydrates, tautomers, and pharmaceutically acceptable salts thereof.

5. A compound claim 4 wherein:

R¹ is pyridyl, methoxy substituted pyridyl-N-oxide, pyrimidyl, methyl substituted imidazolyl, methyl substituted pyrazolyl optionally substituted with Br, thiophenyl optionally substituted with Br, benzooxazolyl, oxazolyl, thiazolyl, isothiazolyl, or [1,3,4]thiadiazolyl; wherein said pyridyl is optionally substituted with one substituent selected from the group consisting of OCH₃, OCH₂CH₃, OCH(CH₃)₂, OC(CH₃)₃, cyclobutoxy, OCH₂CF₃, OCH₂Ph, F, CN, CH₃, N(CH₃)₂, and Br; or said pyridyl may be substituted with one OCH₃ group and one CH₃; wherein said pyrimidyl is optionally substituted with one N(CH₃)₂ group or one or two OCH₃ groups; wherein said thiazolyl is optionally substituted with CH₂OH, Si(CH₃)₃, CH₃, CH₂CH₃, CH(CH₃)₂, —C≡CH, SCH₃, S(O)CH₃, SO₂CH₃, OH, NH₂, N(CH₃)₂, pyrrolidinyl, OCH₃, OCH(CH₃)₂, NHCN, or said thiazolyl may be substituted on two adjacent carbon atoms to form fused bicyclic system benzothiazol-2-yl, wherein said benzothiazol-2-yl is optionally substituted with Br.(Original);

R² is CF₃, F, Cl, CN, or OCH₃,

R³ is H, F, Cl, or CF₃, alternatively, R² and R³ may be taken together with their attached phenyl to form a benzo[1,3] dioxolyl group;

R⁴ is H, or F;

and hydrates, tautomers, and pharmaceutically acceptable salts thereof.

6. A compound of claim 1 selected from the group consisting of:

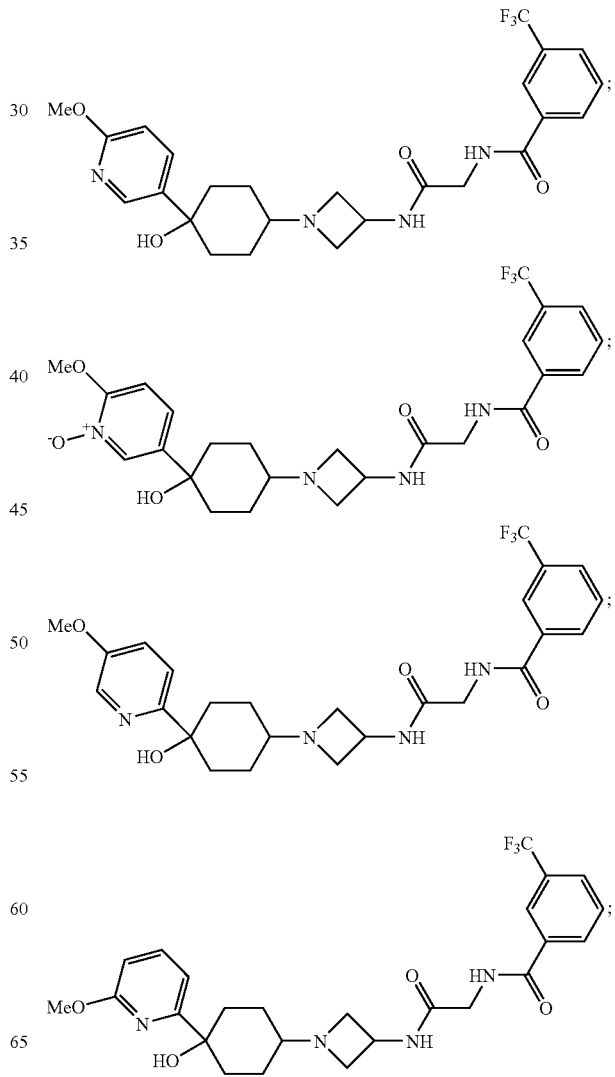

137
-continued
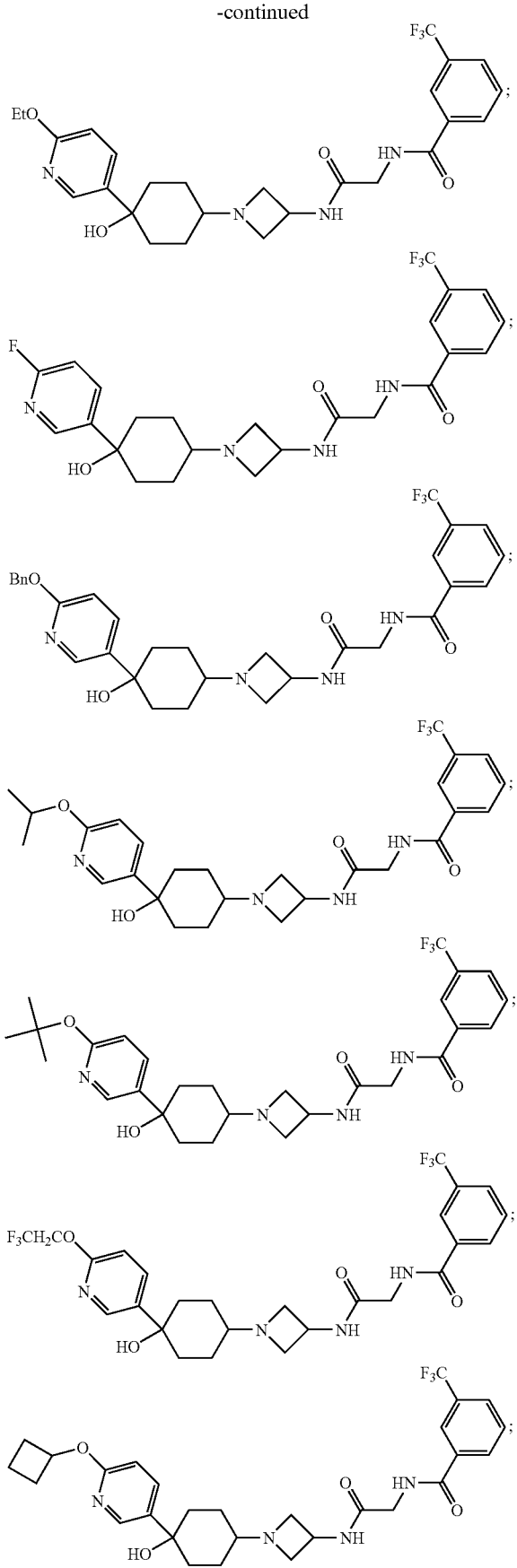
138
-continued
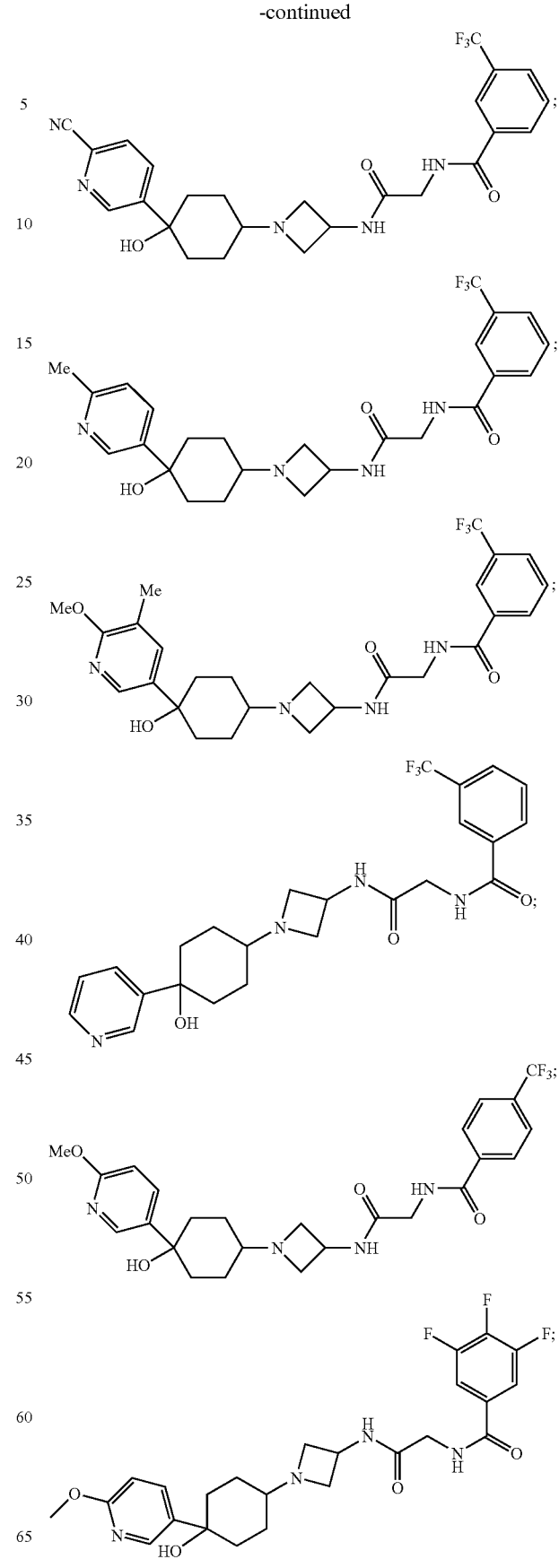

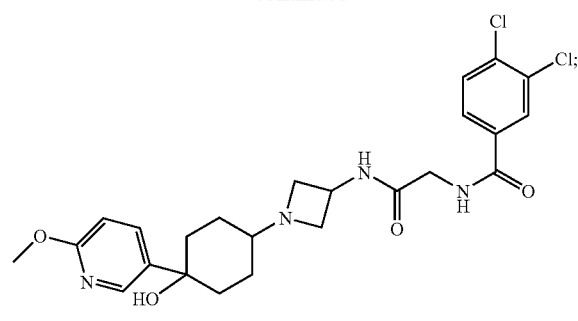
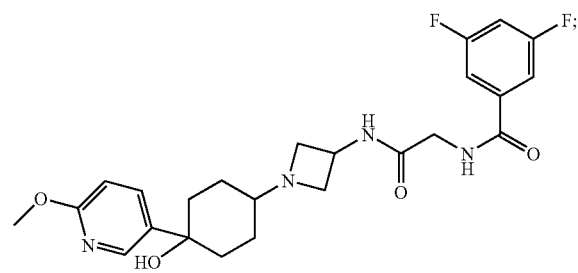
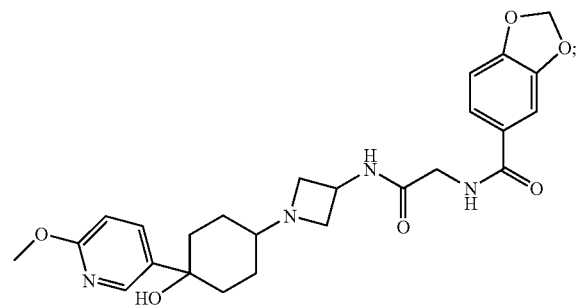
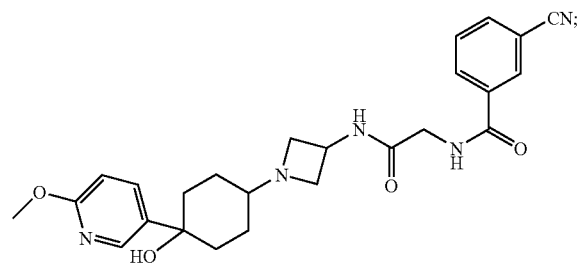
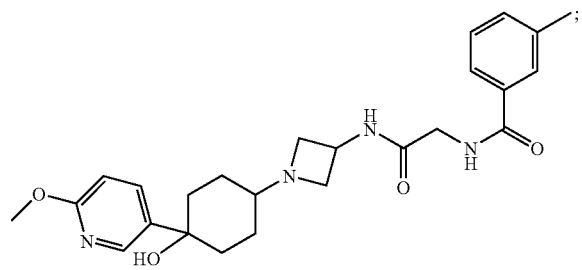
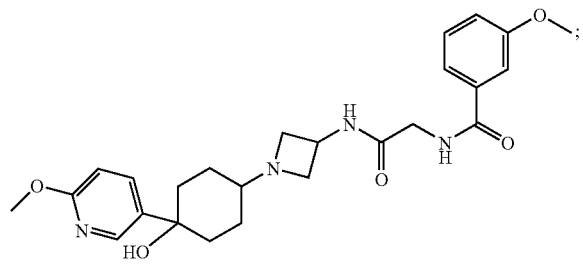
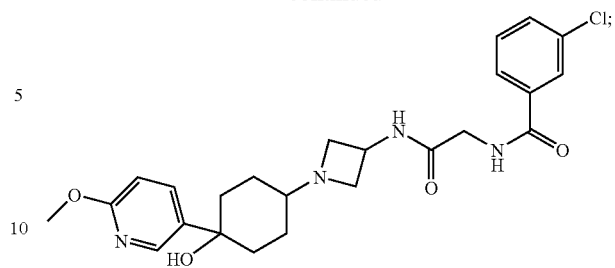
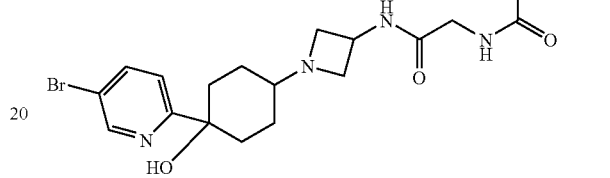
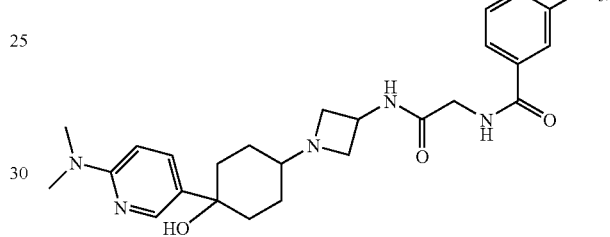
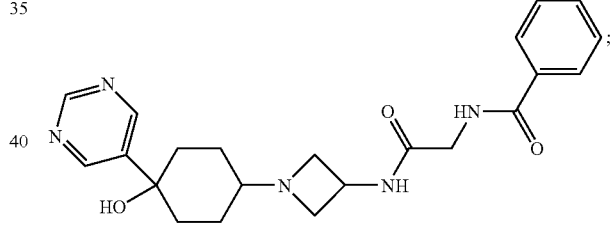
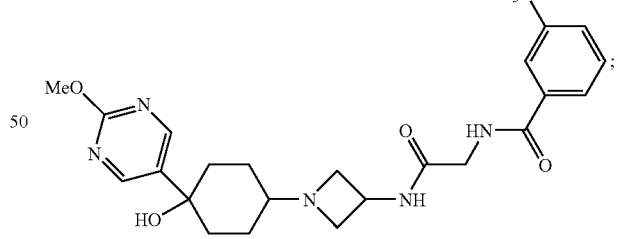
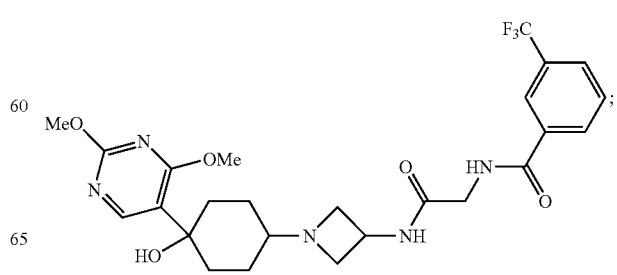

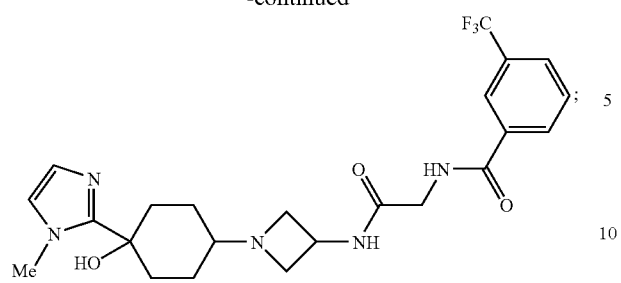
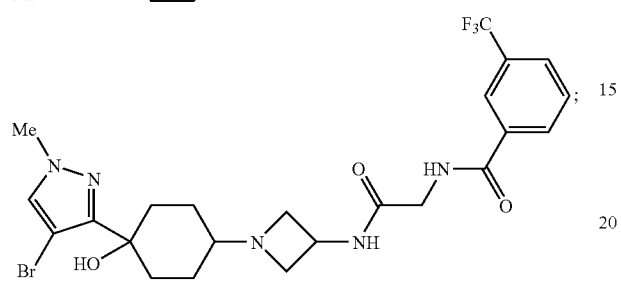
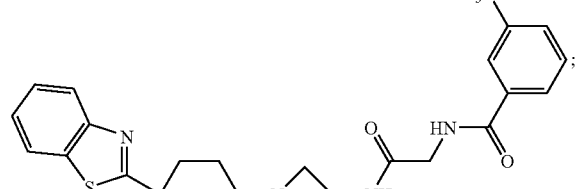
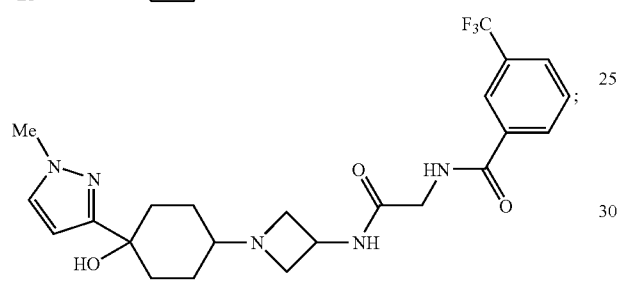
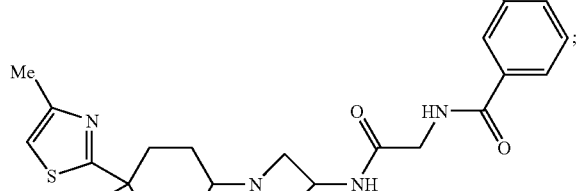
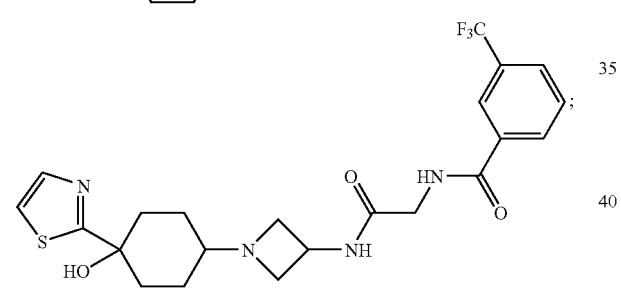
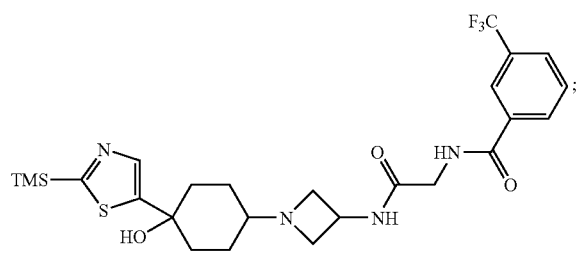
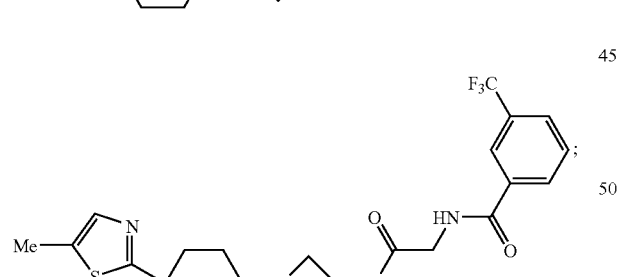
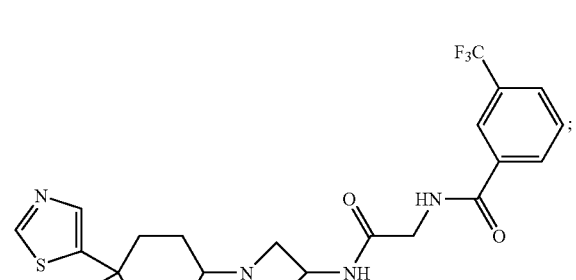
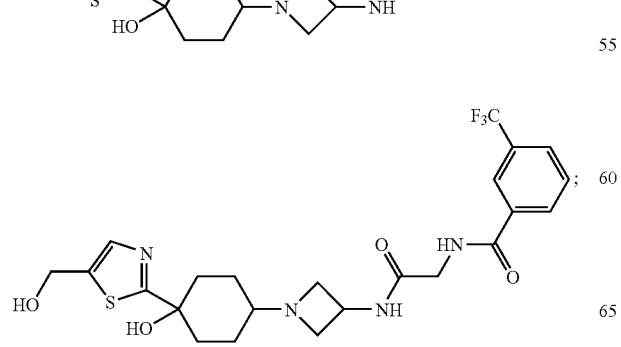
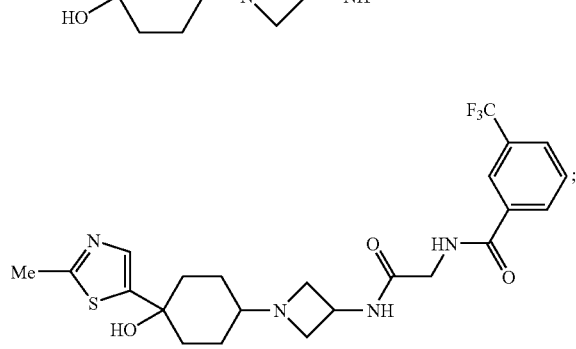

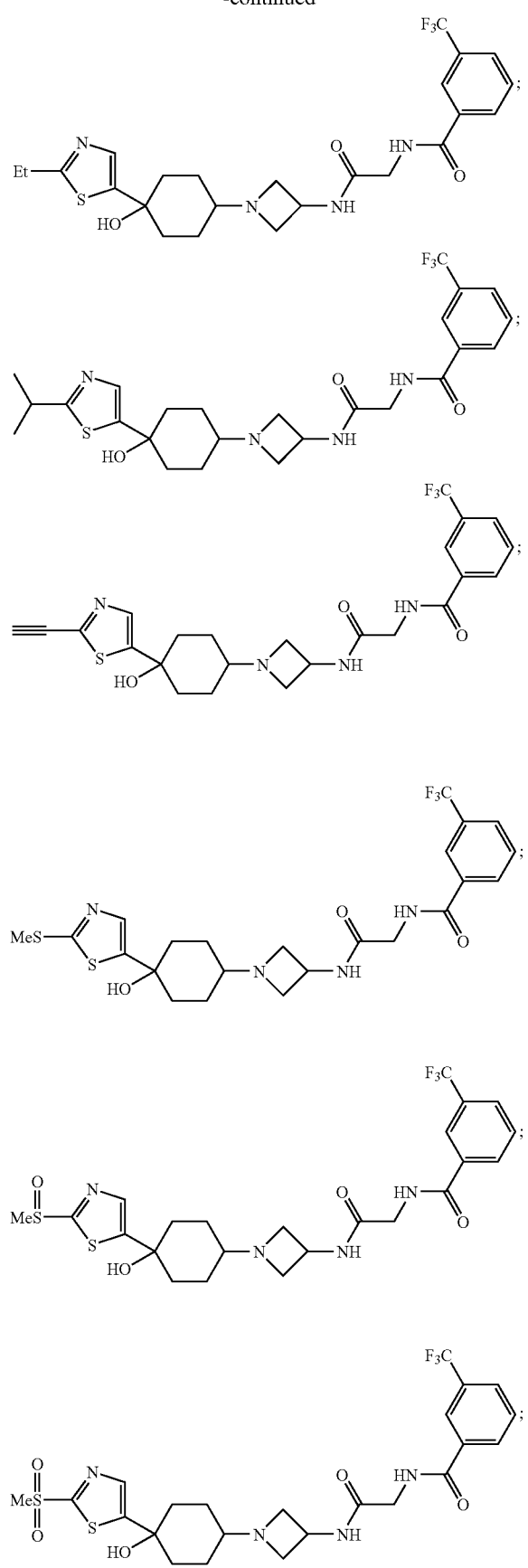
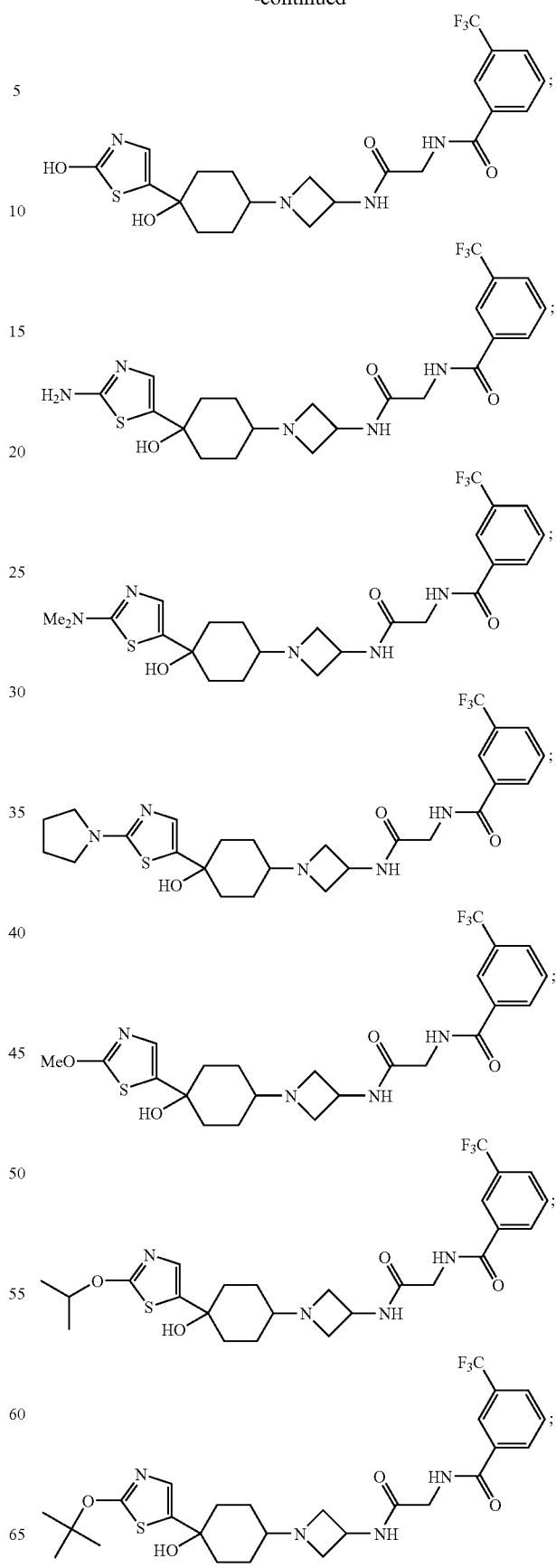

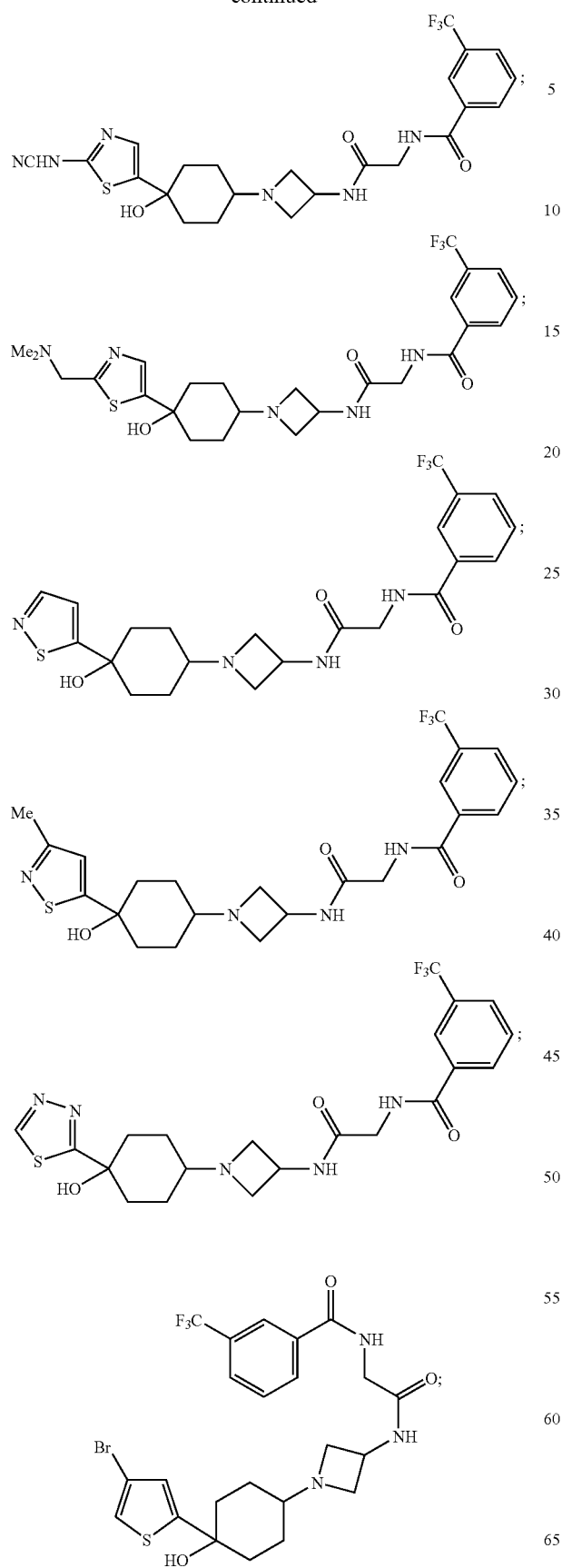
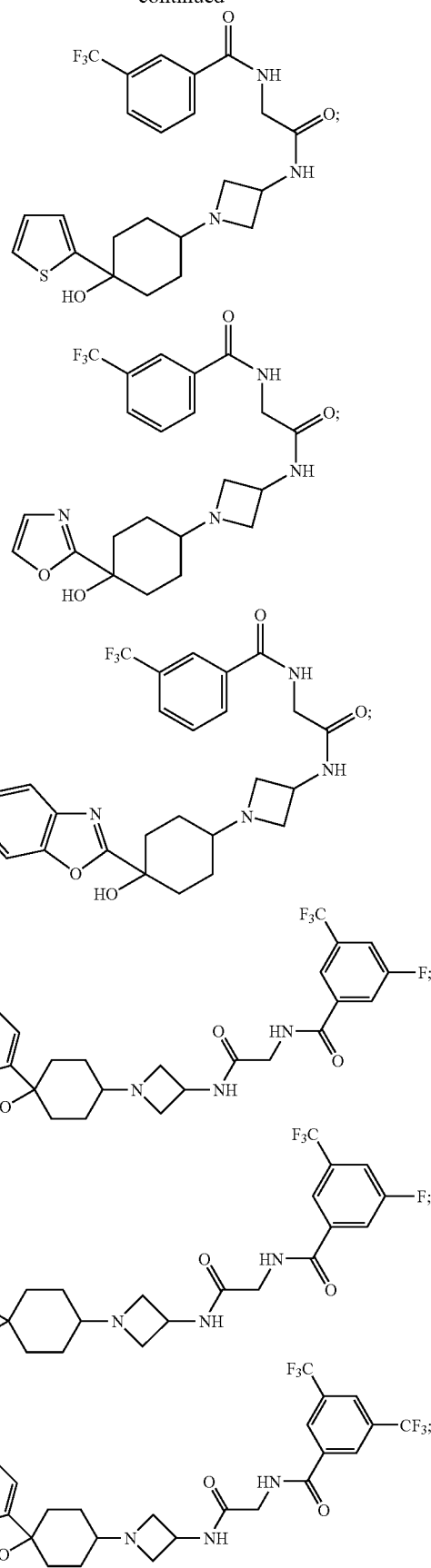

-continued
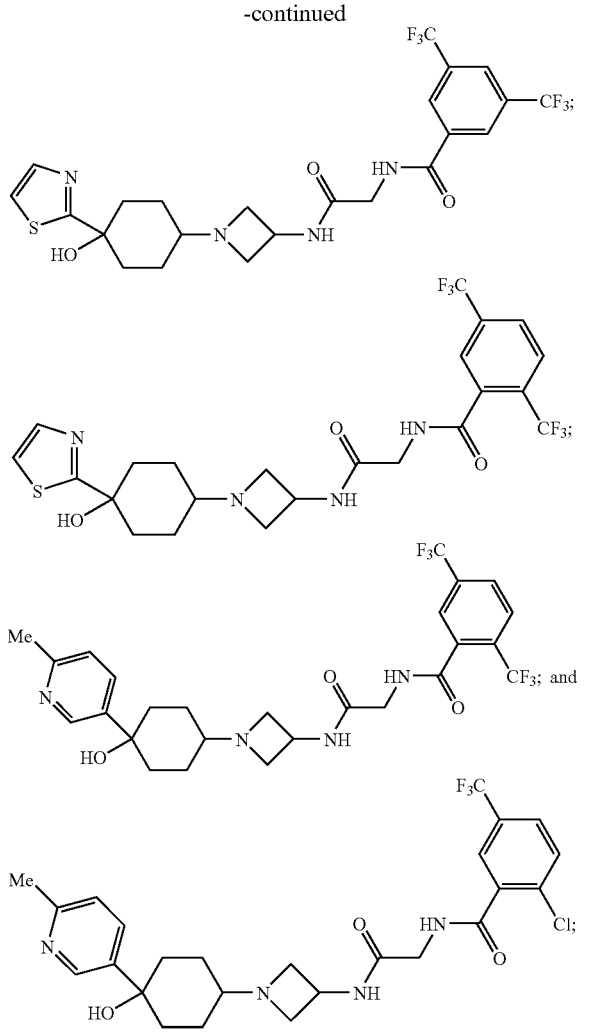
and hydrates, tautomers, and pharmaceutically acceptable salts thereof.
7. A compound of claim 6 selected from the group consisting of:
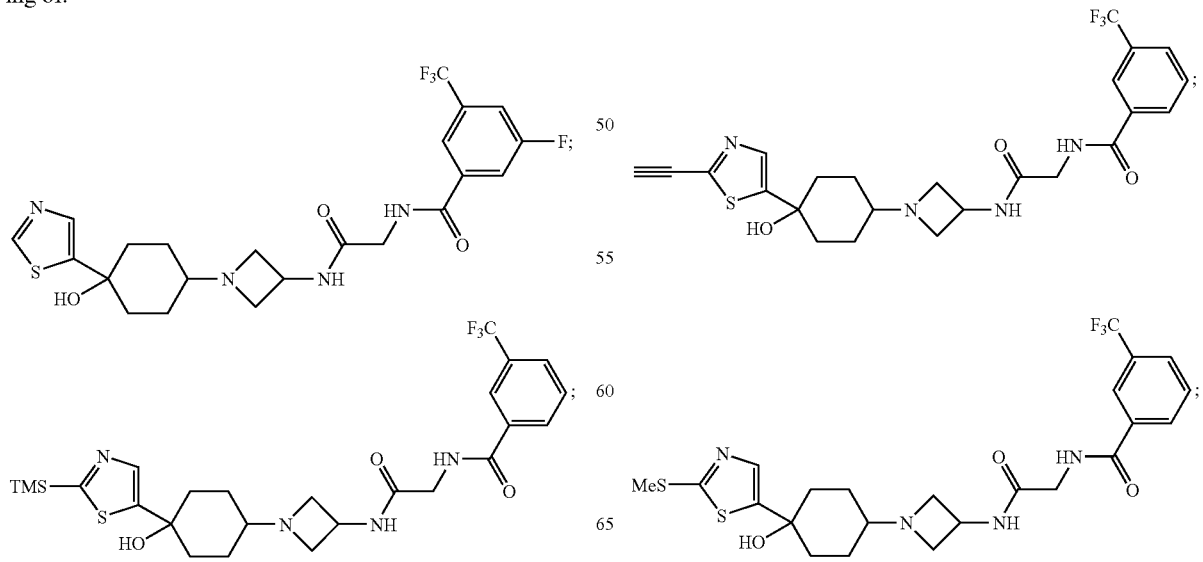
-continued
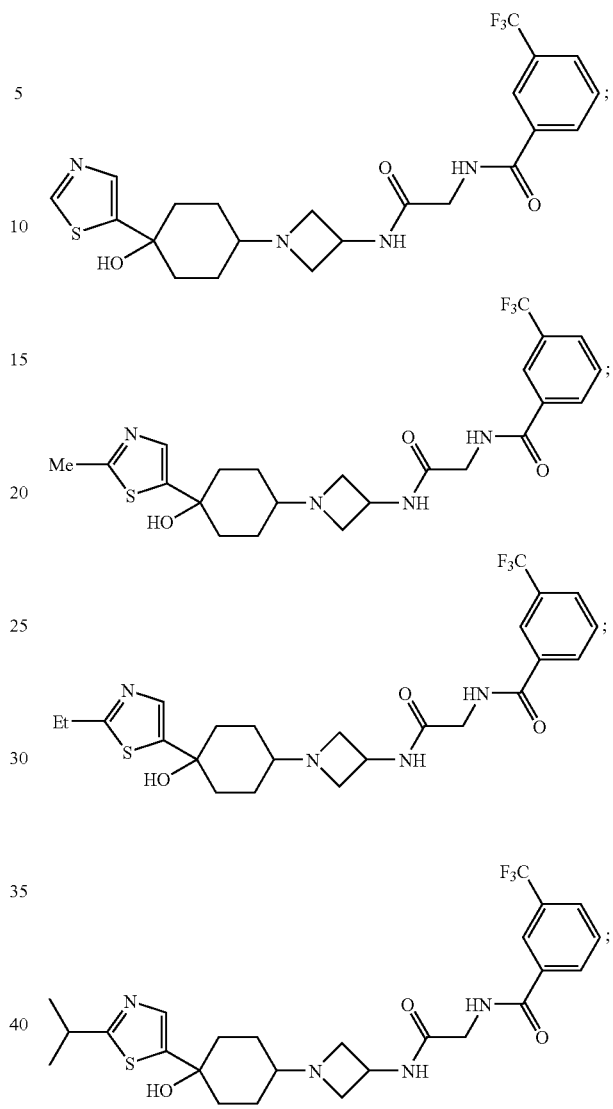

-continued
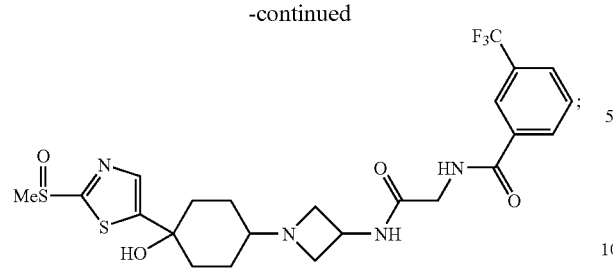
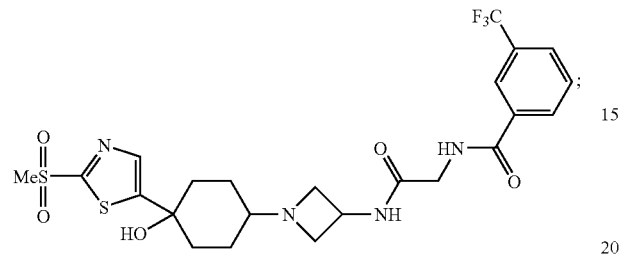
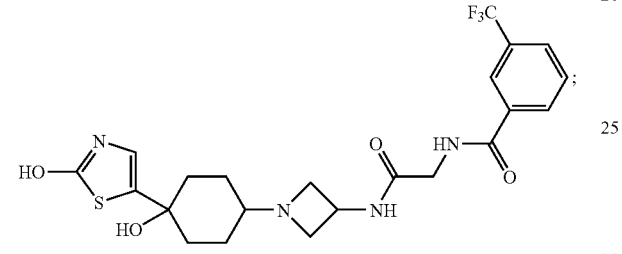
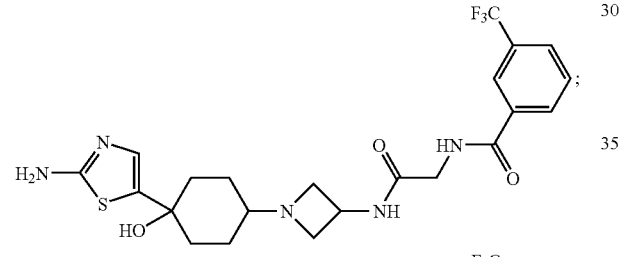
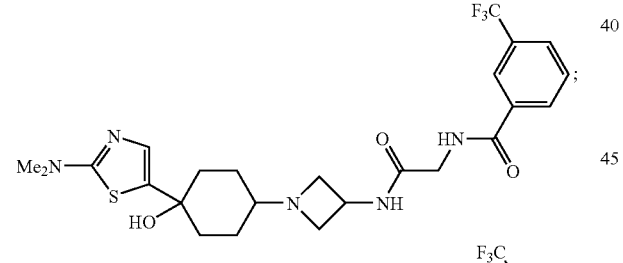
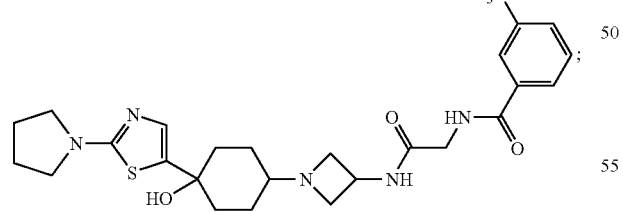
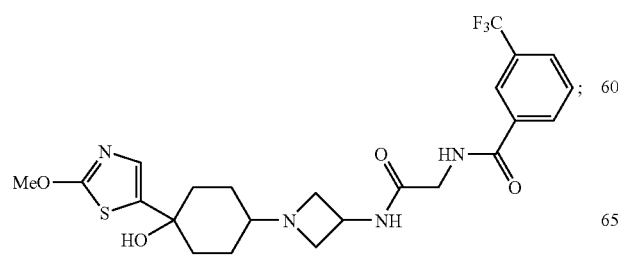
-continued
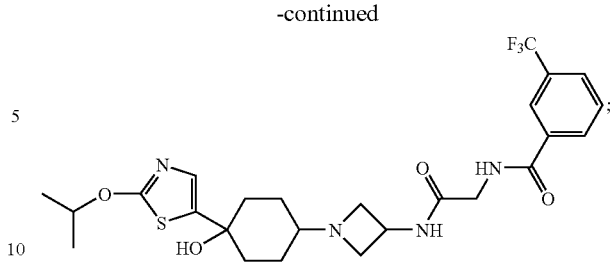
; and
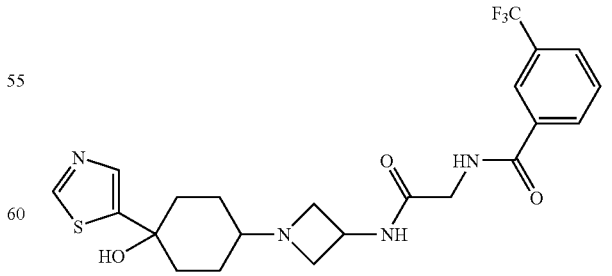
and hydrates, tautomers, and pharmaceutically acceptable salts thereof.
8. A compound of the formula
and hydrates, tautomers, and pharmaceutically acceptable salts thereof.

9. A compound of Formula (Ia)

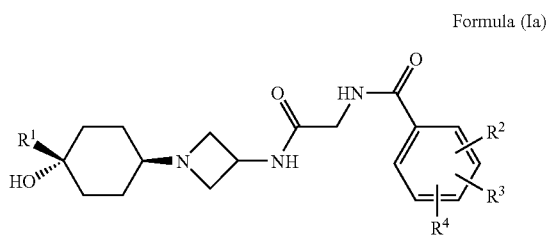

Formula (Ia)

wherein:
R¹ is

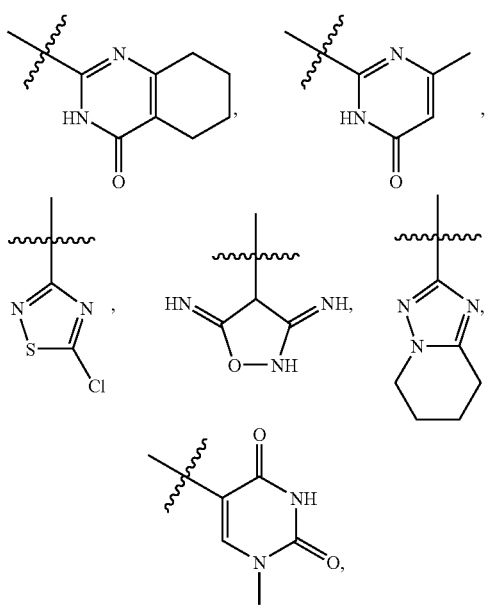

pyridyl, pyridyl-N-oxide, 1H-pyridin-2-onyl, indolyl, pyrazinyl, 3-H-thiazol-2-onyl, pyrimidyl, benzooxazolyl, oxazolyl, thiazolyl, isothiazolyl, pyrazolyl, imidazolyl, thiophenyl, furyl, [1,2,4]oxadiazolyl or [1,3,4]thiadiazolyl; wherein said pyridyl, pyridyl-N-oxide, pyrimidyl, pyrazolyl, imidazolyl, thiophenyl, or thiazolyl is optionally substituted with one substituent selected from the group consisting of $OC_{(1-4)}$alkyl, $OC_{(3-6)}$cycloalkyl, $OCH_2CF_3$, $OCH_2Ph$, F, CN, $CH_2CN$, $C_{(1-4)}$alkyl, $CH_2CF_3$, $N(C_{(1-4)}alkyl)_2$, $C_{(1-4)}$alkylOH, $Si(CH_3)_3$, —C≡CH, $SCH_3$, $S(O)CH_3$, $SO_2CH_3$, pyrrolidinyl, OH, $NH_2$, NHCN, $CO_2H$, $CONH_2$, $NHCO_2C_{(1-4)}$alkyl, $N(SO_2CH_3)_2$, $NHSO_2CH_3$, $NHC(O)CF_3$, $NHC_{(1-4)}$alkyl, $NHCO_2H$, $NHCO_2C_{(1-4)}$alkyl, $NHCOC_{(1-4)}$alkyl, $NHCONH_2$, $NHCONHC_{(1-4)}$alkyl, and Br; or said pyridyl may be substituted with one $OCH_3$ group and one $CH_3$; or wherein said pyrimidyl is optionally substituted with one $N(C_{(1-4)}alkyl)_2$ group or one or two $OCH_3$ groups; or wherein said thiazolyl is optionally substituted on two adjacent carbon atoms to form fused bicyclic system benzothiazol-2-yl, or wherein said benzothiazol-2-yl is optionally substituted with Br or $OCH_3$; or wherein said 1H-pyridin-2-onyl is optionally substituted with one substituent selected from the group consisting of $CH_2CN$, $C_{(1-4)}$alkyl, $CH_2CF_3$, and $CH_2CH_2OH$, or said 1H-pyridin-2-onyl may be optionally substituted with up to 2 methyl groups; or wherein said [1,2,4]oxadiazolyl is optionally substituted on any carbon atom with $CCl_3$, or pyrrolidinyl, or alternatively both hydrogens on said carbon atom of said [1,2,4]oxadiazolyl may be replaced by an oxo group;

R² is $C_{(1-4)}$alkyl, $NH_2$, $NO_2$, $NHCH_2CH_2OH$, $N(C_{(1-4)}alkyl)_2$, $N(SO_2CH_3)_2$, CN, F, Cl, Br, $CF_3$, $C_{(3-6)}$cycloalkyl, heterocyclyl, $OCF_3$, $OCF_2H$, $CF_2H$, or $OC_{(1-4)}$alkyl;

R³ is H, F, Cl, $CF_3$, or $OC_{(1-4)}$alkyl; alternatively, R² and R³ may be taken together with their attached phenyl to form a benzo[1,3]dioxolyl, 2,3-dihydro-benzofuranyl, or 2,3-dihydro-benzo[1,4]dioxinyl group;

R⁴ is H, $OC_{(1-4)}$alkyl, or F;

and hydrates, tautomers, and pharmaceutically acceptable salts thereof.

10. A compound claim 9 wherein:
R¹ is

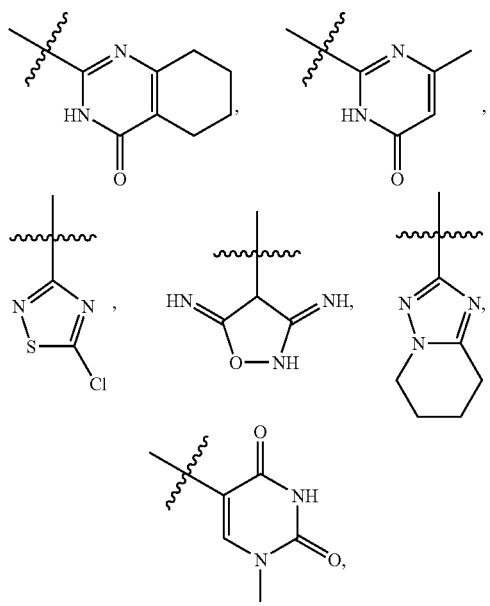

pyridyl, pyridyl-N-oxide, 1H-pyridin-2-onyl, indolyl, pyrazinyl, 3-H-thiazol-2-onyl, pyrimidyl, methyl substituted imidazolyl, methyl substituted pyrazolyl optionally substituted with Br, thiophenyl optionally substituted with Br, benzooxazolyl, oxazolyl, thiazolyl, isothiazolyl, [1,2,4]oxadiazolyl or [1,3,4]thiadiazolyl; wherein said pyridyl, pyridyl-N-oxide, or thiazolyl is optionally substituted with one substituent selected from the group consisting of $OC_{(1-4)}$alkyl, $OC_{(3-6)}$cycloalkyl, $OCH_2CF_3$, $OCH_2Ph$, F, CN, $CH_2CN$, $C_{(1-4)}$alkyl, $CH_2CF_3$, $N(C_{(1-4)}alkyl)_2$, $C_{(1-4)}$alkylOH, $Si(CH_3)_3$, —C≡CH, $SCH_3$, $S(O)CH_3$, $SO_2CH_3$, pyrrolidinyl, OH, $NH_2$, NHCN, $CO_2H$, $CONH_2$, $NHCO_2C_{(1-4)}$alkyl, $N(SO_2CH_3)_2$, $NHSO_2CH_3$, $NHC(O)CH_3$, $NHC(O)CF_3$, $NHC_{(1-4)}$alkyl, and Br; or said pyridyl may be substituted with one $OCH_3$ group and one $CH_3$; wherein said pyrimidyl is optionally substituted with one $N(C_{(1-4)}alkyl)_2$ group or one or two $OCH_3$ groups; wherein said thiazolyl is optionally substituted on two adjacent carbon atoms to form fused bicyclic system benzothiazol-2-yl, wherein said benzothiazol-2-yl is optionally substituted with Br or $OCH_3$; wherein said 1H-pyridin-2-onyl is optionally substituted with one substituent selected from the group consisting of $CH_2CN$, $C_{(1-4)}$alkyl, $CH_2CF_3$, and $CH_2CH_2OH$, or said 1H-pyridin-2-onyl may be optionally substituted with up to 2 methyl groups; wherein said [1,2,4]oxadiazolyl is optionally substituted on any carbon atom with $CCl_3$, or pyrrolidinyl, or alternatively both hydrogens on said carbon atom of said [1,2,4]oxadiazolyl may be replaced by an oxo group;

$R^2$ is $C_{(1-4)}$alkyl, $NH_2$, $NO_2$, $NHCH_2CH_2OH$, $N(C_{(1-4)}$alkyl$)_2$, $N(SO_2CH_3)_2$, CN, F, Cl, Br, $CF_3$, pyrrolidinyl, $OCF_3$, $OCF_2H$, $CF_2H$, or $OC_{(1-4)}$alkyl;

$R^3$ is H, F, Cl, $CF_3$, or $OC_{(1-4)}$alkyl; alternatively, $R^2$ and $R^3$ may be taken together with their attached phenyl to form a benzo[1,3]dioxolyl group;

$R^4$ is H, $OCH_3$, or F;

and hydrates, tautomers, and pharmaceutically acceptable salts thereof.

11. A compound claim 10 wherein:

$R^1$ is pyridyl, pyridyl-N-oxide, pyrimidyl, methyl substituted imidazolyl, methyl substituted pyrazolyl optionally substituted with Br, thiophenyl optionally substituted with Br, benzooxazolyl, oxazolyl, thiazolyl, isothiazolyl, or [1,3,4]thiadiazolyl; wherein said pyridyl, pyridyl-N-oxide, or thiazolyl is optionally substituted with one substituent selected from the group consisting of $OC_{(1-4)}$alkyl, $OC_{(3-6)}$cycloalkyl, $OCH_2CF_3$, $OCH_2Ph$, F, CN, $C_{(1-4)}$alkyl, $N(C_{(1-4)}$alkyl$)_2$, $C_{(1-4)}$alkylOH, $Si(CH_3)_3$, —C≡CH, $SCH_3$, $S(O)CH_3$, $SO_2CH_3$, pyrrolidinyl, OH, $NH_2$, NHCN, and Br; or said pyridyl may be substituted with one $OCH_3$ group and one $CH_3$; wherein said pyrimidyl is optionally substituted with one $N(C_{(1-4)}$alkyl$)_2$ group or one or two $OCH_3$ groups; wherein said thiazolyl is optionally substituted on two adjacent carbon atoms to form fused bicyclic system benzothiazol-2-yl, wherein said benzothiazol-2-yl is optionally substituted with Br or $OCH_3$;

$R^2$ is $NH_2$, $NO_2$, $NHCH_2CH_2OH$, $N(CH_3)_2$, $N(SO_2CH_3)_2$, CN, F, Cl, Br, $CF_3$, pyrrolidinyl, or $OCH_3$;

$R^3$ is H, F, Cl, $CF_3$, or $OCH_3$; alternatively, $R^2$ and $R^3$ may be taken together with their attached phenyl to form a benzo[1,3]dioxolyl group;

$R^4$ is H, or F;

and hydrates, tautomers, and pharmaceutically acceptable salts thereof.

12. A compound claim 11 wherein:

$R^1$ is pyridyl, pyridyl-N-oxide, pyrimidyl, methyl substituted imidazolyl, methyl substituted pyrazolyl optionally substituted with Br, thiophenyl optionally substituted with Br, benzooxazolyl, oxazolyl, thiazolyl, isothiazolyl, or [1,3,4]thiadiazolyl; wherein said pyridyl or pyridyl-N-oxide is optionally substituted with one substituent selected from the group consisting of $OC_{(1-4)}$alkyl, $OC_{(3-6)}$cycloalkyl, $OCH_2CF_3$, $OCH_2Ph$, F, CN, $C_{(1-4)}$alkyl, $N(C_{(1-4)}$alkyl$)_2$, and Br; or said pyridyl may be substituted with one $OCH_3$ group and one $CH_3$; wherein said pyrimidyl is optionally substituted with one $N(C_{(1-4)}$alkyl$)_2$ group or one or two $OCH_3$ groups; wherein said thiazolyl is optionally substituted with $C_{(1-4)}$alkyl, $CH_2OH$, $Si(CH_3)_3$, —C≡CH, $SCH_3$, $S(O)CH_3$, $SO_2CH_3$, OH, $NH_2$, $N(C_{(1-4)}$alkyl$)_2$, pyrrolidinyl, $OC_{(1-4)}$alkyl, NHCN, or said thiazolyl may be substituted on two adjacent carbon atoms to form fused bicyclic system benzothiazol-2-yl, wherein said benzothiazol-2-yl is optionally substituted with Br;

and hydrates, tautomers, and pharmaceutically acceptable salts thereof.

13. A compound claim 12 wherein:

$R^1$ is pyridyl, methoxy substituted pyridyl-N-oxide, pyrimidyl, methyl substituted imidazolyl, methyl substituted pyrazolyl optionally substituted with Br, thiophenyl optionally substituted with Br, benzooxazolyl, oxazolyl, thiazolyl, isothiazolyl, or [1,3,4]thiadiazolyl; wherein said pyridyl is optionally substituted with one substituent selected from the group consisting of $OCH_3$, $OCH_2CH_3$, $OCH(CH_3)_2$, $OC(CH_3)_3$, cyclobutoxy, $OCH_2CF_3$, $OCH_2Ph$, F, CN, $CH_3$, $N(CH_3)_2$, and Br; or said pyridyl may be substituted with one $OCH_3$ group and one $CH_3$; wherein said pyrimidyl is optionally substituted with one $N(CH_3)_2$ group or one or two $OCH_3$ groups; wherein said thiazolyl is optionally substituted with $CH_2OH$, $Si(CH_3)_3$, $CH_3$, $CH_2CH_3$, $CH(CH_3)_2$, —C≡CH, $SCH_3$, $S(O)CH_3$, $SO_2CH_3$, OH, $NH_2$, $N(CH_3)_2$, pyrrolidinyl, $OCH_3$, $OCH(CH_3)_2$, NHCN, or said thiazolyl may be substituted on two adjacent carbon atoms to form fused bicyclic system benzothiazol-2-yl, wherein said benzothiazol-2-yl is optionally substituted with Br;

$R^2$ is $CF_3$, F, Cl, CN, or $OCH_3$, $R^3$ is H, F, Cl, or $CF_3$, alternatively, $R^2$ and $R^3$ may be taken together with their attached phenyl to form a benzo[1,3]dioxolyl group;

$R^4$ is H, or F;

and hydrates, tautomers, and pharmaceutically acceptable salts thereof.

14. A compound of claim 9 selected from the group consisting of:

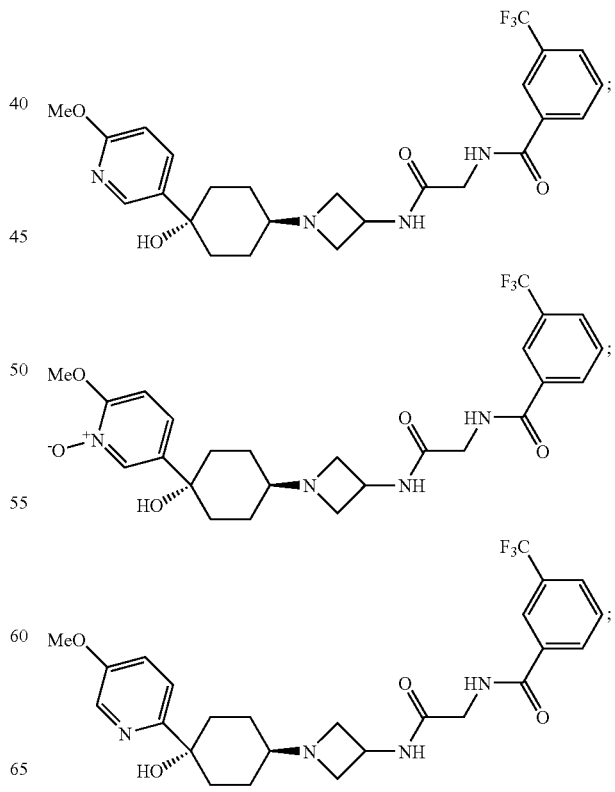

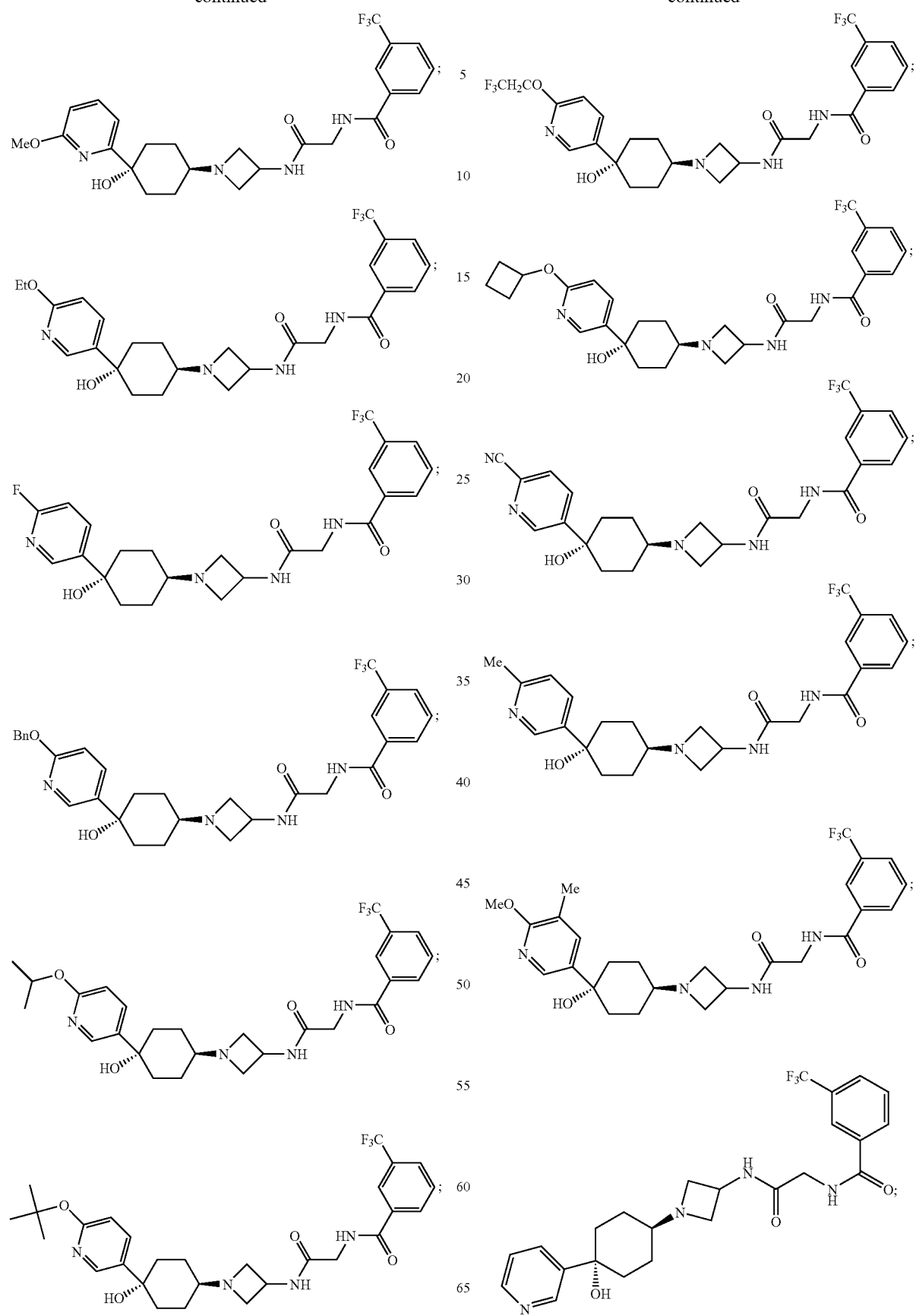

157
-continued
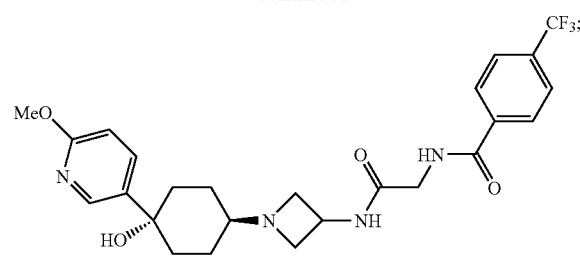
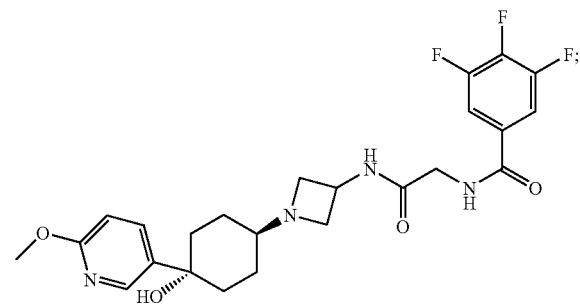
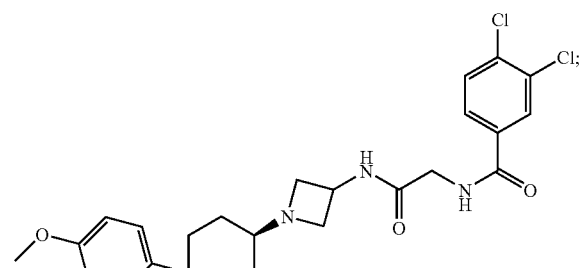
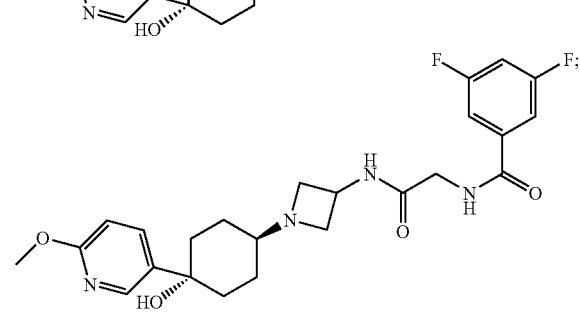
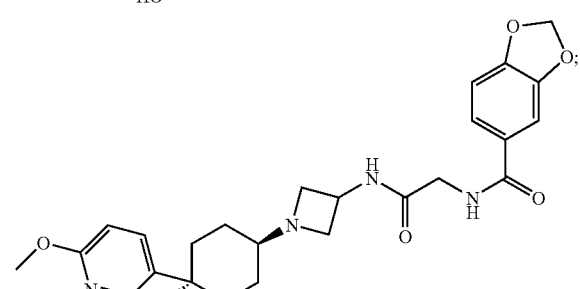
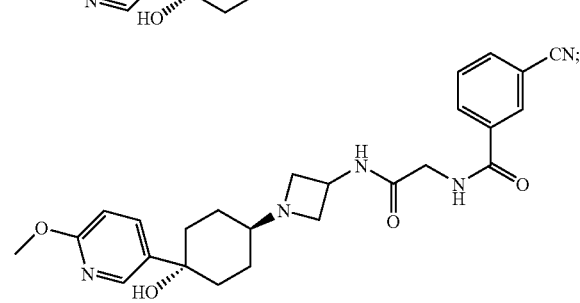
158
-continued
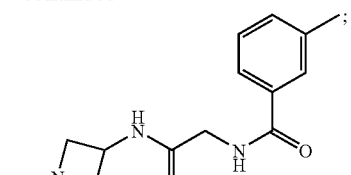
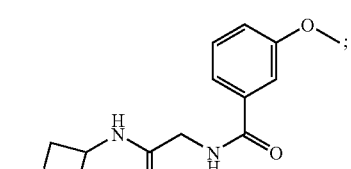
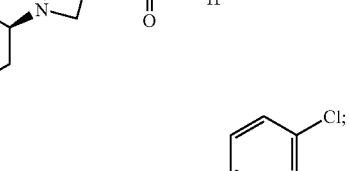
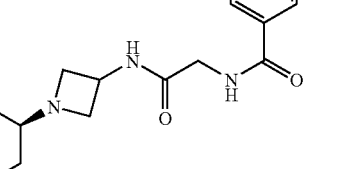
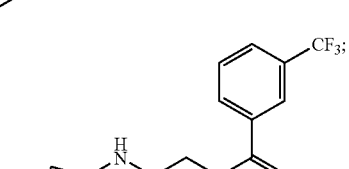
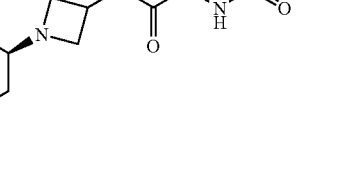
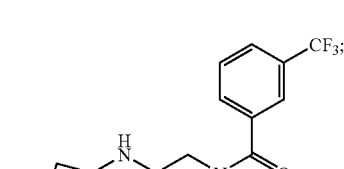
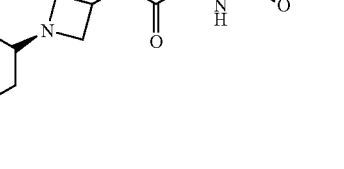
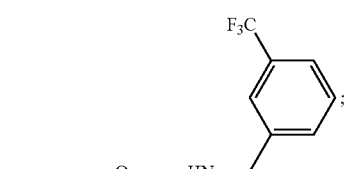
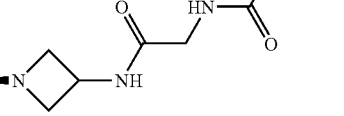

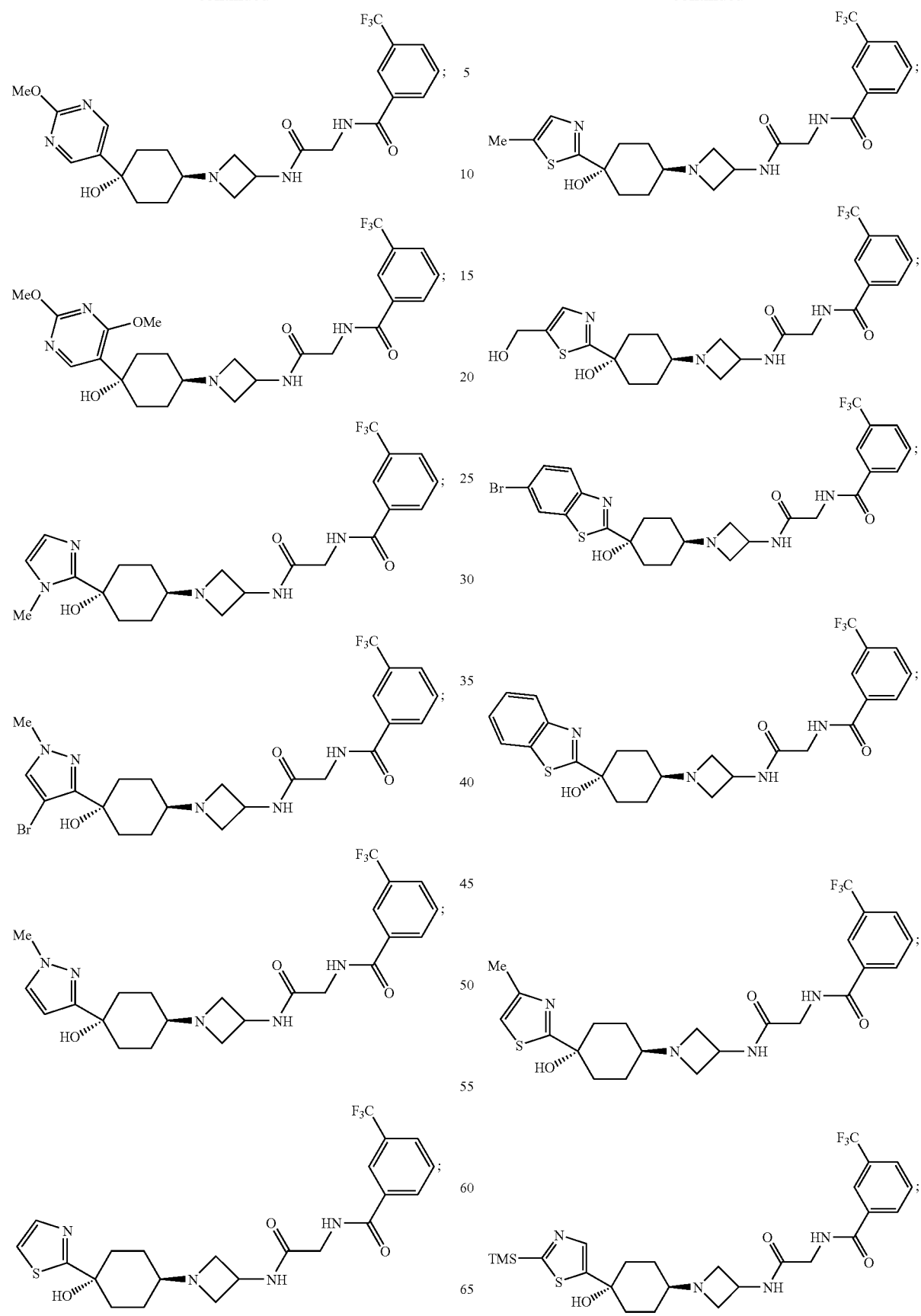

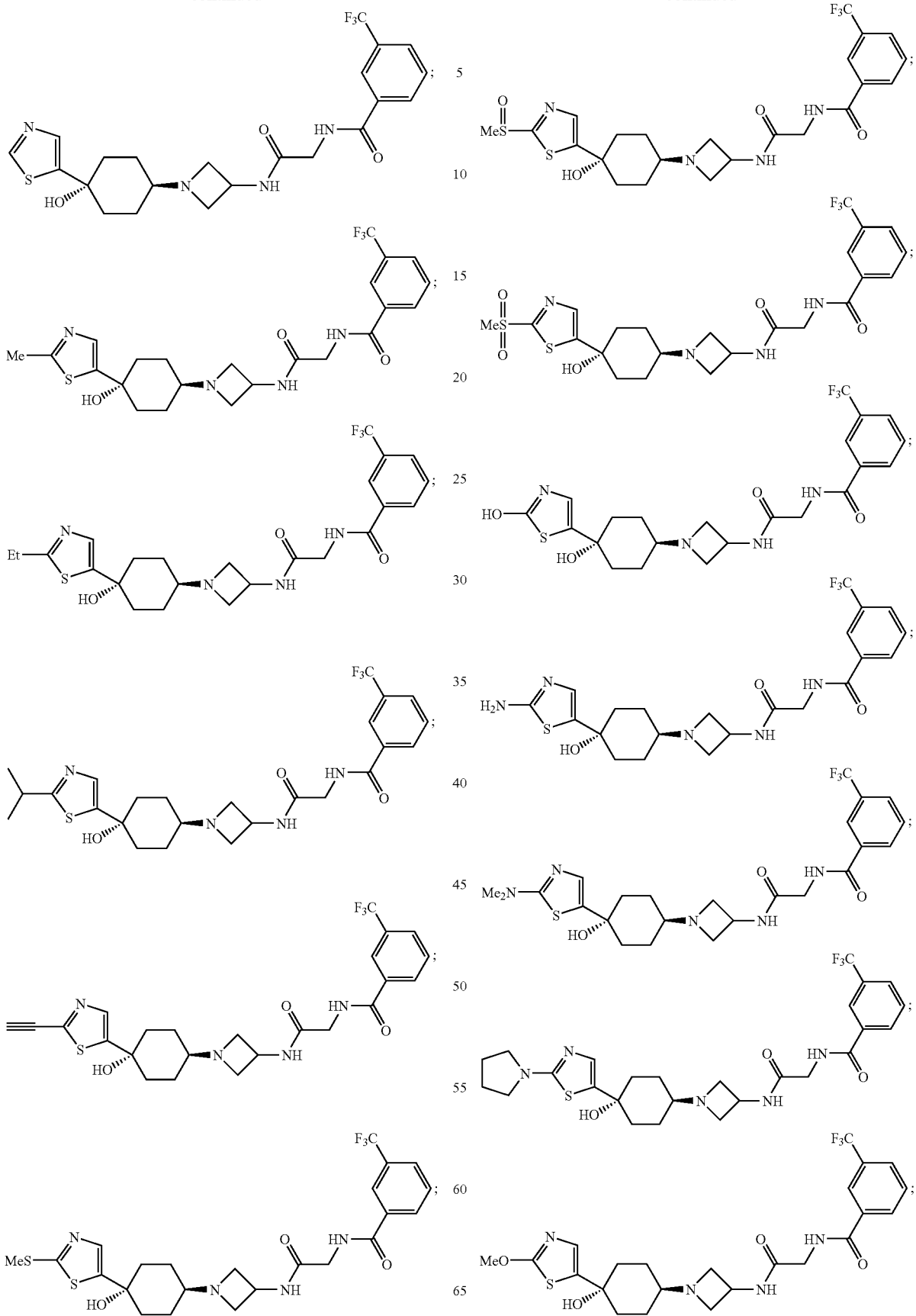

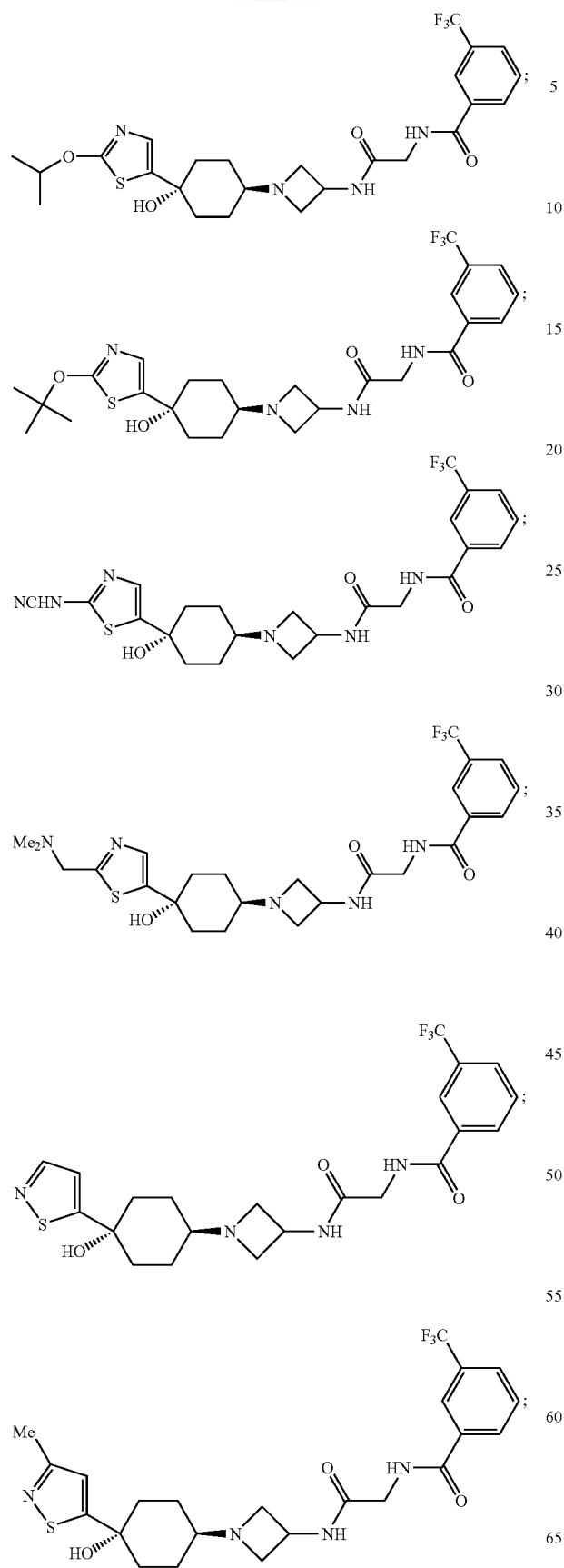
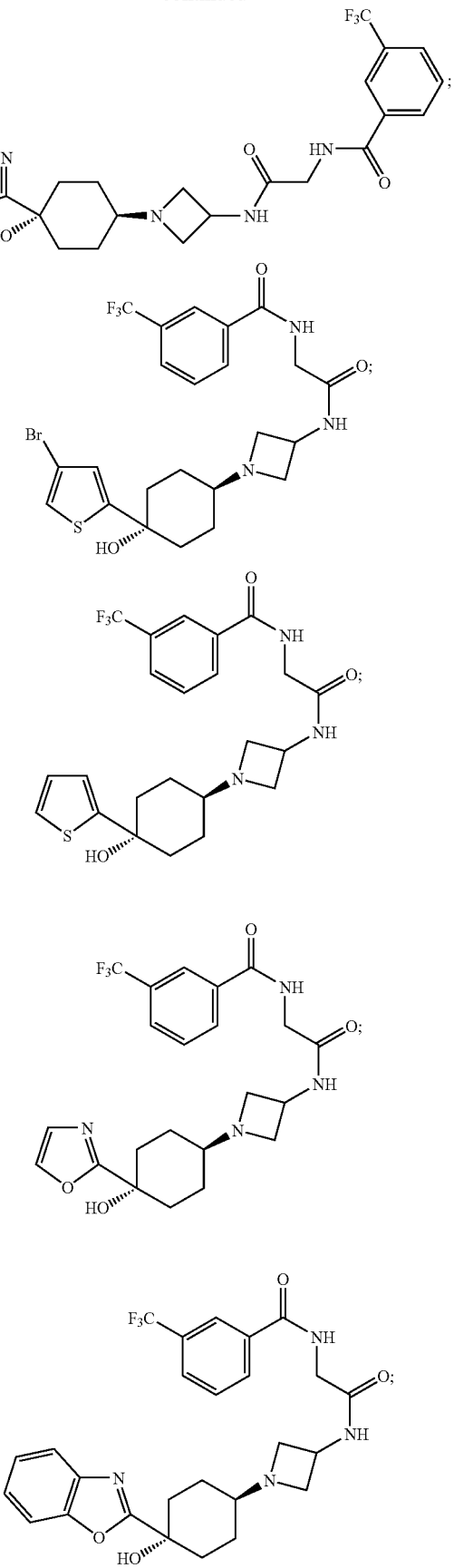

-continued
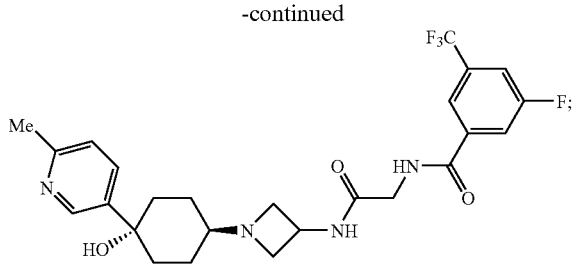
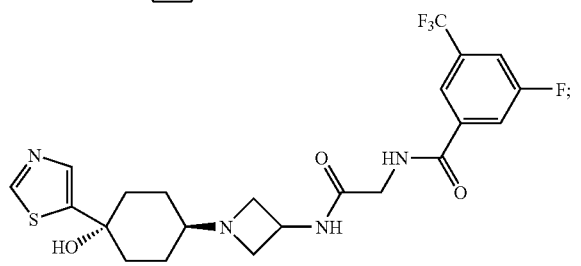
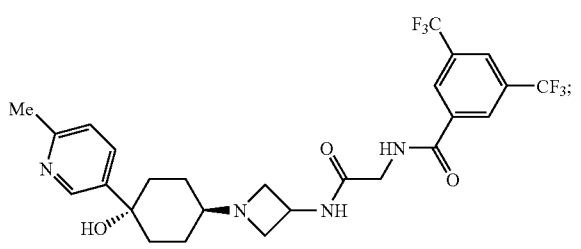
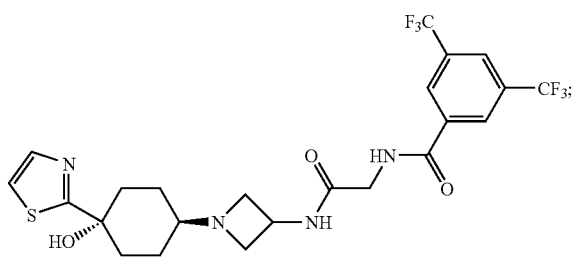
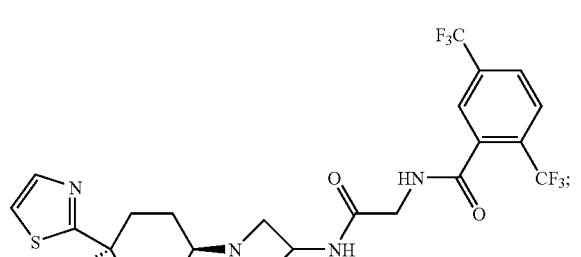
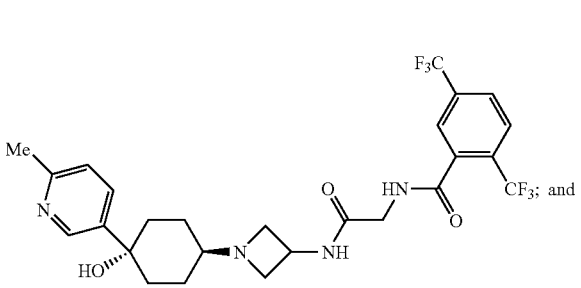
-continued
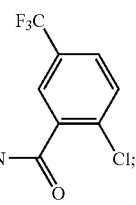
and hydrates, tautomers, and pharmaceutically acceptable salts thereof.
15. A compound of the formula
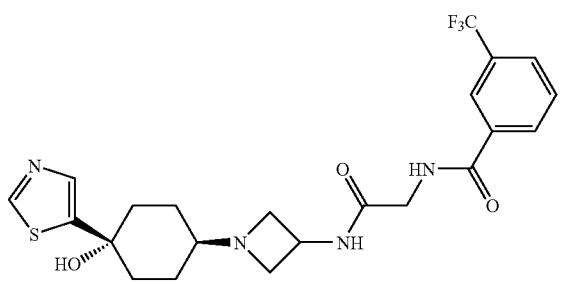 [SMILES: O=C(CNC(=O)c1cccc(C(F)(F)F)c1)NC1CN([C@H]2CC[C@@](O)(c3cncs3)CC2)C1]
and hydrates, tautomers, and pharmaceutically acceptable salts thereof.
16. A compound of claim 15 of the formula
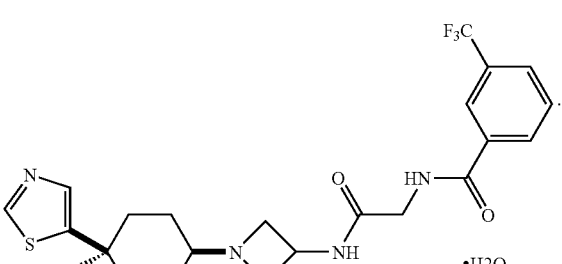
17. A crystalline compound of claim 16 having the following XRPD °2Θ peaks:
| Position [°2θ] |
| --- |
| 7.0 |
| 7.4 |
| 9.3 |
| 11.0 |
| 12.6 |
| 14.3 |
| 14.4 |
| 14.8 |
| 15.3 |
| 17.1 |
| 17.4 |
| 18.3 |
| 18.7 |
| 19.2 |
| 19.7 |
| 21.3 |
| 21.8 |

-continued

| Position [°2θ] |
|---|
| 22.2 |
| 22.9 |
| 23.5 |
| 23.9 |
| 24.5 |
| 24.7 |
| 25.3 |
| 26.3 |
| 28.2 |
| 28.8 |
| 29.5 |

18. A pharmaceutical composition, comprising a compound of claim 1 and a pharmaceutically acceptable carrier.

19. A pharmaceutical composition made by mixing a compound of claim 1 and a pharmaceutically acceptable carrier.

20. A process for making a pharmaceutical composition comprising mixing a compound of claim 1 and a pharmaceutically acceptable carrier.

21. A pharmaceutical composition, comprising a compound of claim 9 and a pharmaceutically acceptable carrier.

22. A pharmaceutical composition made by mixing a compound of claim 9 and a pharmaceutically acceptable carrier.

23. A process for making a pharmaceutical composition comprising mixing a compound of claim 9 and a pharmaceutically acceptable carrier.

24. A method of treating a disorder selected from the group consisting of: rheumatoid arthritis, type I diabetes, type II diabetes, diabetic complications, diabetic nephropathy, diabetic retinopathy, diabetic retinitis, diabetic microangiopathy, obesity, obesity-associated insulin resistance, metabolic syndrome, asthma, and allergic asthma, comprising administering to a subject in need thereof a therapeutically effective amount of a compound of claim 1.

25. A method of treating a disorder selected from the group consisting of type II diabetes, obesity and asthma comprising administering to a subject in need thereof a therapeutically effective amount of a compound of claim 1.

* * * * *